(12) United States Patent
Makita et al.

(10) Patent No.: US 10,987,349 B2
(45) Date of Patent: Apr. 27, 2021

(54) ANTITUMOR AGENT AND BROMODOMAIN INHIBITOR

(71) Applicants: FUJIFILM Corporation, Tokyo (JP); FUJIFILM Toyama Chemical Co., Ltd., Tokyo (JP); NATIONAL INSTITUTE OF ADVANCED INDUSTRIAL SCIENCE AND TECHNOLOGY, Tokyo (JP)

(72) Inventors: Keiko Makita, Ashigarakami-gun (JP); Kazunori Saeki, Ashigarakami-gun (JP); Tadashi Tanaka, Ashigarakami-gun (JP); Masataka Fujino, Ashigarakami-gun (JP); Tohru Natsume, Tokyo (JP); Kentaro Furuya, Toyama (JP)

(73) Assignees: FUJIFILM Corporation, Tokyo (JP); FUJIFILM Toyama Chemical Co., Ltd., Tokyo (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 16/453,393

(22) Filed: Jun. 26, 2019

(65) Prior Publication Data

US 2019/0314360 A1    Oct. 17, 2019

Related U.S. Application Data

(63) Continuation of application No. PCT/JP2017/046901, filed on Dec. 27, 2017.

(30) Foreign Application Priority Data

Dec. 27, 2016 (JP) .............................. JP2016-253157
Jun. 15, 2017 (JP) .............................. JP2017-117482
Oct. 25, 2017 (JP) .............................. JP2017-206012

(51) Int. Cl.
*A61K 31/4704*    (2006.01)
*A61P 35/02*    (2006.01)
*A61P 35/00*    (2006.01)
*A61K 31/4709*    (2006.01)
*A61K 31/4725*    (2006.01)
*A61K 31/497*    (2006.01)
(Continued)

(52) U.S. Cl.
CPC ...... *A61K 31/4704* (2013.01); *A61K 31/4709* (2013.01); *A61K 31/4725* (2013.01); *A61K 31/497* (2013.01); *A61K 31/498* (2013.01); *A61K 31/5377* (2013.01); *A61P 35/00* (2018.01); *A61P 35/02* (2018.01)

(58) Field of Classification Search
CPC ............ A61K 31/4704; A61K 31/4709; A61K 31/4725; A61K 31/497; A61K 31/498; A61K 31/5377; A61P 35/02; A61P 35/00; A61P 43/00
See application file for complete search history.

(56) References Cited

U.S. PATENT DOCUMENTS

| | | |
|---|---|---|
| 5,378,694 A | 1/1995 | Afonso et al. |
| 5,457,099 A | 10/1995 | Shogaki et al. |
| 6,509,352 B1 | 1/2003 | Inaba et al. |

(Continued)

FOREIGN PATENT DOCUMENTS

| | | |
|---|---|---|
| CN | 102143949 A | 8/2011 |
| EA | 007464 B1 | 10/2006 |

(Continued)

OTHER PUBLICATIONS

Office Action dated Jan. 28, 2020 from the Intellectual Property India Patent Office in Indian application 201947025350.

(Continued)

*Primary Examiner* — Sahar Javanmard
(74) *Attorney, Agent, or Firm* — Sughrue Mion, PLLC

(57) ABSTRACT

It is an object of the present invention to provide an antitumor agent, which is further excellent as a treatment agent used in the prevention and/or therapy of tumor associated with a bromodomain, and also to provide a bromodomain inhibitor, which is useful as a treatment agent for diseases or states associated with a bromodomain.

An antitumor agent and a bromodomain inhibitor, comprising a compound represented by the following formula, have an excellent bromodomain inhibitory activity and are useful as treatment agents in the prevention and/or therapy of tumor associated with a bromodomain, and the like:

[Formula 1]

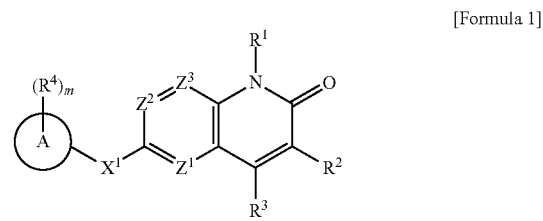

wherein $R^1$ represents a $C_{1-6}$ alkyl group, etc.; $R^2$ represents a hydrogen atom, etc.; $R^3$ represents a halogen atom, etc.; $Z^1$, $Z^2$ and $Z^3$ each represent CH, etc.; $X^1$ represents CONH, etc.; Ring A represents a phenyl group, etc.; $R^4$ represents a halogen atom, etc.; and m represents an integer from 0 to 5.

11 Claims, 3 Drawing Sheets

(51) Int. Cl.
*A61K 31/498* (2006.01)
*A61K 31/5377* (2006.01)

(56) References Cited

U.S. PATENT DOCUMENTS

| | | | |
|---|---|---|---|
| 2004/0082592 | A1 | 4/2004 | Mabire et al. |
| 2004/0235848 | A1 | 11/2004 | Okuzumi et al. |
| 2010/0286127 | A1 | 11/2010 | Miyoshi et al. |
| 2010/0331326 | A1 | 12/2010 | Bock et al. |
| 2017/0291875 | A1 | 10/2017 | Fish et al. |
| 2019/0077761 | A1 | 3/2019 | Tanaka et al. |

FOREIGN PATENT DOCUMENTS

| | | |
|---|---|---|
| JP | 6-73011 A | 3/1994 |
| JP | 6-502845 A | 3/1994 |
| JP | 7-252228 A | 10/1995 |
| TW | 515794 B | 1/2003 |
| WO | 02/051834 A1 | 7/2002 |
| WO | 02/051835 A1 | 7/2002 |
| WO | 03/053926 A1 | 7/2003 |
| WO | 2004/005892 A2 | 1/2004 |
| WO | 2005/018573 A2 | 3/2005 |
| WO | 2009/041026 A1 | 4/2009 |
| WO | 2009/084693 A1 | 7/2009 |
| WO | 2009/140769 A1 | 11/2009 |
| WO | 2010/028015 A2 | 3/2010 |
| WO | 2013/027168 A1 | 2/2013 |
| WO | 2014/159837 A1 | 10/2014 |
| WO | 2016/016316 A1 | 2/2016 |
| WO | 2016/034512 A1 | 3/2016 |
| WO | 2016/077656 A2 | 5/2016 |

OTHER PUBLICATIONS

Elena Ferri, et al.,"Bromodomains: Structure, function and pharmacology of inhibition", Biochemical Pharmacology, 2015, one page, https://doi.org/10.1016/j.bcp.2015.12.005.
Office Action dated Apr. 28, 2020, from the Japanese Patent Office in Japanese application No. 2018-559578.
Office Action dated Mar. 13, 2020 issued in corresponding Russian patent Application No. 2019119836.
Office Action dated Oct. 3, 2019 issued by the Intellectual Property Office of Australia in counterpart Australian application No. 2017385292.
Igoe, Niall et al., "Design of a Biased Potent Small Molecule Inhibitor of the Bromodomain and PHD Finger-Containing (BRPF) Proteins Suitable for Cellular and in Vivo Studies", Journal of Medicinal Chemistry, 2017, vol. 60, No. 2, XP-002795414, pp. 668-680 (total 13 pages).
Extended European Search Report dated Nov. 22, 2019 from European Patent Office in counterpart EP Application No. 17885921.1.
Office Action dated Dec. 18, 2019 in Russian Application No. 2018105867, corresponding to previously-disclosed co-pending U.S. Appl. No. 15/743,758.
Notice of Allowance dated Oct. 30, 2019 in U.S. Appl. No. 15/743,758.
Extended European Search Report dated Feb. 26, 2019, from the European Patent Office in European Application No. 16827761.4 (corresponding to U.S. Appl. No. 15/743,758).
Office Action dated Jun. 14, 2019, from the Intellectual Property Office of Singapore in Application No. 11201800445P (corresponding to U.S. Appl. No. 15/743,758).
International Preliminary Report on Patentability dated Jan. 23, 2018 for International application No. PCT/JP2016/071047 (corresponding to U.S. Appl. No. 15/743,758).
International Search Report for PCT/JP2016/071047, dated Aug. 30, 2016 (corresponding to U.S. Appl. No. 15/743,758).
Kelland, E. E. et al., "In vitro assessment of the direct effect of laquinimod on basic functions of human neural stem cells and oligodendrocyte progenitor cells", Journal of the Neurological Sciences, 2014, pp. 66-74, vol. 346, No. 1-2.
Written Opinion, dated Aug. 30, 2016 for International application No. PCT/JP2016/071047 (corresponding to U.S. Appl. No. 15/743,758).
Office Action dated Jun. 25, 2019 in U.S. Appl. No. 15/743,758.
Takayoshi Suzuki, "Development of Epigenetic Modulators for Cancer Therapy", Magazine of Kyoto Prefectural University of Medicine, vol. 124, No. 12, 2015, pp. 839-847.
Panagis Filippakopoulos et al., "Targeting bromodomains: epigenetic readers of lysine acetylation", Nature Reviews, Drug Discovery, vol. 13, May 2014, pp. 337-356.
International Search Report dated Apr. 10, 2018 from the International Searching Authority in counterpart International Application No. PCT/JP2017/046901.
Written Opinion dated Apr. 10, 2018 from the International Bureau in counterpart International Application No. PCT/JP2017/046901.
International Preliminary Report on Patentability dated Jul. 2, 2019 from the International Bureau in counterpart International Application No. PCT/JP2017/046901.
Clark et al., "Discovery and Synthesis of the First Selective BRD7/9 Bromodomain Inhibitor", Angew. Chem. Int. Ed., 2015, vol. 54, pp. 6217-6221.
Office Action dated Mar. 10, 2020 in Taiwanese Application No. 105122410, corresponding to U.S. Appl. No. 15/743,758.
Office Action dated Jul. 21, 2020, issued by the Canadian Intellectual Property Office in Canadian application No. 3,048,602.
Office Action dated Sep. 29, 2020 from the Korean Intellectual Property Office in KR Application No. 10-2019-7018536.
Office Action dated Jun. 25, 2020, from the Russian Federal Service for Intellectual Property in Russian Application No. 2019119836/04.
Office Action dated Nov. 12, 2020, from the Russian Patent and Trademark Office in Russian application No. 2019119836.

[Fig. 1]
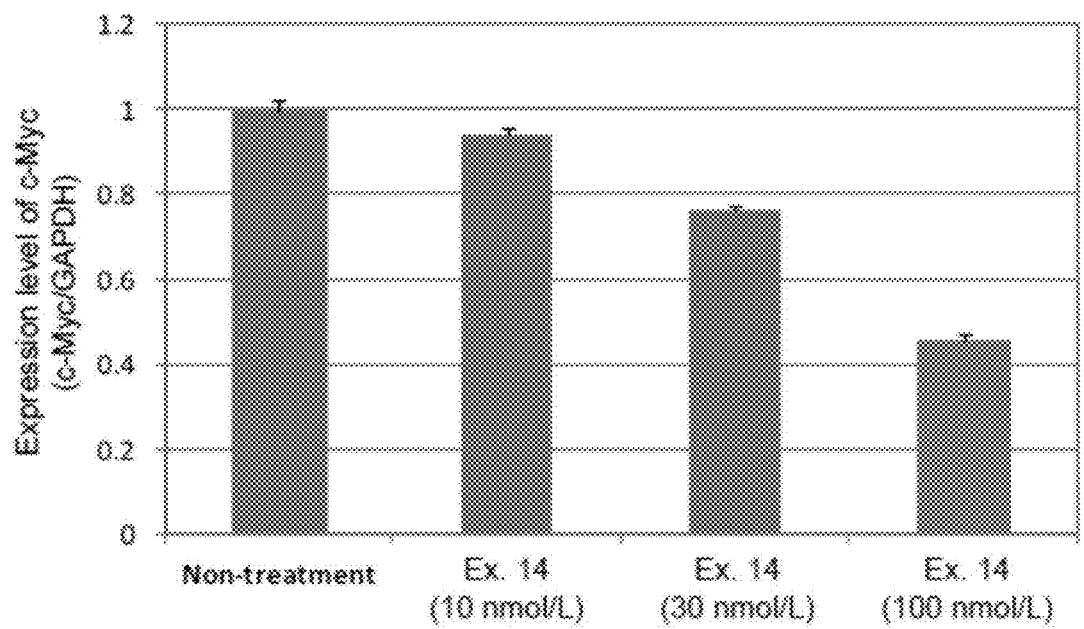
[Fig. 2]
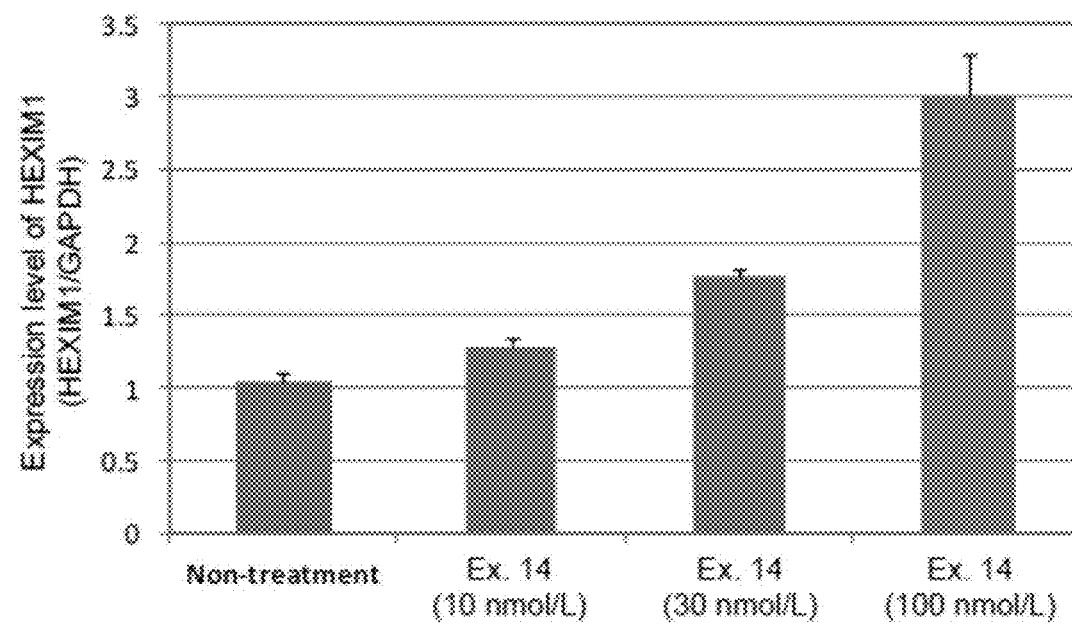

[Fig. 3]
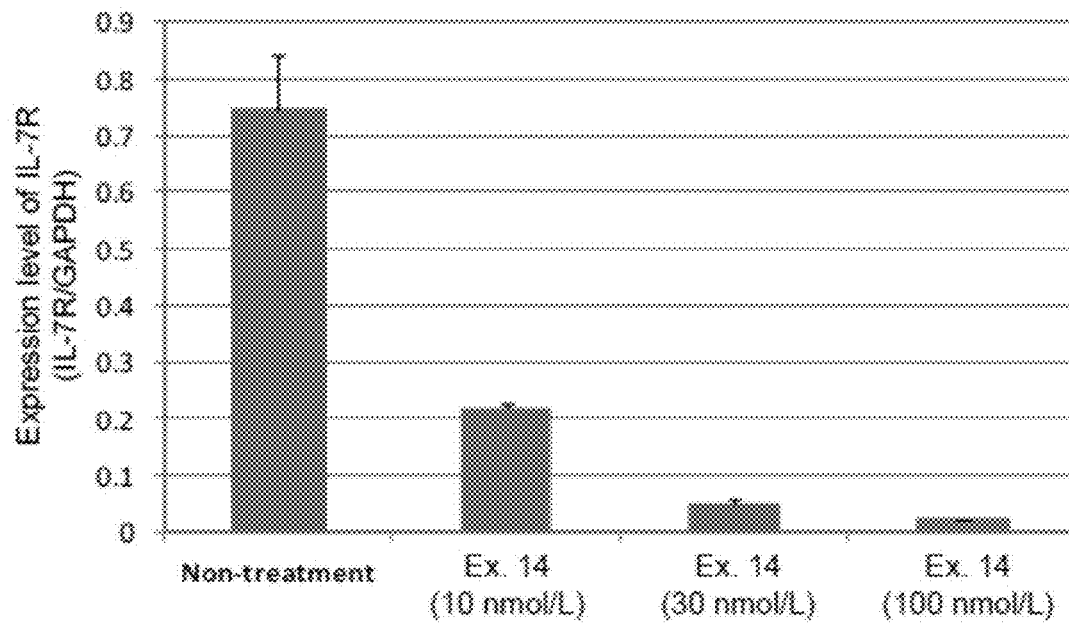
[Fig. 4]
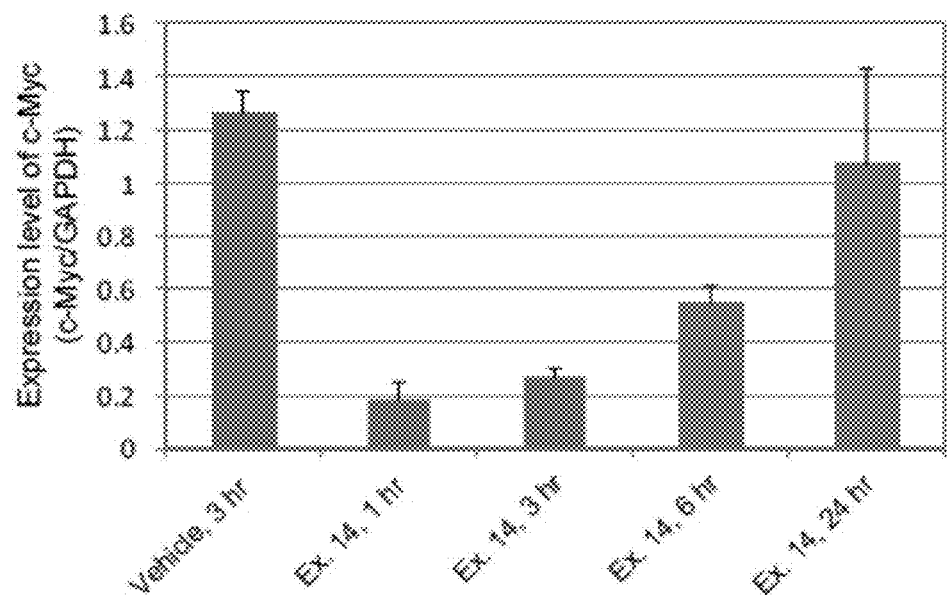

[Fig. 5]
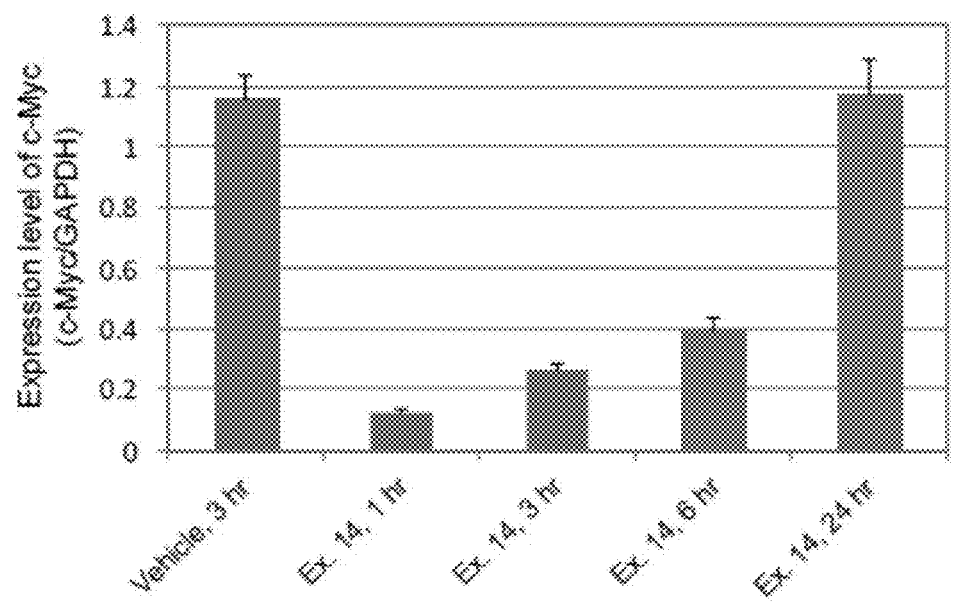

ANTITUMOR AGENT AND BROMODOMAIN INHIBITOR

CROSS-REFERENCE TO RELATED APPLICATIONS

This application is a Continuation of PCT International Application No. PCT/JP2017/046901 filed on Dec. 27, 2017, which claims priority under 35 U.S.C § 119(a) to Japanese Patent Application No. 2016-253157 filed on Dec. 27, 2016, Japanese Patent Application No. 2017-117482 filed on Jun. 15, 2017 and Japanese Patent Application No. 2017-206012 filed on Oct. 25, 2017. Each of the above application(s) is hereby expressly incorporated by reference, in its entirety, into the present application.

TECHNICAL FIELD

The present invention relates to an antitumor agent and a bromodomain inhibitor.

BACKGROUND ART

Bromodomain is a protein domain, which has been known to have a function to recognize the acetylated lysine of histone and to gather regulatory proteins to control a chromatin structure and gene expression (Non-Patent Document 1). Approximately 50 types of bromodomain-containing proteins are present in a human body. An example of the protein containing a bromodomain may be a bromodomain and extra-terminal (BET) family protein having a bromodomain repeated sequence and a specific terminal sequence. As such a BET family protein, bromodomain-containing protein 2 (BRD2), BRD3, BRD4 and BRDT have been known. These proteins each have Bromodomain 1 (BD1) and Bromodomain 2 (BD2) as N-terminal bromodomains.

Histone is a basic protein, which is commonly present in the nucleus of the eukaryotic cells of organisms ranging from multicellular organisms including humans as typical examples to unicellular organisms including fungi (mold and/or yeast) as typical examples, and which binds to genomic DNA via an ionic bond. Such histone generally consists of 5 types of components (H1, H2A, H2B, H3 and H4), and they are highly similar to one another, regardless of organism species. Histone undergoes modifications, such as acetylation, methylation, phosphorylation, ubiquitylation and small ubiquitin-related modification (SUMO), at the N-terminal portion called "histone tail," and the chromatin structure is maintained or is specifically converted to another structure, so that reactions occurring on the chromosomal DNA, such as gene expression, DNA replication and DNA repair, can be controlled. The post-translational modification of histone is an epigenetic regulatory mechanism, and it is considered that this modification is essential for the gene regulation of eukaryotic cells. For example, the acetylation of histone is controlled by a pair of modifying enzymes (i.e., a histone acetylating enzyme and a histone deacetylating enzyme). In general, a deacetylating enzyme dominantly works and thus, histone is maintained in a deacetylated state. However, once cells are stimulated and are thereby activated, the amino group of the lysine residue of histone is acetylated by a histone acetylating enzyme, and the positive charge of the amino group is neutralized, so that the interaction between nucleosomes is loosen, a transcriptional factor is recruited, and transcription is initiated.

In recent years, it has been assumed that acetylated histone H3 or acetylated histone H4, which is formed by acetylation of histone H3 or histone H4, would interact with BRD2, BRD3 and BRD4. The development of a bromodomain inhibitor that targets these BET family proteins has been progressed (Patent Documents 1 and 2, and Non-Patent Documents 1 and 2), and the application of such a bromodomain inhibitor as an antitumor agent has also been progressed.

PRIOR ART DOCUMENTS

Patent Documents

Patent Document 1: International Publication WO 2016/016316
Patent Document 2: International Publication WO 2009/084693

Non-Patent Documents

Non-Patent Document 1: Panagis F et al., Nature Reviews Drug Discovery, Vol. 13, pp. 337 to 356, 2014
Non-Patent Document 2: Suzuki et al., Magazine of Kyoto Prefectural University of Medicine, Vol. 124, pp. 839 to 847, 2015

SUMMARY OF INVENTION

Object to be Solved by the Invention

It is an object of the present invention to provide an antitumor agent, which is further excellent as a treatment agent used in the prevention and/or therapy of tumor associated with a bromodomain. In addition, it is another object of the present invention to provide a bromodomain inhibitor, which is useful as a treatment agent for diseases or states associated with a bromodomain.

Means for Solving the Object

As a result of intensive studies in order to achieve the above objects, the present inventors have found that a nitrogen-containing heterocyclic compound having a specific structure or a salt thereof has an excellent bromodomain inhibitory activity. Moreover, the present inventors have also found that the compound of the present invention having an excellent bromodomain inhibitory activity is also useful as an antitumor agent, thereby completing the present invention.

Specifically, the present invention provides the following.
<1>
An antitumor agent comprising a compound represented by the following formula [1] (hereinafter referred to as "Compound A") or a salt thereof:

[Formula 1]

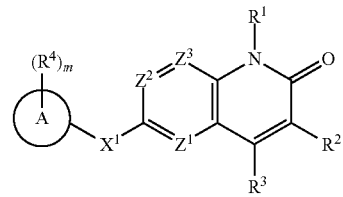

[1]

wherein $R^1$ represents a hydrogen atom or an optionally substituted $C_{1-6}$ alkyl group;
$R^2$ represents a hydrogen atom, a halogen atom, or an optionally substituted $C_{1-6}$ alkyl group;
$R^3$ represents a halogen atom, an optionally substituted $C_{1-6}$ alkyl group, an optionally substituted $C_{2-6}$ alkenyl group, an optionally substituted $C_{3-8}$ cycloalkyl group, an optionally substituted $C_{4-8}$ cycloalkenyl group, an optionally substituted aryl group, an optionally substituted $C_{1-6}$ alkoxy group, an optionally substituted $C_{1-6}$ alkylamino group, an optionally substituted di($C_{1-6}$ alkyl)amino group, or an optionally substituted heterocyclic group;
$Z^1$, $Z^2$ and $Z^3$, which are the same or different, each represent a nitrogen atom or a group represented by the formula $CR^5$ (wherein $R^5$ represents a hydrogen atom, a halogen atom or an optionally substituted $C_{1-6}$ alkyl group);
$X^1$ represents
(1) a group represented by the formula $C(=O)N(R^6)$ (wherein the carbon atom binds to Ring A, and $R^6$ represents a hydrogen atom, an amino-protecting group, or an optionally substituted $C_{1-6}$ alkyl group,
(2) a group represented by the formula $N(R^7)C(=O)$ (wherein the nitrogen atom binds to Ring A, and $R^7$ represents a hydrogen atom, an amino-protecting group, or an optionally substituted $C_{1-6}$ alkyl group; or $R^7$ represents, together with one substituent $R^4$ of Ring A, an optionally substituted $C_{2-4}$ alkylene group, a group represented by the formula $O—Y^1$ (wherein the oxygen atom binds to Ring A, and $Y^1$ represents an optionally substituted $C_{1-3}$ alkylene group), a group represented by the formula $S(O)_n—Y^2$ (wherein the sulfur atom binds to Ring A, $Y^2$ represents an optionally substituted $C_{1-3}$ alkylene group, and n represents an integer from 0 to 2), or a group represented by the formula $N(R^8)—Y^3$ (wherein the nitrogen atom binds to Ring A, $Y^3$ represents an optionally substituted $C_{1-3}$ alkylene group, and $R^8$ represents a hydrogen atom, an amino-protecting group, an optionally substituted $C_{1-6}$ alkyl group, or an optionally substituted aryl group)),
(3) an optionally substituted divalent cyclic hydrocarbon group that is formed by removing each one hydrogen atom on the two adjacent atoms, or
(4) an optionally substituted divalent heterocyclic group that is formed by removing each one hydrogen atom on the two adjacent atoms; Ring A represents a cyclic hydrocarbon group or a heterocyclic group; an m number of $R^4$, which are the same or different, each represent a halogen atom, a cyano group, a nitro group, an amino-protecting group, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{4-8}$ cycloalkenyl group, an optionally substituted aryl group, an optionally substituted $C_{1-6}$ alkoxy group, an optionally substituted aryloxy group, an optionally substituted $C_{1-6}$ alkylamino group, an optionally substituted di($C_{1-6}$ alkyl)amino group, an optionally substituted arylamino group, an optionally substituted carbamoyl group, an optionally substituted sulfamoyl group, an optionally substituted $C_{1-6}$ alkylthio group, an optionally substituted arylthio group, an optionally substituted $C_{1-6}$ alkylsulfonyl group, an optionally substituted arylsulfonyl group, an optionally substituted heterocyclic group, an optionally protected amino group, an optionally protected hydroxyl group, an optionally protected carboxyl group, an optionally substituted $C_{2-5}$ alkylene group formed together by the two adjacent $R^4$,
an optionally substituted $C_{2-4}$ alkylene group formed by one $R^4$ together with $R^7$, a group represented by the formula $O—Y^1$ (wherein the oxygen atom binds to Ring A, and $Y^1$ represents an optionally substituted $C_{1-3}$ alkylene group), which is formed by one $R^4$ together with $R^7$,
a group represented by the formula $S(O)_n—Y^2$ (wherein the sulfur atom binds to Ring A, $Y^2$ represents an optionally substituted $C_{1-3}$ alkylene group, and n represents an integer from 0 to 2), which is formed by one $R^4$ together with $R^7$,
or
a group represented by the formula $N(R^8)—Y^3$ (wherein the nitrogen atom binds to Ring A, $Y^3$ represents an optionally substituted $C_{1-3}$ alkylene group, and $R^8$ represents a hydrogen atom, an amino-protecting group, an optionally substituted $C_{1-6}$ alkyl group, or an optionally substituted aryl group), which is formed by one $R^4$ together with $R^7$; and m represents an integer from 0 to 5.

<2>
The antitumor agent according to the above <1>, wherein $R^2$ represents a hydrogen atom or a $C_{1-6}$ alkyl group; and $Z^1$, $Z^2$ and $Z^3$ each represent CH.

<3>
The antitumor agent according to the above <1> or <2>, wherein $R^3$ represents an optionally substituted $C_{3-8}$ cycloalkyl group or an optionally substituted heterocyclic group.

<4>
The antitumor agent according to any one of the above <1> to <3>, wherein
$R^3$ represents any one of the following heterocyclic groups:

[Formula 2]

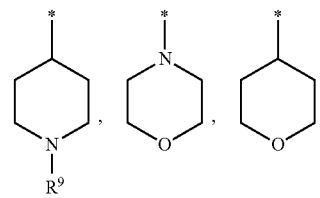

wherein $R^9$ represents a hydrogen atom, an amino-protecting group, or an optionally substituted $C_{1-6}$ alkyl group, and * represents a binding site.

<5>
The antitumor agent according to any one of the above <1> to <4>, wherein Ring A represents a cyclic hydrocarbon group.

<6>
The antitumor agent according to any one of the above <1> to <5>, wherein $X^1$ represents
(2) a group represented by the formula $N(R^7)C(=O)$ (wherein the nitrogen atom binds to Ring A, and $R^7$ represents a hydrogen atom, an amino-protecting group, or an optionally substituted $C_{1-6}$ alkyl group; or $R^7$ represents, together with one substituent $R^4$ of Ring A, an optionally substituted $C_{2-4}$ alkylene group, a group represented by the formula $O—Y^1$ (wherein the oxygen atom binds to Ring A, and $Y^1$ represents an optionally substituted $C_{1-3}$ alkylene group), a group represented by the formula $S(O)_n—Y^2$ (wherein the sulfur atom binds to Ring A, $Y^2$ represents an optionally substituted $C_{1-3}$ alkylene group, and n represents an integer from 0 to 2), or a group represented by the formula $N(R^8)—Y^3$ (wherein the nitrogen atom binds to Ring A, $Y^3$ represents an optionally substituted $C_{1-3}$ alkylene group, and $R^8$ represents a hydrogen atom, an amino-protecting group, an optionally substituted $C_{1-6}$ alkyl group, or an optionally substituted aryl group)), or (4) an optionally substituted divalent heterocyclic group that is formed by removing each one hydrogen atom on the two adjacent atoms.
<7>
The antitumor agent according to any one of the above <1> to <5>, wherein
the compound is represented by the following formula [1-1]:

[Formula 3]

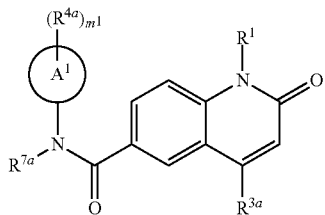

[1-1]

wherein $R^1$ represents a hydrogen atom or an optionally substituted $C_{1-6}$ alkyl group;
$R^{3a}$ represents an optionally substituted $C_{1-6}$ alkyl group, an optionally substituted $C_{3-8}$ cycloalkyl group, or an optionally substituted heterocyclic group;
Ring $A^1$ represents a cyclic hydrocarbon group;
$R^{7a}$ represents an amino-protecting group or an optionally substituted $C_{1-6}$ alkyl group; or
$R^{7a}$ represents, together with one substituent $R^{4a}$ of Ring $A^1$, an optionally substituted $C_{2-3}$ alkylene group, a group represented by the formula $O-Y^{1a}$ (wherein the oxygen atom binds to Ring $A^1$, and $Y^{1a}$ represents an optionally substituted $C_{1-3}$ alkylene group), a group represented by the formula $S(O)_n-Y^{2a}$ (wherein the sulfur atom binds to Ring $A^1$, $Y^{2a}$ represents an optionally substituted $C_{1-3}$ alkylene group, and n represents an integer from 0 to 2), or a group represented by the formula $N(R^{8a})-Y^{3a}$ (wherein the nitrogen atom binds to Ring $A^1$, $Y^{3a}$ represents an optionally substituted $C_{1-3}$ alkylene group, and $R^{8a}$ represents a hydrogen atom or an optionally substituted $C_{1-6}$ alkyl group),
an $m^1$ number of $R^{4a}$, which are the same or different, each represent a halogen atom, a cyano group, an optionally substituted $C_{1-3}$ alkyl group, an optionally substituted carbamoyl group, an optionally substituted $C_{1-3}$ alkylsulfonyl group, an optionally protected carboxyl group,
an optionally substituted $C_{2-5}$ alkylene group formed together by the two adjacent $R^{4a}$,
an optionally substituted $C_{2-3}$ alkylene group formed by one $R^{4a}$ together with $R^{7a}$,
a group represented by the formula $O-Y^{1a}$ (wherein the oxygen atom binds to Ring $A^1$, and $Y^{1a}$ represents an optionally substituted $C_{1-3}$ alkylene group), which is formed by one $R^{4a}$ together with $R^{7a}$,
a group represented by the formula $S(O)_n-Y^{2a}$ (wherein the sulfur atom binds to Ring $A^1$, $Y^{2a}$ represents an optionally substituted $C_{1-3}$ alkylene group, and n represents an integer from 0 to 2), which is formed by one $R^{4a}$ together with $R^{7a}$, or
a group represented by the formula $N(R^{8a})-Y^{3a}$ (wherein the nitrogen atom binds to Ring $A^1$, $Y^{3a}$ represents an optionally substituted $C_{1-3}$ alkylene group, and $R^{8a}$ represents a hydrogen atom or an optionally substituted $C_{1-6}$ alkyl group), which is formed by one $R^{4a}$ together with $R^{7a}$; and
$m^1$ represents an integer from 0 to 2.

<8>
The antitumor agent according to any one of the above <1> to <6>, wherein
$X^1$ represents an optionally substituted dihydrooxoimidazole-1,5-diyl group, an optionally substituted imidazole-1,2-diyl group, an optionally substituted imidazole-4,5-diyl group, an optionally substituted 1,2,4-triazole-1,5-diyl group, an optionally substituted 1H-pyrazole-4,5-dihyl group, an optionally substituted oxopyrrolidine-1,2-diyl group, an optionally substituted dioxotriazolidine-1,2-diyl group, an optionally substituted dioxopyrazolidine-1,2-diyl group, an optionally substituted oxopyrazoline-1,2-diyl group, an optionally substituted pyridine-2,3-diyl group, or an optionally substituted pyrazine-2,3-diyl group.
<9>
The antitumor agent according to any one of the above <1> to <5>, wherein
the compound is represented by the following formula [1-2]:

[Formula 4]

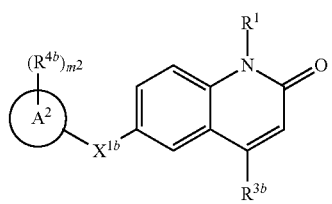

[1-2]

wherein $R^1$ represents a hydrogen atom or an optionally substituted $C_{1-6}$ alkyl group;
$R^{3b}$ represents an optionally substituted $C_{1-6}$ alkyl group, an optionally substituted $C_{3-8}$ cycloalkyl group, or an optionally substituted heterocyclic group;
$X^{1b}$ represents an optionally substituted dihydrooxoimidazole-1,5-diyl group;
Ring $A^2$ represents a cyclic hydrocarbon group;
an $m^2$ number of $R^{4b}$, which are the same or different, each represent a halogen atom or an optionally substituted $C_{1-6}$ alkyl group; and
$m^2$ represents an integer from 0 to 2.
<10>
The antitumor agent according to the above <1>, wherein
the compound is at least one selected from the group consisting of: N-(4-cyclopropyl-1-ethyl-2-oxo-1,2-dihydroquinolin-6-yl)-N-methylbenzamide, 1-ethyl-4-(1-ethylpiperidin-4-yl)-N-methyl-2-oxo-N-phenyl-1,2-dihydroquinoline-6-carboxamide, 6-(3,4-dihydroquinolin-1 (2H)-ylcarbonyl)-1-ethyl-4-(1-methylpiperidin-4-yl)quinolin-2 (1H)-one, 1-ethyl-N-methyl-N-(4-methylphenyl)-4-(1-methylpiperidin-4-yl)-2-oxo-1,2-dihydroquinoline-6-carboxamide, N-(2,3-dihydro-1H-inden-5-yl)-1-ethyl-N-methyl-4-(1-methylpiperidin-4-yl)-2-oxo-1,2-dihydroquinoline-6-carboxamide, 6-(5-(4-chlorophenyl)-2-oxo-2,3-dihydro-1H-imidazol-1-yl)-1-ethyl-4-(morpholin-4-yl)quinolin-2(1H)-one, 6-(5-(4-chlorophenyl)-3-methyl-2-oxo-2,3-dihydro-1H-imidazol-1-yl)-1-ethyl-4-(morpholin-4-yl)quinolin-2(1H)-one, 1-ethyl-4-(morpholin-4-yl)-6-(2-oxo-5-phenyl-3-(propan-2-yl)-2,3-dihydro-1H-imidazol-1-yl)quinolin-2(1H)-one, 1-(4-cyclopropyl-1-ethyl-2-oxo-1,2-dihydroquinolin-6-yl)-2-phenyl-1,2,4-triazolidine-3,5-dione, 4-chloro-N-(1-ethyl-4-(morpholin-4-yl)-2-oxo-1,2-dihydroquinolin-6-yl)-N-methylbenzamide, 4-(1-acetylpiperidin-4-yl)-1-ethyl-N-methyl-N-(4-methylphenyl)-2-oxo-1,2-dihydroquinoline-6-carboxamide, 1-ethyl-N-(3-fluoro-4-methylphenyl)-N-methyl-4-(1-methylpiperidin-4-yl)-2-oxo-1,2-dihydroquinoline-6-carboxamide, N-(3-chloro-4-methylphenyl)-1-ethyl-N-methyl-4-(1-methylpiperidin-4-yl)-2-oxo-1,2-dihydroquinoline-6-carboxamide, and N-(3,4-dimethylphenyl)-1-ethyl-N-methyl-4-(1-methylpiperidin-4-yl)-2-oxo-1,2-dihydroquinoline-6-carboxamide.
<11>
The antitumor agent according to any one of the above <1> to <10>, wherein the tumor is blood cancer, thymoma, myeloma, liver cancer, pancreatic cancer, ovarian cancer, prostate cancer, lung cancer, osteosarcoma, colon cancer, breast cancer, skin cancer, or epithelial cell cancer.
<12>
A bromodomain inhibitor comprising Compound A or a salt thereof.
<13>
The bromodomain inhibitor according to the above <12>, which inhibits the binding of bromodomain to acetylated histone.
<14>
The bromodomain inhibitor according to the above <12> or <13>, wherein the bromodomain is a protein domain comprised in a BET family protein.
<15>
A pharmaceutical composition for use in the therapy of tumor, comprising Compound A or a salt thereof.
<16>
A pharmaceutical composition for use in the therapy of disease associated with a bromodomain, comprising Compound A or a salt thereof.
<17>
A method for therapy of tumor, comprising a step of administering a therapeutically effective amount of Compound A or a salt thereof to mammals including a human.
<18>
A method for treating disease associated with a bromodomain, comprising a step of administering a therapeutically effective amount of Compound A or a salt thereof to mammals including a human.
<19>
Compound A or a salt thereof for use in the therapy of tumor.
<20>
Compound A or a salt thereof for use in the therapy of disease or symptom associated with a bromodomain.
<21>
Use of Compound A or a salt thereof for the production of a pharmaceutical composition for treating tumor.
<22>
Use of Compound A or a salt thereof for the production of a pharmaceutical composition for treating disease associated with a bromodomain.

Advantageous Effects of Invention

The antitumor agent and the bromodomain inhibitor of the present invention have an excellent bromodomain inhibitory activity and are useful as treatment agents in the prevention and/or therapy of tumor associated with a bromodomain, and the like.

BRIEF DESCRIPTION OF DRAWINGS

FIG. 1 is a graph showing the mRNA expression level of a c-Myc gene according to GAPDH correction, in MV4-11 cells treated with the compound of Example 14.

FIG. 2 is a graph showing the mRNA expression level of an HXIM1 gene according to GAPDH correction, in MV4-11 cells treated with the compound of Example 14.

FIG. 3 is a graph showing the mRNA expression level of an IL-7R gene according to GAPDH correction, in MV4-11 cells treated with the compound of Example 14.

FIG. 4 is a graph showing the mRNA expression level of a c-Myc gene according to GAPDH correction in tumor, when the compound of Example 14 was intravenously administered into a cancer-bearing mouse model having subcutaneous transplantation of MV4-11.

FIG. 5 is a graph showing the mRNA expression level of a c-Myc gene according to GAPDH correction in tumor, when the compound of Example 14 was orally administered to a cancer-bearing mouse model having subcutaneous transplantation of MV4-11.

EMBODIMENT OF CARRYING OUT THE INVENTION

Hereafter, the present invention will be described in detail.

In the present invention, the symbol % means % by mass, unless otherwise particularly specified.

In the present invention, individual terms have the following meanings, unless otherwise particularly specified.

The halogen atom means a fluorine atom, a chlorine atom, a bromine atom, or an iodine atom.

The $C_{1-6}$ alkyl group means linear or branched $C_{1-6}$ alkyl groups, such as methyl, ethyl, propyl, isopropyl, butyl, sec-butyl, isobutyl, tert-butyl, pentyl, isopentyl and hexyl groups.

The $C_{1-3}$ alkyl group means a methyl, ethyl, propyl or isopropyl group.

The $C_{2-6}$ alkenyl group means linear or branched $C_{2-6}$ alkenyl groups, such as vinyl, allyl, propenyl, isopropenyl, butenyl, isobutenyl, 1,3-butadienyl, pentenyl and hexenyl groups.

The $C_{2-6}$ alkynyl group means linear or branched $C_{2-6}$ alkynyl groups, such as ethynyl, propynyl, butynyl, pentynyl and hexynyl groups.

The $C_{3-8}$ cycloalkyl group means $C_{3-8}$ cycloalkyl groups, such as cyclopropyl, cyclobutyl, cyclopentyl and cyclohexyl groups.

The $C_{4-8}$ cycloalkenyl group means $C_{4-8}$ cycloalkenyl groups, such as cyclobutenyl, cyclopentenyl, cyclohexenyl and cyclohexanedienyl groups.

The aryl group means a phenyl or naphthyl group.

The aryl $C_{1-6}$ alkyl group means aryl $C_{1-6}$ alkyl groups, such as benzyl, diphenylmethyl, trityl, phenethyl and naphthylmethyl groups.

The $C_{2-5}$ alkylene group means linear or branched $C_{2-5}$ alkylene groups, such as ethylidene, ethylene, trimethylene, propylene, tetramethylene and pentamethylene groups.

The $C_{2-4}$ alkylene group means linear or branched $C_{2-4}$ alkylene groups, such as ethylidene, ethylene, trimethylene, propylene and tetramethylene groups.

The $C_{2-3}$ alkylene group means an ethylidene, ethylene, trimethylene or propylene group.

The $C_{1-3}$ alkylene group means a methylene, ethylidene, ethylene, trimethylene or propylene group.

The $C_{1-6}$ alkoxy group means linear or branched $C_{1-6}$ alkyloxy groups, such as methoxy, ethoxy, propoxy, isopropoxy, butoxy, isobutoxy, sec-butoxy, tert-butoxy, pentyloxy and hexyloxy groups.

The aryloxy group means a phenoxy or naphthyloxy group.

The C$_{1-6}$ alkoxy C$_{1-6}$ alkyl group means C$_{1-6}$ alkyloxy C$_{1-6}$ alkyl groups, such as methoxymethyl and 1-ethoxyethyl groups.

The aryl C$_{1-6}$ alkoxy C$_{1-6}$ alkyl group means aryl C$_{1-6}$ alkyloxy C$_{1-6}$ alkyl groups, such as benzyloxymethyl and phenethyloxymethyl groups.

The C$_{2-6}$ alkanoyl group means linear or branched C$_{2-6}$ alkanoyl groups, such as acetyl, propionyl, valeryl, isovaleryl and pivaloyl groups.

The aroyl group means a benzoyl or naphthoyl group.

The heterocyclic carbonyl group means a furoyl, thenoyl, pyrrolidinylcarbonyl, piperidinylcarbonyl, piperazinylcarbonyl, morpholinylcarbonyl or pyridinylcarbonyl group.

The acyl group means a formyl group, a C$_{2-6}$ alkanoyl group, an aroyl group, or a heterocyclic carbonyl group.

The C$_{1-6}$ alkoxycarbonyl group means linear or branched C$_{1-6}$ alkyloxycarbonyl groups, such as methoxycarbonyl, ethoxycarbonyl, propoxycarbonyl, isopropoxycarbonyl, tert-butoxycarbonyl and 1,1-dimethylpropoxycarbonyl groups.

The aryloxycarbonyl group means a phenyloxycarbonyl or naphthyloxycarbonyl group.

The aryl C$_{1-6}$ alkoxycarbonyl group means aryl C$_{1-6}$ alkyloxycarbonyl groups, such as benzyloxycarbonyl and phenethyloxycarbonyl groups.

The C$_{1-6}$ alkylamino group means linear or branched C$_{1-6}$ alkylamino groups, such as methylamino, ethylamino, propylamino, isopropylamino, butylamino, sec-butylamino, tert-butylamino, pentylamino and hexylamino groups.

The di(C$_{1-6}$ alkyl)amino group means linear or branched di(C$_{1-6}$ alkyl)amino groups, such as dimethylamino, diethylamino, dipropylamino, diisopropylamino, dibutylamino, di(tert-butyl)amino, dipentylamino, dihexylamino, (ethyl)(methyl)amino, and (methyl)(propyl)amino groups.

The arylamino group means a phenylamino or naphthylamino group.

The C$_{1-6}$ alkylthio group means linear or branched C$_{1-6}$ alkylthio groups, such as methylthio, ethylthio, and propylthio groups.

The arylthio group means a phenylthio or naphthylthio group.

The C$_{1-6}$ alkylsulfonyl group means linear or branched C$_{1-6}$ alkylsulfonyl groups, such as methylsulfonyl, ethylsulfonyl, and propylsulfonyl groups.

The C$_{1-3}$ alkylsulfonyl group means linear or branched C$_{1-3}$ alkylsulfonyl groups, such as methylsulfonyl, ethylsulfonyl, and propylsulfonyl group groups.

The arylsulfonyl group means a benzenesulfonyl, p-toluenesulfonyl or naphthalenesulfonyl group.

The C$_{1-6}$ alkylsulfonyloxy group means linear or branched C$_{1-6}$ alkylsulfonyloxy groups, such as methylsulfonyloxy, ethylsulfonyloxy and propylsulfonyloxy groups.

The arylsulfonyloxy group means a benzenesulfonyloxy, p-toluenesulfonyloxy or naphthalenesulfonyloxy group.

The silyl group means a trimethylsilyl, triethylsilyl or tributylsilyl group.

The cyclic amino group means a cyclic amino group, which comprises one or more nitrogen atoms as heteroatoms forming the above-described ring and which may further comprise one or more oxygen atoms or sulfur atoms, such as, for example, aziridinyl, azetidinyl, pyrrolidinyl, piperidinyl, homopiperidinyl, pyrrolyl, dihydropyrrolyl, pyrazolyl, pyrazolinyl, pyrazolidinyl, imidazolyl, imidazolinyl, imidazolidinyl, thiazolinyl, thiazolidinyl, dihydrothiadiazoyl, piperazinyl, homopiperazinyl, morpholinyl, homomorpholinyl, thiomorpholinyl, tetrahydroquinolinyl, tetrahydroisoquinolinyl, decahydroisoquinolinyl, benzomorpholinyl, dihydropyridoxazinyl and quinuclidinyl.

The cyclic hydrocarbon group means a C$_{3-8}$ cycloalkyl group, a C$_{4-8}$ cycloalkenyl group, or an aryl group.

The monocyclic nitrogen-containing heterocyclic group means a monocyclic nitrogen-containing heterocyclic group, which may be optionally substituted with an oxo group and comprises only nitrogen atoms as heteroatoms forming the above-described ring, such as azetidinyl, pyrrolidinyl, oxopyrrolidinyl, pyrrolinyl, pyrrolyl, piperidyl, oxopiperidyl, tetrahydropyridyl, dihydropyridyl, pyridyl, homopiperidinyl, octahydroazocinyl, imidazolidinyl, oxoimidazolidinyl, imidazolinyl, dihydrooxoimidazolyl, imidazolyl, pyrazolidinyl, pyrazolinyl, pyrazolyl, piperazinyl, homopiperazinyl, pyrazinyl, pyridazinyl, pyrimidinyl, triazolidinyl, dioxotriazolidinyl, triazolyl and tetrazolyl groups.

The monocyclic oxygen-containing heterocyclic group means an oxetanyl, tetrahydrofuryl, oxotetrahydrofuryl, furyl, tetrahydropyranyl, oxotetrahydropyranyl, dihydropyranyl or pyranyl group.

The monocyclic sulfur-containing heterocyclic group means a tetrahydrothienyl, oxotetrahydrothienyl or thienyl group.

The monocyclic nitrogen-oxygen-containing heterocyclic group means a monocyclic nitrogen-oxygen-containing heterocyclic group, which may be optionally substituted with an oxo group and which only contains nitrogen atoms and oxygen atoms as heteroatoms forming the above-described ring, such as oxazolyl, isooxazolyl, oxoisooxazolyl, oxadiazolyl and morpholinyl groups.

The monocyclic nitrogen-sulfur-containing heterocyclic group means a monocyclic nitrogen-sulfur-containing heterocyclic group, which may be optionally substituted with an oxo group and which only contains nitrogen atoms and sulfur atoms as heteroatoms forming the above-described ring, such as thiazolyl, isothiazolyl, thiadiazoyl, thiomorpholinyl, 1-oxidothiomorpholinyl and 1,1-dioxidothiomorpholinyl groups.

The monocyclic heterocyclic group means a monocyclic nitrogen-containing heterocyclic group, a monocyclic oxygen-containing heterocyclic group, a monocyclic sulfur-containing heterocyclic group, a monocyclic nitrogen-oxygen-containing heterocyclic group, or a monocyclic nitrogen-sulfur-containing heterocyclic group.

The bicyclic nitrogen-containing heterocyclic group means a bicyclic nitrogen-containing heterocyclic group, which may be optionally substituted with an oxo group and which only contains nitrogen atoms as heteroatoms forming the above-described ring, such as indolinyl, oxoindolinyl, indolyl, isoindolinyl, oxoisoindolinyl, isoindolyl, pyrrolopyridinyl, indazolyl, benzoimidazolyl, benzotriazolyl, tetrahydroquinolinyl, oxotetrahydroquinolinyl, dihydroquinolinyl, oxodihydroquinolinyl, quinolinyl, dihydroisoquinolinyl, octahydroisoquinolinyl, oxooctahydroisoquinolinyl, tetrahydroisoquinolinyl, decahydroisoquinolinyl, isoquinolinyl, dihydroquinazolinyl, cinnolinyl, phthalazinyl, quinazolinyl, tetrahydroquinoxalinyl, oxotetrahydroquinoxalinyl, hydroquinoxalinyl, quinoxalinyl, naphthyridinyl, purinyl, pteridinyl and quinuclidinyl groups.

The bicyclic oxygen-containing heterocyclic group means a bicyclic oxygen-containing heterocyclic group, which may be optionally substituted with an oxo group and which only contains oxygen atoms as heteroatoms forming the above-described ring, such as 2,3-dihydrobenzofuranyl, oxo-2,3-dihydrobenzofuranyl, benzofuranyl, isobenzofuranyl, chromanyl, oxochromanyl, chromenyl, isochromanyl, oxoisochromanyl, 1,3-benzodioxolyl, 1,3-benzodioxanyl and 1,4-benzodioxanyl groups.

The bicyclic sulfur-containing heterocyclic group means a bicyclic sulfur-containing heterocyclic group, which may be optionally substituted with an oxo group and which only contains sulfur atoms as heteroatoms forming the above-described ring, such as 2,3-dihydrobenzothienyl, oxo-2,3-dihydrobenzothienyl and benzothienyl groups.

The bicyclic nitrogen-oxygen-containing heterocyclic group means a bicyclic nitrogen-oxygen-containing heterocyclic group, which may be optionally substituted with an oxo group and which only contains nitrogen atoms and oxygen atoms as heteroatoms forming the above-described ring, such as dihydrobenzoxazolyl, oxodihydrobenzoxazolyl, benzoxazolyl, benzisoxazolyl, benzoxadiazolyl, benzomorpholinyl, oxobenzomorpholinyl, dihydropyranopyridyl, oxodihydropyranopyridyl, dihydrodioxinopyridyl, oxodihydrodioxinopyridyl and dihydropyridoxazinyl groups.

The bicyclic nitrogen-sulfur-containing heterocyclic group means a bicyclic nitrogen-sulfur-containing heterocyclic group, which may be optionally substituted with an oxo group and which only contains nitrogen atoms and sulfur atoms as heteroatoms forming the above-described ring, such as dihydrobenzothiazolyl, oxodihydrobenzothiazolyl, benzothiazolyl, benzoisothiazolyl and benzothiadiazoyl groups.

The bicyclic heterocyclic group means a bicyclic nitrogen-containing heterocyclic group, a bicyclic oxygen-containing heterocyclic group, a bicyclic sulfur-containing heterocyclic group, a bicyclic nitrogen-oxygen-containing heterocyclic group, or a bicyclic nitrogen-sulfur-containing heterocyclic group.

The heterocyclic group means a monocyclic heterocyclic group or a bicyclic heterocyclic group.

The $C_{3-8}$ cycloalkane means cyclopropane, cyclobutane, cyclopentane, cyclohexane, cycloheptane, or cyclooctane.

The $C_{4-8}$ cycloalkene means $C_{4-8}$ cycloalkenes such as cyclobutene, cyclopentene, cyclopentadiene, cyclohexene, cyclohexadiene, and cycloheptene.

The cyclic hydrocarbon means $C_{3-8}$ cycloalkane, $C_{4-8}$ cycloalkene, benzene, or naphthalene.

The nitrogen-containing heterocyclic ring means a nitrogen-containing heterocyclic ring, which may be optionally substituted with an oxo group and which only contains nitrogen atoms as heteroatoms forming the above-described ring, such as azetidine, pyrrolidine, oxopyrrolidine, pyrroline, pyrrole, piperidine, oxopiperidine, tetrahydropyridine, dihydropyridine, oxodihydropyridine, pyridine, homopiperidine, octahydroazocine, imidazolidine, oxoimidazolidine, imidazoline, dihydrooxoimidazole, imidazole, pyrazolidine, dioxopyrazolidine, pyrazoline, oxopyrazoline, pyrazole, piperazine, homopiperazine, pyrazine, pyridazine, pyrimidine, triazolidine, dioxotriazolidine, triazole, tetrazole, 1H-benzimidazole, and quinoxaline.

The oxygen-containing heterocyclic ring means oxetane, tetrahydrofuran, oxotetrahydrofuran, furan, tetrahydropyran, oxotetrahydropyran, dihydropyran, or pyran.

The sulfur-containing heterocyclic ring means tetrahydrothiophene, oxotetrahydrothiophene, or thiophene.

The nitrogen-oxygen-containing heterocyclic ring means a monocyclic nitrogen-oxygen-containing heterocyclic ring, which may be optionally substituted with an oxo group and which only contains nitrogen atoms and oxygen atoms as heteroatoms forming the above-described ring, such as oxazole, isoxazole, oxoisoxazole, oxadiazole, and morpholine.

The nitrogen-sulfur-containing heterocyclic ring means a monocyclic nitrogen-sulfur-containing heterocyclic ring, which may be optionally substituted with an oxo group and which only contains nitrogen atoms and sulfur atoms as heteroatoms forming the above-described ring, such as thiazole, isothiazole, thiadiazole, thiomorpholine, 1-oxidothiomorpholin, and 1,1-dioxidothiomorpholine.

The heterocyclic ring means a nitrogen-containing heterocyclic ring, an oxygen-containing heterocyclic ring, a sulfur-containing heterocyclic ring, a nitrogen-oxygen-containing heterocyclic ring, or a nitrogen-sulfur-containing heterocyclic ring.

The divalent cyclic hydrocarbon group formed by removing each one hydrogen atom on the two adjacent atoms means a group that is formed by removing two hydrogen atoms binding to the two adjacent atoms from a cyclic hydrocarbon, such as cyclopropane-1,2-diyl, cyclobutane-1,2-diyl, cyclobutene-1,2-diyl, cyclopentane-1,2-diyl, cyclopentene-1,2-diyl, cyclopentadiene-1,2-diyl, cyclohexane-1,2-diyl, cyclohexene-1,2-diyl, cyclohexadiene-1,2-diyl, cycloheptane-1,2-diyl, cycloheptene-1,2-diyl, cyclooctane-1,2-diyl, benzene-1,2-diyl, naphthalene-1,2-diyl, and naphthalene-2,3-diyl.

The divalent heterocyclic group formed by removing each one hydrogen atom on the two adjacent atoms means a group that is formed by removing two hydrogen atoms binding to the two adjacent atoms from a heterocyclic ring, and that may be optionally substituted with an oxo group, such as azetidine-1,2-diyl, pyrrolidine-1,2-diyl, oxopyrrolidine-1,2-diyl, oxopyrrolidine-3,4-diyl, pyrroline-3,4-diyl, pyrrole-3,4-diyl, piperidine-2,3-diyl, piperidine-3,4-diyl, oxopiperidine-2,3-diyl, tetrahydropyridine-1,2-diyl, tetrahydropyridine-2,3-diyl, tetrahydropyridine-3,4-diyl, dihydropyridine-2,3-diyl, dihydropyridine-3,4-diyl, dihydropyridine-1,2-diyl, oxodihydropyridine-1,2-diyl, pyridine-2,3-diyl, pyridine-3,4-diyl, homopiperidine-2,3-diyl, homopiperidine-3,4-diyl, octahydroazocine-2,3-diyl, imidazolidine-1,5-diyl, oxoimidazolidine-1,5-diyl, 1,2-dihydroimidazole-3,4-diyl, 4,5-dihydroimidazole-1,2-diyl, dihydrooxoimidazole-1,5-diyl, 2H-imidazole-4,5-diyl, imidazole-1,2-diyl, imidazole-1,5-diyl, imidazole-4,5-diyl, pyrazolidine-1,2-diyl, dioxopyrazolidine-1,2-diyl, pyrazoline-1,2-diyl, oxopyrazoline-1,2-diyl, pyrazoline-1,5-diyl, 1H-pyrazole-3,4-diyl, 1H-pyrazole-4,5-diyl, 1H-pyrazole-1,5-diyl, piperazine-1,2-diyl, piperazine-2,3-diyl, homopiperazine-1,2-diyl, homopiperazine-2,3-diyl, pyrazine-2,3-diyl, pyridazine-3,4-diyl, pyrimidine-4,5-diyl, 1,2,4-triazolidine-1,2-diyl, dioxotriazolidine-1,2-diyl, 1,2,3-triazole-1,5-diyl, 1,2,4-triazole-1,5-diyl, 1,2,4-triazole-3,4-diyl, tetrazole-1,5-diyl, 1H-benzimidazole-1,2-diyl, quinoxaline-2,3-diyl, oxetane-2,3-diyl, tetrahydrofuran-2,3-diyl, oxotetrahydrofuran-2,3-diyl, furan-2,3-diyl, tetrahydropyran-2,3-diyl, oxotetrahydropyran-2,3-diyl, dihydropyran-2,3-diyl, pyran-2,3-diyl, tetrahydrothiophene-2,3-diyl, oxotetrahydrothiophene-2,3-diyl, thiophene-3,4-diyl, oxazole-4,5-diyl, isoxazole-3,4-diyl, dihydrooxoisoxazole-3,4-diyl, 1,2,3-oxadiazole-4,5-diyl, morpholine-2,3-diyl, morpholine-3,4-diyl, thiazole-4,5-diyl, isothiazole-4,5-diyl, 1,2,3-thiadiazole-4,5-diyl, thiomorpholine-2,3-diyl, 1-oxidothiomorpholine-2,3-diyl, and 1,1-dioxidothiomorpholine-2,3-diyl.

The leaving group means a halogen atom, a $C_{1-6}$ alkylsulfonyloxy group, or an arylsulfonyloxy group. The $C_{1-6}$ alkylsulfonyloxy group and the arylsulfonyloxy group may be optionally substituted with one or more groups selected from Substituent Group A.

Substituent Group A: a halogen atom, a carbamoyl group optionally substituted with one or more groups selected from Substituent Group B, a sulfamoyl group optionally substituted with one or more groups selected from Substituent Group B, an acyl group optionally substituted with one or more groups selected from Substituent Group B, a $C_{1-6}$ alkyl group optionally substituted with one or more groups selected from Substituent Group B, a $C_{2-6}$ alkenyl group optionally substituted with one or more groups selected from Substituent Group B, a $C_{3-8}$ cycloalkyl group optionally substituted with one or more groups selected from Substituent Group B, a $C_{4-8}$ cycloalkenyl group optionally substituted with one or more groups selected from Substituent Group B, a $C_{1-6}$ alkoxy group optionally substituted with one or more groups selected from Substituent Group B, a $C_{1-6}$ alkylsulfonyl group optionally substituted with one or more groups selected from Substituent Group B, an arylsulfonyl group optionally substituted with one or more groups selected from Substituent Group B, a $C_{1-6}$ alkylamino group optionally substituted with one or more groups selected from Substituent Group B, a di($C_{1-6}$ alkyl)amino group optionally substituted with one or more groups selected from Substituent Group B, an aryl group optionally substituted with one or more groups selected from Substituent Group B, a heterocyclic group optionally substituted with one or more groups selected from Substituent Group B, an arylamino group optionally substituted with one or more groups selected from Substituent Group B, a cyano group, an optionally protected amino group, an optionally protected hydroxyl group, an optionally protected carboxyl group, and an oxo group.

Substituent Group B: a halogen atom, acyl group, a $C_{1-6}$ alkyl group optionally substituted with one or more groups selected from Substituent Group C, a $C_{3-8}$ cycloalkyl group optionally substituted with one or more groups selected from Substituent Group C, a $C_{1-6}$ alkoxy group optionally substituted with one or more groups selected from Substituent Group C, a $C_{1-6}$ alkylamino group, a di($C_{1-6}$ alkyl)amino group, an aryl group optionally substituted with one or more groups selected from Substituent Group C, a heterocyclic group optionally substituted with one or more groups selected from Substituent Group C, a cyano group, an optionally protected amino group, an optionally protected hydroxyl group, an optionally protected carboxyl group, and an oxo group.

Substituent Group C: a halogen atom, an optionally protected amino group, an optionally protected hydroxyl group, and an optionally protected carboxyl group.

The hydroxyl-protecting group includes all groups that can be used as common hydroxyl group-protecting groups. Examples of such a hydroxyl-protecting group include the groups described in Greene's Protective Groups in Organic Synthesis, 5$^{th}$ edition, pp. 17 to 471, 2014, John Wiley & Sons, INC. Specific examples include a $C_{1-6}$ alkyl group, an aryl $C_{1-6}$ alkyl group, a $C_{1-6}$ alkoxy $C_{1-6}$ alkyl group, an acyl group, a $C_{1-6}$ alkoxycarbonyl group, an aryl $C_{1-6}$ alkoxycarbonyl group, a $C_{1-6}$ alkylsulfonyl group, an arylsulfonyl group, a silyl group, a tetrahydrofuryl group, and a tetrahydropyranyl group. These groups may be optionally substituted with one or more groups selected from Substituent Group A.

The carboxyl-protecting group includes all groups that can be used as common carboxyl group-protecting groups. Examples of such a carboxyl-protecting group include the groups described in Greene's Protective Groups in Organic Synthesis, 5$^{th}$ edition, pp. 686 to 836, 2014, John Wiley & Sons, INC. Specific examples include a $C_{1-6}$ alkyl group, an aryl $C_{1-6}$ alkyl group, a $C_{1-6}$ alkoxy $C_{1-6}$ alkyl group, an aryl $C_{1-6}$ alkoxy $C_{1-6}$ alkyl group, and a silyl group. These groups may be optionally substituted with one or more groups selected from Substituent Group A.

The amino-protecting group includes all groups that can be used as common amino group-protecting groups. Examples of such an amino-protecting group include the groups described in Greene's Protective Groups in Organic Synthesis, 5$^{th}$ edition, pp. 895 to 1193, 2014, John Wiley & Sons, INC. Specific examples include an aryl $C_{1-6}$ alkyl group, a $C_{1-6}$ alkoxy $C_{1-6}$ alkyl group, an acyl group, a $C_{1-6}$ alkoxycarbonyl group, an aryl $C_{1-6}$ alkoxycarbonyl group, an aryloxycarbonyl group, a $C_{1-6}$ alkylsulfonyl group, an arylsulfonyl group, and a silyl group. These groups may be optionally substituted with one or more groups selected from Substituent Group A.

Aliphatic hydrocarbons mean pentane, hexane, heptane, cyclohexane, methylcyclohexane, or ethylcyclohexane.

Halogenated hydrocarbons mean dichloromethane, chloroform, or dichloroethane.

Ethers mean diethyl ether, diisopropyl ether, tetrahydrofuran, 2-methyltetrahydrofuran, 1,4-dioxane, anisole, ethylene glycol dimethyl ether, diethylene glycol dimethyl ether, or diethylene glycol diethyl ether.

Alcohols mean methanol, ethanol, propanol, 2-propanol, butanol, 2-methyl-2-propanol, ethylene glycol, propylene glycol, or diethylene glycol.

Ketones mean acetone, 2-butanone, or 4-methyl-2-pentanone.

Esters mean methyl acetate, ethyl acetate, propyl acetate, isopropyl acetate, or butyl acetate.

Amides mean N,N-dimethylformamide, N,N-dimethylacetamide, or N-methylpyrrolidone.

Nitriles mean acetonitrile or propionitrile.

Sulfoxides mean dimethyl sulfoxide or sulfolane.

Aromatic hydrocarbons mean benzene, toluene, or xylene.

Inorganic base means sodium hydroxide, potassium hydroxide, sodium hydrogen carbonate, sodium carbonate, sodium hydride, potassium carbonate, tripotassium phosphate, potassium acetate, cesium fluoride, or cesium carbonate.

Organic base means sodium methoxide, sodium ethoxide, tert-butoxy sodium, tert-butoxy potassium, triethylamine, N,N-diisopropylethylamine, 1,8-diazabicyclo(5.4.0)undec-7-ene (DBU), pyridine, N,N-dimethyl-4-aminopyridine, or 4-methylmorpholine.

The present invention relates to an antitumor agent and a bromodomain inhibitor, comprising the compound represented by the formula [1] or a salt thereof.

In the present invention, the tumor has a concept including benign tumor, malignant tumor, carcinoma, cancer, and the like.

In the present invention, the antitumor agent is preferably an antineoplastic agent, and it has a concept including a carcinostatic agent, an anticancer agent, or the like. The antitumor agent of the present invention has the effect of reducing or extinguishing a cancerous tumor, or suppressing an increase in the cancerous tumor, for the purpose of preventing and/or treating carcinoma.

Prevention means inhibition of the onset, reduction in the onset risk, retardation in the onset, or the like.

Therapy means the improvement of a target disease or condition, suppression (maintaining or retardation) of the progression, or the like.

Treatment means prevention, therapy or the like performed on various types of diseases.

The treatment agent means a substance subjected to various types of diseases for the purpose of prevention, therapy, or the like.

The target, to which the measures are taken, is a human or a non-human animal in need thereof.

The type of tumor, to which the antitumor agent of the present invention is applied, is not particularly limited. Specific examples include blood cancer, thymoma, myeloma, liver cancer, pancreatic cancer, ovarian cancer, prostate cancer, lung cancer, osteosarcoma, colon cancer, breast cancer, skin cancer, and epithelial cell cancer; preferred examples include blood cancer, thymoma, uterine cancer, lung cancer, colon cancer, and pancreatic cancer; and more preferred examples include blood cancer and thymoma. In the present invention, the blood cancer includes lymphoma and leukemia, and a preferred example is acute myeloid leukemia.

The antitumor agent and the bromodomain inhibitor of the present invention are assumed to inhibit the binding of bromodomain in a protein to acetylated histone.

A compound inhibiting the binding of such a bromodomain to an acetylated protein, more specifically, a compound inhibiting the binding of a bromodomain to an acetylated lysine residue has been discovered. Such a compound is referred to as a "bromodomain inhibitor" in the present description.

In the present invention, it is preferable to use a compound that inhibits the binding of bromodomain-containing protein to acetylated histone H3 or acetylated histone H4, which is formed by acetylation of histone H3 or histone H4. The bromodomain-containing protein is preferably a protein belonging to a BET family. As a BET family protein, not only a human-derived protein, but also fly-derived and yeast-derived proteins and the like have been known. In the present invention, it is desirable to use a compound that is assumed to inhibit the binding of a human-derived BET family protein to acetylated histone. Specific examples of the human-derived BET family protein include BRD2, BRD3, BRD4, and BRDT. Preferred examples include BRD2, BRD3, and BRD4.

Moreover, the present invention provides a pharmaceutical composition for use in the therapy of tumor, and a pharmaceutical composition for use in the therapy of disease associated with a bromodomain, both of which comprise the above-described Compound A or a salt thereof.

From a further viewpoint of the present invention, provided are: use of Compound A or a salt thereof for the production of the above-described pharmaceutical composition; a method for treating tumor, comprising a step of administering a therapeutically effective amount of the above-described Compound A or a salt thereof to mammals including a human; and a method for treating disease associated with a bromodomain, comprising a step of administering a therapeutically effective amount of the above-described Compound A or a salt thereof to mammals including a human.

The disease associated with a bromodomain means all diseases that can be prevented or treated by inhibiting the bromodomain.

An example of the disease associated with a bromodomain is tumor. Examples of the tumor include blood cancer, thymoma, myeloma, liver cancer, pancreatic cancer, ovarian cancer, prostate cancer, lung cancer, osteosarcoma, colon cancer, breast cancer, skin cancer, and epithelial cell cancer.

In the present invention, the bromodomain inhibitor is considered to have effectiveness for the therapy of disease or pathological condition, to which it is applied. The bromodomain inhibitor is preferably applied to tumor.

In the present invention, the following compound is preferable: Formula [1]

[Formula 5]

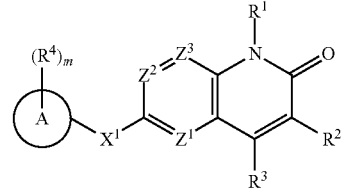

[1]

$R^1$ represents a hydrogen atom or an optionally substituted $C_{1-6}$ alkyl group.

The $C_{1-6}$ alkyl group of $R^1$ may be optionally substituted with one or more groups selected from Substituent Group A.

A compound in which $R^1$ is a $C_{1-6}$ alkyl group is preferable, a compound in which $R^1$ is a $C_{1-3}$ alkyl group is more preferable, and a compound in which $R^1$ is an ethyl group is further preferable.

$R^2$ represents a hydrogen atom, a halogen atom or an optionally substituted $C_{1-6}$ alkyl group.

The $C_{1-6}$ alkyl group of $R^2$ may be optionally substituted with one or more groups selected from Substituent Group B.

A compound in which $R^2$ is a hydrogen atom or an optionally substituted $C_{1-6}$ alkyl group is preferable, a compound in which $R^2$ is a hydrogen atom or a $C_{1-6}$ alkyl group is more preferable, and a compound in which $R^2$ is a hydrogen atom is further preferable.

$R^3$ represents a halogen atom, an optionally substituted $C_{1-6}$ alkyl group, an optionally substituted $C_{2-6}$ alkenyl group, an optionally substituted $C_{3-8}$ cycloalkyl group, an optionally substituted $C_{4-8}$ cycloalkenyl group, an optionally substituted aryl group, an optionally substituted $C_{1-6}$ alkoxy group, an optionally substituted $C_{1-6}$ alkylamino group, an optionally substituted di($C_{1-6}$ alkyl)amino group, or an optionally substituted heterocyclic group.

The $C_{1-6}$ alkyl group, $C_{2-6}$ alkenyl group, $C_{3-8}$ cycloalkyl group, $C_{4-8}$ cycloalkenyl group, aryl group, $C_{1-6}$ alkoxy group, $C_{1-6}$ alkylamino group, di($C_{1-6}$ alkyl)amino group and heterocyclic group of $R^3$ may be optionally substituted with one or more groups selected from Substituent Group A.

A compound, in which $R^3$ is a halogen atom, an optionally substituted $C_{1-6}$ alkyl group, an optionally substituted $C_{2-6}$ alkenyl group, an optionally substituted $C_{3-8}$ cycloalkyl group, an optionally substituted $C_{4-8}$ cycloalkenyl group, an optionally substituted aryl group, an optionally substituted di($C_{1-6}$ alkyl)amino group, or an optionally substituted heterocyclic group, is preferable.

A compound, in which $R^3$ is an optionally substituted $C_{1-6}$ alkyl group, an optionally substituted $C_{3-8}$ cycloalkyl group, an optionally substituted aryl group, or an optionally substituted heterocyclic group, is more preferable.

A compound, in which $R^3$ is an optionally substituted $C_{1-6}$ alkyl group, an optionally substituted $C_{3-8}$ cycloalkyl group, or an optionally substituted heterocyclic group, is even more preferable.

A compound, in which $R^3$ is an optionally substituted $C_{3-8}$ cycloalkyl group or an optionally substituted heterocyclic group, is further preferable.

A compound, in which $R^3$ is an optionally substituted heterocyclic group, is particularly preferable.

A compound, in which $R^3$ is any one of the heterocyclic groups represented by the following formulae:

[Formula 6]

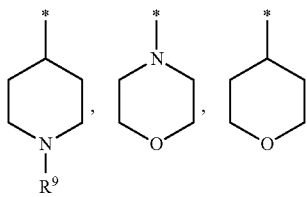

wherein $R^9$ and * have the same meanings as above, is most preferable.

$R^9$ represents a hydrogen atom, an amino-protecting group, or an optionally substituted $C_{1-6}$ alkyl group.

The $C_{1-6}$ alkyl group of $R^9$ may be optionally substituted with one or more groups selected from Substituent Group A.

A compound in which $R^9$ is an amino-protecting group or an optionally substituted $C_{1-6}$ alkyl group is preferable.

A compound in which $R^9$ is an optionally substituted $C_{1-6}$ alkyl group is more preferable.

A compound in which $R^9$ is an optionally substituted $C_{1-3}$ alkyl group is further preferable.

$Z^1$, $Z^2$ and $Z^3$, which are the same or different, each represent a nitrogen atom or a group represented by the formula $CR^5$ (wherein $R^5$ has the same meanings as above).

A compound, in which $Z^1$, $Z^2$ and $Z^3$ each represent a group represented by the formula $CR^5$ (wherein $R^5$ has the same meanings as above), is preferable, and a compound, in which $Z^1$, $Z^2$ and $Z^3$ each represent CH, is more preferable.

$R^5$ represents a hydrogen atom, a halogen atom, or an optionally substituted $C_{1-6}$ alkyl group.

The $C_{1-6}$ alkyl group of $R^5$ may be optionally substituted with one or more groups selected from Substituent Group A.

A compound, in which $R^5$ is a hydrogen atom or a halogen atom, is preferable, and a compound, in which $R^5$ is a hydrogen atom, is more preferable.

$X^1$ represents (1) a group represented by the formula $C(=O)N(R^6)$ (wherein $R^6$ has the same meanings as above), (2) a group represented by the formula $N(R^7)C(=O)$ (wherein $R^7$ has the same meanings as above), (3) an optionally substituted divalent cyclic hydrocarbon group that is formed by removing each one hydrogen atom on the two adjacent atoms, or (4) an optionally substituted divalent heterocyclic group that is formed by removing each one hydrogen atom on the two adjacent atoms.

The optionally substituted divalent cyclic hydrocarbon group that is formed by removing each one hydrogen atom on the two adjacent atoms and the optionally substituted divalent heterocyclic group that is formed by removing each one hydrogen atom on the two adjacent atoms, which are represented by $X^1$, may be optionally substituted with one or more groups selected from Substituent Group A.

A compound, in which $X^1$ represents (2) the group represented by the formula $N(R^7)C(=O)$ (wherein $R^7$ has the same meanings as above) or (4) the optionally substituted divalent heterocyclic group that is formed by removing each one hydrogen atom on the two adjacent atoms, is preferable.

$R^7$ represents a hydrogen atom, an amino-protecting group, or an optionally substituted $C_{1-6}$ alkyl group. Otherwise, $R^7$ represents, together with one substituent $R^4$ of Ring A, an optionally substituted $C_{2-4}$ alkylene group, a group represented by the formula $O-Y^1$ (wherein $Y^1$ and n have the same meanings as above), a group represented by the formula $S(O)_n-Y^2$ (wherein $Y^2$ and n have the same meanings as above), or a group represented by the formula $N(R^8)-Y^3$ (wherein $Y^3$ and $R^8$ have the same meanings as above).

The $C_{1-6}$ alkyl group of $R^7$ may be optionally substituted with one or more groups selected from Substituent Group A.

The $C_{2-4}$ alkylene group formed by $R^7$ together with one substituent $R^4$ of Ring A may be optionally substituted with one or more groups selected from Substituent Group A.

A compound, in which $R^7$ represents an amino-protecting group or an optionally substituted $C_{1-6}$ alkyl group, or represents, together with one substituent $R^4$ of Ring A, an optionally substituted $C_{2-3}$ alkylene group, a group represented by the formula $O-Y^{1a}$ (wherein $Y^{1a}$ and n have the same meanings as above), a group represented by the formula $S(O)_n-Y^{2a}$ (wherein $Y^{2a}$ and n have the same meanings as above), or a group represented by the formula $N(R^{8a})-Y^{3a}$ (wherein $Y^{3a}$ and $R^{8a}$ have the same meanings as above), is preferable.

A compound, in which $R^7$ represents an optionally substituted $C_{1-3}$ alkyl group, or represents, together with one substituent $R^4$ of Ring A, an optionally substituted $C_{2-3}$ alkylene group or a group represented by the formula $N(R^{8a})-Y^{3a}$ (wherein $Y^{3a}$ and $R^{8a}$ have the same meanings as above), is more preferable.

A compound, in which $R^7$ represents an optionally substituted $C_{1-3}$ alkyl group, or represents, together with one substituent $R^4$ of Ring A, an optionally substituted $C_{2-3}$ alkylene group, is even more preferable.

A compound, in which $R^7$ represents a $C_{1-6}$ alkyl group optionally substituted with one or more groups selected from the group consisting of a hydroxyl group, an aryl group and a $C_{1-6}$ alkoxy group, is further preferable.

$Y^1$ represents an optionally substituted $C_{1-3}$ alkylene group.

The $C_{1-3}$ alkylene group of $Y^1$ may be optionally substituted with one or more groups selected from Substituent Group A.

A compound in which $Y^1$ represents a $C_{1-3}$ alkylene group is preferable, and a compound in which $Y^1$ represents an ethylene group is more preferable.

$Y^{1a}$ represents an optionally substituted $C_{1-3}$ alkylene group.

The $C_{1-3}$ alkylene group of $Y^{1a}$ may be optionally substituted with one or more groups selected from Substituent Group A.

A compound in which $Y^{1a}$ represents a $C_{1-3}$ alkylene group is preferable, and a compound in which $Y^{1a}$ represents an ethylene group is more preferable.

$Y^2$ represents an optionally substituted $C_{1-3}$ alkylene group.

The $C_{1-3}$ alkylene group of $Y^2$ may be optionally substituted with one or more groups selected from Substituent Group A.

A compound in which $Y^2$ represents a $C_{1-3}$ alkylene group is preferable, and a compound in which $Y^2$ represents an ethylene group is more preferable.

$Y^{2a}$ represents an optionally substituted $C_{1-3}$ alkylene group.

The $C_{1-3}$ alkylene group of $Y^{2a}$ may be optionally substituted with one or more groups selected from Substituent Group A.

A compound in which $Y^{2a}$ represents a $C_{1-3}$ alkylene group is preferable, and a compound in which $Y^{2a}$ represents an ethylene group is more preferable.

$Y^3$ represents an optionally substituted $C_{1-3}$ alkylene group.

The $C_{1-3}$ alkylene group of $Y^3$ may be optionally substituted with one or more groups selected from Substituent Group A.

A compound in which $Y^3$ represents a $C_{1-3}$ alkylene group is preferable, and a compound in which $Y^3$ represents an ethylene group is more preferable.

$Y^{3a}$ represents an optionally substituted $C_{1-3}$ alkylene group.

The $C_{1-3}$ alkylene group of $Y^{3a}$ may be optionally substituted with one or more groups selected from Substituent Group A.

A compound in which $Y^{3a}$ represents a $C_{1-3}$ alkylene group is preferable, and a compound in which $Y^{3a}$ represents an ethylene group is more preferable.

n represents an integer from 0 to 2.

A compound in which n is 0 or 2 is preferable, and a compound in which n is 0 is more preferable.

R represents a hydrogen atom, an amino-protecting group, an optionally substituted $C_{1-6}$ alkyl group, or an optionally substituted aryl group.

The $C_{1-6}$ alkyl group and the aryl group, which are represented by $R^8$, may be optionally substituted with one or more groups selected from Substituent Group A.

A compound in which $R^8$ represents a hydrogen atom or an optionally substituted $C_{1-6}$ alkyl group is preferable, and a compound in which $R^8$ represents a hydrogen atom is more preferable.

$R^{8a}$ represents a hydrogen atom or an optionally substituted $C_{1-6}$ alkyl group.

The $C_{1-6}$ alkyl group of $R^{8a}$ may be optionally substituted with one or more groups selected from Substituent Group A.

A compound in which $R^{8a}$ represents a hydrogen atom or a $C_{1-3}$ alkyl group is preferable, and a compound in which $R^{8a}$ represents a hydrogen atom is more preferable.

In another aspect, a compound, in which $X^1$ is a group represented by the formula $N(R^7)C(=O)$ (wherein $R^7$ has the same meanings as above), is preferable.

A compound, in which $X^1$ is a group represented by the formula $N(R^{7a})C(=O)$ (wherein $R^{7a}$ has the same meanings as above), is more preferable.

The preferred range of $R^7$ and $R^{7a}$ is the same as the range of $R^7$ in the compound represented by the formula [1].

In another aspect, a compound, in which $X^1$ represents an optionally substituted divalent heterocyclic group that is formed by removing each one hydrogen atom on the two adjacent atoms, is preferable.

A compound, in which $X^1$ represents an optionally substituted dihydrooxoimidazole-1,5-diyl group, an optionally substituted imidazole-1,2-diyl group, an optionally substituted imidazole-4,5-diyl group, an optionally substituted 1,2,4-triazole-1,5-diyl group, an optionally substituted 1H-pyrazole-4,5-dihyl group, an optionally substituted oxopyrrolidine-1,2-diyl group, an optionally substituted dioxotriazolidine-1,2-diyl group, an optionally substituted dioxopyrazolidine-1,2-diyl group, an optionally substituted oxopyrazoline-1,2-diyl group, an optionally substituted pyridine-2,3-diyl group, or an optionally substituted pyrazine-2,3-diyl group, is more preferable.

A compound, in which $X^1$ represents an optionally substituted dihydrooxoimidazole-1,5-diyl group, is further preferable.

The dihydrooxoimidazole-1,5-diyl group, imidazole-1,2-diyl group, imidazole-4,5-diyl group, 1,2,4-triazole-1,5-diyl group, 1H-pyrazole-4,5-dihyl group, oxopyrrolidine-1,2-diyl group, dioxotriazolidine-1,2-diyl group, dioxopyrazolidine-1,2-diyl group, oxopyrazoline-1,2-diyl group, pyridine-2,3-diyl group, and pyrazine-2,3-diyl group, which are represented by $X^1$, may be optionally substituted with one or more groups selected from Substituent Group A.

In a further aspect, a compound, in which $X^1$ represents a group represented by the formula $C(=O)N(R^6)$ (wherein $R^6$ has the same meanings as above) or an optionally substituted divalent cyclic hydrocarbon group that is formed by removing each one hydrogen atom on the two adjacent atoms, is preferable.

Ring A represents a cyclic hydrocarbon group or a heterocyclic group.

A compound in which Ring A represents a cyclic hydrocarbon group is preferable, a compound in which Ring A represents an aryl group is more preferable, and a compound in which Ring A represents a phenyl group is further preferable.

An m number of $R^4$, which are the same or different, each represent a halogen atom, a cyano group, a nitro group, an amino-protecting group, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{4-8}$ cycloalkenyl group, an optionally substituted aryl group, an optionally substituted $C_{1-6}$ alkoxy group, an optionally substituted aryloxy group, an optionally substituted $C_{1-6}$ alkylamino group, an optionally substituted di($C_{1-6}$ alkyl)amino group, an optionally substituted arylamino group, an optionally substituted carbamoyl group, an optionally substituted sulfamoyl group, an optionally substituted $C_{1-6}$ alkylthio group, an optionally substituted arylthio group, an optionally substituted $C_{1-6}$ alkylsulfonyl group, an optionally substituted arylsulfonyl group, an optionally substituted heterocyclic group, an optionally protected amino group, an optionally protected hydroxyl group, or an optionally protected carboxyl group. Herein, two adjacent $R^4$ may together form an optionally substituted $C_{2-5}$ alkylene group. Further, one $R^4$ may form, together with $R^7$, an optionally substituted $C_{2-4}$ alkylene group, a group represented by the formula $O-Y^1$ (wherein $Y^1$ has the same meanings as above), a group represented by the formula $S(O)_n-Y^2$ (wherein $Y^2$ and n have the same meanings as above), or a group represented by the formula $N(R^8)-Y^3$ (wherein $Y^3$ and $R^8$ have the same meanings as above).

The $C_{1-6}$ alkyl group, $C_{2-6}$ alkenyl group, $C_{2-6}$ alkynyl group, $C_{3-8}$ cycloalkyl group, $C_{4-8}$ cycloalkenyl group, aryl group, $C_{1-6}$ alkoxy group, aryloxy group, $C_{1-6}$ alkylamino group, di($C_{1-6}$ alkyl)amino group, arylamino group, carbamoyl group, sulfamoyl group, $C_{1-6}$ alkylthio group, arylthio group, $C_{1-6}$ alkylsulfonyl group, arylsulfonyl group, and heterocyclic group, which are represented by $R^4$, may be optionally substituted with one or more groups selected from Substituent Group A.

The $C_{2-5}$ alkylene group formed together by the two adjacent $R^4$ may be optionally substituted with one or more groups selected from Substituent Group A.

The $C_{2-4}$ alkylene group formed by $R^4$ together with $R^7$ may be optionally substituted with one or more groups selected from Substituent Group A.

Preferable is a compound, in which an m number of $R^4$, which are the same or different, each represent a halogen atom, a cyano group, an amino-protecting group, an optionally substituted $C_{1-6}$ alkyl group, an optionally substituted $C_{2-6}$ alkenyl group, an optionally substituted $C_{3-8}$ cycloalkyl group, an optionally substituted $C_{4-8}$ cycloalkenyl group, an optionally substituted aryl group, an optionally substituted $C_{1-6}$ alkoxy group, an optionally substituted $C_{1-6}$ alkylamino group, an optionally substituted di($C_{1-6}$ alkyl)amino group, an optionally substituted arylamino group, an optionally substituted carbamoyl group, an optionally substituted sulfamoyl group, an optionally substituted $C_{1-6}$ alkylsulfonyl group, an optionally substituted heterocyclic group, an optionally protected amino group, an optionally protected hydroxyl group, an optionally protected carboxyl group, an optionally substituted $C_{2-5}$ alkylene group formed together by the two adjacent $R^4$, an optionally substituted $C_{2-3}$ alkylene group formed by one $R^4$ together with $R^7$, a group represented by the formula O—$Y^{1a}$ (wherein $Y^{1a}$ has the same meanings as above), which is formed by one $R^4$ together with $R^7$, a group represented by the formula S(O)$_n$—$Y^{2a}$ (wherein $Y^{2a}$ has the same meanings as above), which is formed by one $R^4$ together with $R^7$, or a group represented by the formula N($R^{8a}$)—$Y^{3a}$ (wherein $R^{8a}$ and $Y^{3a}$ have the same meanings as above), which is formed by one $R^4$ together with $R^7$.

More preferable is a compound, in which an m number of $R^4$, which are the same or different, each represent a halogen atom, a cyano group, an optionally substituted $C_{1-6}$ alkyl group, an optionally substituted aryl group, an optionally substituted $C_{1-6}$ alkoxy group, an optionally substituted di($C_{1-6}$ alkyl)amino group, an optionally substituted carbamoyl group, an optionally substituted $C_{1-6}$ alkylsulfonyl group, an optionally substituted heterocyclic group, an optionally protected amino group, an optionally protected hydroxyl group, an optionally protected carboxyl group, an optionally substituted $C_{2-5}$ alkylene group formed together by the two adjacent $R^4$, an optionally substituted $C_{2-3}$ alkylene group formed by one $R^4$ together with $R^7$, or a group represented by the formula N($R^{8a}$)—$Y^{3a}$ (wherein $R^{8a}$ and $Y^{3a}$ have the same meanings as above), which is formed by one $R^4$ together with $R^7$.

Further preferable is a compound, in which an m number of $R^4$, which are the same or different, each represent a halogen atom, a cyano group, an optionally substituted $C_{1-3}$ alkyl group, an optionally substituted $C_{1-3}$ alkoxy group, an optionally substituted carbamoyl group, an optionally substituted $C_{1-3}$ alkylsulfonyl group, an optionally substituted heterocyclic group, an optionally protected amino group, an optionally protected carboxyl group, an optionally substituted $C_{2-5}$ alkylene group formed together by the two adjacent $R^4$, an optionally substituted $C_{2-3}$ alkylene group formed by one $R^4$ together with $R^7$, or a group represented by the formula N($R^{8a}$)—$Y^{3a}$ (wherein $R^{8a}$ and $Y^{3a}$ have the same meanings as above), which is formed by one $R^4$ together with $R^7$.

m represents an integer from 0 to 5.

A compound in which m represents an integer from 0 to 2 is preferable.

In another aspect, the compound is preferably a compound represented by the following formula [1-1]:

[Formula 7]

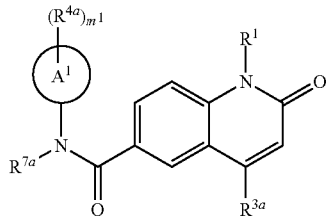

[1-1]

wherein $R^1$, $R^{3a}$, $R^{4a}$, $R^{7a}$, $A^1$ and $m^1$ have the same meanings as above.

The preferred range of $R^1$ is the same as the range of $R^1$ in the compound represented by the formula [1].

$R^{3a}$ represents an optionally substituted $C_{1-6}$ alkyl group, an optionally substituted $C_{3-8}$ cycloalkyl group, or an optionally substituted heterocyclic group.

The $C_{1-6}$ alkyl group, $C_{3-8}$ cycloalkyl group, and heterocyclic group, which are represented by $R^{3a}$, may be optionally substituted with one or more groups selected from Substituent Group A.

A compound in which $R^{3a}$ represents an optionally substituted heterocyclic group is preferable.

More preferable is a compound, in which $R^{3a}$ represents a heterocyclic group represented by any one of the following formulae:

[Formula 8]

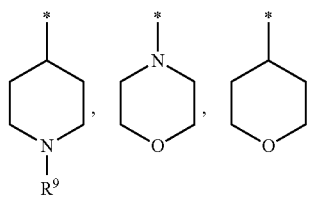

wherein $R^9$ and * have the same meanings as above.

$R^9$ represents a hydrogen atom, an amino-protecting group, or an optionally substituted $C_{1-6}$ alkyl group.

The preferred range of $R^9$ is the same as the range of $R^9$ in the compound represented by the formula [1].

$R^{7a}$ represents an amino-protecting group or an optionally substituted $C_{1-6}$ alkyl group.

The $C_{1-6}$ alkyl group of $R^{7a}$ may be optionally substituted with one or more groups selected from Substituent Group A.

A compound in which $R^{7a}$ represents an optionally substituted $C_{1-3}$ alkyl group is preferable.

More preferable is a compound, in which $R^{7a}$ represents a $C_{1-6}$ alkyl group optionally substituted with one or more groups selected from a hydroxyl group, an aryl group and a $C_{1-6}$ alkoxy group.

Ring $A^1$ represents a cyclic hydrocarbon group.

A compound in which Ring $A^1$ represents an aryl group is preferable, and a compound in which Ring $A^1$ represents a phenyl group is more preferable.

An $m^1$ number of $R^{4a}$, which are the same or different, each represent a halogen atom, a cyano group, an optionally substituted $C_{1-3}$ alkyl group, an optionally substituted carbamoyl group, an optionally substituted $C_{1-3}$ alkylsulfonyl group, an optionally protected carboxyl group, an optionally substituted $C_{2-5}$ alkylene group formed together by the two adjacent $R^{4a}$, an optionally substituted $C_{2-3}$ alkylene group formed by one $R^{4a}$ together with $R^{7a}$, a group represented by the formula O—$Y^{1a}$ (wherein the oxygen atom binds to Ring $A^1$, and $Y^{1a}$ represents an optionally substituted $C_{1-3}$ alkylene group), which is formed by one $R^{4a}$ together with $R^{7a}$, a group represented by the formula $S(O)_n$—$Y^{2a}$ (wherein the sulfur atom binds to Ring $A^1$, $Y^{2a}$ represents an optionally substituted $C_{1-3}$ alkylene group, and n represents an integer from 0 to 2), which is formed by one $R^{4a}$ together with $R^{7a}$, or a group represented by the formula $N(R^{8a})$—$Y^{3a}$ (wherein the nitrogen atom binds to Ring $A^1$, and $R^{8a}$ and $Y^{3a}$ have the same meanings as above), which is formed by one $R^{4a}$ together with $R^{7a}$.

The $C_{1-3}$ alkyl group, carbamoyl group and $C_{1-3}$ alkylsulfonyl group, which are represented by $R^{4a}$, may be optionally substituted with one or more groups selected from Substituent Group A.

Preferable is a compound, in which an $m^1$ number of $R^{4a}$, which are the same or different, each represent a halogen atom, a cyano group, an optionally substituted $C_{1-3}$ alkyl group, an optionally substituted carbamoyl group, an optionally substituted $C_{1-3}$ alkylsulfonyl group, an optionally protected carboxyl group, an optionally substituted $C_{2-5}$ alkylene group formed together by the two adjacent $R^{4a}$, an optionally substituted $C_{2-3}$ alkylene group formed by one $R^{4a}$ together with $R^{7a}$, or a group represented by the formula $N(R^{8a})$—$Y^{3a}$ (wherein $R^{8a}$ and $Y^{3a}$ have the same meanings as above), which is formed by one $R^{4a}$ together with $R^{7a}$.

More preferable is a compound, in which an $m^1$ number of $R^{4a}$, which are the same or different, each represent a halogen atom, a cyano group, an optionally substituted $C_{1-3}$ alkyl group, an optionally substituted carbamoyl group, an optionally substituted $C_{1-3}$ alkylsulfonyl group, an optionally protected carboxyl group, an optionally substituted $C_{2-5}$ alkylene group formed together by the two adjacent $R^{4a}$, or an optionally substituted $C_{2-3}$ alkylene group formed by one $R^{4a}$ together with $R^{7a}$.

$R^{8a}$ represents a hydrogen atom or an optionally substituted $C_{1-6}$ alkyl group.

The $C_{1-6}$ alkyl group of $R^{8a}$ may be optionally substituted with one or more groups selected from Substituent Group A.

A compound in which $R^{8a}$ represents a hydrogen atom or a $C_{1-6}$ alkyl group is preferable, and a compound in which $R^{8a}$ represents a hydrogen atom is more preferable.

$m^1$ represents an integer from 0 to 2.

The preferred range of $Y^{1a}$ is the same as the range of $Y^{1a}$ in the compound represented by the formula [1].

The preferred range of $Y^{2a}$ is the same as the range of $Y^{2a}$ in the compound represented by the formula [1].

The preferred range of $Y^{3a}$ is the same as the range of $Y^{3a}$ in the compound represented by the formula [1].

The preferred range of n is the same as the range of n in the compound represented by the formula [1].

In another aspect, the compound is preferably a compound represented by the following formula [1-2]:

[Formula 9]

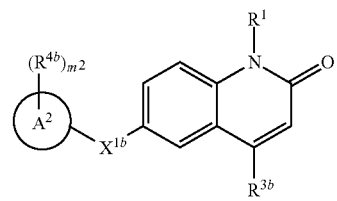

[1-2]

wherein $R^1$, $R^{3b}$, $R^{4b}$, $X^{1b}$, $A^2$ and $m^2$ have the same meanings as above.

The preferred range of $R^1$ is the same as the range of $R^1$ in the compound represented by the formula [1].

$R^{3b}$ represents an optionally substituted $C_{1-6}$ alkyl group, an optionally substituted $C_{3-8}$ cycloalkyl group, or an optionally substituted heterocyclic group.

The $C_{1-6}$ alkyl group, $C_{3-8}$ cycloalkyl group and heterocyclic group, which are represented by $R^{3b}$, may be optionally substituted with one or more groups selected from Substituent Group A.

The preferred range of $R^{3b}$ is the same as the range of $R^{3a}$ in the compound represented by the formula [1-1].

$X^{1b}$ represents an optionally substituted dihydrooxoimidazole-1,5-diyl group.

The dihydrooxoimidazole-1,5-diyl group of $X^{1b}$ may be optionally substituted with one or more groups selected from Substituent Group A.

Preferable is a compound, in which $X^{1b}$ represents an optionally substituted dihydrooxoimidazole-1,5-diyl group represented by the following formula:

[Formula 10]

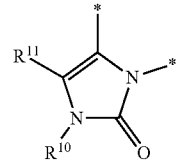

wherein $R^{10}$ represents a hydrogen atom, an optionally substituted $C_{1-6}$ alkyl group, an optionally substituted aryl group, or an optionally substituted heterocyclic group, $R^{11}$ represents a hydrogen atom, a halogen atom, an optionally substituted $C_{1-6}$ alkyl group, an optionally substituted $C_{1-6}$ alkoxy group, an optionally substituted aryl group, or an optionally substituted heterocyclic group, and * represents a binding site.

The $C_{1-6}$ alkyl group, aryl group and heterocyclic group, which are represented by $R^{10}$, may be optionally substituted with one or more groups selected from Substituent Group A.

More preferable is a compound, in which $R^{10}$ represents a hydrogen atom, an optionally substituted $C_{1-6}$ alkyl group, or an optionally substituted aryl group; even more preferable is a compound, in which $R^{10}$ represents a hydrogen atom or an optionally substituted $C_{1-6}$ alkyl group; and further preferable is a compound, in which $R^{10}$ represents a hydrogen atom.

The $C_{1-6}$ alkyl group, $C_{1-6}$ alkoxy group, aryl group and heterocyclic group, which are represented by $R^{11}$, may be optionally substituted with one or more groups selected from Substituent Group A.

A compound in which $R^{11}$ represents a hydrogen atom or an optionally substituted $C_{1-6}$ alkyl group is more preferable, and a compound in which $R^{11}$ represents a hydrogen atom is further preferable.

A compound, in which $R^{10}$ represents a hydrogen atom and $R^{11}$ represents a hydrogen atom, is particularly preferable.

Ring $A^2$ represents a cyclic hydrocarbon group.

A compound in which Ring $A^2$ represents an aryl group is preferable, and a compound in which Ring $A^2$ represents a phenyl group is more preferable.

Examples of a preferred compound in the present invention include the following compounds: N-(4-cyclopropyl-1-ethyl-2-oxo-1,2-dihydroquinolin-6-yl)-N-methylbenzamide, 1-ethyl-4-(1-ethylpiperidin-4-yl)-N-methyl-2-oxo-N-phenyl-1,2-dihydroquinoline-6-carboxamide, 6-(3,4-dihydroquinolin-1 (2H)-ylcarbonyl)-1-ethyl-4-(1-methylpiperidin-4-yl)quinolin-2(1H)-one, 1-ethyl-N-methyl-N-(4-methylphenyl)-4-(1-methylpiperidin-4-yl)-2-oxo-1,2-dihydroquinoline-6-carboxamide, N-(2,3-dihydro-1H-inden-5-yl)-1-ethyl-N-methyl-4-(1-methylpiperidin-4-yl)-2-oxo-1,2-dihydroquinoline-6-carboxamide, 6-(5-(4-chlorophenyl)-2-oxo-2,3-dihydro-1H-imidazol-1-yl)-1-ethyl-4-(morpholin-4-yl)quinolin-2(1H)-one, 6-(5-(4-chlorophenyl)-3-methyl-2-oxo-2,3-dihydro-1H-imidazol-1-yl)-1-ethyl-4-(morpholin-4-yl)quinolin-2(1H)-one, 1-ethyl-4-(morpholin-4-yl)-6-(2-oxo-5-phenyl-3-(propan-2-yl)-2,3-dihydro-1H-imidazol-1-yl)quinolin-2(1H)-one, 1-(4-cyclopropyl-1-ethyl-2-oxo-1,2-dihydroquinolin-6-yl)-2-phenyl-1,2,4-triazolidine-3,5-dione, 4-chloro-N-(1-ethyl-4-(morpholin-4-yl)-2-oxo-1,2-dihydroquinolin-6-yl)-N-methylbenzamide, 4-(1-acetylpiperidin-4-yl)-1-ethyl-N-methyl-N-(4-methylphenyl)-2-oxo-1,2-dihydroquinoline-6-carboxamide, 1-ethyl-N-(3-fluoro-4-methylphenyl)-N-methyl-4-(1-methylpiperidin-4-yl)-2-oxo-1,2-dihydroquinoline-6-carboxamide, N-(3-chloro-4-methylphenyl)-1-ethyl-N-methyl-4-(1-methylpiperidin-4-yl)-2-oxo-1,2-dihydroquinoline-6-carboxamide, and N-(3,4-dimethylphenyl)-1-ethyl-N-methyl-4-(1-methylpiperidin-4-yl)-2-oxo-1,2-dihydroquinoline-6-carboxamide.

More preferable is at least one compound selected from the following compounds, or a salt thereof: N-(4-cyclopropyl-1-ethyl-2-oxo-1,2-dihydroquinolin-6-yl)-N-methylbenzamide, 1-ethyl-4-(1-ethylpiperidin-4-yl)-N-methyl-2-oxo-N-phenyl-1,2-dihydroquinoline-6-carboxamide, 6-(3,4-dihydroquinolin-1 (2H)-ylcarbonyl)-1-ethyl-4-(1-methylpiperidin-4-yl)quinolin-2(1H)-one, 1-ethyl-N-methyl-N-(4-methylphenyl)-4-(1-methylpiperidin-4-yl)-2-oxo-1,2-dihydroquinoline-6-carboxamide, N-(2,3-dihydro-1H-inden-5-yl)-1-ethyl-N-methyl-4-(1-methylpiperidin-4-yl)-2-oxo-1,2-dihydroquinoline-6-carboxamide, 6-(5-(4-chlorophenyl)-2-oxo-2,3-dihydro-1H-imidazol-1-yl)-1-ethyl-4-(morpholin-4-yl)quinolin-2(1H)-one, 6-(5-(4-chlorophenyl)-3-methyl-2-oxo-2,3-dihydro-1H-imidazol-1-yl)-1-ethyl-4-(morpholin-4-yl)quinolin-2(1H)-one, 1-ethyl-4-(morpholin-4-yl)-6-(2-oxo-5-phenyl-3-(propan-2-yl)-2,3-dihydro-1H-imidazol-1-yl)quinolin-2(1H)-one, 1-(4-cyclopropyl-1-ethyl-2-oxo-1,2-dihydroquinolin-6-yl)-2-phenyl-1,2,4-triazolidine-3,5-dione and 4-chloro-N-(1-ethyl-4-(morpholin-4-yl)-2-oxo-1,2-dihydroquinolin-6-yl)-N-methylbenzamide; and particularly preferable is at least one compound selected from the following compounds, or a salt thereof: 6-(3,4-dihydroquinolin-1 (2H)-ylcarbonyl)-1-ethyl-4-(1-methylpiperidin-4-yl)quinolin-2(1H)-one, 1-ethyl-N-methyl-N-(4-methylphenyl)-4-(1-methylpiperidin-4-yl)-2-oxo-1,2-dihydroquinoline-6-carboxamide, N-(2,3-dihydro-1H-inden-5-yl)-1-ethyl-N-methyl-4-(1-methylpiperidin-4-yl)-2-oxo-1,2-dihydroquinoline-6-carboxamide, 6-(5-(4-chlorophenyl)-2-oxo-2,3-dihydro-1H-imidazol-1-yl)-1-ethyl-4-(morpholin-4-yl)quinolin-2(1H)-one, 6-(5-(4-chlorophenyl)-3-methyl-2-oxo-2,3-dihydro-1H-imidazol-1-yl)-1-ethyl-4-(morpholin-4-yl)quinolin-2(1H)-one and 1-ethyl-4-(morpholin-4-yl)-6-(2-oxo-5-phenyl-3-(propan-2-yl)-2,3-dihydro-1H-imidazol-1-yl)quinolin-2(1H)-one.

Examples of the salt of the compound represented by the formula [1] include generally known salts of basic groups such as amino groups, and salts of acidic groups such as hydroxyl or carboxyl groups.

Examples of the salts of basic groups include: salts with mineral acids such as hydrochloric acid, hydrobromic acid, nitric acid and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid and trifluoroacetic acid; and salts with sulfonic acids such as methanesulfonic acid, benzenesulfonic acid, p-toluenesulfonic acid, mesitylenesulfonic acid and naphthalenesulfonic acid.

Examples of the salts of acidic groups include: salts with alkaline metals such as sodium and potassium; salts with alkaline-earth metals such as calcium and magnesium; ammonium salts; and salts with nitrogen-containing organic bases such as trimethylamine, triethylamine, tributylamine, pyridine, N,N-dimethylaniline, N-methylpiperidine, 4-methylmorpholine, diethylamine, dicyclohexylamine, procaine, dibenzylamine, N-benzyl-β-phenethylamine, 1-efenamin and N,N'-dibenzylethylenediamine.

Among the above-described salts, pharmacologically acceptable salts are preferable.

In a case where isomers (e.g., optical isomers, geometrical isomers, tautomers, etc.) are present in the compound represented by the formula [1], the present invention includes these isomers, and also includes solvates, hydrates, and various shapes of crystals.

Next, a method for producing the compound of the present invention will be described.

The compound of the present invention is produced by combining known methods. The present compound can be produced, for example, by the following production method.

[Production Method 1]

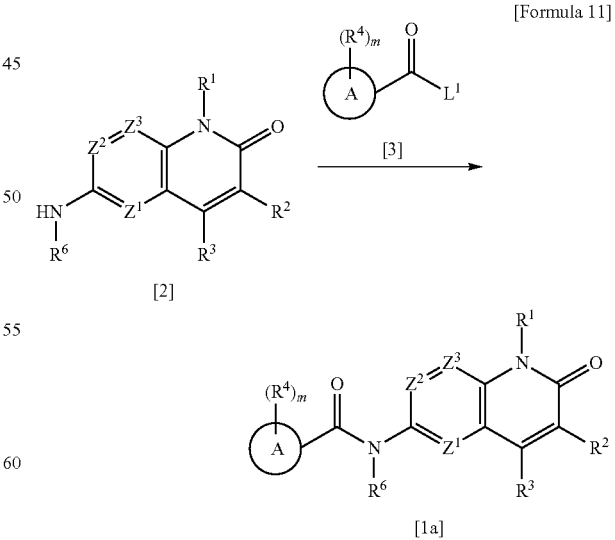

wherein $L^1$ represents a hydroxyl group or a leaving group; and $R^1$, $R^2$, $R^3$, $R^4$, $R^6$, $Z^1$, $Z^2$, $Z^3$, A and m have the same meanings as above.

(1-1) Case where $L^1$ is Hydroxyl Group

As a compound represented by the formula [3], for example, p-chlorobenzoic acid or the like has been known.

The compound represented by the formula [1a] can be produced by allowing the compound represented by the formula [3] to react with the compound represented by the formula [2] in the presence of a condensing agent or an acid halide, and in the presence of a base.

The solvent used in this reaction is not particularly limited, as long as it does not affect the reaction. Examples of the solvent include halogenated hydrocarbons, ethers, esters, amides, nitriles, sulfoxides, and aromatic hydrocarbons. These solvents may be used in combination.

Preferred solvents include halogenated hydrocarbons, ethers, esters, and amides. Among these, halogenated hydrocarbons and amides are more preferable.

The amount of the solvent used is not particularly limited, but the solvent may be used in an amount of 1 to 500 times (v/w), with respect to the amount of the compound represented by the formula [2].

Examples of the base used in this reaction include inorganic bases and organic bases.

Preferred bases are organic bases. Among the organic bases, triethylamine, N,N-diisopropylethylamine and 4-methylmorpholine are more preferable; and N,N-diisopropylethylamine and 4-methylmorpholine are further preferable.

The base may be used in an amount of 1 to 50 times, and preferably 1 to 10 times, with respect to the molar amount of the compound represented by the formula [2].

Examples of the condensing agent used in this reaction include: carbodiimides, such as N,N'-diisopropylcarbodiimide (DIC), N,N'-di-(tert-butyl)carbodiimide, N,N'-dicyclohexylcarbodiimide (DCC), N-(tert-butyl)-N'-ethylcarbodiimide (BEC), N-cyclohexyl-N'-(2-morpholinoethyl)carbodiimide (CMC), and 1-ethyl-3-(3-dimethylaminopropyl)carbodiimide (EDC); imidazoliums, such as 1,1'-carbonyldiimidazole (CDI) and 1,1'-carbonyldi(1,2,4-triazole) (CDT); acid azides, such as diphenylphosphoryl azide; acid cyanides, such as diethylphosphoryl cyanide; 2-ethoxy-1-ethoxycarbonyl-1,2-dihydroquinoline; and uroniums, such as O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), O-(benzotriazol-1-yl)-N,N,N',N'-bis(tetramethylene)uronium hexafluorophosphate (HBPyU), O-(benzotriazol-1-yl)-N,N,N',N'-bis(pentamethylene)uronium hexafluorophosphate (HBPipU), O-(6-chlorobenzotriazol-1-yl)-N,N,N',N'-tetramethyluronium hexafluorophosphate (HCTU), O-(3,4-dihydro-4-oxo-1,2,3-benzotriazin-3-yl)-N,N,N',N'-tetramethyluronium hexafluorophosphate (HDBTU), O-(2-oxo-1(2H)pyridyl)-N,N,N',N'-tetramethyluronium hexafluorophosphate (TPTU), O-((ethoxycarbonyl)cyanomethyleneamino)-N,N,N',N'-tetramethyluronium hexafluorophosphate (HOTU), O-((ethoxycarbonyl)cyanomethyleneamino)-N,N,N',N'-tetramethyluronium tetrafluoroborate (TOTU), N,N,N',N'-tetramethyl-O—(N-succinimidyl)uronium hexafluorophosphate (HSTU), N,N,N',N'-tetramethyl-O—(N-succinimidyl)uronium tetrafluoroborate (TSTU), dipyrrolidino(N-succinimidyloxy)carbenium hexafluorophosphate (HSPyU), and S-(1-oxido-2-pyridyl)-N,N,N',N'-tetramethylthiouronium tetrafluoroborate (TOTT).

Preferred condensing agents are carbodiimides, and among the carbodiimides, EDC is more preferable.

The condensing agent may be used in an amount of 1 to 50 times, and preferably 1 to 5 times, with respect to the molar amount of the compound represented by the formula [2].

When carbodiimides are used as condensing agents, an additive is preferably added.

Preferred examples of such an additive include 1-hydroxybenzotriazole (HOBT), 1-hydroxy-7-azabenzotriazole (HOAT), and ethyl (hydroxyimino)cyanoacetate. Among these, HOBT and ethyl (hydroxyimino)cyanoacetate are preferable.

The additive may be used in an amount of 0.01 to 10 times, and preferably 0.1 to 1 time, with respect to the molar amount of the compound represented by the formula [2].

Examples of the acid halide used in this reaction include: oxalyl chloride; carboxylic acid halides, such as acetyl chloride and trifluoroacetyl chloride; sulfonic acid halides, such as methanesulfonyl chloride and tosyl chloride; and chloroformic acid esters, such as ethyl chloroformate and isobutyl chloroformate.

The used amount of the compound represented by the formula [3] is not particularly limited, but the compound represented by the formula [3] may be used in an amount of 1 to 10 times, with respect to the molar amount of the compound represented by the formula [2].

This reaction may be carried out at −30° C. to 150° C., preferably at 0° C. to 100° C., for 30 minutes to 48 hours.

(1-2) Case where $L^1$ is Leaving Group

As a compound represented by the formula [3], for example, p-chlorobenzoyl chloride or the like has been known.

The compound represented by the formula [1a] can be produced by allowing the compound represented by the formula [3] to react with the compound represented by the formula [2] in the presence of a base.

The solvent used in this reaction is not particularly limited, as long as it does not affect the reaction. Examples of the solvent include halogenated hydrocarbons, ethers, esters, amides, nitriles, sulfoxides, and aromatic hydrocarbons. These solvents may be used in combination.

Preferred solvents include halogenated hydrocarbons, ethers, and esters. Among these, halogenated hydrocarbons are more preferable.

The amount of the solvent used is not particularly limited, but the solvent may be used in an amount of 1 to 500 times (v/w), with respect to the amount of the compound represented by the formula [2].

Examples of the base used in this reaction include inorganic bases and organic bases.

Preferred bases are organic bases. Among the organic bases, triethylamine, N,N-diisopropylethylamine, 4-methylmorpholine, and pyridine are more preferable; and N,N-diisopropylethylamine, 4-methylmorpholine, and pyridine are further preferable.

The base may be used in an amount of 1 to 50 times, and preferably 1 to 10 times, with respect to the molar amount of the compound represented by the formula [2].

The used amount of the compound represented by the formula [3] is not particularly limited, but the compound represented by the formula [3] may be used in an amount of 1 to 10 times, with respect to the molar amount of the compound represented by the formula [2].

This reaction may be carried out at −30° C. to 150° C., preferably at 0° C. to 100° C., for 30 minutes to 48 hours.

[Production Method 2]

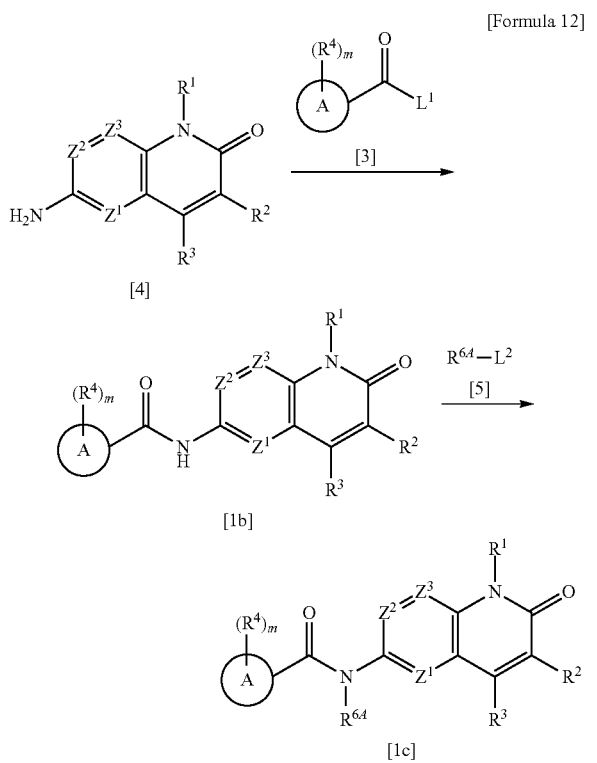

wherein $R^{6A}$ represents an optionally substituted $C_{1-6}$ alkyl group; $L^2$ represents a leaving group; and $R^1$, $R^2$, $R^3$, $R^4$, $L^1$, $Z^1$, $Z^2$, $Z^3$, A and m have the same meanings as above.

<First Step>

The compound represented by the formula [1b] can be produced by allowing the compound represented by the formula [3] to react with the compound represented by the formula [4].

This reaction may be carried out in accordance with Production Method 1.

<Second Step>

As a compound represented by the formula [5], for example, methyl iodide or the like has been known.

The compound represented by the formula [1c] can be produced by allowing the compound represented by the formula [5] to react with the compound represented by the formula [1b] in the presence of a base.

The solvent used in this reaction is not particularly limited, as long as it does not affect the reaction. Examples of the solvent include halogenated hydrocarbons, ethers, ketones, esters, amides, nitriles, sulfoxides, and aromatic hydrocarbons. These solvents may be used in combination.

Preferred solvents are ethers and amides. Among these, amides are more preferable.

The amount of the solvent used is not particularly limited, but the solvent may be used in an amount of 1 to 500 times (v/w), with respect to the amount of the compound represented by the formula [1b].

Examples of the base used in this reaction include: organic bases, such as sodium methoxide, sodium ethoxide, potassium tert-butoxide, pyridine, dimethylaminopyridine, and triethylamine; and inorganic bases, such as sodium hydride, sodium hydroxide, potassium hydroxide, sodium hydrogen carbonate, potassium carbonate, and sodium carbonate. Preferred bases are sodium hydride and potassium carbonate.

The used amount of the base is not particularly limited, but the base may be used in an amount of 1 to 20 times, and preferably 1 to 5 times, with respect to the molar amount of the compound represented by the formula [1b].

The used amount of the compound represented by the formula [5] is not particularly limited, but the compound represented by the formula [5] may be used in an amount of 1 to 10 times, with respect to the molar amount of the compound represented by the formula [1b].

This reaction may be carried out at −30° C. to 150° C., preferably at 0° C. to 100° C., for 30 minutes to 48 hours.

[Production Method 3]

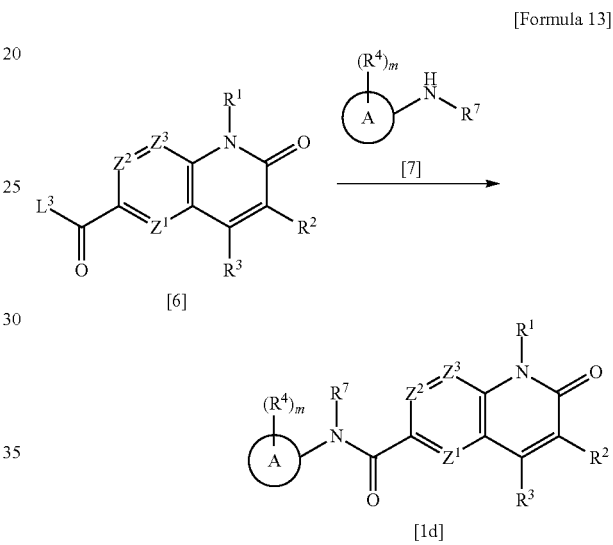

wherein $L^3$ represents a hydroxyl group or a leaving group; and $R^1$, $R^2$, $R^3$, $R^4$, $R^7$, $Z^1$, $Z^2$, $Z^3$, A and m have the same meanings as above.

As a compound represented by the formula [7], for example, N-methylaniline or the like has been known.

The compound represented by the formula [1d] can be produced by allowing the compound represented by the formula [7] to react with the compound represented by the formula [6].

This reaction may be carried out in accordance with Production Method 1.

[Production Method 4]

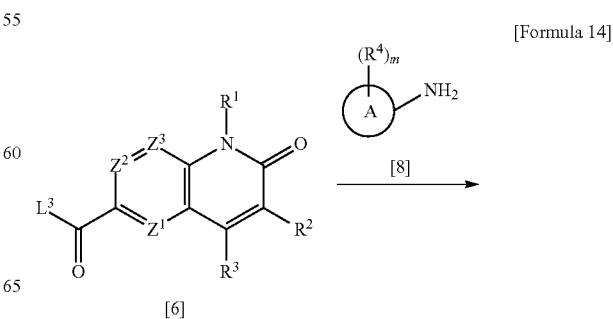

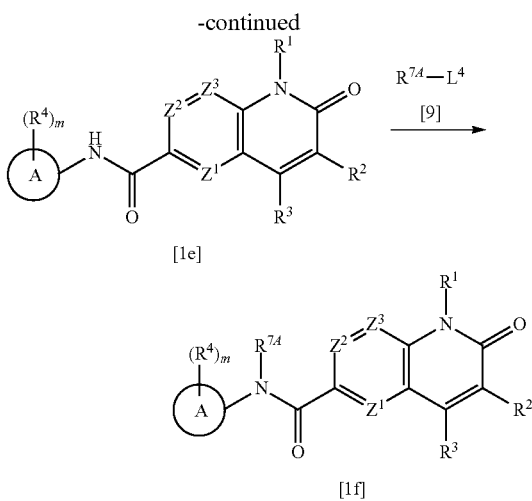

wherein $R^{7A}$ represents an optionally substituted $C_{1-6}$ alkyl group; $L^4$ represents a leaving group; and $R^1$, $R^2$, $R^3$, $R^4$, $L^3$, $Z^1$, $Z^2$, $Z^3$, A and m have the same meanings as above.

<First Step>

The compound represented by the formula [1e] can be produced by allowing the compound represented by the formula [8] to react with the compound represented by the formula [6].

This reaction may be carried out in accordance with Production Method 1.

<Second Step>

As a compound represented by the formula [9], for example, methyl iodide or the like has been known.

The compound represented by the formula [1f] can be produced by allowing the compound represented by the formula [9] to react with the compound represented by the formula [1e].

This reaction may be carried out in accordance with <Second Step> of Production Method 2.

[Production Method 5]

[Formula 15]

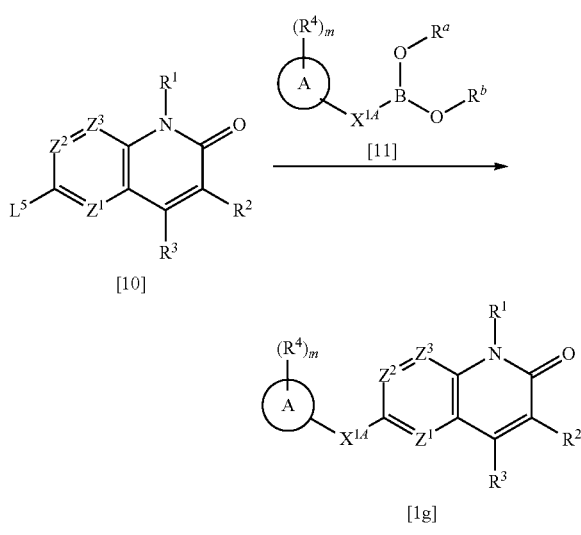

wherein $R^a$ represents a hydrogen atom or an optionally substituted $C_{1-6}$ alkyl group; $R^b$ represents a hydrogen atom or an optionally substituted $C_{1-6}$ alkyl group; or $R^a$ and $R^b$ together represent an optionally substituted $C_{1-3}$ alkylene group; $L^5$ represents a leaving group; $X^{1A}$ represents an optionally substituted divalent cyclic hydrocarbon group that is formed by removing each one hydrogen atom on the two adjacent atoms, or an optionally substituted divalent heterocyclic group that is formed by removing each one hydrogen atom on the two adjacent atoms; and $R^1$, $R^2$, $R^3$, $R^4$, $Z^1$, $Z^2$, $Z^3$, A and m have the same meanings as above.

As a compound represented by the formula [11], for example, 2-biphenylboric acid or the like has been known.

The compound represented by the formula [1g] can be produced by allowing the compound represented by the formula [11] to react with the compound represented by the formula [10] in the presence or absence of a base, in the presence of a palladium catalyst, and in the presence or absence of a ligand.

The solvent used in this reaction is not particularly limited, as long as it does not affect the reaction. Examples of the solvent include water, alcohols, halogenated hydrocarbons, ethers, ketones, esters, amides, nitriles, sulfoxides, and aromatic hydrocarbons. These solvents may be used in combination.

Preferred solvents include mixed solvents of aromatic hydrocarbons and water, and mixed solvents of ethers and water.

The amount of the solvent used is not particularly limited, but the solvent may be used in an amount of 1 to 500 times (v/w), with respect to the amount of the compound represented by the formula [10].

Examples of the palladium catalyst used in this reaction include: palladium metals such as palladium-carbon and palladium black; inorganic palladium salts such as palladium chloride; organic palladium salts such as palladium acetate; chloro(2-(dicyclohexylphosphino)-3,6-dimethoxy-2',4',6'-triisopropyl-1,1'-biphenyl)(2-(2-aminoethyl)phenyl)palladium(II); organic palladium complexes such as tetrakis(triphenylphosphine)palladium(0), bis(triphenylphosphine)palladium(II) dichloride, bis(di-tert-butyl(4-dimethylaminophenyl)phosphine)dichloropalladium(II), 1,1'-bis(diphenylphosphino)ferrocenepalladium(II) dichloride, (E)-di(Q-acetato)bis(o-(di-o-tolylphosphino)benzyl)dipalladium(II), and tris(dibenzylideneacetone)dipalladium(0); and polymer-supported organic palladium complexes, such as polymer-supported bis(acetato)triphenylphosphinepalladium(II) and polymer-supported di(acetato)dicyclohexylphenylphosphinepalladium(II). Among these, organic palladium complexes are preferable.

The palladium catalyst may be used in an amount of 0.00001 to 1 time, and preferably 0.01 to 0.2 times, with respect to the molar amount of the compound represented by the formula [10].

Examples of the ligand used as desired in this reaction include: trialkylphosphines such as trimethylphosphine and tri-tert-butylphosphine; tricycloalkylphosphines such as tricyclohexylphosphine; triarylphosphines such as triphenylphosphine and tritolylphosphine; trialkylphosphites such as trimethylphosphite, triethylphosphite, and tributylphosphite; tricycloalkylphosphites such as tricyclohexylphosphite; triarylphosphites such as triphenylphosphite; imidazolium salts such as 1,3-bis(2,4,6-trimethylphenyl)imidazolium chloride; diketones such as acetylacetone and octafluoroacetylacetone; amines such as trimethylamine, triethylamine, tripropylamine, triisopropylamine, and tributylamine; 1,1'-bis(diphenylphosphino)ferrocene; 2,2'- bis(diphenylphosphino)-1,1'-binaphthyl; 2-dicyclohexylphosphino-2',6'-dimethoxybiphenyl; 2-dicyclohexylphosphino-2',4',6'-triisopropylbiphenyl; 2-(di-tert-butylphosphino)-2',4',6'-triisopropylbiphenyl; 2-dicyclohexylphosphino-2'-(N,N-dimethylamino)biphenyl; 4,5-bis(diphenylphosphino)-9,9-dimethylxanthene; and 2-(di-tert-butylphosphino)biphenyl.

The ligand may be used in an amount of 0.00001 to 1 time, and preferably 0.02 to 0.5 times, with respect to the molar amount of the compound represented by the formula [10].

Examples of the base used as desired in this reaction include inorganic bases and organic bases. Among these, inorganic bases such as sodium hydrogen carbonate, sodium carbonate, potassium carbonate, cesium carbonate, and tripotassium phosphate are preferable.

The base may be used in an amount of 1 to 50 times, and preferably 2 to 10 times, with respect to the molar amount of the compound represented by the formula [10].

The compound represented by the formula [11] may be used in an amount of 1 to 50 times, and preferably 1 to 2 times, with respect to the molar amount of the compound represented by the formula [10].

This reaction may be generally carried out under an inert gas (e.g., nitrogen and/or argon) atmosphere, at 0° C. to 160° C., preferably at 20° C. to 120° C., for 1 minute to 96 hours.

[Production Method 6]

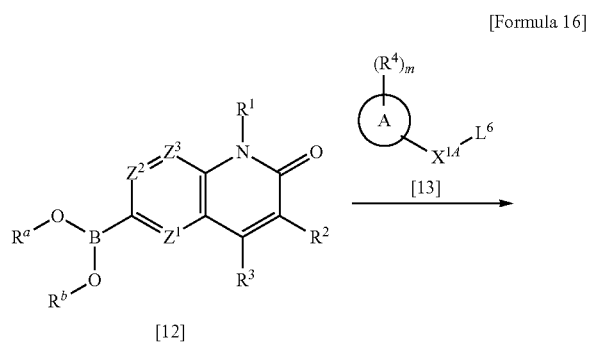

[Formula 16]

[12]

[1h]

wherein $L^6$ represents a leaving group; and $R^1$, $R^2$, $R^3$, $R^4$, $R^a$, $R^b$, $X^{1A}$, $Z^1$, $Z^2$, $Z^3$, A and m have the same meanings as above.

The compound represented by the formula [1h] can be produced by allowing the compound represented by the formula [13] to react with the compound represented by the formula [12].

This reaction may be carried out in accordance with Production Method 5.

[Production Method 7]

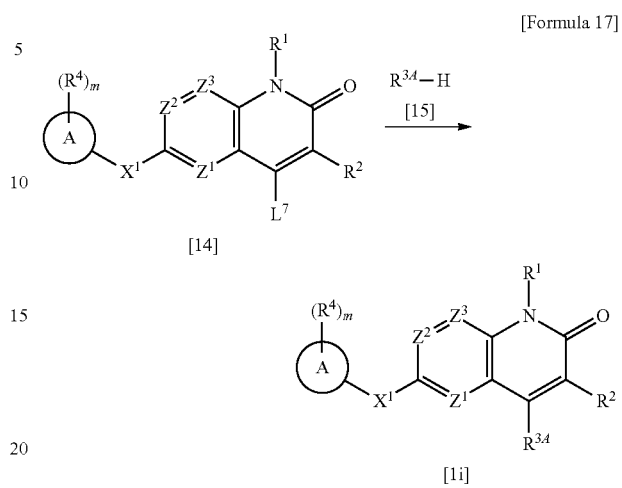

[Formula 17]

[14]

[1i]

wherein $R^{3A}$ represents an optionally substituted $C_{1-6}$ alkylamino group, an optionally substituted di($C_{1-6}$ alkyl) amino group, or an optionally substituted cyclic amino group; $L^7$ represents a leaving group; and $R^1$, $R^2$, $R^4$, $X^1$, $Z^1$, $Z^2$, $Z^3$, A and m have the same meanings as above.

As a compound represented by the formula [15], for example, morpholine or the like has been known.

The compound represented by the formula [1i] can be produced by allowing the compound represented by the formula [15] to react with the compound represented by the formula [14] in the presence or absence of a base.

The solvent used in this reaction is not particularly limited, as long as it does not affect the reaction. Examples of the solvent include halogenated hydrocarbons, ethers, esters, amides, nitriles, sulfoxides, and aromatic hydrocarbons. These solvents may be used in combination.

Preferred solvents include halogenated hydrocarbons, ethers, esters and amides. Among these, amides are more preferable.

The amount of the solvent used is not particularly limited, but the solvent may be used in an amount of 1 to 500 times (v/w), with respect to the amount of the compound represented by the formula [14].

Examples of the base used in this reaction include inorganic bases and organic bases.

Preferred bases are organic bases. Among the organic bases, triethylamine, N,N-diisopropylethylamine, and 4-methylmorpholine are more preferable; and N,N-diisopropylethylamine and 4-methylmorpholine are further preferable.

The base may be used in an amount of 1 to 50 times, and preferably 1 to 10 times, with respect to the molar amount of the compound represented by the formula [14].

The used amount of the compound represented by the formula [15] is not particularly limited, but the compound represented by the formula [15] may be used in an amount of 1 to 10 times, with respect to the molar amount of the compound represented by the formula [14].

This reaction may be carried out at −30° C. to 150° C., preferably at 0° C. to 150° C., for 30 minutes to 48 hours.

Next, methods for producing raw materials used to produce the compound of the present invention will be described.

[Production Method A]

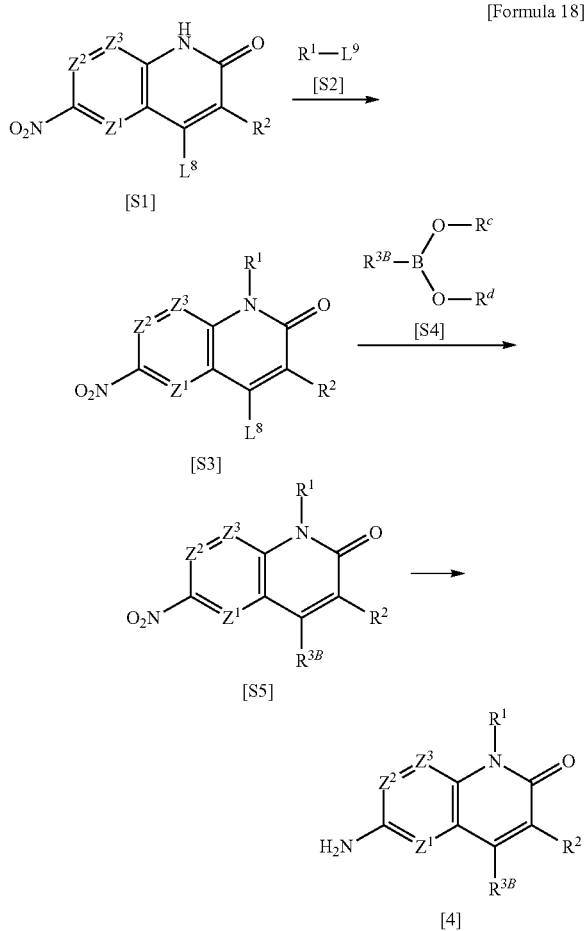

wherein $R^{3B}$ represents an optionally substituted $C_{1-6}$ alkyl group, an optionally substituted $C_{3-8}$ cycloalkyl group, an optionally substituted aryl group, or an optionally substituted heterocyclic group; $R^c$ represents a hydrogen atom or an optionally substituted $C_{1-6}$ alkyl group; $R^d$ represents a hydrogen atom or an optionally substituted $C_{1-6}$ alkyl group; or $R^c$ and $R^d$ together represent an optionally substituted $C_{1-3}$ alkylene group; $L^8$ represents a leaving group; $L^9$ represents a leaving group; and $R^1$, $R^2$, $Z^1$, $Z^2$ and $Z^3$ have the same meanings as above.

<First Step>

As a compound represented by the formula [S1], for example, 4-chloro-6-nitroquinolin-2(1H)-one or the like has been known.

As a compound represented by the formula [S2], for example, ethyl iodide or the like has been known.

The compound represented by the formula [S3] can be produced by allowing the compound represented by the formula [S2] to react with the compound represented by the formula [S1] in the presence of a base.

The solvent used in this reaction is not particularly limited, as long as it does not affect the reaction. Examples of the solvent include halogenated hydrocarbons, ethers, esters, amides, nitriles, sulfoxides, and aromatic hydrocarbons. These solvents may be used in combination.

Preferred solvents are amides and sulfoxides. Among these, amides are more preferable.

The amount of the solvent used is not particularly limited, but the solvent may be used in an amount of 1 to 500 times (v/w), with respect to the amount of the compound represented by the formula [S1].

Examples of the base used in this reaction include inorganic bases and organic bases.

Preferred bases are inorganic base. Among the inorganic bases, cesium carbonate is more preferable.

The base may be used in an amount of 1 to 50 times, and preferably 1 to 10 times, with respect to the molar amount of the compound represented by the formula [S1].

The used amount of the compound represented by the formula [S2] is not particularly limited, but the compound represented by the formula [S2] may be used in an amount of 1 to 10 times, with respect to the molar amount of the compound represented by the formula [S1].

This reaction may be carried out at −30° C. to 150° C., preferably at 0° C. to 100° C., for 30 minutes to 48 hours.

<Second Step>

As a compound represented by the formula [S4], for example, cyclopropylboric acid or the like has been known.

The compound represented by the formula [S5] can be produced by allowing the compound represented by the formula [S4] to react with the compound represented by the formula [S3] in the presence of a base, in the presence of a palladium catalyst, and in the presence or absence of a ligand.

This reaction may be carried out in accordance with Production Method 5.

<Third Step>

The compound represented by the formula [4] can be produced by subjecting the compound represented by the formula [S5] to a reduction reaction. This reaction may be carried out according to the method described in Richard C. Larock et al., Comprehensive Organic Transformations, 2nd edition, pp. 823 to 827, 1999, John Wiley & Sons, INC., or a method equivalent thereto. Specifically, a catalytic hydrogenation reaction using a metal catalyst, a reduction reaction using a metal such as iron or zinc, and the like are applied.

When the compound represented by the formula [S5] is subjected to a catalytic hydrogenation reaction, the used solvent is not particularly limited, as long as it does not affect the reaction. Examples of the solvent used herein include water, alcohols, amides, halogenated hydrocarbons, aromatic hydrocarbons, ethers, acetonitrile, ketones, esters, acetic acid, and pyridine. These solvents may also be used in combination.

Examples of the metal catalyst used in this reaction include: palladium metals such as palladium-carbon and palladium black; palladium salts such as palladium oxide and palladium hydroxide; nickel metals such as Raney nickel; and platinum salts such as platinum oxide.

The metal catalyst may be used in an amount of 0.001 to 5 times (w/w), and preferably 0.01 to 1 time (w/w), with respect to the amount of the compound represented by the formula [S5].

Examples of the hydrogen source include: hydrogen; formic acid; formates such as sodium formate, ammonium formate, and triethylammonium formate; cyclohexene; and cyclohexadiene.

The hydrogen source may be used in an amount of 2 to 100 times, and preferably 2 to 10 times, with respect to the molar amount of the compound represented by the formula [S5].

This reaction may be carried out at 0° C. to 200° C., preferably at 0° C. to 100° C., for 1 minute to 24 hours.

When the compound represented by the formula [S5] is subjected to a reduction reaction using a metal, the used solvent is not particularly limited, as long as it does not affect the reaction. Examples of the solvent used herein include water, alcohols, amides, halogenated hydrocarbons, aromatic hydrocarbons, ethers, acetonitrile, ketones, and esters. These solvents may also be used in combination.

Examples of the metal used in this reaction include iron, zinc, tin, and tin(II) chloride.

The metal is used in an amount of 1 to 50 times, and preferably 1 to 10 times, with respect to the molar amount of the compound represented by the formula [S5].

Examples of the acid used as desired in this reaction include hydrogen chloride, hydrogen bromide, acetic acid, and ammonium chloride.

The acid may be used in an amount of 0.001 to 100 times (v/w), and preferably 0.01 to 20 times (v/w), with respect to the amount of the compound represented by the formula [S5].

This reaction may be carried out at 0° C. to 200° C., preferably at 0° C. to 100° C., for 1 minute to 24 hours.

[Production Method B]

[Formula 19]

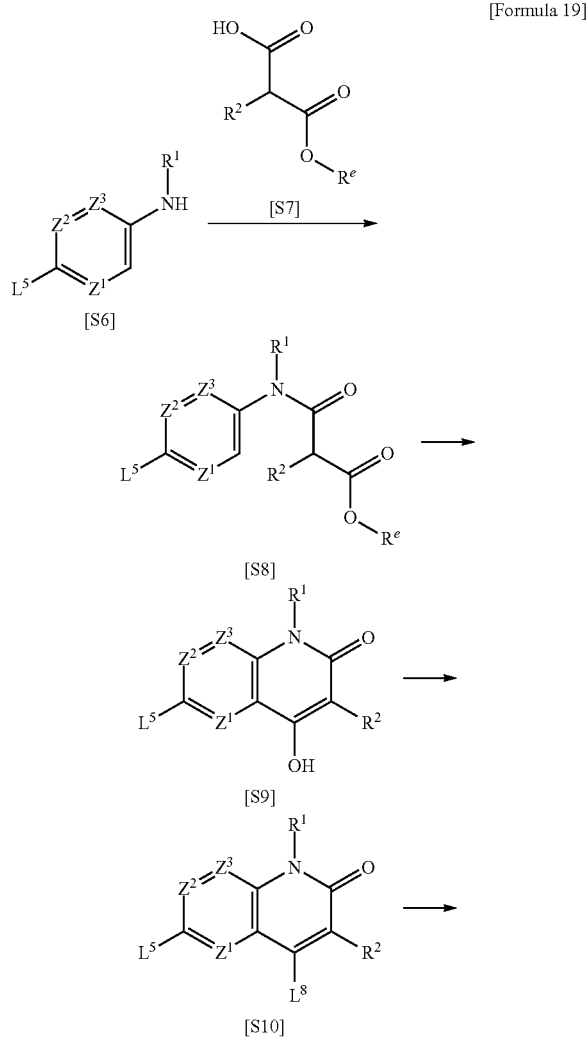

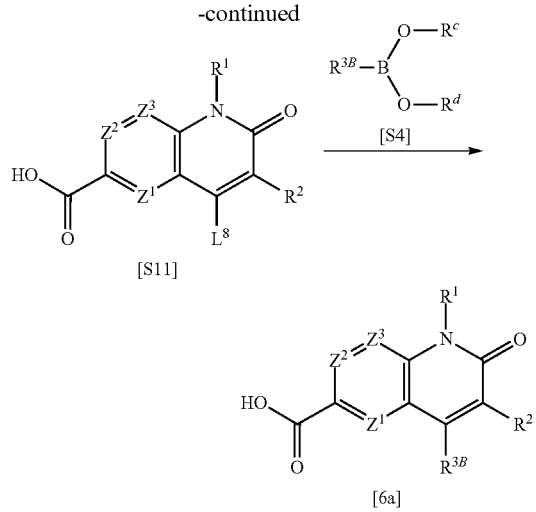

wherein $R^e$ represents a carboxyl-protecting group; and $R^1$, $R^2$, $R^{3B}$, $R^c$, $R^d$, $L^5$, $L^8$, $Z^1$, $Z^2$ and $Z^3$ have the same meanings as above.

<First Step>

As a compound represented by the formula [S6], for example, N-ethyl-4-iodoaniline or the like has been known.

As a compound represented by the formula [S7], for example, 3-tert-butoxy-3-oxopropionic acid or the like has been known.

The compound represented by the formula [S8] can be produced by allowing the compound represented by the formula [S7] to react with the compound represented by the formula [S6] in the presence of a condensing agent or an acid halide and in the presence of a base.

This reaction may be carried out in accordance with Production Method 1.

<Second Step>

The compound represented by the formula [S9] can be produced by allowing a dehydrating agent to react with the compound represented by the formula [S8].

The solvent used in this reaction is not particularly limited, as long as it does not affect the reaction. Examples of the solvent include halogenated hydrocarbons, ethers, esters, amides, nitriles, sulfoxides, and aromatic hydrocarbons. These solvents may be used in combination.

Preferred solvents are amides and sulfoxides. Among these, amides are more preferable.

The amount of the solvent used is not particularly limited, but the solvent may be used in an amount of 1 to 500 times (v/w), with respect to the amount of the compound represented by the formula [S8].

Examples of the dehydrating agent used in this reaction include phosphorus pentoxide, phosphorus pentachloride, phosphoryl chloride, and thionyl chloride.

The dehydrating agent may be used in an amount of 1 to 50 times, and preferably 1 to 10 times, with respect to the molar amount of the compound represented by the formula [S8].

This reaction may be carried out at −30° C. to 150° C., preferably at 0° C. to 100° C., for 30 minutes to 48 hours.

<Third Step>

When $L^8$ is, for example, a halogen atom, the compound represented by the formula [S10] can be produced by allowing a halogenating agent to react with the compound represented by the formula [S9].

The solvent used in this reaction is not particularly limited, as long as it does not affect the reaction. Examples of the solvent include aliphatic hydrocarbons, halogenated hydrocarbons, ethers, ketones, esters, amides, nitriles, sulfoxides, and aromatic hydrocarbons. These solvents may be used in combination.

Preferred solvents are aromatic hydrocarbons.

The amount of the solvent used is not particularly limited, but the solvent may be used in an amount of 1 to 500 times (v/w), with respect to the amount of the compound represented by the formula [S9].

Examples of the halogenating agent used in this reaction include phosphorus oxychloride, phosphoryl chloride, and thionyl chloride.

The halogenating agent may be used in an amount of 1 to 50 times, and preferably 1 to 10 times, with respect to the molar amount of the compound represented by the formula [S9]. In addition, such a halogenating agent may also be used as a solvent.

This reaction may be carried out at −30° C. to 150° C., preferably at 0° C. to 100° C., for 30 minutes to 48 hours.

<Fourth Step>

The compound represented by the formula [S11] can be produced by allowing sodium formate to react with the compound represented by the formula [S10] in the presence of a base and in the presence of a palladium catalyst.

The solvent used in this reaction is not particularly limited, as long as it does not affect the reaction. Examples of the solvent include halogenated hydrocarbons, ethers, esters, amides, nitriles, sulfoxides, and aromatic hydrocarbons. These solvents may be used in combination.

Preferred solvents are amides and sulfoxides. Among these, amides are more preferable.

The amount of the solvent used is not particularly limited, but the solvent may be used in an amount of 1 to 500 times (v/w), with respect to the amount of the compound represented by the formula [S10].

The base used in this reaction may be, for example, an organic base.

The base may be used in an amount of 1 to 50 times, and preferably 1 to 10 times, with respect to the molar amount of the compound represented by the formula [S10].

Examples of the palladium catalyst used in this reaction include: palladium metals such as palladium-carbon and palladium black; inorganic palladium salts such as palladium chloride; organic palladium salts such as palladium acetate; chloro(2-(dicyclohexylphosphino)-3,6-dimethoxy-2',4',6'-triisopropyl-1,1'-biphenyl)(2-(2-aminoethyl)phenyl)palladium(II); organic palladium complexes, such as tetrakis(triphenylphosphine)palladium(0), bis(triphenylphosphine)palladium(II) dichloride, bis(di-tert-butyl(4-dimethylaminophenyl)phosphine)dichloropalladium(II), 1,1'-bis(diphenylphosphino)ferrocenepalladium(II) dichloride, (E)-di(Q-acetato)bis(o-(di-o-tolylphosphino)benzyl)dipalladium(II), and tris(dibenzylideneacetone)dipalladium(0); and polymer-supported organic palladium complexes, such as polymer-supported bis(acetato)triphenylphosphinepalladium(II) and polymer-supported di(acetato)dicyclohexylphenylphosphinepalladium(II). Among these, organic palladium complexes are preferable.

The palladium catalyst may be used in an amount of 0.00001 to 1 time, and preferably 0.01 to 0.2 times, with respect to the molar amount of the compound represented by the formula [S10].

The sodium formate may be used in an amount of 1 to 50 times, and preferably 1 to 10 times, with respect to the molar amount of the compound represented by the formula [S10].

This reaction may be carried out at −30° C. to 150° C., preferably at 0° C. to 100° C., for 30 minutes to 48 hours.

<Fifth Step>

As a compound represented by the formula [S4], for example, tert-butyl 4-(4,4,5,5-tetramethyl-1,3,2-dioxaborolan-2-yl)-3,6-dihydropyridine-1(2H)-carboxylate or the like has been known.

The compound represented by the formula [6a] can be produced by allowing the compound represented by the formula [S4] to react with the compound represented by the formula [S11] in the presence of a base, in the presence of a palladium catalyst, and in the presence or absence of a ligand.

This reaction may be carried out in accordance with Production Method 5.

With regard to the compounds used in the above-described production methods, when solvates, hydrates, and various shapes of crystals are present, these solvates, hydrates, and various shapes of crystals can also be used.

With regard to the compounds used in the above-described production methods, which have, for example, amino groups, hydroxyl groups or carboxyl groups, these groups may be previously protected by common protecting groups, and after completion of the reaction, these protecting groups can be removed by known methods.

The compounds obtained by the above-described production methods can be derived to other compounds by being subjected to a known reaction such as condensation, addition, oxidation, reduction, transposition, substitution, halogenation, dehydration or hydrolysis, or by combining these reactions with one another, as appropriate.

When the compound represented by the formula [1] is used as a medicament, pharmaceutical aids that are commonly used in formulation, such as excipients, carriers and diluents, may be mixed into the compound, as appropriate. These can be orally or parenterally administered according to an ordinary method, in the form of a tablet, a capsule, a powder agent, a syrup agent, a granule, a pill, a suspending agent, an emulsion, a liquid agent, a powdery preparation, a suppository, an eye drop, a nasal drop, an ear drop, a patch, an ointment or an injection. In addition, the administration method, the applied dose, and the number of administrations can be selected, as appropriate, depending on the age, body weight, and symptoms of a patient. In general, the medicament may be administered to an adult, via oral or parenteral (e.g., injection, intravenous drip, administration into a rectal site, etc.) administration, at a daily dose of 0.01 to 1000 mg/kg, once or divided over several administrations.

The pharmaceutical composition means a composition comprising pharmaceutical aids used in formulation, such as excipients, carriers and diluents, as appropriate, as well as the compound of the present invention or a salt thereof serving as an active ingredient.

Next, the present invention will be described in the following Reference Examples, Examples and Test Examples. However, these examples are not intended to limit the scope of the present invention.

Unless otherwise specified, in purification using column chromatography, an automated purification apparatus ISOLERA (Biotage) or a medium-pressure liquid chromatograph YFLC-Wprep2XY.N (YAMAZEN CORPORATION) was used.

Unless otherwise specified, as a carrier used in silica gel column chromatography, SNAP KP-Sil Cartridge (Biotage), or HI-FLASH COLUMN W001, W002, W003, W004 or W005 (YAMAZEN CORPORATION) was used.

As a carrier used in basic silica gel column chromatography, SNAP KP-NH Cartridge (Biotage) was used.

The mixing ratio in an eluent indicates a volume ratio. For example, the phrase "gradient elution of hexane:ethyl acetate=100:0-50:50" means that an eluent of 100% hexane/0% ethyl acetate has been finally converted to an eluent of 50% hexane/50% ethyl acetate.

As a flow-type hydrogenation reactor, H-Cube (ThalesNano) was used.

As a microwave apparatus, Initiator+ or Initiator Sixty (both of which are manufactured by Biotage) was used.

MS spectrum was measured using ACQUITY SQD LC/MS System (Waters, ionization method: ESI (ElectroSpray Ionization) method), M-8000 (Hitachi, Ltd., ionization method: ESI method), LCMS-2010EV (Shimadzu Corporation, ionization method: an ionization method in which ESI and APCI (Atmospheric Pressure ChemicalIonization) are simultaneously carried out), or JMS-T100LP (DART) (JEOL, ionization method: DART (Direct Analysis in Real Time) method).

NMR spectrum was measured using tetramethylsilane as an internal reference, employing Bruker AV300 (Bruker) or JNM-AL400 (JEOL). All δ values were indicated by ppm.

The abbreviations used in the NMR measurement have the following meanings.

s: Singlet
brs: Broad singlet
d: Doublet
dd: Double doublet
t: Triplet
q: Quartet
quint: Quintet
m: Multiplet
DMSO-$D_6$: Deuterated dimethyl sulfoxide The abbreviations used in Reference Examples and Examples have the following meanings.

Bn: Benzyl
Me: Methyl

Reference Example 1

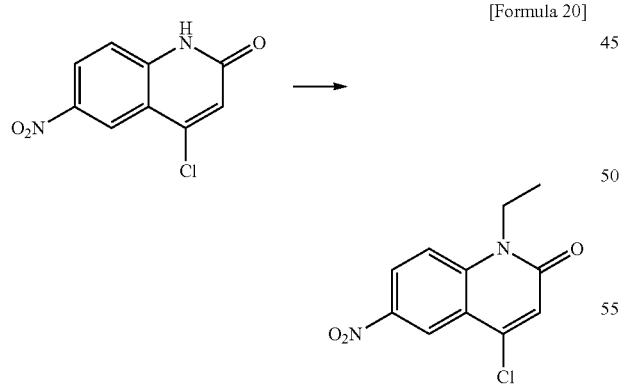

[Formula 20]

53.8 g of Cesium carbonate was added to a suspension of 18.5 g of 4-chloro-6-nitroquinolin-2(1H)-one in 150 mL of N,N-dimethylacetamide at 40° C. to 50° C. Under cooling on ice, 7.91 mL of ethyl iodide was added to the reaction mixture, and the obtained mixture was then stirred at room temperature for 3 hours. To the reaction mixture, ethyl acetate and water were added, and the obtained mixture was then adjusted to pH 2.0 with 2 mol/L hydrochloric acid. A solid was collected by filtration, and was then washed with water to obtain a slightly brown solid. To the obtained solid, ethyl acetate and diisopropyl ether were added, and a solid was collected by filtration, and was then washed with ethyl acetate to obtain 8.88 g of 4-chloro-1-ethyl-6-nitroquinolin-2(1H)-one in the form of a slightly brown solid.

$^1$H-NMR (CDCl$_3$) δ: 1.39 (3H, t, J=7.3 Hz), 4.39 (2H, q, J=7.3 Hz), 7.01 (1H, s), 7.51 (1H, d, J=9.9 Hz), 8.48 (1H, dd, J=9.2, 2.6 Hz), 8.94 (1H, d, J=2.6 Hz).

Reference Example 2

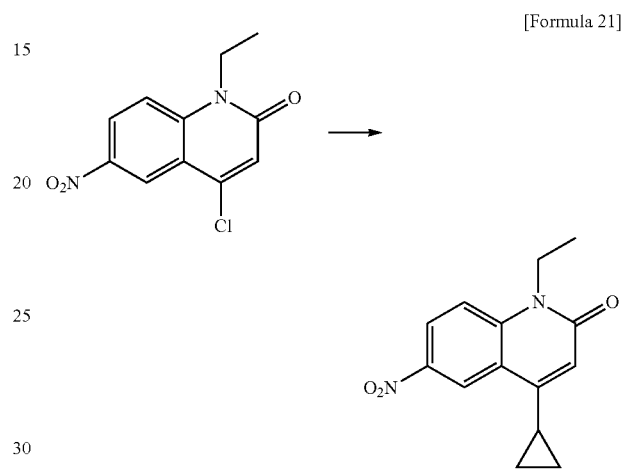

[Formula 21]

A mixture of 5.17 g of 4-chloro-1-ethyl-6-nitroquinolin-2(1H)-one, 4.26 g of cyclopropylboric acid monohydrate, 10.9 g of sodium carbonate, 0.44 g of bis(di-tert-butyl(4-dimethylaminophenyl)phosphine)dichloropalladium(II), 50 mL of ethylene glycol dimethyl ether, and 5.0 mL of water was heated to reflux under a nitrogen atmosphere for 3 hours. Thereafter, the reaction mixture was cooled to room temperature, and ethyl acetate and water were then added thereto. An organic layer was separated, was then successively washed with water and a saturated sodium chloride aqueous solution, and was then dried over anhydrous magnesium sulfate. The solvent was distilled away under reduced pressure. Diisopropyl ether, ethyl acetate and hexane were added to the obtained residue, and a solid was collected by filtration and was then washed with diisopropyl ether to obtain 4.81 g of 4-cyclopropyl-1-ethyl-6-nitroquinolin-2(1H)-one in the form of a slightly brown solid.

$^1$H-NMR (CDCl$_3$): 0.79-0.87 (2H, m), 1.15-1.24 (2H, m), 1.37 (3H, t, J=7.3 Hz), 2.11-2.23 (1H, m), 4.37 (2H, q, J=7.Hz), 6.54 (1H, s), 7.47 (1H, d, J=9.2 Hz), 8.42 (1H, dd, J=9.2, 2.6 Hz), 9.00 (1H, d, J=2.6 Hz).

Reference Example 3

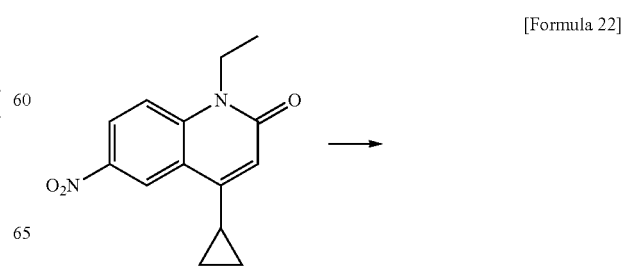

[Formula 22]

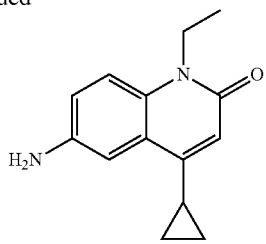

A mixture of 4.8 g of 4-cyclopropyl-1-ethyl-6-nitroquinolin-2(1H)-one, 0.68 g of ammonium chloride, 3.91 g of iron powder, 48 mL of ethanol and 9.6 mL of water was heated to reflux for 1 hour. The reaction mixture was cooled to room temperature, water and ethyl acetate were then added thereto, and insoluble matters were then removed by filtration. The filtrate cake was washed with ethyl acetate and water. The filtrate was gathered with the washing solution, and an organic layer was then separated. The organic layer was washed with water and a saturated sodium chloride aqueous solution, and was then dried over anhydrous magnesium sulfate. The solvent was distilled away under reduced pressure. Diisopropyl ether and ethyl acetate were added to the obtained residue, and a solid was then collected by filtration, so as to obtain 3.92 g of 6-amino-4-cyclopropyl-1-ethylquinolin-2(1H)-one in the form of a light yellow solid.

$^1$H-NMR (CDCl$_3$) δ:0.71-0.79 (2H, m), 0.99-1.08 (2H, m), 1.33 (3H, t, J=7.3 Hz), 1.96-2.08 (1H, m), 3.74 (2H, brs), 4.31 (2H, q, J=7.1 Hz), 6.42 (1H, s), 6.99 (1H, dd, J=9.2, 2.6 Hz), 7.23 (1H, d, J=9.2 Hz), 7.38 (1H, d, J=2.6 Hz).

Reference Example 4

[Formula 23]

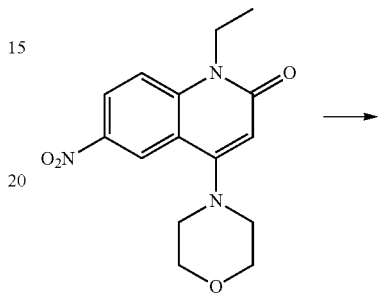

A mixture of 2.0 g of 4-chloro-1-ethyl-6-nitroquinolin-2(1H)-one, 10 mL of N,N-dimethylacetamide and 3.46 mL of morpholine was stirred at an external temperature of 130° C. to 140° C. for 2 hours. Thereafter, the reaction mixture was cooled to room temperature, and the solvent was then distilled away under reduced pressure. Water was added to the obtained residue, and a solid was collected by filtration and was then washed with diisopropyl ether to obtain 2.29 g of 1-ethyl-4-(morpholin-4-yl)-6-nitroquinolin-2(1H)-one in the form of a slightly brown solid.

$^1$H-NMR (CDCl$_3$) δ: 1.37 (3H, t, J=7.3 Hz), 3.10-3.18 (4H, m), 3.95-4.03 (4H, m), 4.36 (2H, q, J=7.0 Hz), 6.27 (1H, s), 7.46 (1H, d, J=9.2 Hz), 8.38 (1H, dd, J=9.2, 2.6 Hz), 8.71 (1H, d, J=2.6 Hz).

Reference Example 5

[Formula 24]

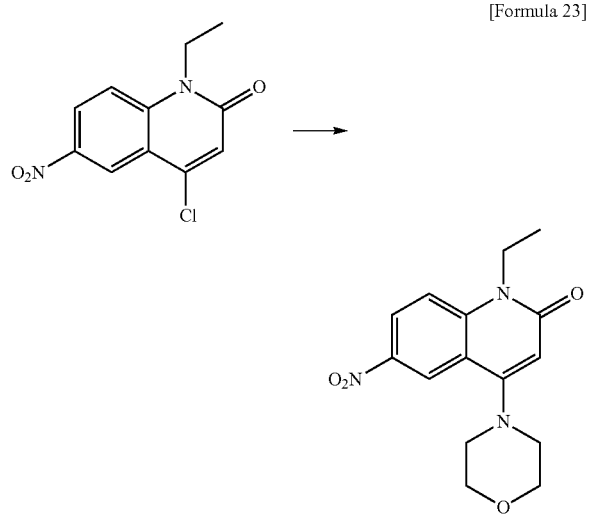

A mixture of 2.27 g of 1-ethyl-4-(morpholin-4-yl)-6-nitroquinolin-2(1H)-one, 0.26 g of ammonium chloride, 1.46 g of iron powder, 20 mL of ethanol and 4.0 mL of water was heated to reflux for 3 hours 20 minutes. Thereafter, 20 mL of dioxane and 20 mL of ethyl acetate were added to the reaction mixture, and the obtained mixture was then heated to reflux for 3 hours. The reaction mixture was cooled to room temperature, and was then left at rest overnight. Thereafter, the reaction mixture was heated to reflux for 1 hour. After that, 100 mL of chloroform was added to the reaction mixture, and the obtained mixture was then heated to reflux for 1 hour. To the reaction mixture, 0.26 g of ammonium chloride and 0.73 g of iron powder were added, and the obtained mixture was then heated to reflux for 5 hours. Thereafter, the reaction mixture was cooled to room temperature, and insoluble matters were then removed by filtration. A filtrate cake was washed with chloroform and water. The filtrate was gathered with the washing solution, and an organic layer was then separated. The organic layer was washed with a saturated sodium chloride aqueous solution, and was then dried over anhydrous magnesium sulfate. The solvent was distilled away under reduced pressure. Diisopropyl ether was added the obtained residue, and a solid was then collected by filtration to obtain 1.76 g of 6-amino-1-ethyl-4-(morpholin-4-yl)quinolin-2(1H)-one in the form of a slightly brown solid.

$^1$H-NMR (CDCl$_3$) δ: 1.32 (3H, t, J=7.3 Hz), 3.04-3.12 (4H, m), 3.71 (2H, brs), 3.89-3.96 (4H, m), 4.29 (2H, q, J=7.0 Hz), 6.18 (1H, s), 6.96 (1H, dd, J=8.6, 2.6 Hz), 7.09 (1H, d, J=3.3 Hz), 7.24 (1H, d, J=9.2 Hz).

Reference Example 6

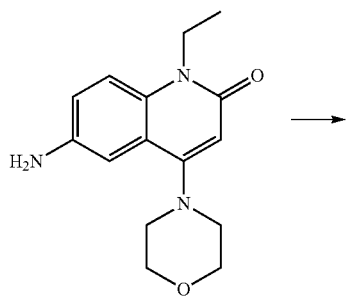

[Formula 25]

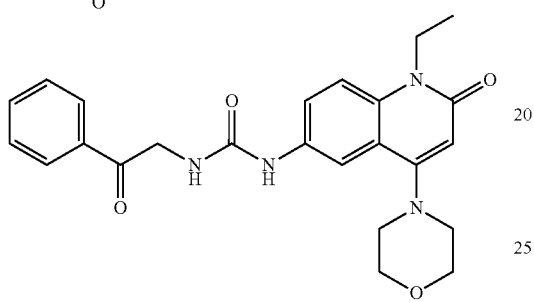

0.46 g of 1,1'-Carbonyldiimidazole was added to a solution of 0.7 g of 6-amino-1-ethyl-4-(morpholin-4-yl)quinolin-2(1H)-one in 14 mL of dichloromethane, and the obtained mixture was then stirred at room temperature for 4 hour. Thereafter, 0.54 mL of triethylamine was added to the reaction mixture at room temperature. To the reaction mixture, 0.48 g of 2-amino-1-phenylethanone hydrochloride was added under cooling on ice, and the obtained mixture was then stirred at room temperature for 3 hours. Thereafter, chloroform and water were added to the reaction mixture, and the obtained mixture was then adjusted to pH 2.0 with 2 mol/L hydrochloric acid. An organic layer was separated, was then washed with a saturated sodium chloride aqueous solution and was then dried over anhydrous magnesium sulfate. The solvent was distilled away under reduced pressure. Diisopropyl ether and ethyl acetate were added to the obtained residue, and a solid was then collected by filtration to obtain 0.86 g of 1-(1-ethyl-4-(morpholin-4-yl)-2-oxo-1,2-dihydroquinolin-6-yl)-3-(2-oxo-2-phenylethyl)urea in the form of a slightly brown solid.

$^1$H-NMR (CDCl$_3$): 1.34 (3H, t, J=6.9 Hz), 3.10-3.17 (4H, m), 3.89-3.97 (4H, m), 4.32 (2H, q, J=7.0 Hz), 4.86 (2H, d, J=4.0 Hz), 5.93-6.01 (1H, m), 6.22 (1H, s), 6.98 (1H, s), 7.34 (1H, d, J=9.2 Hz), 7.42-7.56 (3H, m), 7.59-7.68 (1H, m), 7.96-8.03 (3H, m).

Reference Example 7

[Formula 26]

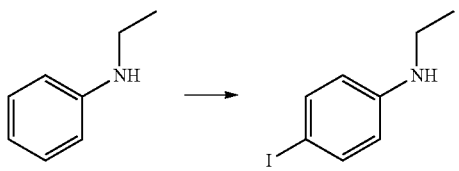

6.7 g of Sodium hydrogen carbonate was added to a solution of 5 mL of N-ethylaniline in dichloromethane (50 mL) and methanol (25 mL) at room temperature, and thereafter, 13.8 g of benzyltrimethylammonium dichloroiodate was added thereto. The obtained mixture was stirred at room temperature for 30 minutes, and ethyl acetate and water were then added to the reaction mixture. An organic layer was separated, was then successively washed with water and a saturated sodium chloride aqueous solution and was then dried over anhydrous magnesium sulfate. The solvent was distilled away under reduced pressure to obtain 9.8 g of N-ethyl-4-iodoaniline in the form of a slightly brown solid.

$^1$H-NMR (CDCl$_3$) δ:1.24 (3H, t, J=6.9 Hz), 3.12 (2H, q, J=7.0 Hz), 3.60 (1H, brs), 6.34-6.42 (2H, m), 7.37-7.45 (2H, m).

Reference Example 8

[Formula 27]

8.38 g of 1-Ethyl-3-(3-dimethylaminopropyl)carbodiimide hydrochloride was added to a mixture of 9.8 g of N-ethyl-4-iodoaniline, 7.0 g of 3-tert-butoxy-3-oxopropionic acid and 50 mL of dichloromethane under cooling on ice, and the obtained mixture was then stirred at room temperature for 2 hour. To the reaction mixture, 6.1 mL of triethylamine and 5.34 g of N,N-dimethyl-4-aminopyridine were added, and the obtained mixture was then stirred at room temperature for 1 hour. To the reaction mixture, 1.75 g of 3-tert-butoxy-3-oxopropionic acid and 4.2 g of 1-ethyl-3-(3-dimethylaminopropyl)carbodiimide hydrochloride were added, and the obtained mixture was then stirred at room temperature for 1 hour. To the reaction mixture, water and ethyl acetate were added. An organic layer was separated, was then washed with a saturated sodium hydrogen carbonate aqueous solution and 1 mol/L hydrochloric acid twice, and was then dried over anhydrous magnesium sulfate. The solvent was distilled away under reduced pressure. Diisopropyl ether and ethyl acetate were added to the obtained residue, and a solid was collected by filtration and was then washed with diisopropyl ether to obtain 8.1 g of tert-butyl 3-(ethyl(4-iodophenyl)amino)-3-oxopropanoate in the form of a white solid.

$^1$H-NMR (CDCl$_3$) δ: 1.12 (3H, t, J=7.3 Hz), 1.42 (9H, s), 3.07 (2H, s), 3.75 (2H, q, J=7.0H z), 6.94-7.01 (2H, m), 7.71-7.79 (2H, m).

Reference Example 9

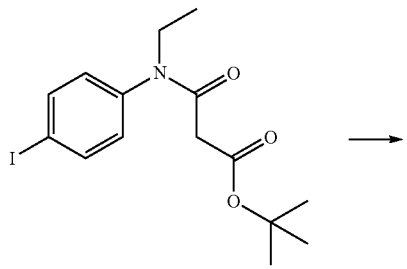

8.1 g of tert-Butyl 3-(ethyl(4-iodophenyl)amino)-3-oxo-propanoate was added to 40 mL of methanesulfonic acid at room temperature. 5.91 g of Diphosphorus pentaoxide was added to the obtained mixture, and the thus obtained mixture was then stirred at an external temperature of 50° C. to 60° C. for 30 minutes. Thereafter, the temperature of the reaction mixture was elevated, and the reaction mixture was then stirred at an external temperature of 100° C. to 110° C. for 30 minutes. Thereafter, the reaction mixture was cooled to room temperature, and ice water was then added to the reaction mixture. A solid was collected by filtration, and was then washed with water to obtain 6.55 g of 1-ethyl-4-hydroxy-6-iodoquinolin-2(1H)-one in the form of a slightly brown solid.

$^1$H-NMR (DMSO-D$_6$) δ: 1.14 (3H, t, J=7.3 Hz), 4.17 (2H, q, J=7.0 Hz), 5.86 (1H, s), 7.36 (1H, d, J=9.2 Hz), 7.88 (1H, dd, J=8.6, 2.0 Hz), 8.14 (1H, d, J=2.0 Hz), 11.56 (1H, brs).

Reference Example 10

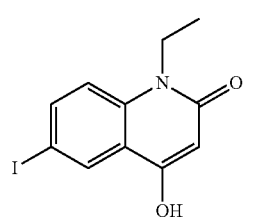

6.5 g of 1-Ethyl-4-hydroxy-6-iodoquinolin-2(1H)-one was added to 25 mL of phosphorus oxychloride at room temperature, and the obtained mixture was then stirred at an external temperature of 90° C. to 100° C. for 30 minutes. Thereafter, the reaction mixture was cooled to room temperature, and water was then added to the reaction mixture. Ethyl acetate was added to the obtained mixture, and an organic layer was separated. The organic layer was washed with a saturated sodium chloride aqueous solution, and was then dried over anhydrous magnesium sulfate. The solvent was distilled away under reduced pressure. The obtained residue was purified by silica gel column chromatography [ethyl acetate]. To the obtained residue, diisopropyl ether, ethyl acetate and hexane were added, and a solid was then collected by filtration, so as to obtain 4.87 g of 4-chloro-1-ethyl-6-iodoquinolin-2(1H)-one in the form of a slightly brown solid.

$^1$H-NMR (DMS O-D$_6$) δ:1.19 (3H, t, J=7.3 Hz), 4.25 (2H, q, J=7.0 Hz), 6.98 (1H, s), 7.52 (1H, d, J=9.2 Hz), 8.01 (1H, dd, J=9.2, 2.0 Hz), 8.19 (1H, d, J=2.0 Hz).

Reference Example 11

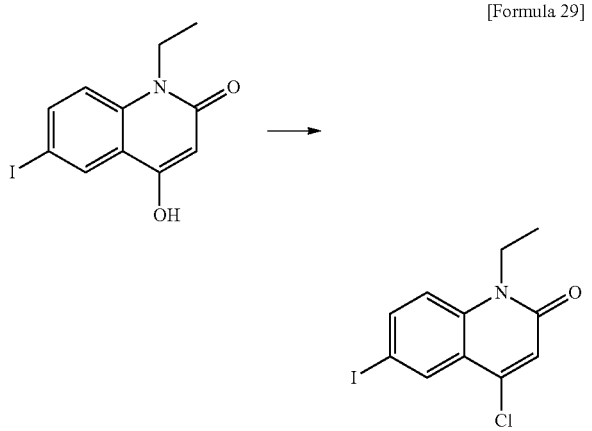

A mixture of 1.48 g of 4-chloro-1-ethyl-6-iodoquinolin-2(1H)-one, 0.9 g of sodium formate, 0.56 g of lithium chloride, 1.51 mL of N,N-diisopropylethylamine, 0.86 mL of acetic anhydride, 0.12 g of tris(dibenzylideneacetone)dipalladium(0) and 10 mL of N,N-dimethylacetamide was stirred under a nitrogen atmosphere at an external temperature of 90° C. for 4 hours. Thereafter, the reaction mixture was cooled to room temperature, and insoluble matters were then removed by filtration. A filtrate cake was washed with a 5 mol/L sodium hydroxide aqueous solution and water. The filtrate was gathered with the washing solution, and the obtained mixture was then adjusted to pH 2.0 with 6 mol/L hydrochloric acid. Thereafter, diisopropyl ether and ethyl acetate were added to the mixture. A solid was collected by filtration, and was then washed with diisopropyl ether to obtain 1.06 g of 4-chloro-1-ethyl-2-oxo-1,2-dihydroquinoline-6-carboxylic acid in the form of a slightly brown solid.

$^1$H-NMR (DMS O-D$_6$) δ: 1.23 (3H, t, J=7.3 Hz), 4.31 (2H, q, J=7.0 Hz), 7.06 (1H, s), 7.80 (1H, d, J=9.2 Hz), 8.22 (1H, dd, J=8.6, 2.0 Hz), 8.51 (1H, d, J=2.0 Hz), 13.27 (1H, brs).

Reference Example 12

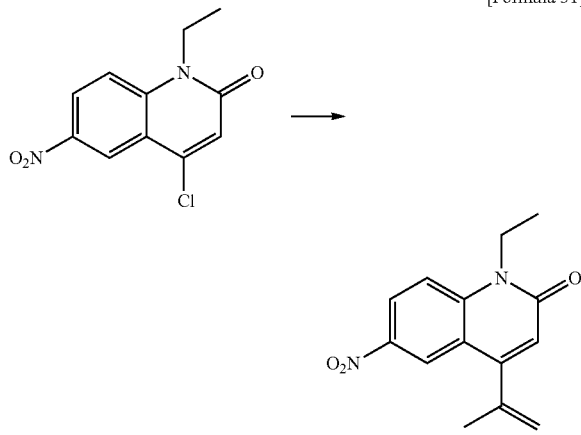

[Formula 31]

A mixture of 10.1 g of 4-chloro-1-ethyl-6-nitroquinolin-2(1H)-one, 8.07 g of isopropenyl boronic acid pinacol ester, 17.38 g of tripotassium phosphate, 0.28 g of bis(di-tert-butyl (4-dimethylaminophenyl)phosphine)dichloropalladium(II), 225 mL of dioxane and 90 mL of water was heated to reflux under a nitrogen atmosphere for 3 hours 10 minutes. Thereafter, 0.28 g of bis(di-tert-butyl(4-dimethylaminophenyl) phosphine)dichloropalladium(II) was added to the reaction mixture, and the obtained mixture was then heated to reflux for 30 minutes. Thereafter, 0.28 g of bis(di-tert-butyl(4-dimethylaminophenyl)phosphine)dichloropalladium(II) was added to the reaction mixture, and the obtained mixture was then heated to reflux for 1 hour 30 minutes. After that, the reaction mixture was cooled to room temperature, and ethyl acetate and water were then added thereto. An organic layer was separated, and a water layer was then extracted with ethyl acetate twice. The organic layer was gathered with the extract, and the obtained mixture was washed with a saturated sodium chloride aqueous solution and was then dried over anhydrous magnesium sulfate. The solvent was distilled away under reduced pressure. Diisopropyl ether and ethyl acetate were added to the obtained residue, and a solid was then collected by filtration to obtain 10.19 g of 1-ethyl-6-nitro-4-(prop-1-en-2-yl)quinolin-2(1H)-one in the form of a yellow solid.

$^1$H-NMR (CDCl$_3$) δ: 1.40 (3H, t, J=7.2 Hz), 2.14-2.19 (3H, m), 4.40 (2H, q, J=7.2 Hz), 5.13-5.18 (1H, m), 5.49-5.53 (1H, m), 6.66 (1H, s), 7.48 (1H, d, J=9.3 Hz), 8.40 (1H, dd, J=9.3, 2.7 Hz), 8.64 (1H, d, J=2.7 Hz).

Reference Example 13

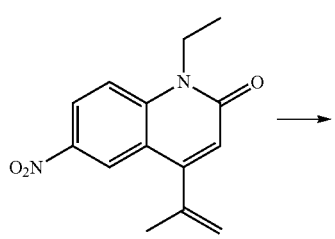

[Formula 32]

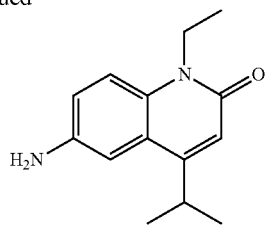

2.5 g of 10% Palladium-carbon was added to a solution of 5.0 g of 1-ethyl-6-nitro-4-(prop-1-en-2-yl)quinolin-2(1H)-one in methanol (450 mL) and dioxane (50 mL), and the obtained mixture was then stirred under a hydrogen atmosphere at room temperature for 2 hours. Thereafter, insoluble matters were removed by filtration, and the solvent was then distilled away under reduced pressure to obtain 3.86 g of 6-amino-1-ethyl-4-(propan-2-yl)quinolin-2(1H)-one in the form of a yellow foam.

$^1$H-NMR (CDCl$_3$): 1.31 (6H, d, J=6.8 Hz), 1.27-1.38 (3H, m), 3.23-3.35 (1H, m), 4.32 (2H, q, J=7.2 Hz), 6.63 (1H, s), 6.98 (1H, dd, J=9.0, 2.4 Hz), 7.10 (1H, d, J=2.4 Hz), 7.23-7.30 (1H, m).

Reference Example 14

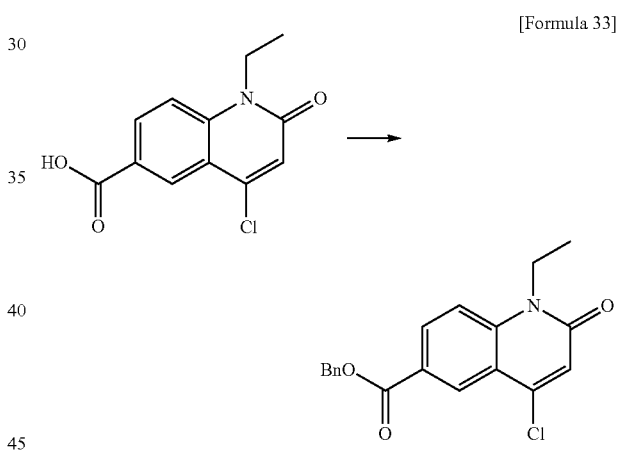

[Formula 33]

0.83 g of Potassium carbonate and 0.51 mL of benzyl chloride were added to a suspension of 1.01 g of 4-chloro-1-ethyl-2-oxo-1,2-dihydroquinoline-6-carboxylic acid in 5 mL of N,N-dimethylformamide, and the obtained mixture was then stirred at an external temperature of 80° C. for 1 hour. Thereafter, the reaction mixture was cooled to room temperature, ethyl acetate and water were then added thereto, and the obtained mixture was then adjusted to pH 2.0 with 6 mol/L hydrochloric acid. An organic layer was separated, and a water layer was then extracted with ethyl acetate. The organic layer was gathered with the extract, was then successively washed with water and a saturated sodium chloride aqueous solution and was then dried over anhydrous magnesium sulfate. The solvent was distilled away under reduced pressure. The obtained residue was purified by silica gel column chromatography [gradient elution of hexane:ethyl acetate=80:20-70:30]. To the obtained residue, diisopropyl ether was added, and a solid was then collected by filtration, so as to obtain 1.09 g of benzyl 4-chloro-1-ethyl-2-oxo-1,2-dihydroquinoline-6-carboxylate in the form of a white solid.

$^1$H-NMR (CDCl$_3$) δ:1.36 (3H, t, J=7.2 Hz), 4.36 (2H, q, J=7.2 Hz), 5.43 (2H, s), 6.93 (1H, s), 7.34-7.52 (6H, m), 8.30 (1H, dd, J=9.0, 2.0 Hz), 8.75 (1H, d, J=2.0 Hz).

Reference Example 15

[Formula 34]

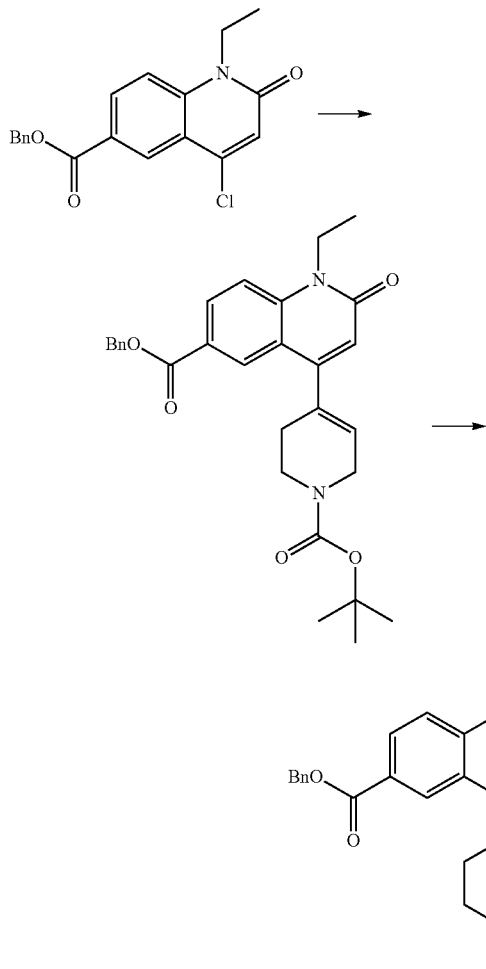

A mixture of 1.09 g of benzyl 4-chloro-1-ethyl-2-oxo-1,2-dihydroquinoline-6-carboxylate, 1.18 g of tert-butyl 4-(4,4,5,5-tetramethyl-1,3,2-dioxaborolan-2-yl)-3,6-dihydropyridine-1(2H)-carboxylate, 1.36 g of tripotassium phosphate, 68 mg of bis(di-tert-butyl(4-dimethylaminophenyl)phosphine)dichloropalladium(II), 23 mL of dioxane and 9 mL of water was heated to reflux under a nitrogen atmosphere for 30 minutes. Thereafter, the reaction mixture was cooled to room temperature, and ethyl acetate and water were then added thereto. An organic layer was separated, and a water layer was then extracted with ethyl acetate twice. The organic layer was gathered with the extract, and the obtained mixture was washed with a saturated sodium chloride aqueous solution, and was then dried over anhydrous magnesium sulfate. The solvent was distilled away under reduced pressure. The obtained residue was purified by silica gel column chromatography [gradient elution of hexane:ethyl acetate=70:30-60:40] to obtain benzyl 4-(1-(tert-butoxycarbonyl)-1,2,3,6-tetrahydropyridin-4-yl)-1-ethyl-2-oxo-1,2-di hydroquinoline-6-carboxylate in the form of a yellow oily substance.

To a solution of the obtained benzyl 4-(1-(tert-butoxycarbonyl)-1,2,3,6-tetrahydropyridin-4-yl)-1-ethyl-2-oxo-1,2-di hydroquinoline-6-carboxylate in 4 mL of formic acid, 2.5 mL of a 37% formaldehyde aqueous solution was added, and the obtained mixture was then stirred at an external temperature of 80° C. for 1 hour 30 minutes. Thereafter, the reaction mixture and ethyl acetate were added to a sodium hydrogen carbonate aqueous solution. An organic layer was separated, and a water layer was then extracted with ethyl acetate twice. The organic layer was gathered with the extract, and the obtained mixture was washed with a saturated sodium chloride aqueous solution, and was then dried over anhydrous sodium sulfate. The solvent was distilled away under reduced pressure. The obtained residue was purified by silica gel column chromatography [gradient elution of chloroform:methanol=100:0-70:30], to obtain 1.17 g of benzyl 1-ethyl-4-(1-methyl-1,2,3,6-tetrahydropyridin-4-yl)-2-oxo-1,2-dihydroquinoline-6-carboxylate in the form of a light brown solid.

$^1$H-NMR (CDCl$_3$) δ:1.37 (3H, t, J=7.2 Hz), 2.45 (3H, s), 2.42-2.53 (2H, m), 2.71 (2H, t, J=5.6 Hz), 3.13-3.21 (2H, m), 4.37 (2H, q, J=7.2 Hz), 5.39 (2H, s), 5.80-5.87 (1H, m), 6.58 (1H, s), 7.33-7.50 (6H, m), 8.21 (1H, dd, J=9.0, 2.0 Hz), 8.45 (1H, d, J=2.0 Hz).

Reference Example 16

[Formula 35]

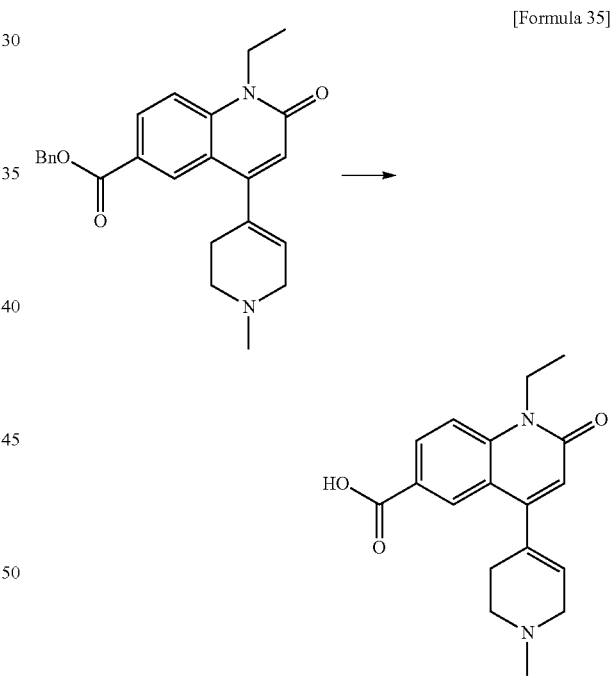

118 mg of 10% Palladium-carbon was added to a solution of 118 mg of benzyl 1-ethyl-4-(1-methyl-1,2,3,6-tetrahydropyridin-4-yl)-2-oxo-1,2-dihydroquinoline-6-carboxylate in 20 mL of methanol, and the obtained mixture was then stirred under a hydrogen atmosphere at room temperature for 3 hours 15 minutes. Thereafter, insoluble matters were removed by filtration, and the solvent was then distilled away under reduced pressure. Ethyl acetate was added to the obtained residue, and a solid was then collected by filtration to obtain 62 mg of 1-ethyl-4-(1-methylpiperidin-4-yl)-2-oxo-1,2-dihydroquinoline-6-carboxylic acid in the form of a white solid.

$^1$H-NMR (D$_2$O) δ: 1.12 (3H, t, J=7.3 Hz), 1.70-1.85 (2H, m), 2.01-2.12 (2H, m), 2.81 (3H, s), 3.13-3.23 (2H, m), 3.24-3.34 (1H, m), 3.48-3.57 (2H, m), 4.13 (2H, q, J=7.3 Hz), 6.41 (1H, s), 7.51 (1H, d, J=9.0 Hz), 7.98 (1H, d, J=9.0 Hz), 8.25 (1H, s).

Reference Example 17

[Formula 36]

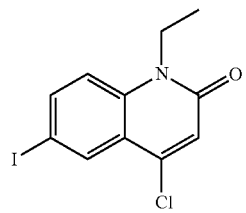

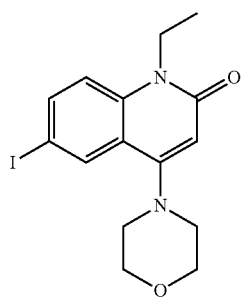

A mixture of 0.39 g of 4-chloro-1-ethyl-6-iodoquinolin-2(1H)-one, 2.0 mL of N,N-dimethylacetamide and 0.51 mL of morpholine was stirred in a sealed tube at an external temperature of 130° C. to 140° C. for 1 hour 30 minutes. Thereafter, the reaction mixture was cooled to room temperature, and the solvent was then distilled away under reduced pressure. Ethyl acetate and water were added to the obtained residue, and the obtained mixture was then adjusted to pH 2.0 with 2 mol/L hydrochloric acid. An organic layer was separated, was then washed with a saturated sodium chloride aqueous solution, and was then dried over anhydrous magnesium sulfate. The solvent was distilled away under reduced pressure. Diisopropyl ether and hexane were added to the obtained residue, and a solid was then collected by filtration, so as to obtain 0.33 g of 1-ethyl-6-iodo-4-(morpholin-4-yl)quinolin-2(1H)-one in the form of a slightly brown solid.

$^1$H-NMR (CDCl$_3$) δ: 1.32 (3H, t, J=7.3 Hz), 3.04-3.13 (4H, m), 3.90-3.99 (4H, m), 4.28 (2H, q, J=7.3 Hz), 6.18 (1H, s), 7.14 (1H, d, J=9.2 Hz), 7.79 (1H, dd, J=8.9, 2.3 Hz), 8.10 (1H, d, J=8.9 Hz).

Reference Example 18

[Formula 37]

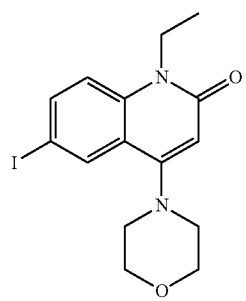

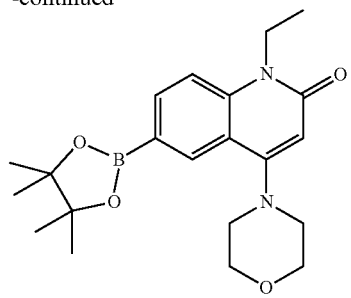

A mixture of 0.25 g of 1-ethyl-6-iodo-4-(morpholin-4-yl)quinolin-2(1H)-one, 53 mg of 1,1'-bis(diphenylphosphino)ferrocenepalladium(II) dichloride, 0.19 g of potassium acetate, 0.17 g of bis(pinacolato)diboron and 3.0 mL of dioxane was heated to reflux under a nitrogen atmosphere for 4 hours. Thereafter, the reaction mixture was cooled to room temperature, and ethyl acetate and water were then added thereto. An organic layer was separated, was then washed with a saturated sodium chloride aqueous solution and was then dried over anhydrous magnesium sulfate. The solvent was distilled away under reduced pressure. The obtained residue was purified by silica gel column chromatography [gradient elution of hexane:ethyl acetate=80:20-0:100], to obtain 66 mg of 1-ethyl-4-(morpholin-4-yl)-6-(4,4,5,5-tetramethyl-1,3,2-dioxaborolan-2-yl)quinolin-2(1H)-one in the form of a slightly brown oily substance.

$^1$H-NMR (CDCl$_3$) δ: 1.20-1.45 (15H, m), 3.05-3.22 (4H, m), 3.90-4.05 (4H, m), 4.25-4.41 (2H, m), 6.14-6.22 (1H, m), 7.33-7.43 (1H, m), 7.89-8.00 (1H, m), 8.23-8.33 (1H, m)

Reference Example 19

[Formula 38]

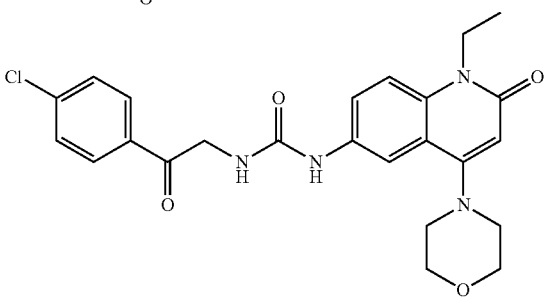

0.65 g of 1,1'-Carbonyldiimidazole was added to a solution of 1.0 g of 6-amino-1-ethyl-4-(morpholin-4-yl)quinolin-2(1H)-one in 10 mL of dichloromethane, and the obtained mixture was then stirred at an external temperature of 40° C. to 50° C. for 2 hours. Thereafter, 0.76 mL of triethylamine and 0.84 g of 2-amino-1-(4-chlorophenyl) ethanone hydrochloride were added to the reaction mixture under cooling on ice, and the obtained mixture was then stirred at room temperature for 2 hours. Thereafter, chloroform and water were added to the reaction mixture, and the obtained mixture was then adjusted to pH 2.0 with 2 mol/L hydrochloric acid. An organic layer was separated, was then washed with water and a saturated sodium chloride aqueous solution and was then dried over anhydrous magnesium sulfate. The solvent was distilled away under reduced pressure. The obtained residue was purified by silica gel column chromatography [gradient elution of chloroform:methanol=100:0-90:10]. Diisopropyl ether and ethyl acetate were added to the obtained residue, and a solid was then collected by filtration, so as to obtain 0.74 g of 1-(2-(4-chlorophenyl)-2-oxoethyl)-3-(1-ethyl-4-(morpholin-4-yl)-2-oxo-1,2-dihydroquinolin-6-yl)urea in the form of a slightly brown solid.

$^1$H-NMR (DMSO-D$_6$) δ: 1.17 (3H, t, J=7.0 Hz), 3.01-3.08 (4H, m), 3.79-3.86 (4H, m), 4.20 (2H, q, J=7.1 Hz), 4.70 (2H, d, J=5.1 Hz), 5.99 (1H, s), 6.50 (1H, t, J=5.2 Hz), 7.47 (1H, d, J=9.3 Hz), 7.56 (1H, dd, J=9.1, 2.6 Hz), 7.61-7.67 (2H, m), 8.01-8.07 (3H, m), 9.07 (1H, s).

Reference Example 20

[Formula 39]

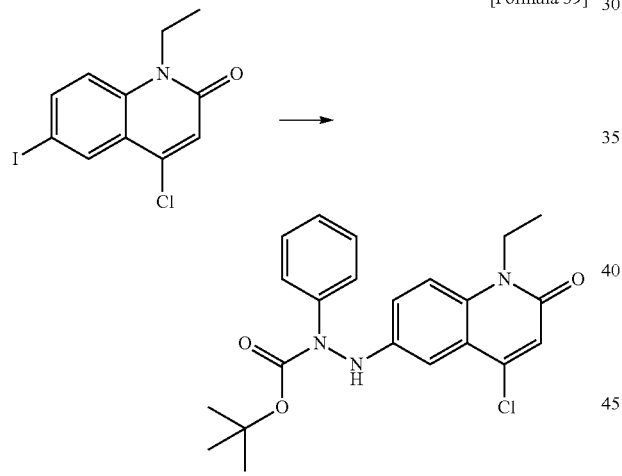

A mixture of 11.14 g of 4-chloro-1-ethyl-6-iodoquinolin-2(1H)-one, 7.93 g of tert-butyl 1-phenylhydrazinecarboxylate, 581 mg of tri-tert-butylphosphonium tetrafluoroborate, 375 mg of palladium acetate, 16.32 g of cesium carbonate and 160 mL of toluene was heated to reflux under a nitrogen atmosphere for 1 hour 30 minutes. Thereafter, the reaction mixture was cooled to room temperature, and water was then added thereto. An organic layer was separated, and a water layer was then extracted with ethyl acetate. The organic layer was gathered with the extract, and the obtained mixture was washed with a saturated sodium chloride aqueous solution and was then dried over anhydrous sodium sulfate. The solvent was distilled away under reduced pressure. The obtained residue was purified by silica gel column chromatography (gradient elution of hexane:ethyl acetate=80:20-60:40), to obtain 6.01 g of tert-butyl 2-(4-chloro-1-ethyl-2-oxo-1,2-dihydroquinolin-6-yl)-1-phenylhydrazinecarboxylate in the form of a yellow solid.

$^1$H-NMR (CDCl$_3$) δ:1.33 (3H, t, J=7.2 Hz), 1.43 (9H, s), 4.31 (2H, q, J=7.1 Hz), 6.58 (1H, s), 6.87 (1H, s), 7.13-7.20 (2H, m), 7.29-7.39 (3H, m), 7.45 (1H, d, J=2.7 Hz), 7.54-7.60 (2H, m).

Reference Example 21

[Formula 40]

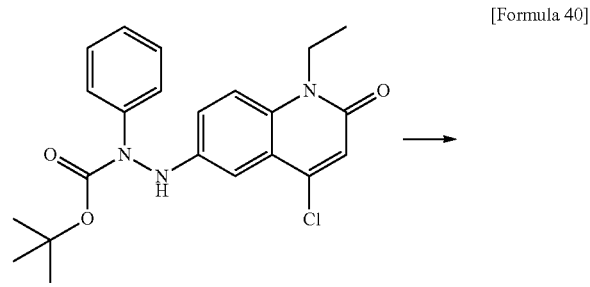

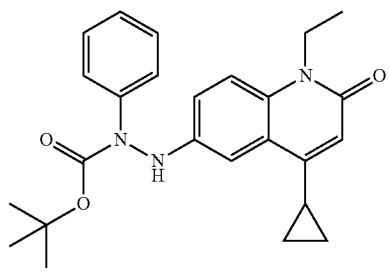

A mixture of 690 mg of tert-butyl 2-(4-chloro-1-ethyl-2-oxo-1,2-dihydroquinolin-6-yl)-1-phenylhydrazinecarboxylate, 172 mg of cyclopropylboric acid, 1.06 g of tripotassium phosphate, 35 mg of bis(di-tert-butyl(4-dimethylaminophenyl)phosphine)dichloropalladium(II), 12 mL of dioxane and 4.0 mL of water was stirred using a microwave apparatus at 140° C. for 5 minutes. Thereafter, the reaction mixture was cooled to room temperature, and ethyl acetate and water were then added thereto. An organic layer was separated, and a water layer was then extracted with ethyl acetate. The organic layer was gathered with the extract, and the obtained mixture was washed with a saturated sodium chloride aqueous solution and was then dried over anhydrous magnesium sulfate. The solvent was distilled away under reduced pressure. The obtained residue was purified by silica gel column chromatography (gradient elution of hexane:ethyl acetate=60:40-40:60), to obtain 527 mg of tert-butyl 2-(4-cyclopropyl-1-ethyl-2-oxo-1,2-dihydroquinolin-6-yl)-1-phenylhydrazinecarboxylate in the form of a light yellow solid.

$^1$H-NMR (CDCl$_3$) δ:0.67-0.73 (2H, m), 0.94-1.01 (2H, m), 1.32 (3H, t, J=7.1 Hz), 1.41 (9H, s), 1.90-2.00 (1H, m), 4.31 (2H, q, J=7.2 Hz), 6.44 (1H, d, J=0.98 Hz), 6.56 (1H, s), 7.08-7.19 (2H, m), 7.25-7.39 (3H, m), 7.52 (1H, d, J=2.4 Hz), 7.57-7.63 (2H, m).

Reference Example 22

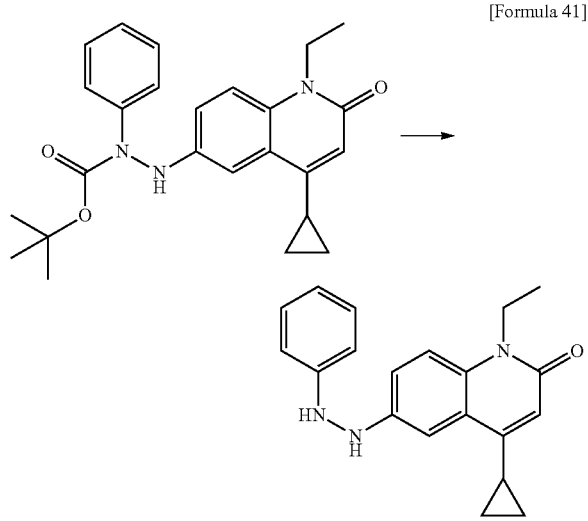

A mixture of 200 mg of tert-butyl 2-(4-cyclopropyl-1-ethyl-2-oxo-1,2-dihydroquinolin-6-yl)-1-phenylhydrazinecarboxylate and 2 mL of a 20% sodium ethoxide-ethanol solution was stirred using a microwave apparatus at 140° C. for 2 minutes. Thereafter, the reaction mixture was cooled to room temperature, and ethyl acetate and water were then added thereto. An organic layer was separated, was then successively washed with water and a saturated sodium chloride aqueous solution and was then dried over anhydrous magnesium sulfate. The solvent was distilled away under reduced pressure. Diisopropyl ether was added to the obtained residue, and a solid was collected by filtration and was then washed with diisopropyl ether, so as to obtain 115 mg of 4-cyclopropyl-1-ethyl-6-(2-phenylhydrazinyl)quinolin-2(1H)-one in the form of a light yellow solid.

$^1$H-NMR (DMS O-D$_6$) δ:0.62-0.69 (2H, m), 0.87-0.95 (2H, m), 1.15 (3H, t, J=7.0 Hz), 1.90-2.00 (1H, m), 4.18 (2H, q, J=7.0 Hz), 6.20 (1H, s), 6.65 (1H, t, J=7.2 Hz), 6.74-6.81 (2H, m), 7.08-7.15 (3H, m), 7.41 (1H, d, J=9.3 Hz), 7.45 (1H, d, J=2.4 Hz), 7.69-7.77 (2H, m).

Reference Example 23

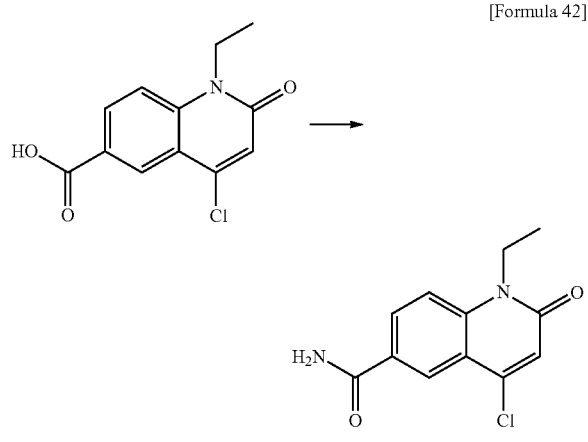

2.6 mL of Oxalyl chloride and 10 µL of N,N-dimethylformamide were added to a suspension of 4.0 g of 4-chloro-1-ethyl-2-oxo-1,2-dihydroquinoline-6-carboxylic acid in 25 mL of tetrahydrofuran at room temperature, and the obtained mixture was then stirred for 3 hours. Thereafter, the reaction mixture and 100 mL of water were added to a 28% ammonium aqueous solution under cooling on ice. A solid was collected by filtration, and was then washed with water to obtain 3.70 g of 4-chloro-1-ethyl-2-oxo-1,2-dihydroquinoline-6-carboxamide in the form of a slightly brown solid.

$^1$H-NMR (DMS O-D$_6$) δ: 1.22 (3H, t, J=7.1 Hz), 4.31 (2H, q, J=7.2 Hz), 7.02 (1H, s), 7.52 (1H, brs), 7.76 (1H, d, J=9.0 Hz), 8.22 (1H, dd, J=8.9, 2.1 Hz), 8.25 (1H, brs), 8.50 (1H, d, J=2.2 Hz).

Reference Example 24

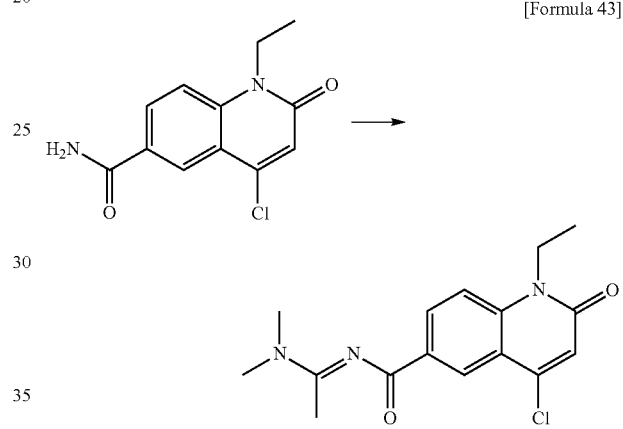

A mixture of 2.0 g of 4-chloro-1-ethyl-2-oxo-1,2-dihydroquinoline-6-carboxamide and 10 mL of 1,1-dimethoxy-N,N-dimethylethanamine was heated to reflux for 4 hours. Thereafter, the reaction mixture was cooled to room temperature, and diisopropyl ether was then added to the reaction mixture. A solid was collected by filtration, and was then washed with diisopropyl ether to obtain 2.13 g of 4-chloro-N-((1E)-1-(dimethylamino)ethylidene)-1-ethyl-2-oxo-1,2-dihydroquinoline-6-carboxamide in the form of a slightly brown solid.

$^1$H-NMR (DMSO-D$_6$) δ:1.22 (3H, t, J=7.1 Hz), 2.31 (3H, s), 3.16 (3H, s), 3.19 (3H, s), 4.30 (2H, q, J=7. Hz), 7.00 (1H, s), 7.72 (1H, d, J=8.8 Hz), 8.33 (1H, dd, J=8.8, 2.0 Hz), 8.64 (1H, d, J=2.0 Hz).

Reference Example 25

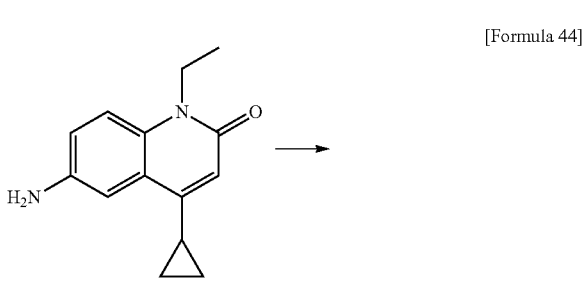

-continued

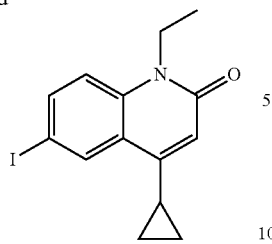

1.25 g of p-Toluenesulfonic acid monohydrate was added to a solution of 0.50 g of 6-amino-4-cyclopropyl-1-ethylquinolin-2(1H)-one in 9 mL of acetonitrile. Under cooling on ice, 0.91 g of potassium iodide and 0.30 g of sodium nitrite in 1.3 mL of an aqueous solution were added to the mixture, and the thus obtained mixture was stirred for 10 minutes, and was then stirred at room temperature for 1 hour. Thereafter, to the reaction mixture, water, a saturated sodium carbonate aqueous solution, a 1% sodium thiosulfate aqueous solution and ethyl acetate were added. An organic layer was separated, and a water layer was then extracted with ethyl acetate. The organic layer was gathered with the extract, and the obtained mixture was washed with a saturated sodium chloride aqueous solution and was then dried over anhydrous sodium sulfate. The solvent was distilled away under reduced pressure. The obtained residue was purified by silica gel column chromatography [gradient elution of hexane:ethyl acetate=70:30-40:60]. To the obtained residue, diisopropyl ether was added, and a solid was then collected by filtration, so as to obtain 0.31 g of 4-cyclopropyl-1-ethyl-6-iodoquinolin-2(1H)-one in the form of a light yellow solid.

$^1$H-NMR (CDCl$_3$) δ:0.75-0.79 (2H, m), 1.07-1.12 (2H, m), 1.32 (3H, t, J=7.2 Hz), 2.01-2.08 (1H, m), 4.30 (2H, q, J=7.2 Hz), 6.43 (1H, d, J=1.2 Hz), 7.14 (1H, d, J=8.8 Hz), 7.81 (1H, dd, J=8.8, 2.0 Hz), 8.38 (1H, d, J=2.0 Hz).

Reference Example 26

[Formula 45]

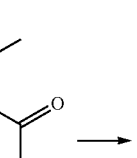

4-Chloro-1-ethyl-6-(4,4,5,5-tetramethyl-1,3,2-dioxaborolan-2-yl)quinolin-2(1H)-one was obtained from 4-chloro-1-ethyl-6-iodoquinolin-2(1H)-one by the same method as that of Reference Example 18.

$^1$H-NMR (CDCl$_3$): 1.35 (3H, t, J=7.2 Hz), 1.38 (12H, s), 4.36 (2H, q, J=7.2 Hz), 6.88 (1H, s), 7.39 (1H, d, J=8.5 Hz), 8.03 (1H, dd, J=8.5, 1.5 Hz), 8.46 (1H, d, J=1.5 Hz).

Reference Example 27

[Formula 46]

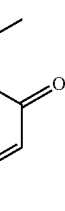

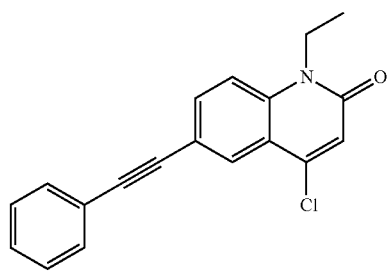

A mixture of 334 mg of 4-chloro-1-ethyl-6-iodoquinolin-2(1H)-one, 112 mg of ethynylbenzene, 2 mg of copper(I) iodide, 5 mg of triphenylphosphine, 2 mg of dichloropalladium, 0.42 mL of triethylamine and 5 mL of tetrahydrofuran was stirred under a nitrogen atmosphere at room temperature for 2 hours. Thereafter, to the reaction mixture, ethyl acetate, water and 1 mol/L hydrochloric acid were added. An organic layer was separated, and a water layer was then extracted with ethyl acetate. The organic layer was gathered with the extract, and the obtained mixture was washed with a saturated sodium chloride aqueous solution and was then dried over anhydrous magnesium sulfate. The solvent was distilled away under reduced pressure. To the obtained residue, diisopropyl ether was added, and a solid was then collected by filtration, so as to obtain 160 mg of 4-chloro-1-ethyl-6-(phenylethynyl)quinolin-2(1H)-one in the form of a brown solid.

$^1$H-NMR (CDCl$_3$) δ: 1.37 (3H, t, J=7.2 Hz), 4.36 (2H, q, J=7.2 Hz), 6.92 (1H, s), 7.35-7.42 (4H, m), 7.55-7.60 (2H, m), 7.76 (1H, dd, J=8.8, 2.0 Hz), 8.20 (1H, d, J=2.0 Hz).

Reference Example 28

[Formula 47]

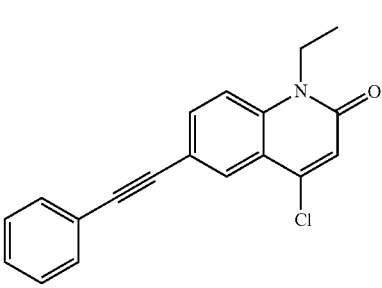

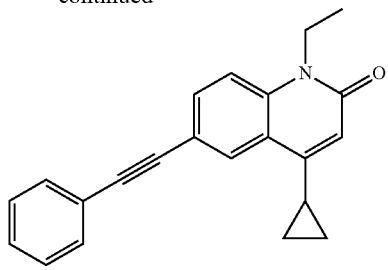

A mixture of 154 mg of 4-chloro-1-ethyl-6-(phenylethynyl)quinolin-2(1H)-one, 52 mg of cyclopropylboric acid, 318 mg of tripotassium phosphate, 11 mg of bis(di-tert-butyl(4-dimethylaminophenyl)phosphine)dichloropalladium(II), 3 mL of dioxane and 1 mL of water was stirred using a microwave apparatus at 140° C. for 15 minutes. Thereafter, the reaction mixture was cooled to room temperature, and ethyl acetate, water and 2 mol/L hydrochloric acid were then added thereto. An organic layer was separated, and a water layer was then extracted with ethyl acetate. The organic layer was gathered with the extract, and the obtained mixture was washed with a saturated sodium chloride aqueous solution and was then dried over anhydrous magnesium sulfate. The solvent was distilled away under reduced pressure. The obtained residue was purified by silica gel chromatography [gradient elution of hexane:ethyl acetate=80:20-60:40]. To the obtained residue, diisopropyl ether was added, and a solid was then collected by filtration, so as to obtain 100 mg of 4-cyclopropyl-1-ethyl-6-(phenylethynyl)quinolin-2(1H)-one in the form of a white solid.

$^1$H-NMR (CDCl$_3$) δ: 0.77-0.83 (2H, m), 1.08-1.16 (2H, m), 1.36 (3H, t, J=7.1 Hz), 2.08-2.19 (1H, m), 4.35 (2H, q, J=7.2 Hz), 6.45-6.49 (1H, m), 7.34-7.42 (4H, m), 7.55-7.61 (2H, m), 7.71 (1H, dd, J=8.9, 1.8 Hz), 8.27 (1H, d, J=2.0 Hz).

Reference Example 29

[Formula 48]

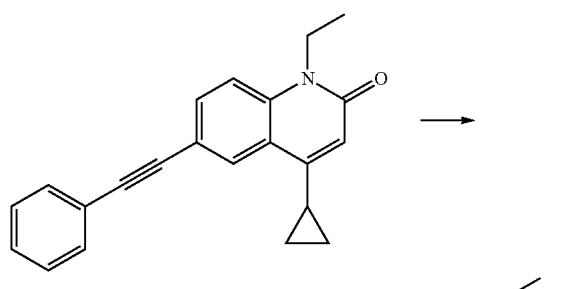

A mixture of 31 mg of 4-cyclopropyl-1-ethyl-6-(phenylethynyl)quinolin-2(1H)-one, 24 mg of magnesium sulfate, 19 mg of potassium permanganate, 5 mg of sodium hydrogen carbonate, 3 mL of acetone and 1.7 mL of water was stirred at room temperature for 20 minutes. Thereafter, 43 mg of potassium permanganate was added to the reaction mixture, and the obtained mixture was then stirred at room temperature for 1 hour. Thereafter, 30 mg of sodium nitrite and a 10% sulfuric acid aqueous solution were added to the reaction mixture, and insoluble matters were then removed by filtration. A filtrate cake was washed with ethyl acetate and water. The filtrate was gathered with the washing solution. An organic layer was separated, and a water layer was then extracted with ethyl acetate. The organic layer was gathered with the extract, and the obtained mixture was washed with a saturated sodium chloride aqueous solution and was then dried over anhydrous magnesium sulfate. The solvent was distilled away under reduced pressure. The obtained residue was purified by silica gel chromatography [gradient elution of hexane:ethyl acetate=60:40-30:70], to obtain 20 mg of 1-(4-cyclopropyl-1-ethyl-2-oxo-1,2-dihydroquinolin-6-yl)-2-phenylethane-1,2-dione.

$^1$H-NMR (CDCl$_3$) δ: 0.74-0.80 (2H, m), 1.05-1.12 (2H, m), 1.35 (3H, t, J=7.1 Hz), 2.07-2.16 (1H, m), 4.36 (2H, q, J=7.2 Hz), 6.46-6.49 (1H, m), 7.46 (1H, d, J=9.0 Hz), 7.54 (2H, t, J=7.9 Hz), 7.69 (1H, t, J=7.4 Hz), 8.02 (2H, dd, J=8.3, 1.2 Hz), 8.14 (1H, dd, J=8.9, 2.1 Hz), 8.77 (1H, d, J=2.0 Hz).

Reference Example 30

[Formula 49]

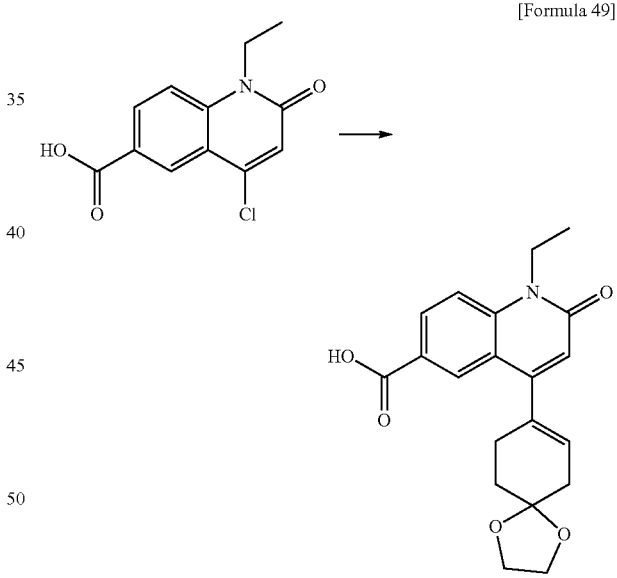

A mixture of 503 mg of 4-chloro-1-ethyl-2-oxo-1,2-dihydroquinoline-6-carboxylic acid, 639 mg of 8-(4,4,5,5-tetramethyl-1,3,2-dioxaborolan-2-yl)-1,4-dioxaspiro[4.5]dec-7-ene, 849 mg of tripotassium phosphate, 42 mg of bis(di-tert-butyl(4-dimethylaminophenyl)phosphine)dichloropalladium(II), 12 mL of dioxane and 4 mL of water was stirred using a microwave apparatus at 140° C. for 5 minutes. Thereafter, the reaction mixture was cooled to room temperature, and ethyl acetate and water were then added to the reaction mixture. A water layer was separated and was then washed with ethyl acetate twice. The water layer was adjusted to pH 2.0 by addition of 6 mol/L hydrochloric acid, and tetrahydrofuran was then added thereto. An organic layer was separated, and a water layer was then extracted with ethyl acetate twice. The organic layer was gathered with the extract, and the obtained mixture was washed with a saturated sodium chloride aqueous solution and was then dried over anhydrous magnesium sulfate. The solvent was distilled away under reduced pressure. Ethyl acetate was added to the obtained residue, and a solid was then collected by filtration, so as to obtain 590 mg of 4-(1,4-dioxaspiro[4.5]dec-7-en-8-yl)-1-ethyl-2-oxo-1,2-dihydroquinoline-6-carboxylic acid in the form of a light brown solid.

$^1$H-NMR (DMS O-D$_6$) δ: 1.21 (3H, t, J=7.0 Hz), 1.85 (2H, t, J=6.2 Hz), 2.39-2.56 (4H, m), 3.94-4.00 (4H, m), 4.29 (2H, q, J=7. Hz), 5.71-5.76 (1H, m), 6.41 (1H, s), 7.69 (1H, d, J=9.0 Hz), 8.11 (1H, dd, J=8.9, 2.1 Hz), 8.26 (1H, d, J=2.2 Hz), 13.02 (1H, brs).

Reference Example 31

[Formula 50]

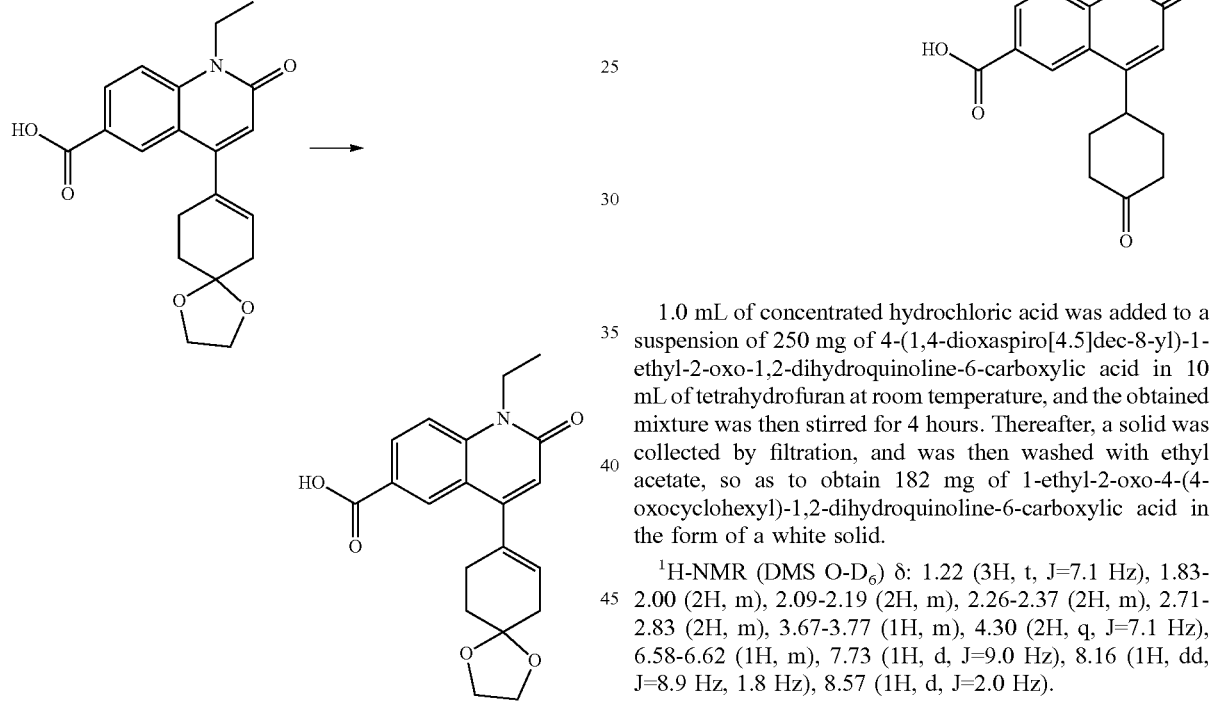

291 mg of 20% Palladium hydroxide-carbon was added to a mixture of 583 mg of 4-(1,4-dioxaspiro[4.5]dec-7-en-8-yl)-1-ethyl-2-oxo-1,2-dihydroquinoline-6-carboxylic acid, 20 mL of dioxane and 100 mL of methanol. The obtained mixture was stirred under a hydrogen atmosphere at room temperature for 30 minutes. Thereafter, insoluble matters were removed by filtration, and the solvent was then distilled away under reduced pressure. To the obtained residue, diisopropyl ether was added, and a solid was then collected by filtration, so as to obtain 502 mg of 4-(1,4-dioxaspiro[4.5]dec-8-yl)-1-ethyl-2-oxo-1,2-dihydroquinoline-6-carboxylic acid in the form of a white solid.

$^1$H-NMR (DMSO-D$_6$) δ: 1.22 (3H, t, J=7.0 Hz), 1.60-1.93 (8H, m), 3.10-3.25 (1H, m), 3.87-3.96 (4H, m), 4.29 (2H, q, J=6.9 Hz), 6.46-6.51 (1H, m), 7.66-7.73 (1H, m), 8.13 (1H, dd, J=8.7 Hz, 1.6 Hz), 8.45 (1H, d, J=1.5 Hz), 13.06 (1H, brs).

Reference Example 32

[Formula 51]

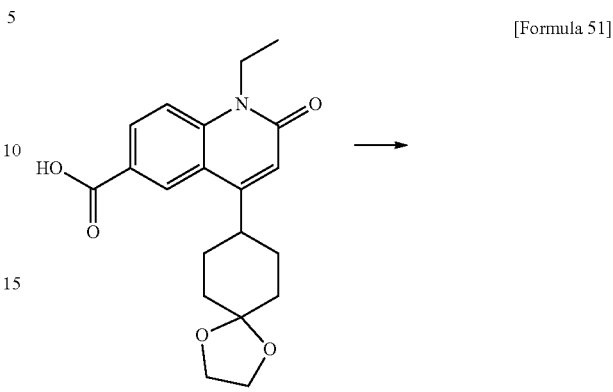

1.0 mL of concentrated hydrochloric acid was added to a suspension of 250 mg of 4-(1,4-dioxaspiro[4.5]dec-8-yl)-1-ethyl-2-oxo-1,2-dihydroquinoline-6-carboxylic acid in 10 mL of tetrahydrofuran at room temperature, and the obtained mixture was then stirred for 4 hours. Thereafter, a solid was collected by filtration, and was then washed with ethyl acetate, so as to obtain 182 mg of 1-ethyl-2-oxo-4-(4-oxocyclohexyl)-1,2-dihydroquinoline-6-carboxylic acid in the form of a white solid.

$^1$H-NMR (DMS O-D$_6$) δ: 1.22 (3H, t, J=7.1 Hz), 1.83-2.00 (2H, m), 2.09-2.19 (2H, m), 2.26-2.37 (2H, m), 2.71-2.83 (2H, m), 3.67-3.77 (1H, m), 4.30 (2H, q, J=7.1 Hz), 6.58-6.62 (1H, m), 7.73 (1H, d, J=9.0 Hz), 8.16 (1H, dd, J=8.9 Hz, 1.8 Hz), 8.57 (1H, d, J=2.0 Hz).

Example 1

[Formula 52]

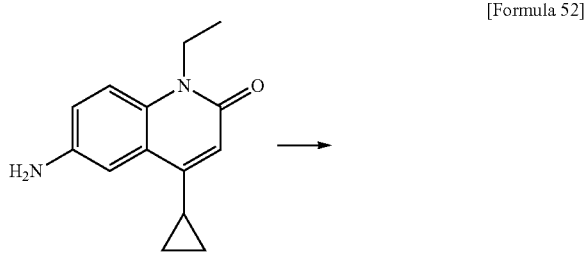

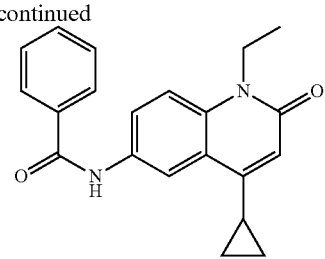

0.73 mL of Benzoyl chloride was added to a suspension of 1.2 g of 6-amino-4-cyclopropyl-1-ethylquinolin-2(1H)-one in 6 mL of pyridine, and the obtained mixture was then stirred at room temperature for 1 hour. Thereafter, to the reaction mixture, ethyl acetate and water were added, and the obtained mixture was then adjusted to pH 2.0 with 2 mol/L hydrochloric acid. An organic layer was separated, was then washed with water and a saturated sodium chloride aqueous solution and was then dried over anhydrous magnesium sulfate. The solvent was distilled away under reduced pressure. Diisopropyl ether and ethyl acetate were added to the obtained residue, and a solid was then collected by filtration, so as to obtain 1.75 g of N-(4-cyclopropyl-1-ethyl-2-oxo-1,2-dihydroquinolin-6-yl)benzamide in the form of a slightly brown solid.

$^1$H-NMR (DMS O-D$_6$) δ:0.75-0.84 (2H, m), 1.02-1.11 (2H, m), 1.20 (3H, t, J=6.9 Hz), 2.09-2.21 (1H, m), 4.26 (2H, q, J=7.1 Hz), 6.32 (1H, s), 7.44-7.66 (4H, m), 7.91-8.09 (3H, m), 8.65 (1H, d, J=2.0 Hz), 10.45 (1H, s).

Example 2

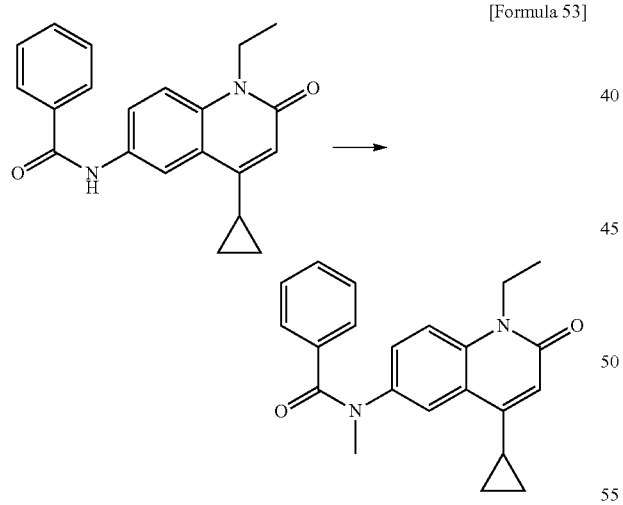

[Formula 53]

0.25 g of 60% Sodium hydride was added to a solution of 1.75 g of N-(4-cyclopropyl-1-ethyl-2-oxo-1,2-dihydroquinolin-6-yl)benzamide in 15 mL of N,N-dimethylacetamide under cooling on ice, and the obtained mixture was then stirred for 10 minutes. Thereafter, 0.43 mL of methyl iodide was added to the reaction mixture under cooling on ice, and the obtained mixture was then stirred at room temperature for 1 hour. Thereafter, ethyl acetate and water were added to the reaction mixture, the obtained mixture was then adjusted to pH 2.0 with 6 mol/L hydrochloric acid, and a solid was then collected by filtration. An organic layer in the filtrate was separated, was then washed with water and a saturated sodium chloride aqueous solution and was then dried over anhydrous magnesium sulfate. The solvent was distilled away under reduced pressure. Diisopropyl ether, ethyl acetate and water were added to the obtained residue and the filtrated solid, and thereafter, a solid was collected by filtration, and was then washed with water and diisopropyl ether, so as to obtain 1.45 g of N-(4-cyclopropyl-1-ethyl-2-oxo-1,2-dihydroquinolin-6-yl)-N-methylbenzamide in the form of a slightly brown solid.

$^1$H-NMR (DMSO-D$_6$) δ:0.48-0.57 (2H, m), 0.86-0.95 (2H, m), 1.13 (3H, t, J=6.9 Hz), 1.93-2.06 (1H, m), 3.44 (3H, s), 4.19 (2H, q, J=6.8 Hz), 6.24 (1H, s), 7.16-7.33 (5H, m), 7.46-7.58 (2H, m), 7.76-7.81 (1H, m).

Example 3

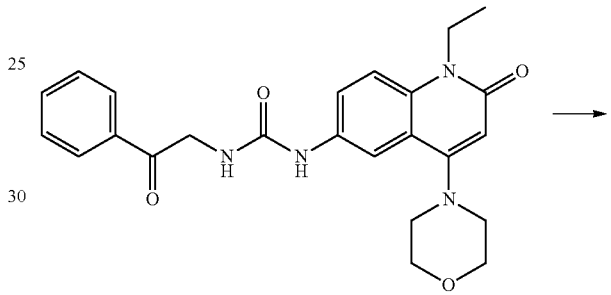

[Formula 54]

5.0 mL of Concentrated hydrochloric acid was added to a suspension of 0.86 g of 1-(1-ethyl-4-(morpholin-4-yl)-2-oxo-1,2-dihydroquinolin-6-yl)-3-(2-oxo-2-phenylethyl)urea in 5.0 mL of dioxane at room temperature, and the obtained mixture was then stirred for 2 hours. Thereafter, water was added to the reaction mixture, and a solid was collected by filtration, and was then washed with water and diisopropyl ether, so as to obtain 0.72 g of 1-ethyl-4-(morpholin-4-yl)-6-(2-oxo-5-phenyl-2,3-dihydro-1H-imidazol-1-yl)quinolin-2(1H)-one in the form of a slightly brown solid.

$^1$H-NMR (DMS O-D$_6$): 1.19 (3H, t, J=7.3 Hz), 2.54-2.65 (4H, m), 3.44-3.53 (4H, m), 4.17-4.29 (2H, m), 5.98 (1H, s), 6.87 (1H, d, J=2.6 Hz), 7.05-7.12 (2H, m), 7.14-7.31 (4H, m), 7.59-7.68 (2H, m), 10.57-10.63 (1H, m).

Example 4

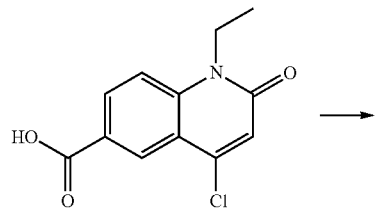

[Formula 55]

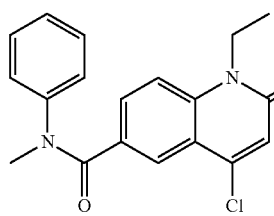

1.25 mL of Oxalyl chloride and 10 μL of N,N-dimethylformamide were added to a suspension of 3.0 g of 4-chloro-1-ethyl-2-oxo-1,2-dihydroquinoline-6-carboxylic acid in 30 mL of tetrahydrofuran at room temperature, and the obtained mixture was then stirred for 2 hours. Thereafter, 1.55 mL of N-methylaniline and 1.81 mL of triethylamine were added to the reaction mixture under cooling on ice, and the obtained mixture was then stirred at room temperature for 1 hour. Thereafter, to the reaction mixture, ethyl acetate and water were added. An organic layer was separated, was then washed with water and a saturated sodium chloride aqueous solution and was then dried over anhydrous magnesium sulfate. The solvent was distilled away under reduced pressure. The obtained residue was purified by silica gel column chromatography [gradient elution of hexane:ethyl acetate=50:50-20:80]. Diisopropyl ether and ethyl acetate were added to the obtained residue, and a solid was then collected by filtration, so as to obtain 2.01 g of 4-chloro-1-ethyl-N-methyl-2-oxo-N-phenyl-1,2-dihydroquinoline-6-carboxamide in the form of a slightly brown solid.

$^1$H-NMR (CDCl$_3$) δ: 1.28 (3H, t, J=6.9 Hz), 3.55 (3H, s), 4.26 (2H, q, J=7.3 Hz), 6.81 (1H, s), 7.07-7.13 (2H, m), 7.15-7.32 (4H, m), 7.65 (1H, dd, J=9.2, 2.0 Hz), 7.94 (1H, d, J=2.0 Hz).

Example 5

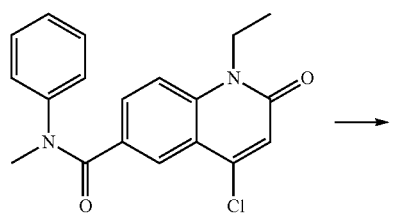

[Formula 56]

A mixture of 2.0 g of 4-chloro-1-ethyl-N-methyl-2-oxo-N-phenyl-1,2-dihydroquinoline-6-carboxamide, 2.18 g of tert-butyl 4-(4,4,5,5-tetramethyl-1,3,2-dioxaborolan-2-yl)-3,6-dihydropyridine-1(2H)-carboxylate, 1.24 g of sodium carbonate, 0.21 g of bis(di-tert-butyl(4-dimethylaminophenyl)phosphine)dichloropalladium(II), 20 mL of ethylene glycol dimethyl ether and 4.0 mL of water was heated to reflux under a nitrogen atmosphere for 3 hours. Thereafter, the reaction mixture was cooled to room temperature, and ethyl acetate and water were then added thereto. An organic layer was separated, was then successively washed with water and a saturated sodium chloride aqueous solution and was then dried over anhydrous magnesium sulfate. The solvent was distilled away under reduced pressure. The obtained residue was purified by silica gel chromatography [gradient elution of hexane:ethyl acetate=50:50-0:100], to obtain 2.9 g of tert-butyl 4-(1-ethyl-6-(methyl(phenyl)carbamoyl)-2-oxo-1,2-dihydroquinolin-4-yl)-3,6-dihydropyridine-1(2H)-carboxylate in the form of a slightly brown foam.

$^1$H-NMR (CDCl$_3$) δ:1.32 (3H, t, J=6.9 Hz), 1.56 (9H, s), 1.94-2.14 (2H, m), 3.53 (3H, s), 3.57 (2H, t, J=5.6 Hz), 3.99-4.06 (2H, m), 4.30 (2H, q, J=7.0 Hz), 5.42 (1H, brs), 6.41 (1H, s), 6.99-7.07 (2H, m), 7.10-7.19 (1H, m), 7.22-7.33 (3H, m), 7.35-7.41 (1H, m), 7.77 (1H, dd, J=9.2, 2.0 Hz).

Example 6

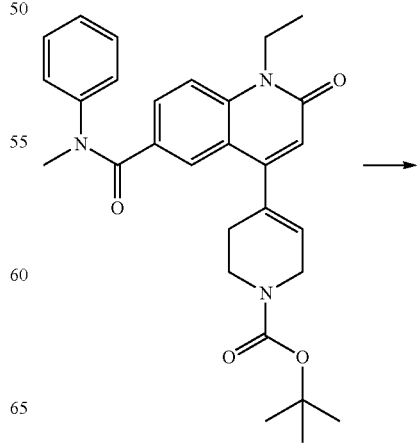

[Formula 57]

-continued

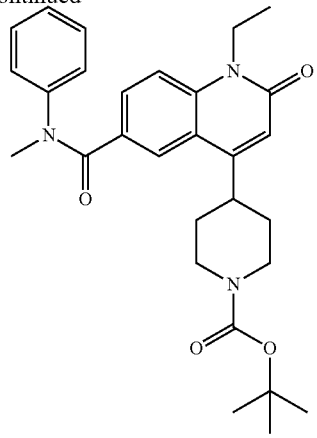

A mixture of 1.47 g of tert-butyl 4-(1-ethyl-6-(methyl (phenyl)carbamoyl)-2-oxo-1,2-dihydroquinolin-4-yl)-3,6-dihydropyridine-1(2H)-carboxylate, 0.44 g of 5% palladium-carbon, 0.29 g of ammonium formate and 15 mL of methanol was heated to reflux under a nitrogen atmosphere for 1 hour 30 minutes. Thereafter, the reaction mixture was cooled to room temperature, and insoluble matters were then removed by filtration. A filtrate cake was washed with ethyl acetate. The filtrate was gathered with the washing solution and the solvent was then distilled away under reduced pressure. To the obtained residue, 0.44 g of 5% palladium-carbon, 0.29 g of ammonium formate and 15 mL of methanol were added, and the obtained mixture was then heated to reflux under a nitrogen atmosphere for 2 hours. Thereafter, the reaction mixture was cooled to room temperature, and insoluble matters were then removed by filtration. A filtrate cake was washed with ethyl acetate. The filtrate was gathered with the washing solution and the solvent was then distilled away under reduced pressure. To the obtained residue, diisopropyl ether was added, and a solid was collected by filtration, and was then washed with diisopropyl ether, so as to obtain 1.26 g of tert-butyl 4-(1-ethyl-6-(methyl(phenyl)carbamoyl)-2-oxo-1,2-dihydroquinolin-4-yl)piperidine-1-carboxylate in the form of a white solid.

$^1$H-NMR (CDCl$_3$) δ: 1.31 (3H, t, J=7.3 Hz), 1.40-1.58 (4H, m), 1.50 (9H, s), 2.62-2.85 (3H, m), 3.56 (3H, s), 4.15-4.34 (4H, m), 6.49 (1H, s), 7.04-7.11 (2H, m), 7.12-7.20 (1H, m), 7.23-7.33 (3H, m), 7.61 (1H, d, J=2.0 Hz), 7.73 (1H, dd, J=8.6, 2.0 Hz).

Example 7

[Formula 58]

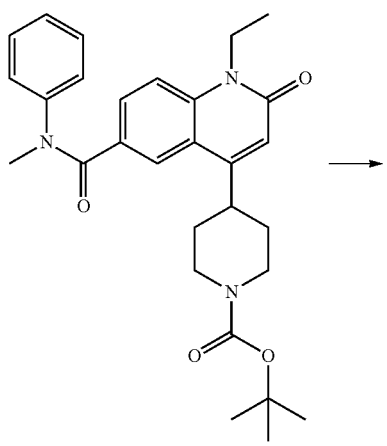

-continued

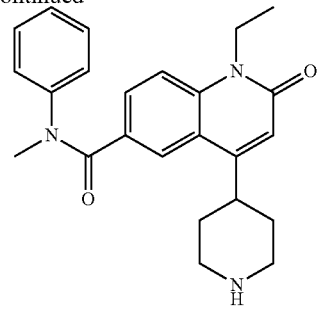

A mixture of 1.26 g of tert-butyl 4-(1-ethyl-6-(methyl (phenyl)carbamoyl)-2-oxo-1,2-dihydroquinolin-4-yl)piperidine-1-carboxylate in 5 mL of dichloromethane and 5 mL of trifluoroacetic acid was stirred at room temperature for 30 minutes, and thereafter, the solvent was distilled away under reduced pressure. To the obtained residue, ethyl acetate and a saturated sodium hydrogen carbonate aqueous solution were added, and an organic layer was separated. A water layer was extracted with ethyl acetate, and was further extracted with chloroform twice. The organic layer was gathered with the extract, and the obtained mixture was then dried over anhydrous magnesium sulfate. The solvent was distilled away under reduced pressure to obtain 1.0 g of 1-ethyl-N-methyl-2-oxo-N-phenyl-4-(piperidin-4-yl)-1,2-dihydroquinoline-6-carboxamide in the form of a white solid.

$^1$H-NMR (CDCl$_3$) δ: 1.31 (3H, t, J=7.3 Hz), 1.55-1.67 (4H, m), 2.67-2.90 (3H, m), 3.22-3.34 (2H, m), 3.56 (3H, s), 4.29 (2H, q, J=7.3 Hz), 6.55 (1H, s), 7.05-7.20 (3H, m), 7.22-7.32 (3H, m), 7.62 (1H, d, J=2.0 Hz), 7.71 (1H, dd, J=8.6, 2.0 Hz).

Example 8

[Formula 59]

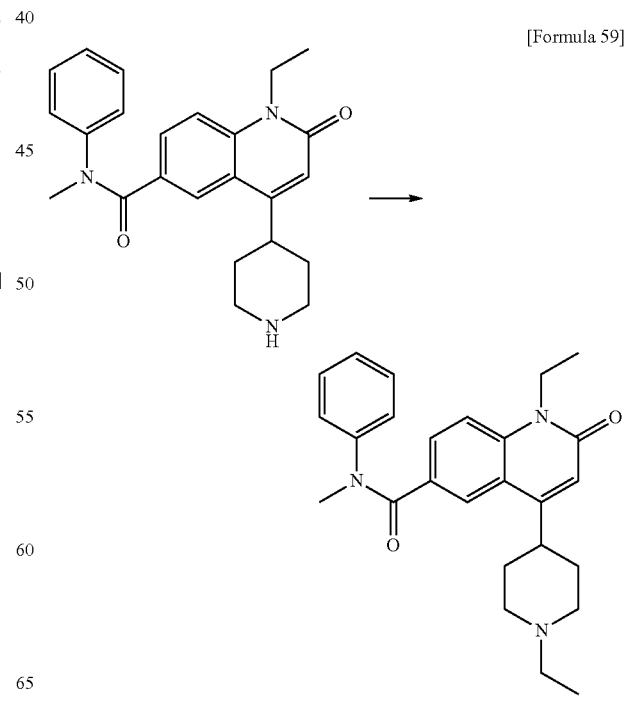

0.71 g of Potassium carbonate and 0.25 mL of ethyl iodide were added to a suspension of 1.0 g of 1-ethyl-N-methyl-2-oxo-N-phenyl-4-(piperidin-4-yl)-1,2-dihydroquinoline-6-carboxamide in acetone (15 mL) and tetrahydrofuran (8 mL), and thereafter, the obtained mixture was stirred at room temperature for 30 minutes, and was then stirred at an external temperature of 40° C. for 2 hours. Thereafter, 0.24 g of potassium carbonate and 82 µL of ethyl iodide were added to the reaction mixture, and the obtained mixture was then stirred at an external temperature of 40° C. for 1 hour. Thereafter, the solvent was distilled away under reduced pressure. To the obtained residue, ethyl acetate and water were added, and an organic layer was separated. The organic layer was washed with a saturated sodium chloride aqueous solution, and was then dried over anhydrous magnesium sulfate. The solvent was distilled away under reduced pressure. The obtained residue was purified by basic silica gel column chromatography [gradient elution of hexane:ethyl acetate=50:50-0:100]. To the obtained residue, diisopropyl ether was added, and a solid was then collected by filtration, so as to obtain 0.76 g of 1-ethyl-4-(1-ethylpiperidin-4-yl)-N-methyl-2-oxo-N-phenyl-1,2-dihydroquinoline-6-carboxamide in the form of a white solid.

$^1$H-NMR (DMSO-D$_6$): 1.05 (3H, t, J=7.3 Hz), 1.15 (3H, t, J=7.3 Hz), 1.31-1.52 (4H, m), 1.92-2.06 (2H, m), 2.40 (2H, q, J=7.0 Hz), 2.47-2.63 (1H, m), 2.86-2.98 (2H, m), 3.43 (3H, s), 4.20 (2H, q, J=7.0 Hz), 6.36 (1H, s), 7.10-7.32 (5H, m), 7.50-7.58 (2H, m), 7.73 (1H, dd, J=8.9, 1.7 Hz).

Example 9

[Formula 60]

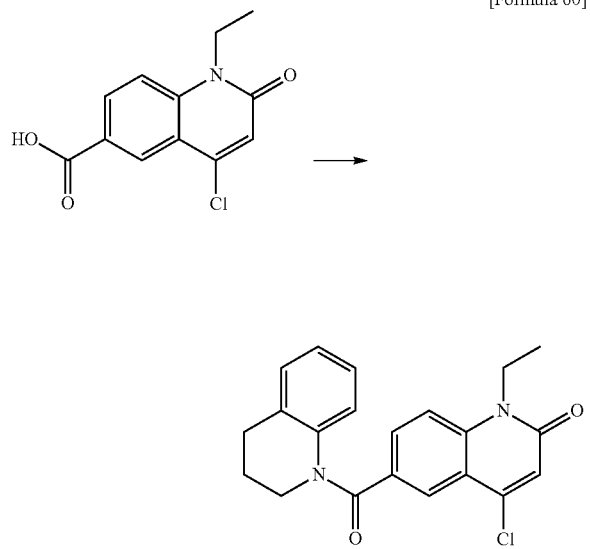

4-Chloro-6-(3,4-dihydroquinolin-1(2H)-ylcarbonyl)-1-ethylquinolin-2(1H)-one was obtained from 4-chloro-1-ethyl-2-oxo-1,2-dihydroquinoline-6-carboxylic acid by the same method as that of Example 4.

$^1$H-NMR (CDCl$_3$) δ: 1.31 (3H, t, J=7.2 Hz), 2.10 (2H, quint, J=6.6 Hz), 2.88 (2H, t, J=6.6 Hz), 3.96 (2H, t, J=6.7 Hz), 4.30 (2H, q, J=7.2 Hz), 6.65 (1H, d, J=7.8 Hz), 6.83-6.90 (2H, m), 7.00-7.06 (1H, m), 7.18-7.28 (2H, m), 7.56 (1H, dd, J=8.8, 2.0 Hz), 8.09 (1H, d, J=2.2 Hz).

Example 10

[Formula 61]

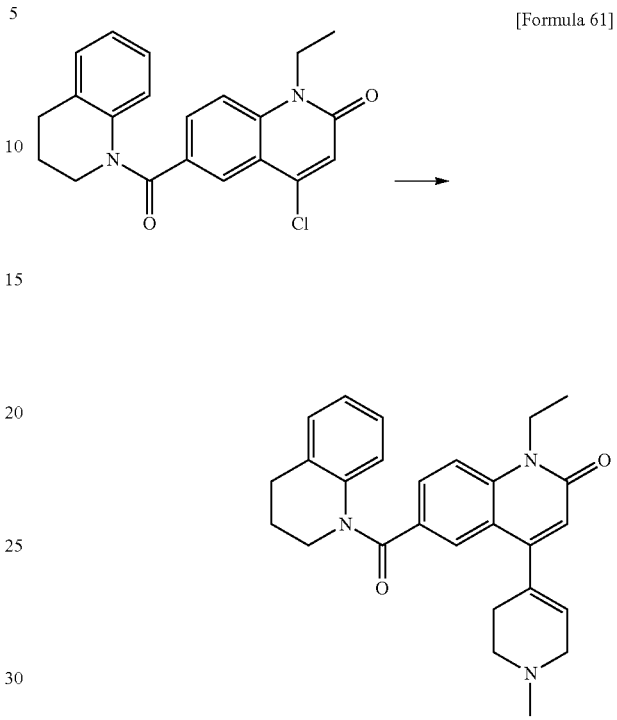

A mixture of 64 mg of 4-chloro-6-(3,4-dihydroquinolin-1(2H)-ylcarbonyl)-1-ethylquinolin-2(1H)-one, 47 mg of 1-methyl-4-(4,4,5,5-tetramethyl-1,3,2-dioxaborolan-2-yl)-1,2,3,6-tetrahydropyridine, 55 mg of sodium carbonate, 12.3 mg of bis(di-tert-butyl(4-dimethylaminophenyl)phosphine)dichloropalladium(II), 2 mL of ethylene glycol dimethyl ether and 0.2 mL of water was heated to reflux under a nitrogen atmosphere for 2 hours. Thereafter, the reaction mixture was cooled to room temperature, and ethyl acetate and water were then added thereto. An organic layer was separated, was then successively washed with water and a saturated sodium chloride aqueous solution and was then dried over anhydrous magnesium sulfate. The solvent was distilled away under reduced pressure. The obtained residue was purified by basic silica gel chromatography [gradient elution of hexane:ethyl acetate=50:50-0:100], to obtain 62 mg of 6-(3,4-dihydroquinolin-1 (2H)-ylcarbonyl)-1-ethyl-4-(1-methyl-1,2,3,6-tetrahydropyridin-4-yl)quinolin-2(1H)-one in the form of a slightly brown foam.

$^1$H-NMR (CDCl$_3$) δ:1.35 (3H, t, J=6.9 Hz), 2.05-2.18 (4H, m), 2.41 (3H, s), 2.45-2.55 (2H, m), 2.87 (2H, t, J=6.6 Hz), 2.94-3.02 (2H, m), 3.95 (2H, t, J=6.6 Hz), 4.33 (2H, q, J=7.1 Hz), 5.29-5.36 (1H, m), 6.47 (1H, s), 6.54 (1H, d, J=7.9 Hz), 6.80-6.89 (1H, m), 6.94-7.02 (1H, m), 7.18 (1H, d, J=7.3 Hz), 7.35 (1H, d, J=9.2 Hz), 7.49 (1H, d, J=2.0 Hz), 7.77 (1H, dd, J=8.6, 2.0 Hz).

Example 11

[Formula 62]

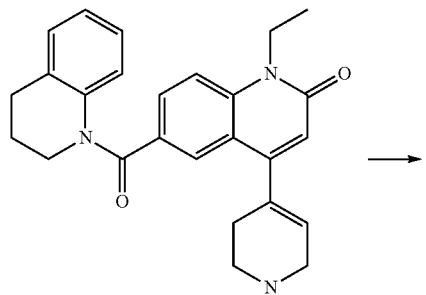

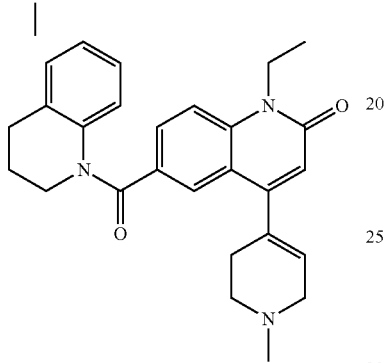

A mixture of 60 mg of 6-(3,4-dihydroquinolin-1 (2H)-ylcarbonyl)-1-ethyl-4-(1-methyl-1,2,3,6-tetrahydropyridin-4-yl)quinolin-2(1H)-one in methanol (15 mL) and ethyl acetate (15 mL) was subjected to a hydrogenation reaction (25° C., 1 bar, flow rate: 2 mL/min, 10% palladium-carbon), using a flow-type hydrogenation reactor. The solvent was distilled away under reduced pressure, and the obtained residue was then purified by basic silica gel column chromatography [gradient elution of hexane:ethyl acetate=50:50-0:100]. Diisopropyl ether and ethyl acetate were added to the obtained residue, and a solid was then collected by filtration, so as to obtain 10 mg of 6-(3,4-dihydroquinolin-1 (2H)-ylcarbonyl)-1-ethyl-4-(1-methylpiperidin-4-yl)quinolin-2(1H)-one in the form of a white solid.

$^1$H-NMR (DMS O-D$_6$) δ: 1.18 (3H, t, J=6.9 Hz), 1.24-1.52 (4H, m), 1.80-1.94 (2H, m), 1.95-2.10 (2H, m), 2.19 (3H, s), 2.50-2.65 (1H, m), 2.70-2.81 (2H, m), 2.87 (2H, t, J=6.3 Hz), 3.81 (2H, t, J=6.6 Hz), 4.24 (2H, q, J=6.8 Hz), 6.38 (1H, s), 6.58 (1H, d, J=7.9 Hz), 6.84 (1H, t, J=7.3 Hz), 6.96 (1H, t, J=7.3 Hz), 7.22 (1H, d, J=7.3 Hz), 7.50-7.55 (1H, m), 7.62 (1H, d, J=9.2 Hz), 7.73-7.81 (1H, m).

Example 12

[Formula 63]

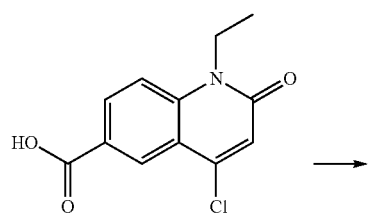

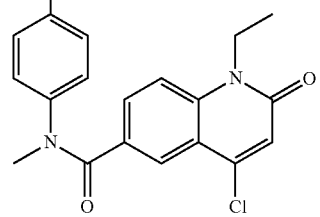

4-Chloro-1-ethyl-N-methyl-N-(4-methylphenyl)-2-oxo-1,2-dihydroquinoline-6-carboxamide was obtained from 4-chloro-1-ethyl-2-oxo-1,2-dihydroquinoline-6-carboxylic acid by the same method as that of Example 4.

$^1$H-NMR (CDCl$_3$) δ: 1.29 (3H, t, J=7.2 Hz), 2.29 (3H, s), 3.51 (3H, s), 4.26 (2H, q, J=7.1H z), 6.81 (1H, s), 6.98 (2H, d, J=8.3 Hz), 7.07 (2H, d, J=8.3 Hz), 7.20 (1H, d, J=8.8 Hz), 7.65 (1H, dd, J=8.8, 2.0 Hz), 7.94 (1H, d, J=2.0 Hz).

Example 13

[Formula 64]

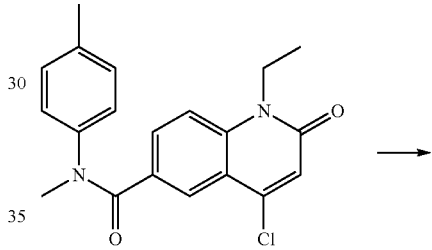

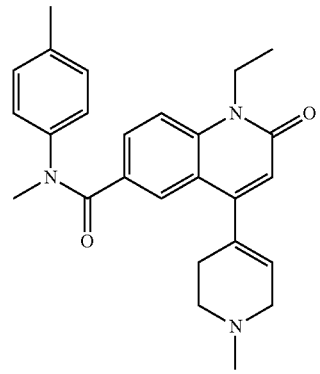

1-Ethyl-N-methyl-N-(4-methylphenyl)-4-(1-methyl-1,2,3,6-tetrahydropyridin-4-yl)-2-oxo-1,2-dihydroquinoline-6-carboxamide was obtained from 4-chloro-1-ethyl-N-methyl-N-(4-methylphenyl)-2-oxo-1,2-dihydroquinoline-6-carboxamide by the same method as that of Example 10.

$^1$H-NMR (CDCl$_3$) δ:1.31 (3H, t, J=7.2 Hz), 2.14-2.21 (2H, m), 2.26 (3H, s), 2.45 (3H, s), 2.61 (2H, t, J=5.6 Hz), 3.04-3.11 (2H, m), 3.50 (3H, s), 4.29 (2H, q, J=7.1 Hz), 5.36-5.42 (1H, m), 6.45 (2H, s), 6.92 (2H, d, J=8.3 Hz), 7.03 (2H, d, J=8.5 Hz), 7.27 (1H, d, J=8.8 Hz), 7.51 (1H, d, J=2.0 Hz), 7.69 (1H, dd, J=8.9, 2.1 Hz).

Example 14

[Formula 65]

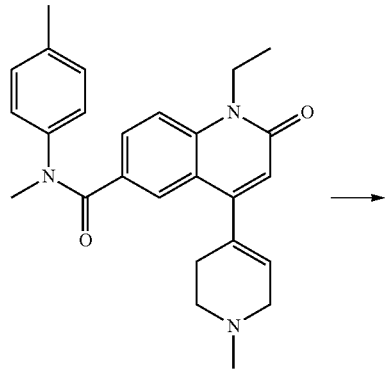

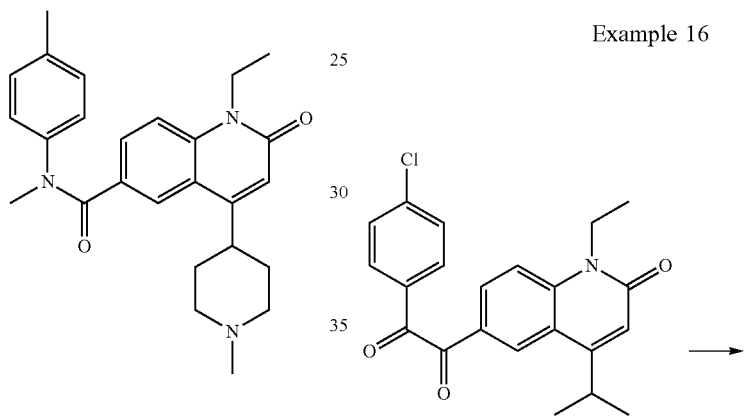

1-Ethyl-N-methyl-N-(4-methylphenyl)-4-(1-methylpiperidin-4-yl)-2-oxo-1,2-dihydroquinoline-6-carboxamide was obtained from 1-ethyl-N-methyl-N-(4-methylphenyl)-4-(1-methyl-1,2,3,6-tetrahydropyridin-4-yl)-2-oxo-1,2-dihydroquinoline-6-carboxamide by the same method as that of Reference Example 13.

$^1$H-NMR (CDCl$_3$) δ: 1.30 (3H, t, J=7.1 Hz), 1.50-1.71 (4H, m), 1.99-2.10 (2H, m), 2.26 (3 H, s), 2.36 (3H, s), 2.48-2.59 (1H, m), 2.91-3.00 (2H, m), 3.53 (3H, s), 4.28 (2H, q, J=7.2H z), 6.55 (1H, s), 6.96 (2H, d, J=8.3 Hz), 7.06 (2H, d, J=8.0 Hz), 7.25-7.30 (1H, m), 7.60 (1H, d, J=2.0 Hz), 7.71 (1H, dd, J=8.8, 2.0 Hz).

Example 15

[Formula 66]

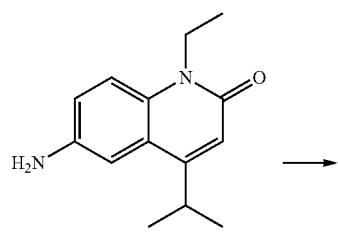

Example 16

[Formula 67]

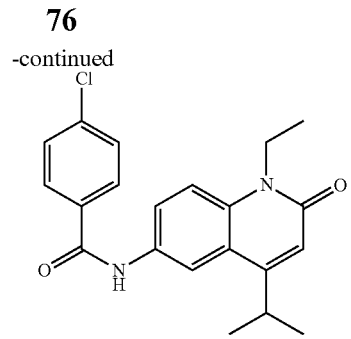

4-Chloro-N-(1-ethyl-2-oxo-4-(propan-2-yl)-1,2-dihydroquinolin-6-yl)benzamide was obtained from 6-amino-1-ethyl-4-(propan-2-yl)quinolin-2(1H)-one and 4-chlorobenzoyl chloride by the same method as that of Example 1.

$^1$H-NMR (CDCl$_3$) δ:1.34 (6H, d, J=6.6 Hz), 1.31-1.40 (3H, m), 3.34-3.47 (1H, m), 4.37 (2H, q, J=7.1 Hz), 6.67 (1H, s), 7.42 (1H, d, J=9.2 Hz), 7.48 (2H, d, J=8.3 Hz), 7.77 (1H, dd, J=9.2, 2.3 Hz), 7.91 (2H, d, J=8.3 Hz), 8.23 (1H, s), 8.33 (1H, d, J=2.3 Hz).

4-Chloro-N-(1-ethyl-2-oxo-4-(propan-2-yl)-1,2-dihydroquinolin-6-yl)-N-methylbenzamide was obtained from 4-chloro-N-(1-ethyl-2-oxo-4-(propan-2-yl)-1,2-dihydroquinolin-6-yl)benzamide by the same method as that of Example 2.

$^1$H-NMR (CDCl$_3$) δ: 1.12 (6H, d, J=6.8 Hz), 1.34 (3H, t, J=7.2 Hz), 3.01-3.14 (1H, m), 3.53 (3H, s), 4.31 (2H, q, J=7.2 Hz), 6.61 (1H, s), 7.12-7.19 (2H, m), 7.24-7.29 (2H, m), 7.31-7.37 (3H, m).

Example 17

[Formula 68]

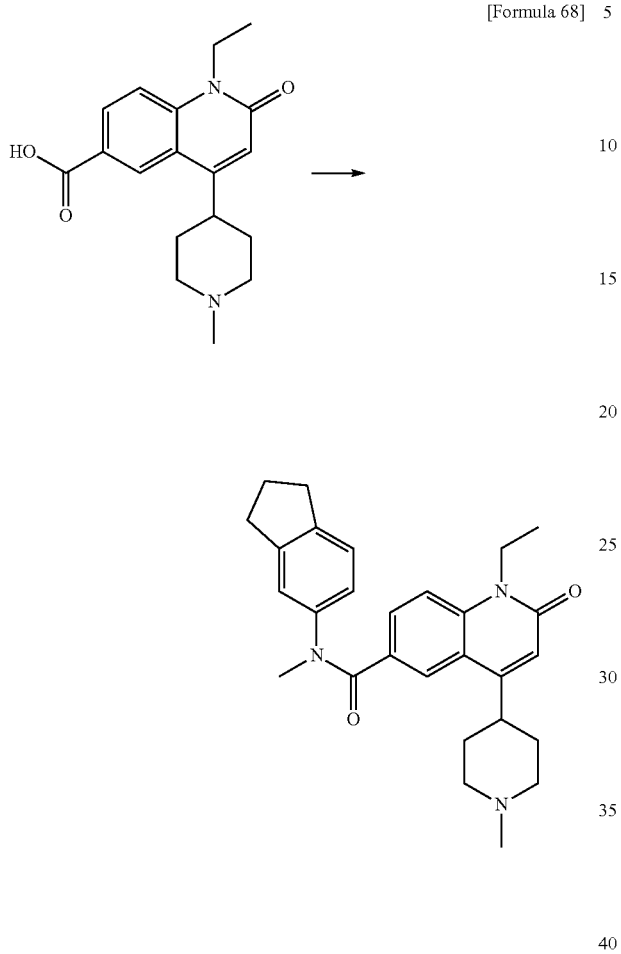

A mixture of 80 mg of 1-ethyl-4-(1-methylpiperidin-4-yl)-2-oxo-1,2-dihydroquinoline-6-carboxylic acid, 80 μL of N-methyl-2,3-dihydro-1H-inden-5-amine, 3 mL of dichloromethane, 90 mg of 1-ethyl-3-(3-dimethylaminopropyl)carbodiimide hydrochloride, 63 mg of 1-hydroxy-7-azabenzotriazole and 0.3 mL of triethylamine was stirred at an external temperature of 70° C. to 80° C. in a sealed tube for 3 hours. Thereafter, the reaction mixture was cooled to room temperature, and the solvent was then distilled away under reduced pressure. To the obtained residue, 1 mL of a 2 mol/L sodium hydroxide aqueous solution, 4 mL of tetrahydrofuran and 2 mL of methanol were added, and the obtained mixture was then stirred at an external temperature of 40° C. to 50° C. for 20 minutes. Thereafter, the solvent was distilled away under reduced pressure. To the reaction mixture, ethyl acetate and a saturated sodium chloride aqueous solution were added, and an organic layer was separated, and a water layer was then extracted with ethyl acetate. The organic layer was gathered with the extract, and the obtained mixture was then dried over anhydrous magnesium sulfate. The solvent was distilled away under reduced pressure. The obtained residue was purified by silica gel column chromatography [gradient elution of chloroform:methanol=100:0-80:20], to obtain 8 mg of N-(2,3-dihydro-1H-inden-5-yl)-1-ethyl-N-methyl-4-(1-methylpiperidin-4-yl)-2-oxo-1,2-dihydroquinoline-6-carboxamide in the form of a white solid.

$^1$H-NMR (DMSO-D$_6$) δ:1.15 (3H, t, J=7.0 Hz), 1.36-1.57 (4H, m), 1.89-2.06 (4H, m), 2.24 (3H, s), 2.69-2.89 (6H, m), 3.29-3.37 (1H, m), 3.39 (3H, s), 4.21 (2H, q, J=7.1 Hz), 6.38 (1H, s), 6.84-6.92 (1H, m), 7.07 (1H, d, J=8.0 Hz), 7.15 (1H, s), 7.52-7.61 (2H, m), 7.75 (1H, dd, J=8.9, 1.6 Hz).

Example 18

[Formula 69]

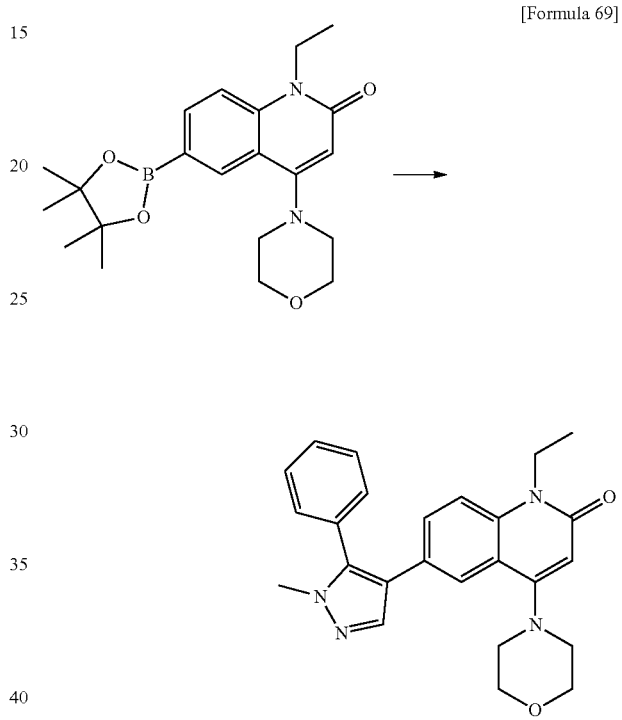

1-Ethyl-6-(1-methyl-5-phenyl-1H-pyrazol-4-yl)-4-(morpholin-4-yl)quinolin-2(1H)-one was obtained from 1-ethyl-4-(morpholin-4-yl)-6-(4,4,5,5-tetramethyl-1,3,2-dioxaborolan-2-yl)quinolin-2(1H)-one and 4-bromo-1-methyl-5-phenyl-1H-pyrazole by the same method as that of Reference Example 2.

$^1$H-NMR (DMSO-D$_6$) δ:1.17 (3H, t, J=6.9 Hz), 2.65-2.76 (4H, m), 3.42-3.53 (4H, m), 3.74 (3H, s), 4.21 (2H, q, J=6.8 Hz), 5.95 (1H, s), 7.35 (1H, d, J=2.0 Hz), 7.37-7.64 (7H, m), 7.81 (1H, s).

Examples 19 to 244

In accordance with the procedures described in the present description, the obtained compounds were subjected to a known reaction such as condensation, addition, oxidation, reduction, transposition, substitution, halogenation, dehydration or hydrolysis, or by combining these reactions with one another, as appropriate, so as to produce the compounds shown in Tables 1 to 25.

TABLE 1

| Example No. | Structural Formula | Compound Name | MS |
| --- | --- | --- | --- |
| 19 | | N-(1-ethyl-4-(1-methylpiperidin-4-yl)-2-oxo-1,2-dihydroquinolin-6-yl)-N-methylbenzamide | 404(M + H) |
| 20 | | N-(1-ethyl-4-(octahydroisoquinolin-2(1H)-yl)-2-oxo-1,2-dihyroquinolin-6-yl)-N-methylbenzamide | 444(M + H) |
| 21 | | N-(1-ethyl-4-(morpholin-4-yl)-2-oxo-1,2-dihydroquinolin-6-yl)-2-hydroxy-N-methylbenzamide | 408(M + H) |
| 22 | | N-(1-ethyl-4-(morpholin-4-yl)-2-oxo-1,2-dihydroquinolin-6-yl)-N-methyl-2-trifluoromethoxy)benzamide | 476(M + H) |
| 23 | | 2-cyano-N-(1-ethyl-4-(morpholin-4-yl)-2-oxo-1,2-dihydroquinolin-6-yl)-N-methylbenzamide | 417(M + H) |

TABLE 1-continued

| Example No. | Structural Formula | Compound Name | MS |
|---|---|---|---|
| 24 | | N-(1-ethyl-4-(morpholin-4-yl)-2-oxo-1,2-dihydroquinolin-6-yl)-N-methyl-4-propylbenzamide | 434(M + H) |
| 25 | | 3-ethoxy-N-(1-ethyl-4-(morpholin-4-yl)-2-oxo-1,2-dihydroquinolin-6-yl)-N-methylbenzamide | 436(M + H) |
| 26 | | N-(1-ethyl-4-(morpholin-4-yl)-2-oxo-1,2-dihydroquinolin-6-yl)-N-methyl-2-(trifluoromethyl)benzamide | 460(M + H) |
| 27 | | N-(1-ethyl-4-(morpholin-4-yl)-2-oxo-1,2-dihydroquinolin-6-yl)-2-fluoro-N-methylbenzamide | 410(M + H) |

TABLE 2

| Example No | Structural Formula | Compound Name | MS |
|---|---|---|---|
| 28 | | N-(4-((E)-2-cyclopropylvinyl)-1-ethyl-2-oxo-1,2-dihydroquinolin-6-yl)-N-methylbenzamide | 373(M + H) |

TABLE 2-continued

| Example No | Structural Formula | Compound Name | MS |
|---|---|---|---|
| 29 | | N-(1-ethyl-4-((1E)-4-hydroxybut-1-en-1-yl)-2-oxo-1,2-dihydroquinolin-6-yl)-N-methylbenzamide | 377(M + H) |
| 30 | | N-(4-butyl-1-ethyl)-2-oxo-1,2-dihydroquinolin-6-yl)-N-methylbenzamide | 363(M + H) |
| 31 | | 4-cyclopropyl-N-(1-ethyl-4-(morpholin-4-yl)-2-oxo-1,2-dihydroquinolin-6-yl)-N-methylbenzamide | 432(M + H) |
| 32 | | 4-((E)-2-cyclopropylvinyl)-N-(1-ethyl-4-(morpholin-4-yl)-2-oxo-1,2-dihydroquinolin-6-yl)-N-methylbenzamide | 458(M + H) |
| 33 | | N-(1-ethyl-4-(morpholin-4-yl)-2-oxo-1,2 dihydroquinolin-6-yl)-N-methyl-4-(1-methyl-1,2,3,6-tetrahydropyridin-4-yl)benzamide | 487(M + H) |
| 34 | | 4-cyclohex-1-en-1-yl)(1-ethyl-4-(morpholin-4-yl)-2-oxo-1,2-dihydroquinolin-6-yl)-N-methylbenzamide | 472(M + H) |

TABLE 2-continued

| Example No | Structural Formula | Compound Name | MS |
|---|---|---|---|
| 35 | | N-(4-(2-cyclopropylethyl)-1-ethyl-2-oxo-1,2-dihydroquinolin-6-yl)-N-methylbenzamide | 375(M + H) |
| 36 | | N-(1,4-diethyl)-2-oxo-1,2-dihydroquinolin-6-yl)-N-methylbenzamide | 335(M + H) |

TABLE 3

| Example No. | Structural Formula | Compound Name | MS |
|---|---|---|---|
| 37 | | N-(1-ethyl-4-(4-hydroxybutyl)-2-oxo-1,2-dihydroquinolin-6-yl)-N-methylbenzamide | 379 (M + H) |
| 38 | | 4-(2-cyclopropylethyl)-N-(1-ethyl-4-(morpholin-4-yl)-2-oxo-1,2-dihydroquinolin-6-yl)-N-methylbenzamide | 460 (M + H) |

TABLE 3-continued

| Example No. | Structural Formula | Compound Name | MS |
|---|---|---|---|
| 39 | | N-(1-ethyl-4-(morpholin-4-yl)-2-oxo-1,2-dihydroquinolin-6-yl)-N-methyl-4-(1-methylpiperidin-4-yl)benzamide | 489 (M + H) |
| 40 | | 4-cyclohexyl-N-(1-ethyl-4-(morpholin-4-yl)-2-oxo-1,2-(dihydroquinolin-6-y1)-N-methylbenazamide | 474 (M + H) |
| 41 | | N-(1-ethyl-4-(morpholin-4-yl)-2-oxo-1,2-dihydroquinolin-6-yl)-4-((1E)-4-hydroxybut-1-en-1-yl)-N-methylbenzamide | 462 (M + H) |
| 42 | | N-(1-ethyl-4-(4-morpholin-4-yl)-2-oxo-1,2-dihydroquinolin-6-yl)-N-methyl-4-sulfamoylbenzamide | 471 (M + H) |
| 43 | | N-(1-ethyl-4-(morpholin-4-yl)-2-oxo-1,2-dihydroquinolin-6-yl)-N-methyl-4-(methylsulfonyl)benzamide | 470 (M + H) |

TABLE 3-continued

| Example No. | Structural Formula | Compound Name | MS |
|---|---|---|---|
| 44 | | 4-(dimethylamino)-N-(1-ethyl-4-(morpholin-4-yl)-2-oxo-1,2-dihydroquinolin-6-yl)-N-methylbenzamide | 435 (M + H) |
| 45 | | 4-ethyl-N-(1-ethyl-4-(morpholin-4-yl)-2-oxo-1,2-dihydroquinolin-6-yl)-N-methylbenzamide | 420 (M + H) |

TABLE 4

| Example No. | Structural Formula | Compound Name | MS |
|---|---|---|---|
| 46 | | N-(1-ethyl-4-(morpholin-4-yl)-2-oxo-1,2-dihydroquinolin-6-yl)-N-methyl-4-(propan-2-yl)benzamide | 434 (M + H) |
| 47 | | 2-amino-N-(4-cyclopropyl-1-ethyl-2-oxo-1,2-dihydroquinolin-6-yl)-N-methyl-4-(trifluoromethyl)benzamide | 430 (M + H) |
| 48 | | 2-amino-N-(4-cyclopropyl-1-ethyl-2-oxo-1,2-dihydroquinolin-6-yl)-4-fluoro-N-methylbenzamide | 380 (M + H) |

TABLE 4-continued

| Example No. | Structural Formula | Compound Name | MS |
|---|---|---|---|
| 49 | 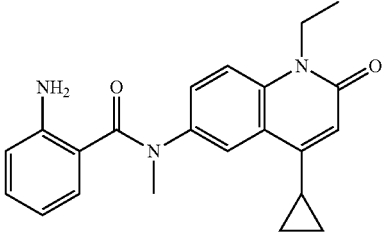 [SMILES: CCn1c(=O)cc(C2CC2)c2cc(N(C)C(=O)c3ccccc3N)ccc21] | 2-amino-N-(4-cyclopropyl-1-ethyl-2-oxo-1,2-dihydroquinolin-6-yl)-N-methylbenzamide | 362 (M + H) |
| 50 | 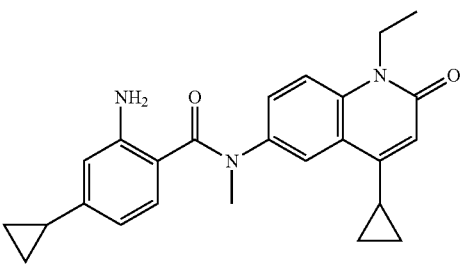 [SMILES: CCn1c(=O)cc(C2CC2)c2cc(N(C)C(=O)c3ccc(C4CC4)cc3N)ccc21] | 2-amino-4-cyclopropyl-N-(4-cyclopropyl-1-ethyl-2-oxo-1,2-dihydroquinolin-6-yl)-N-methylbenzamide | 402 (M + H) |
| 51 | 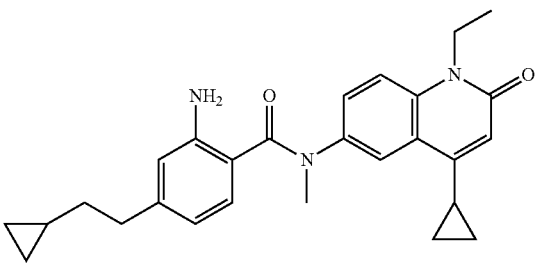 [SMILES: CCn1c(=O)cc(C2CC2)c2cc(N(C)C(=O)c3ccc(CCC4CC4)cc3N)ccc21] | 2-amino-4-(2-cyclopropylethyl)-N-(4-cyclopropyl-1-ethyl-2-oxo-1,2-dihydroquinolin-6-yl)-N-methylbenzamide | 430 (M + H) |
| 52 | 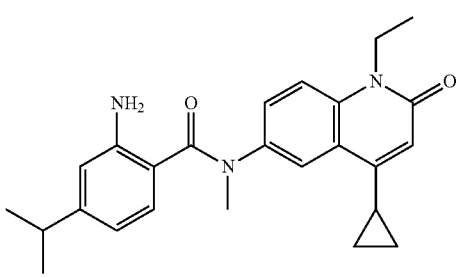 [SMILES: CCn1c(=O)cc(C2CC2)c2cc(N(C)C(=O)c3ccc(C(C)C)cc3N)ccc21] | 2-amino-N-(4-cyclopropyl-1-ethyl-2-oxo-1,2-dihydroquinolin-6-yl)-N-methyl-4-(propan-2-yl)benzamide | 404 (M + H) |
| 53 | 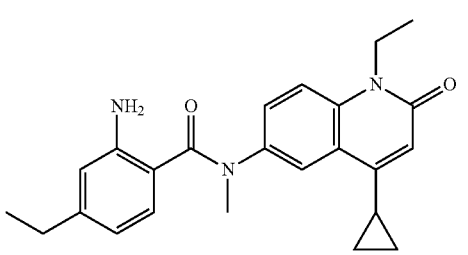 [SMILES: CCc1ccc(C(=O)N(C)c2ccc3c(c2)c(C2CC2)cc(=O)n3CC)c(N)c1] | 2-amino-N-(4-cyclopropyl-1-ethyl-2-oxo-1,2-dihydroquinolin-6-yl)-4-ethyl-N-methylbenzamide | 390 (M + H) |
| 54 | 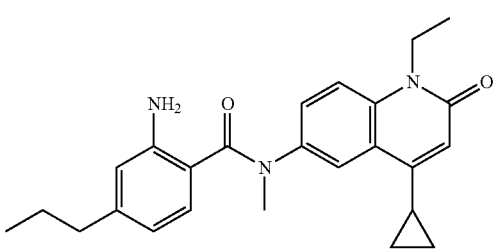 [SMILES: CCCc1ccc(C(=O)N(C)c2ccc3c(c2)c(C2CC2)cc(=O)n3CC)c(N)c1] | 2-amino-N-(4-cyclopropyl-1-ethyl-2-oxo-1,2-dihydroquinolin-6-yl)-N-methyl-4-propylbenzamide | 404 (M + H) |

TABLE 4-continued

| Example No. | Structural Formula | Compound Name | MS |
|---|---|---|---|
| 55 | | N-(1-ethyl-2-oxo-4-(propan-2-yl)-1,2-dihydroquinolin-6-yl)-N-methylbenzamide | 349 (M + H) |

TABLE 5

| Example No. | Structural Formula | Compound Name | MS |
|---|---|---|---|
| 56 | | N-(4-cyclopropyl-1-ethyl-2-oxo-1,2-dihydroquinolin-6-yl)-N-methyl-4-propylbenzamide | 389 (M + H) |
| 57 | | N-(4-cyclopropyl-1-ethyl-2-oxo-1,2-dihydroquinolin-6-yl)-N-methyl-4-(propan-2-yl)benzamide | 389 (M + H) |
| 58 | | N-(4-cyclopropyl-1-ethyl-2-oxo-1,2-dihydroquinolin-6-yl)-N-ethyl-N-methylbenzamide | 375 (M + H) |
| 59 | | 4-(2-cyclopropylethyl)-N-(4-cyclopropyl-1-ethyl-2-oxo-1,2-dihydroquinolin-6-yl)-N-methylbenzamide | 415 (M + H) |

TABLE 5-continued

| Example No. | Structural Formula | Compound Name | MS |
|---|---|---|---|
| 60 | | 4-cyclopropyl-N-(4-cyclopropyl-1-ethyl-2-oxo-1,2-dihydroquinolin-6-yl)-N-methylbenzamide | 387 (M + H) |
| 61 | | N-(4-cyclopropyl-1-ethyl-2-oxo-1,2-dihydroquinolin-6-yl)-4-fluoro-N-methylbenzamide | 365 (M + H) |
| 62 | | 2-amino-N-(1-ethyl-2-oxo-4-(propan-2-yl)-1,2-dihydroquinolin-6-yl)-N-methylbenzamide | 382 (M + H) |
| 63 | | 2-amino-4-cyclopropyl-N-(1-ethyl-2-oxo-4-(propan-2-yl)-1,2-dihydroquinolin-6-yl)-N-methylbenzamide | 404 (M + H) |
| 64 | | 2-amino-N-(1-ethyl-2-oxo-4-(propan-2-yl)-1,2-dihydroquinolin-6-yl)-N-methylbenzamide | 364 (M + H) |
| 65 | | 2-amino-N-(1-ethyl-2-oxo-4-(propan-2-yl)-1,2-dihydroquinolin-6-yl)-N-methyl-4-(trifluoromethyl)benzamide | 432 (M + H) |

TABLE 6

| Example No. | Structural Formula | Compound Name | MS |
|---|---|---|---|
| 66 | | 2-amino-N-(1-ethyl-2-oxo-4-(propan-2-yl)-1,2-dihydroquinolin-6-yl)-N-methyl-4-(propan-2-yl)benzamide | 406 (M + H) |
| 67 | | 2-amino-4-ethyl-N-(1-ethyl-2-oxo-4-(propan-2-yl)-1,2-dihydroquinolin-6-yl)-N-methylbenzamide | 392 (M + H) |
| 68 | | 2-amino-N-(1-ethyl-2-oxo-4-(propan-2-yl)-1,2-dihydroquinolin-6-yl)-N-methyl-4-propylbenzamide | 406 (M + H) |
| 69 | | N-(4-cyclopropyl-1-ethyl-2-oxo-1,2-dihydroquinolin-6-yl)-4-(dimethylamino)-N-methylbenzamide | 390 (M + H) |
| 70 | | N-(4-cyclopropyl-1-ethyl-2-oxo-1,2-dihydroquinolin-6-yl)-4-(ethylamino)-N-methylbenzamide | 390 (M + H) |
| 71 | | N-(4-cyclopropyl-1-ethyl-2-oxo-1,2-dihydroquinolin-6-yl)-N-methyl-4-(phenylamino)benzamide | 438 (M + H) |

TABLE 6-continued

| Example No. | Structural Formula | Compound Name | MS |
|---|---|---|---|
| 72 | | N-(4-cyclopropyl-1-ethyl-2-oxo-1,2-dihydroquinolin-6-yl)-N-methyl-4-(methyl(propyl)amino)benzamide | 418 (M + H) |
| 73 | | N-(4-cyclopropyl-1-ethyl-2-oxo-1,2-dihydroquinolin-6-yl)-N-methyl-4-(piperidin-1-yl)benzamide | 430 (M + H) |
| 74 | | 2-amino-N-(1-ethyl-4-methyl-2-oxo-1,2-dihydroquinolin-6-yl)-4-fluoro-N-methylbenzamide | 354 (M + H) |
| 75 | | N-(4-(butan-2-yl)-1-ethyl-2-oxo-1,2-dihydroquinolin-6-yl)-N-methylbenzamide | 363 (M + H) |

TABLE 7

| Example No. | Structural Formula | Compound Name | MS |
|---|---|---|---|
| 76 | | N-(4-cyclopropyl-1-ethyl-2-oxo-1,2-dihydroquinolin-6-yl)-N,2-dimethylbenzamide | 361 (M + H) |

TABLE 7-continued

| Example No. | Structural Formula | Compound Name | MS |
|---|---|---|---|
| 77 | | N-(4-cyclopropyl-1-ethyl-2-oxo-1,2-dihydroquinolin-6-yl)-N,3-dimethylbenzamide | 361 (M + H) |
| 78 | | N-(4-cyclopropyl-1-ethyl-2-oxo-1,2-dihydroquinolin-6-yl)-N,4-dimethylbenzamide | 361 (M + H) |
| 79 | | N-(4-cyclopropyl-1-ethyl-2-oxo-1,2-dihydroquinolin-6-yl)-2-methoxy-N-methylbenzamide | 377 (M + H) |
| 80 | | N-(4-cyclopropyl-1-ethyl-2-oxo-1,2-dihydroquinolin-6-yl)-3-methoxy-N-methylbenzamide | 377 (M + H) |
| 81 | | N-(4-cyclopropyl-1-ethyl-2-oxo-1,2-dihydroquinolin-6-yl)-4-(diethylamino)-N-methylbenzamide | 418 (M + H) |
| 82 | | 4-tert-butyl-N-(4-cyclopropyl-1-ethyl-2-oxo-1,2-dihydroquinolin-6-yl)-2-hydroxy-N-methylbenzamide | 403 (M + H) |

TABLE 7-continued

| Example No. | Structural Formula | Compound Name | MS |
|---|---|---|---|
| 83 | | N-(4-cyclopropyl-1-ethyl-2-oxo-1,2-dihydroquinolin-6-yl)-2-hydroxy-N-methylbenzamide | 363 (M + H) |
| 84 | | N-(4-cyclopropyl-1-ethyl-2-oxo-1,2-dihydroquinolin-6-yl)-3-hydroxy-N-methylbenzamide | 363 (M + H) |
| 85 | | 3-amino-N-(4-cyclopropyl-1-ethyl-2-oxo-1,2-dihydroquinolin-6-yl)-N-methylbenzamide | 362 (M + H) |

TABLE 8

| Example No. | Structural Formula | Compound Name | MS |
|---|---|---|---|
| 86 | | 4-amino-N-(4-cyclopropyl-1-ethyl-2-oxo-1,2-dihydroquinolin-6-yl)-N-methylbenzamide | 362 (M + H) |
| 87 | | N-(4-cyclopropyl-1-ethyl-2-oxo-1,2-dihydroquinolin-6-yl)-3-(dimethylamino)-N-methylbenzamide | 390 (M + H) |

TABLE 8-continued

| Example No. | Structural Formula | Compound Name | MS |
|---|---|---|---|
| 88 | | 4-(acetylamino)-N-(4-cyclopropyl-1-ethyl-2-oxo-1,2-dihydroquinolin-6-yl)-N-methylbenzamide | 404 (M + H) |
| 89 | | 3-(acetylamino)-N-(4-cyclopropyl-1-ethyl-2-oxo-1,2-dihydroquinolin-6-yl)-N-methylbenzamide | 404 (M + H) |
| 90 | | 2-(acetylamino)-N-(4-cyclopropyl-1-ethyl-2-oxo-1,2-dihydroquinolin-6-yl)-N-methylbenzamide | 404 (M + H) |
| 91 | | N-(4-cyclopropyl-1-ethyl-2-oxo-1,2-dihydroquinolin-6-yl)-N-methyl-4-((methylsulfonyl)amino)benzamide | 440 (M + H) |
| 92 | | N-(4-cyclopropyl-1-ethyl-2-oxo-1,2-dihydroquinolin-6-yl)-N-methyl-3-((methylsulfonyl)amino)benzamide | 440 (M + H) |
| 93 | | N-(4-cyclopropyl-1-ethyl-2-oxo-1,2-dihydroquinolin-6-yl)-N-methyl-2-((methylsulfonyl)amino)benzamide | 440 (M + H) |

TABLE 8-continued

| Example No. | Structural Formula | Compound Name | MS |
|---|---|---|---|
| 94 | | 2-amino-N-(4-cyclopropyl-1-ethyl-2-oxo-1,2-dihydroquinolin-6-yl)-N,4-methylbenzamide | 376 (M + H) |
| 95 | | N-(4-cyclopropyl-1-ethyl-2-oxo-1,2-dihydroquinolin-6-yl)-N-methyl-2-(methylamino)benzamide | 376 (M + H) |
| 96 | | N-(4-cyclopropyl-1-ethyl-2-oxo-1,2-dihydroquinolin-6-yl)-2-(dimethylamino)-N-methylbenzamide | 390 (M + H) |

TABLE 9

| Example No. | Structural Formula | Compound Name | MS |
|---|---|---|---|
| 97 | | N-(1-ethyl-4-(1-(2-hydroxyethyl)piperidin-4-yl)-2-oxo-1,2-dihydroquinolin-6-yl)-N-methylbenzamide | 434 (M + H) |

TABLE 9-continued

| Example No. | Structural Formula | Compound Name | MS |
|---|---|---|---|
| 98 | | N-(1-ethyl-4-(1-(2-methoxyethyl)piperidin-4-yl)-2-oxo-1,2-dihydroquinolin-6-yl)-N-methylbenzamide | 448 (M + H) |
| 99 | | 3-chloro-N-(1-ethyl-4-piperidin-4-yl)-2-oxo-1,2-dihydroquinolin-6-yl)-N-methylbenzamide | 425 (M + H) |
| 100 | | N-(1-ethyl-2-oxo-4-(1-(2,2,2-trifluoroethyl)piperidin-4-yl)-1,2-dihydroquinolin-6-yl)-N,4-dimethylbenzamide | 486 (M + H) |
| 101 | | 3-chloro-N-(1-ethyl-2-oxo-4-(1-(2,2,2-trifluoroethyl)piperidin-4-yl)-1,2-dihydroquinolin-6-yl)-N-methylbenzamide | 507 (M + H) |

TABLE 9-continued

| Example No. | Structural Formula | Compound Name | MS |
|---|---|---|---|
| 102 | | 3-chloro-N-(4-(1-(cyanomethyl)piperidin-4-yl)-1-ethyl-2-oxo-1,2-dihydroquinolin-6-yl)-N-methylbenzamide | 464 (M + H) |
| 103 | | N-(1-ethyl-2-oxo-4-(4-oxocyclohexyl)-1,2-dihydroquinolin-6-yl)-N-methylbenzamide | 401 (M + H) |

TABLE 10

| Example No. | Structural Formula | Compound Name | MS |
|---|---|---|---|
| 104 | | N-(4-(1-(cyanomethyl)piperidin-4-yl)-1-ethyl)-2-oxo-1,2-dihydroquinolin-6-yl)-N-methylbenzamide | 429 (M + H) |
| 105 | | N-(1-ethyl-2-oxo-4-(propan-2-yl)-1,2-dihydroquinolin-6-yl)-2-hydroxy-N,4-dimethylbenzamide | 377 (M + H) |

TABLE 10-continued

| Example No. | Structural Formula | Compound Name | MS |
|---|---|---|---|
| 106 | | 3-chloro-N-(1-ethyl-2-oxo-4-(propan-2-yl)-1,2-dihydroquinolin-6-yl)-N-methylbenzamide | 384 (M + H) |
| 107 | | N-(1-ethyl-2-oxo-4-(propan-2-yl)-1,2-dihydroquinolin-6-yl)-2-hydroxy-N,5-dimethylbenzamide | 377 (M + H) |
| 108 | | 2-(acetylamino)-N-(1-ethyl-2-oxo-4-(propan-2-yl)-1,2-dihydroquinolin-6-yl)-N,4-dimethylbenzamide | 418 (M + H) |
| 109 | | 2-(acetylamino)-N-(1-ethyl-2-oxo-4-(propan-2-yl)-1,2-dihydroquinolin-6-yl)-4-fluoro-N-methylbenzamide | 422 (M + H) |
| 110 | | 4-chloro-N-(1-ethyl-4-(1-methylpiperidin-4-yl)-2-oxo-1,2-dihydroquinolin-6-yl)-N-methylbenzamide | 439 (M + H) |
| 111 | | 2-amino-4-chloro-N-(1-ethyl-2-oxo-4-(propan-2-yl)-1,2-dihydroquinolin-6-yl)-N-methylbenzamide | 399 (M + H) |

TABLE 10-continued

| Example No. | Structural Formula | Compound Name | MS |
|---|---|---|---|
| 112 | | 3-amino-4-chloro-N-(1-ethyl-2-oxo-4-(propan-2-yl)-1,2-dihydroquinolin-6-yl)-N-methylbenzamide | 399 (M + H) |
| 113 | | 4-amino-4-chloro-N-(1-ethyl-2-oxo-4-(propan-2-yl)-1,2-dihydroquinolin-6-yl)-N-methylbenzamide | 380 (M + H) |

TABLE 11

| Example No. | Structural Formula | Compound Name | MS |
|---|---|---|---|
| 114 | | 4-chloro-N-(1-ethyl-2-oxo-4-(propan-2-yl)-1,2-dihydroquinolin-6-yl)-2-methoxy-N-methylbenzamide | 414 (M + H) |
| 115 | | 4-chloro-N-(1-ethyl-2-oxo-4-(propan-2-yl)-1,2-dihydroquinolin-6-yl)-3-methoxy-N-methylbenzamide | 414 (M + H) |
| 116 | | 4-chloro-N-(1-ethyl-2-oxo-4-(propan-2-yl)-1,2-dihydroquinolin-6-yl)-3-(3-hydroxypropoxy)-N-methylbenzamide | 458 (M + H) |

TABLE 11-continued

| Example No. | Structural Formula | Compound Name | MS |
| --- | --- | --- | --- |
| 117 | | 4-chloro-3-(3-(dimethylamino)propoxy)-N-(1-ethyl-2-oxo-4-(propan-2-yl)-1,2-dihydroquinolin-6-yl)-N-methylbenzamide | 484 (M + H) |
| 118 | | 4-chloro-N-(1-ethyl-2-oxo-4-(propan-2-yl)-1,2-dihydroquinolin-6-yl)-2-(3-hydroxypropoxy)-N-methylbenzamide | 458 (M + H) |
| 119 | | 4-chloro-N-(1-ethyl-2-oxo-4-(propan-2-yl)-1,2-dihydroquinolin-6-yl)-2-((2-hydroxyethyl)amino)-N-methylbenzamide | 443 (M + H) |
| 120 | | 4-chloro-2-((2-(dimethylamino)ethyl)amino)-N-(1-ethyl-2-oxo-4-(propan-2-yl)-1,2-dihydroquinolin-6-yl)-N-methylbenzamide | 469 (M + H) |
| 121 | | N-(1-ethyl-4-methyl-2-oxo-1,2-dihydroquinolin-6-yl)-N-methylthiophene-2-carboxamide | 327 (M + H) |
| 122 | | N-(1-ethyl-4-methyl-2-oxo-1,2-dihydroquinolin-6-yl)-N-methylthiophene-3-carboxamide | 327 (M + H) |

TABLE 11-continued

| Example No. | Structural Formula | Compound Name | MS |
|---|---|---|---|
| 123 | | N-(1-ethyl-4-methyl-2-oxo-1,2-dihydroquinolin-6-yl)-N-methyl-1H-pyrrole-2-carboxamide | 310 (M + H) |

TABLE 12

| Example No. | Structural Formula | Compound Name | MS |
|---|---|---|---|
| 124 | | N-(1-ethyl-4-(morpholin-4-yl)-2-oxo-1,2-dihydroquinolin-6-yl)-N-methylnaphthalene-2-carboxamide | 442 (M + H) |
| 125 | | N-(1-ethyl-4-(morpholin-4-yl)-2-oxo-1,2-dihydroquinolin-6-yl)-N-methylnaphthalene-1-carboxamide | 442 (M + H) |
| 126 | | 4-tert-butyl-N-(1-ethyl-4-(morpholin-4-yl)-2-oxo-1,2-dihydroquinolin-6-yl)-N-methylbenzamide | 448 (M + H) |

TABLE 12-continued

| Example No. | Structural Formula | Compound Name | MS |
|---|---|---|---|
| 127 | | N-(1-ethyl-4-(morpholin-4-yl)-2-oxo-1,2-dihydroquinolin-6-yl)-4-methoxy-N-methylbenzamide | 422 (M + H) |
| 128 | | N-(1-ethyl-4-(morpholin-4-yl)-2-oxo-1,2-dihydroquinolin-6-yl)-N-methylbiphenyl-4-carboxamide | 468 (M + H) |
| 129 | | 4-cyano-N-(1-ethyl-4-(morpholin-4-yl)-2-oxo-1,2-dihydroquinolin-6-yl)-N-methylbenzamide | 417 (M + H) |
| 130 | | N-(1-ethyl-4-(morpholin-4-yl)-2-oxo-1,2-dihydroquinolin-6-yl)-3-fluoro-N-methylbenzamide | 410 (M + H) |
| 131 | | 3-cyano-N-(1-ethyl-4-(morpholin-4-yl)-2-oxo-1,2-dihydroquinolin-6-yl)-N-methylbenzamide | 417 (M + H) |

TABLE 12-continued

| Example No. | Structural Formula | Compound Name | MS |
|---|---|---|---|
| 132 | | N-(1-ethyl-4-(morpholin-4-yl)-2-oxo-1,2-dihydroquinolin-6-yl)-N-methyl-3-(trifluoromethyl)benzamide | 460 (M + H) |

TABLE 13

| Example No. | Structural Formula | Compound Name | MS |
|---|---|---|---|
| 133 | | N-(1-ethyl-4-(morpholin-4-yl)-2-oxo-1,2-dihydroquinolin-6-yl)-3-methoxy-N-methylbenzamide | 442 (M + H) |
| 134 | | 3-(dimethylamino)-N-(1-ethyl-4-(morpholin-4-yl)-2-oxo-1,2-dihydroquinolin-6-yl)-N-methylbenzamide | 435 (M + H) |
| 135 | | N-(1-ethyl-4-(morpholin-4-yl)-2-oxo-1,2-dihydroquinolin-6-yl)-4-fluoro-N-methylbenzamide | 410 (M + H) |

TABLE 13-continued

| Example No. | Structural Formula | Compound Name | MS |
|---|---|---|---|
| 136 | | N-(1-ethyl-4-(morpholin-4-yl)-2-oxo-1,2-dihydroquinolin-6-yl)-N-methyl-4-(trifluoromethyl)benzamide | 460 (M + H) |
| 137 | | N-(1-ethyl-4-(morpholin-4-yl)-2-oxo-1,2-dihydroquinolin-6-yl)-3-hydroxy-N-methylbenzamide | 408 (M + H) |
| 138 | | 1-ethyl-N-methyl-4-(1-methyl-1,2,3,6-tetrahydropyridin-4-yl)-2-oxo-N-phenyl-1,2-dihydroquinolin-6-carboxamide | 402 (M + H) |
| 139 | | 1-ethyl-N-methyl-4-(1-methylpyridin-4-yl)-2-oxo-N-phenyl-1,2-dihydroquinolin-6-carboxamide | 404 (M + H) |
| 140 | | 4-cyclohex-1-ethyl-N-methyl-2-oxo-N-phenyl-1,2-dihydroquinolin-6-carboxamide | 389 (M + H) |

TABLE 13-continued

| Example No. | Structural Formula | Compound Name | MS |
|---|---|---|---|
| 141 | | 4-cyclohex-1-en-1-yl)-1-ethyl-N-methyl-2-oxo-N-phenyl-1,2-dihydroquinolin-6-carboxamide | 387 (M + H) |

TABLE 14

| Example No. | Structural Formula | Compound Name | MS |
|---|---|---|---|
| 142 | | 4-cyclopropyl-1-ethyl-N-methyl-2-oxo-N-phenyl-1,2-dihydroquinolin-6-carboxamide | 347 (M + H) |
| 143 | | 6-(2,3-dihydro-1H-indol-1-ylcarbonyl)-1-ethyl-4-(1-methylpiperidin-4-yl)quinolin-2(1H)-one | 416 (M + H) |
| 144 | | 4-((1-ethyl-4-(1-methylpiperidin-4-yl)-2-oxo-1,2-dihydroquinolin-6-yl)carbonyl)-3,4-dihydroquinoxalin-2(1H)-one | 445 (M + H) |

TABLE 14-continued

| Example No. | Structural Formula | Compound Name | MS |
|---|---|---|---|
| 145 | | N-(2-cyanophenyl)-4-cyclopropyl-1-ethyl-N-methyl-2-oxo-1,2-dihydroquinoline-6-carboxamide | 372 (M + H) |
| 146 | | 4-cyclopropyl-1-ethyl-N-(4-fluorophenyl)-N-methyl-2-oxo-1,2-dihydroquinoline-6-carboxamide | 365 (M + H) |
| 147 | | 4-cyclopropyl-1-ethyl-N-methyl-2-oxo-N-(4-trifluoromethyl)phenyl)-1,2-dihydroquinoline-6-carboxamide | 415 (M + H) |
| 148 | | 4-cyclopropyl-1-ethyl-N-(2-fluorophenyl)-N-methyl-2-oxo-1,2-dihydroquinoline-6-carboxamide | 365 (M + H) |
| 149 | | 4-cyclopropyl-1-ethyl-N-methyl-2-oxo-N-(2-(trifluoromethyl)phenyl)-1,2-dihydroquinoline-6-carboxamide | 415 (M + H) |
| 150 | | 4-cyclopropyl-1-ethyl-N-methyl-N-(2-methylphenyl)-2-oxo-1,2-dihydroquinoline-6-carboxamide | 361 (M + H) |

TABLE 14-continued

| Example No. | Structural Formula | Compound Name | MS |
|---|---|---|---|
| 151 | 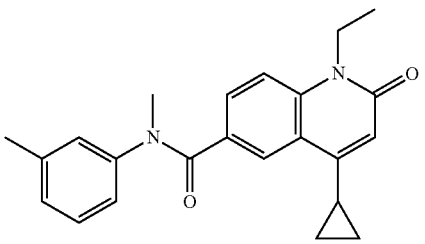 [SMILES: CCn1c(=O)cc(C2CC2)c2cc(C(=O)N(C)c3cccc(C)c3)ccc21] | 4-cyclopropyl-1-ethyl-N-methyl-N-(3-methylphenyl)-2-oxo-1,2-dihydroquinoline-6-carboxamide | 361 (M + H) |

TABLE 15

| Example No. | Structural Formula | Compound Name | MS |
|---|---|---|---|
| 152 | 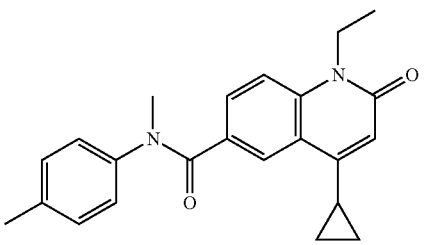 | 4-cyclopropyl-1-ethyl-N-methyl-N-(4-methylphenyl)-2-oxo-1,2-dihydroquinoline-6-carboxamide | 361 (M + H) |
| 153 | 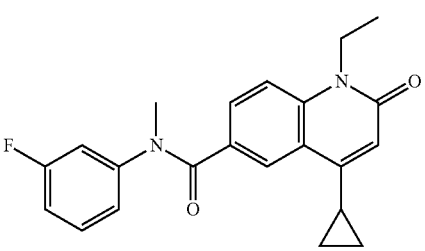 [SMILES: CCn1c(=O)cc(C2CC2)c2cc(C(=O)N(C)c3cccc(F)c3)ccc21] | 4-cyclopropyl-1-ethyl-N-(3-fluorophenyl)-N-methyl-2-oxo-1,2-dihydroquinoline-6-carboxamide | 365 (M + H) |
| 154 | 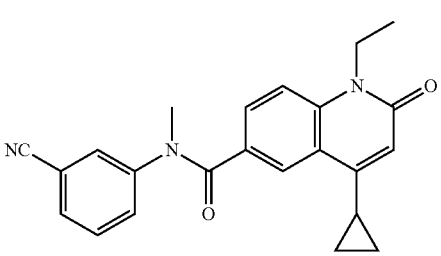 | N-(3-cyanophenyl)-4-cyclopropyl-1-ethyl-N-methyl-2-oxo-1,2-dihydroquinoline-6-carboxamide | 372 (M + H) |
| 155 | 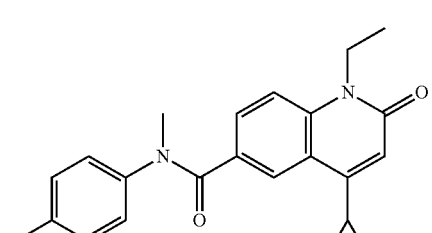 | N-(4-cyanophenyl)-4-cyclopropyl-1-ethyl-N-methyl-2-oxo-1,2-dihydroquinoline-6-carboxamide | 372 (M + H) |

TABLE 15-continued

| Example No. | Structural Formula | Compound Name | MS |
|---|---|---|---|
| 156 | 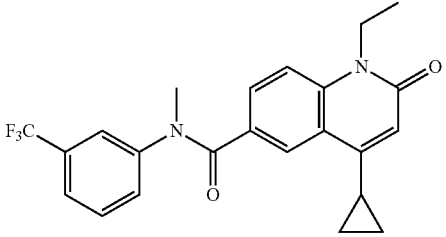 | 4-cyclopropyl-1-ethyl-N-methyl-2-oxo-N-(3-trifluoromethyl)phenyl)-1,2-dihydroquinoline-6-carboxamide | 415 (M + H) |
| 157 | 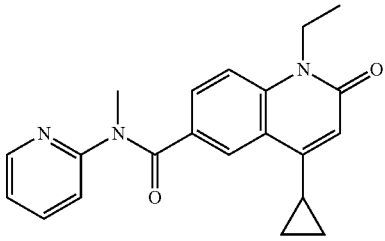 [SMILES: CCn1c(=O)cc(C2CC2)c2cc(C(=O)N(C)c3ccccn3)ccc21] | 4-cyclopropyl-1-ethyl-N-methyl-2-oxo-N-(pyridin-2-yl)-1,2-dihydroquinoline-6-carboxamide | 348 (M + H) |
| 158 | 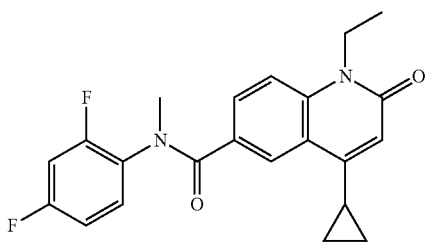 [SMILES: CCn1c(=O)cc(C2CC2)c2cc(C(=O)N(C)c3ccc(F)cc3F)ccc21] | 4-cyclopropyl-N-(2,4-difluorophenyl)-1-ethyl-N-methyl-2-oxo-1,2-dihydroquinoline-6-carboxamide | 383 (M + H) |
| 159 | 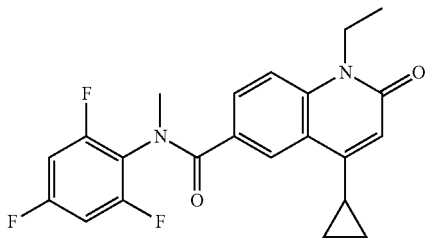 [SMILES: CCn1c(=O)cc(C2CC2)c2cc(C(=O)N(C)c3c(F)cc(F)cc3F)ccc21] | 4-cyclopropyl-1-ethyl-N-methyl-2-oxo-N-(2,4,6-trifluorophenyl)-1,2-dihydroquinoline-6-carboxamide | 401 (M + H) |
| 160 | 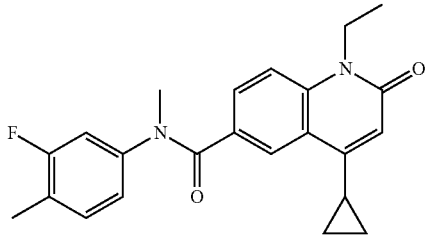 [SMILES: CCn1c(=O)cc(C2CC2)c2cc(C(=O)N(C)c3ccc(C)c(F)c3)ccc21] | 4-cyclopropyl-1-ethyl-N-(3-fluoro-4-methylphenyl)-N-methyl-2-oxo-1,2-dihydroquinoline-6-carboxamide | 379 (M + H) |
| 161 | 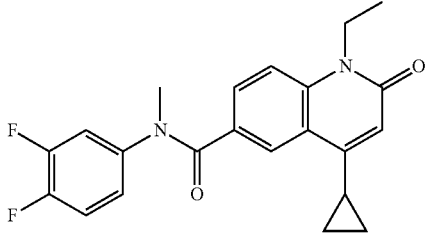 [SMILES: CCn1c(=O)cc(C2CC2)c2cc(C(=O)N(C)c3ccc(F)c(F)c3)ccc21] | 4-cyclopropyl-N-(3,4-difluorophenyl)-1-ethyl-N-methyl-2-oxo-1,2-dihydroquinoline-6-carboxamide | 383 (M + H) |

TABLE 15-continued

| Example No. | Structural Formula | Compound Name | MS |
|---|---|---|---|
| 162 | | 4-cyclopropyl-1-ethyl-N-(4-fluoro-3-methylphenyl)-N-methyl-2-oxo-1,2-dihydroquinoline-6-carboxamide | 379 (M + H) |

TABLE 16

| Example No. | Structural Formula | Compound Name | MS |
|---|---|---|---|
| 163 | | 4-cyclopropyl-1-ethyl-N-methyl-2-oxo-N-(pyridin-4-yl)-1,2-dihydroquinoline-6-carboxamide | 348 (M + H) |
| 164 | | 4-cyclopropyl-1-ethyl-N-methyl-2-oxo-N-(pyridin-3-yl)-1,2-dihydroquinoline-6-carboxamide | 348 (M + H) |
| 165 | | 1-ethyl-N,4-dimethyl-N-(3-methylphenyl)-2-oxo-1,2-dihydroquinoline-6-carboxamide | 335 (M + H) |
| 166 | | 1-ethyl-N,4-dimethyl-N-(4-methylphenyl)-2-oxo-1,2-dihydroquinoline-6-carboxamide | 335 (M + H) |

TABLE 16-continued

| Example No. | Structural Formula | Compound Name | MS |
|---|---|---|---|
| 167 | 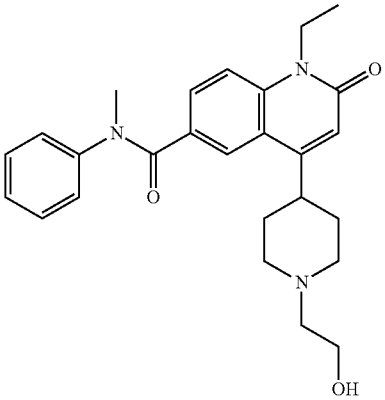 [SMILES: CCn1c(=O)cc(C2CCN(CCO)CC2)c2cc(C(=O)N(C)c3ccccc3)ccc21] | 1-ethyl-4-(1-(2-hydroxyethyl)piperidin-4-yl)-N-methyl-2-oxo-N-phenyl-1,2-dihydroquinoline-6-carboxamide | 434 (M + H) |
| 168 | 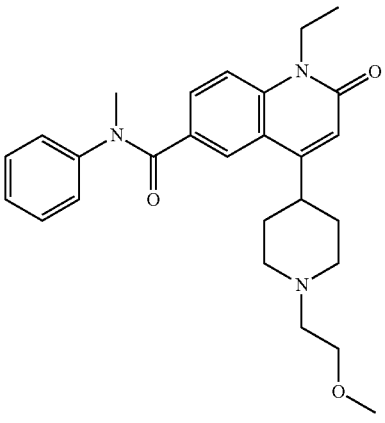 [SMILES: CCn1c(=O)cc(C2CCN(CCOC)CC2)c2cc(C(=O)N(C)c3ccccc3)ccc21] | 1-ethyl-4-(1-(2-methoxyethyl)piperidin-4-yl)-N-methyl-2-oxo-N-phenyl-1,2-dihydroquinoline-6-carboxamide | 448 (M + H) |
| 169 | 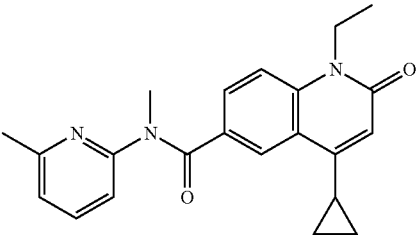 | 4-cyclopropyl-1-ethyl-N-methyl-N-(6-methylpyridin-2-yl)-2-oxo-1,2-dihydroquinoline-6-carboxamide | 362 (M + H) |
| 170 | 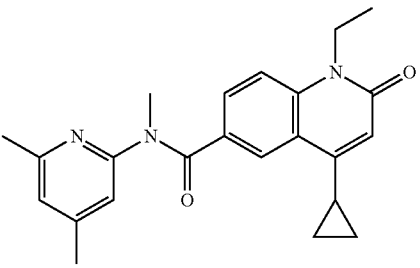 [SMILES: CCn1c(=O)cc(C2CC2)c2cc(C(=O)N(C)c3cc(C)cc(C)n3)ccc21] | 4-cyclopropyl-N-(4,6-dimethylpyridin-2-yl)-1-ethyl-N-methyl-2-oxo-1,2-dihydroquinoline-6-carboxamide | 376 (M + H) |
| 171 | 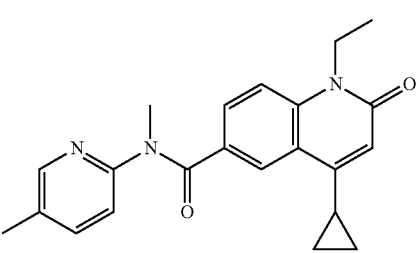 [SMILES: CCn1c(=O)cc(C2CC2)c2cc(C(=O)N(C)c3ccc(C)cn3)ccc21] | 4-cyclopropyl-1-ethyl-N-methyl-N-(5-methylpyridin-2-yl)-2-oxo-1,2-dihydroquinoline-6-carboxamide | 362 (M + H) |

TABLE 16-continued

| Example No. | Structural Formula | Compound Name | MS |
|---|---|---|---|
| 172 | | 4-cyclopropyl-1-ethyl-N-methyl-N-(6-methylpyridin-3-yl)-2-oxo-1,2-dihydroquinoline-6-carboxamide | 362 (M + H) |

TABLE 17

| Example No. | Structural Formula | Compound Name | MS |
|---|---|---|---|
| 173 | | 4-cyclopropyl-1-ethyl-N-methyl-N-(2-methylpyridin-4-yl)-2-oxo-1,2-dihydroquinoline-6-carboxamide | 362 (M + H) |
| 174 | | 1-ethyl-N-methyl-2-oxo-N-phenyl-4-(1-(2,2,2-trifluoroethyl)piperidin-4-yl)-1,2-dihydroquinoline-6-carboxamide | 472 (M + H) |
| 175 | | methyl 2-(((4-cyclopropyl-1-ethyl-2-oxo-1,2-dihydroquinolin-6-yl)carbonyl)(methyl)amino)benzoate | 405 (M + H) |
| 176 | | 3-(((4-cyclopropyl-1-ethyl-2-oxo-1,2-dihydroquinolin-6-yl)carbonyl)(methyl)amino)benzoic acid | 391 (M + H) |

TABLE 17-continued

| Example No. | Structural Formula | Compound Name | MS |
|---|---|---|---|
| 177 | | methyl 4-(((4-cyclopropyl-1-ethyl-2-oxo-1,2-dihydroquinolin-6-yl)carbonyl)(methyl)amino)benzoate | 405 (M + H) |
| 178 | | 2-(((4-cyclopropyl-1-ethyl-2-oxo-1,2-dihydroquinolin-6-yl)carbonyl)(methyl)amino)benzoic acid | 391 (M + H) |
| 179 | | 1-ethyl-4-(1-(2-hydroxyethyl)piperidin-4-yl)-N-methyl-2-oxo-N-(5,6,7,8-tetrahydronaphthalen-2-yl)-1,2-dihydroquinoline-6-carboxamide | 488 (M + H) |
| 180 | | 4-(1-benzoylpiperidin-4-yl)-1-ethyl-N-methyl-N-(4-methylphenyl)-2-oxo-1,2-dihydroquinoline-6-carboxamide | 508 (M + H) |

TABLE 18

| Example No. | Structural Formula | Compound Name | MS |
|---|---|---|---|
| 181 | | 1-ethyl-N-methyl-N-(4-methylphenyl)-4-(1-(methylsulfonyl)piperidin-4-yl)-2-oxo-1,2-dihydroquinoline-6-carboxamide | 480 (M − H) |
| 182 | | 1-ethyl-N-(2-(hydroxymethyl)-4-methylphenyl)-N-methyl-2-oxo-4-(propan-2-yl)-1,2-dihydroquinoline-6-carboxamide | 393 (M + H) |
| 183 | | 1-ethyl-N-methyl-N-(4-methylphenyl)-4-(1-(2-methylpropanoyl)piperidin-4-yl)-2-oxo-1,2-dihydroquinoline-6-carboxamide | 474 (M + H) |
| 184 | | N-(4-chlorophenyl)-1-ethyl-N-methyl-2-oxo-4-(propan-2-yl)-1,2-dihydroquinoline-6-carboxamide | 384 (M + H) |
| 185 | | 1-ethyl-N-methyl-N-(4-methyl-3-(phenylcarbamoyl)phenyl)-2-oxo-4-(propan-2-yl)-1,2-dihydroquinoline-6-carboxamide | 480 (M − H) |

TABLE 18-continued

| Example No. | Structural Formula | Compound Name | MS |
|---|---|---|---|
| 186 | | 1-ethyl-N-methyl-N-(4-methyl-3-(propan-2-ylcarbamoyl)phenyl)-2-oxo-4-(propan-2-yl)-1,2-dihydroquinoline-6-carboxamide | 446 (M − H) |
| 187 | | N-(2-(dimethylcarbamoyl)-4-methylphenyl)-1-ethyl-N-methyl-2-oxo-4-(propan-2-yl)-1,2-dihydroquinoline-6-carboxamide | 434 (M + H) |
| 188 | | 1-ethyl-N-methyl-N-(4-methyl-2-(phenylcarbamoyl)phenyl)-2-oxo-4-(propan-2-yl)-1,2-dihydroquinoline-6-carboxamide | 480 (M − H) |
| 189 | | 1-ethyl-N-methyl-N-(4-methyl-2-(propan-2-ylcarbamoyl)phenyl)-2-oxo-4-(propan-2-yl)-1,2-dihydroquinoline-6-carboxamide | 446 (M − H) |

TABLE 19

| Example No. | Structural Formula | Compound Name | MS |
|---|---|---|---|
| 190 | | 1-ethyl-N-methyl-(4-(1-methylpiperidin-4-yl)-2-oxo-N-(5,6,7,8-tetrahydronaphthalen-2-yl)-1,2-dihydroquinoline-6-carboxamide | 458 (M + H) |

TABLE 19-continued

| Example No. | Structural Formula | Compound Name | MS |
|---|---|---|---|
| 191 | | 1-ethyl-(4-(1-(2-hydroxyethyl)piperidin-4-yl)-N-methyl-2-oxo-N-(6,7,8,9-tetrahydro-5H-benz(7)annulen-2-yl)-1,2-dihydroquinoline-6-carboxamide | 502 (M + H) |
| 192 | | N-(4-chlorophenyl)-1-ethyl-N-methyl-4-(1-(2-methylpropanoyl)piperidin-4-yl)-2-oxo-1,2-dihydroquinoline-6-carboxamide | 494, 496 (M + H) |
| 193 | | 1-ethyl-N-methyl-4-(1-(2-methylpropanoyl)piperidin-4-yl)-2-oxo-N-(4-(trifluoromethyl)phenyl)-1,2-dihydroquinoline-6-carboxamide | 528 (M + H) |
| 194 | | 4-cyano-N-(1-ethyl-2-oxo-4-(propan-2-yl)-1,2-dihydroquinolin-6-yl)-N-methylbenzamide | 374 (M + H) |

TABLE 19-continued

| Example No. | Structural Formula | Compound Name | MS |
|---|---|---|---|
| 195 | | 1-ethyl-N-(2-methoxy-1-methyl-1H-indol-6-yl)-N-methyl-2-oxo-4-(propan-2-yl)-1,2-dihydroquinoline-6-carboxamide | 430 (M − H) |
| 196 | | tert-butyl 6-(((1-ethyl-2-oxo-4-(propan-2-yl)-1,2-dihydroquinolin-6-yl)carbonyl)(methyl)amino)-2,3-dihydro-1H-indole-1-carboxylate | 490 (M + H) |
| 197 | | N-(4-chloro-3-(1H-tetrazol-5-yl)phenyl)-1-ethyl-N-methyl-2-oxo-4-(propan-2-yl)-1,2-dihydroquinoline-6-carboxamide | 451 (M + H) |

TABLE 20

| Example No. | Structural Formula | Compound Name | MS |
|---|---|---|---|
| 198 | | (2-chloro-5-(((1-ethyl-2-oxo-4-(propan-2-yl)-1,2-dihydroquinolin-6-yl)carbonyl)(methyl)amino)phenyl)acetic acid | 442 (M + H) |
| 199 | | N-(4-chloro-3-(2-hydroxyethyl)phenyl)-1-ethyl-N-methyl-2-oxo-4-(propan-2-yl)-1,2-dihydroquinoline-6-carboxamide | 428 (M + H) |

TABLE 20-continued

| Example No. | Structural Formula | Compound Name | MS |
|---|---|---|---|
| 200 | | 1-ethyl-N-(3-((2-hydroxyethyl)carbamoyl)-4-methylphenyl)-N-methyl-2-oxo-4-(propan-2-yl)-1,2-dihydroquinoline-6-carboxamide | 450 (M + H) |
| 201 | | N-(4-chloro-3-methoxyphenyl)-1-ethyl-N-methyl-2-oxo-4-(propan-2-yl)-1,2-dihydroquinoline-6-carboxamide | 414 (M + H) |
| 202 | | N-(3-amino-4-chlorophenyl)-1-ethyl-N-methyl-2-oxo-4-(propan-2-yl)-1,2-dihydroquinoline-6-carboxamide | 399 (M + H) |
| 203 | | 1-ethyl-N-methyl-N-(4-(methylsulfonyl)phenyl)-2-oxo-4-(propan-2-yl)-1,2-dihydroquinoline-6-carboxamide | 427 (M + H) |
| 204 | | N-(3-butylcarbamoyl)-4-methylphenyl)-1-ethyl-N-methyl-4-(1-methylpiperidin-4-yl)-2-oxo-1,2-dihydroquinoline-6-carboxamide | 517 (M + H) |

TABLE 20-continued

| Example No. | Structural Formula | Compound Name | MS |
|---|---|---|---|
| 205 | | 1-ethyl-N-(3-((2-hydroxyethyl)carbamoyl)-4-methylphenyl)-N-methyl-4-(1-methylpiperidin-4-yl)-2-oxo-1,2-dihydroquinoline-6-carboxamide | 505 (M + H) |
| 206 | | 1-ethyl-N-methyl-N-(4-methyl-2-(methylcarbamoyl)phenyl)-4-(1-methylpiperidin-4-yl)-2-oxo-1,2-dihydroquinoline-6-carboxamide | 475 (M + H) |

TABLE 21

| Example No. | Structural Formula | Compound Name | MS |
|---|---|---|---|
| 207 | | 1-ethyl-N-methyl-4-(1-methylpiperidin-4-yl)-N-(4-methyl-2-(propan-2-ylcarbamoyl)phenyl)-2-oxo-1,2-dihydroquinoline-6-carboxamide | 503 (M + H) |
| 208 | | 1-ethyl-N-(2-((2-hydroxyethyl)carbamoyl)4-methylphenyl)-N-methyl-4-(1-methylpiperidin-4-yl)-2-oxo-1,2-dihydroquinoline-6-carboxamide | 505 (M + H) |

TABLE 21-continued

| Example No. | Structural Formula | Compound Name | MS |
|---|---|---|---|
| 209 | | 1-ethyl-N-(3-(2-methoxyethyl)-4-methylphenyl)-N-methyl-4-(1-methylpiperidin-4-yl)-2-oxo-1,2-dihydroquinoline-6-carboxamide | 476 (M + H) |
| 210 | | 1-ethyl-N-(3-(2-hydroxyethyl)-4-methylphenyl)-N-methyl-4-(1-methylpiperidin-4-yl)-2-oxo-1,2-dihydroquinoline-6-carboxamide | 462 (M + H) |
| 211 | | 1-ethyl-N-methyl-2-oxo-N-phenyl-4-(trifluoromethyl)-1,2-dihydroquinoline-6-carboxamide | 375 (M + H) |
| 212 | | 1-ethyl-N-methyl-N-(4-methylphenyl)-2-oxo-4-(trifluoromethyl)-1,2-dihydroquinoline-6-carboxamide | 389 (M + H) |
| 213 | | 1-ethyl-N-(3-fluoro-4-(trifluoromethyl)phenyl)-N-methyl-2-oxo-4-(propan-2-yl)-1,2-dihydroquinoline-6-carboxamide | 435 (M + H) |

TABLE 21-continued

| Example No. | Structural Formula | Compound Name | MS |
|---|---|---|---|
| 214 | | 1-ethyl-N-methyl-2-oxo-4-(propan-2-yl)-N-(3-(trifluoromethyl)phenyl)-1,2-dihydroquinoline-6-carboxamide | 417 (M + H) |
| 215 | | N-(2-cyano-4-methylphenyl)-1-ethyl-N-methyl-2-oxo-4-(propan-2-yl)-1,2-dihydroquinoline-6-carboxamide | 388 (M + H) |

TABLE 22

| Example No. | Structural Formula | Compound Name | MS |
|---|---|---|---|
| 216 | | 1-ethyl-N-methyl-N-(6-methylpyridin-3-yl)-2-oxo-4-(tetrahydro-2H-pyran-4-yl)-1,2-dihydroquinoline-6-carboxamide | 406 (M + H) |
| 217 | | 1-ethyl-N-methyl-N-(3-methylphenyl)-2-oxo-4-(propan-2-yl)-1,2-dihydroquinoline-6-carboxamide | 363 (M + H) |
| 218 | | 1-ethyl-N-(isoquinolin-6-yl)-N-methyl-2-oxo-4-(propan-2-yl)-1,2-dihydroquinoline-6-carboxamide | 400 (M + H) |

TABLE 22-continued

| Example No. | Structural Formula | Compound Name | MS |
|---|---|---|---|
| 219 | 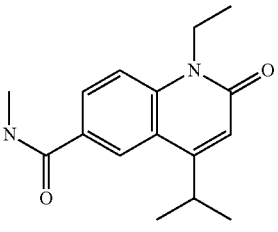 | N-(4-chloro-2-cyanophenyl)-1-ethyl-N-methyl-2-oxo-4-(propan-2-yl)-1,2-dihydroquinoline-6-carboxamide | 408 (M + H) |
| 220 | 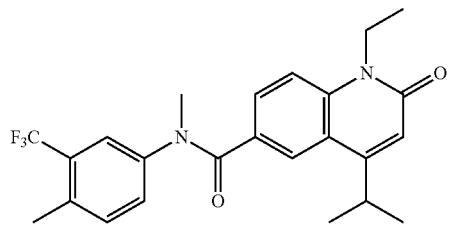 [SMILES: CCn1c(=O)cc(C(C)C)c2cc(C(=O)N(C)c3ccc(C)c(C(F)(F)F)c3)ccc21] | 1-ethyl-N-methyl-N-(4-methyl-3-(trifluoromethyl)phenyl)-2-oxo-4-(propan-2-yl)-1,2-dihydroquinoline-6-carboxamide | 431 (M + H) |
| 221 | 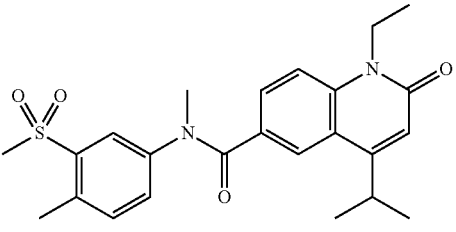 [SMILES: CCn1c(=O)cc(C(C)C)c2cc(C(=O)N(C)c3ccc(C)c(S(C)(=O)=O)c3)ccc21] | 1-ethyl-N-methyl-N-(4-methyl-3-(methylsulfonyl)phenyl)-2-oxo-4-(propan-2-yl)-1,2-dihydroquinoline-6-carboxamide | 441 (M + H) |
| 222 | 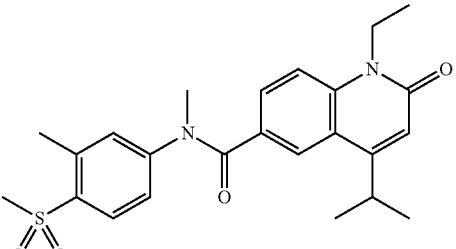 | 1-ethyl-N-methyl-N-(3-methyl-4-(methylsulfonyl)phenyl)-2-oxo-4-(propan-2-yl)-1,2-dihydroquinoline-6-carboxamide | 441 (M + H) |
| 223 | 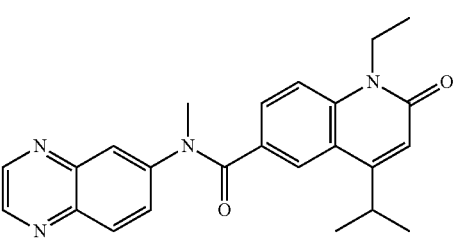 [SMILES: CCn1c(=O)cc(C(C)C)c2cc(C(=O)N(C)c3ccc4nccnc4c3)ccc21] | 1-ethyl-N-methyl-2-oxo-4-(propan-2-yl)-N-(quinoxalin-6-yl)-1,2-dihydroquinoline-6-carboxamide | 401 (M + H) |
| 224 | 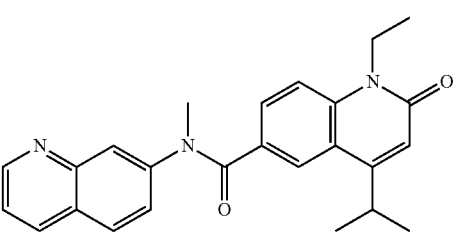 [SMILES: CCn1c(=O)cc(C(C)C)c2cc(C(=O)N(C)c3ccc4cccnc4c3)ccc21] | 1-ethyl-N-methyl-2-oxo-4-(propan-2-yl)-N-(quinolin-7-yl)-1,2-dihydroquinoline-6-carboxamide | 400 (M + H) |

TABLE 22-continued

| Example No. | Structural Formula | Compound Name | MS |
|---|---|---|---|
| 225 | | 1-ethyl-N-methyl-2-oxo-4-(propan-2-yl)-N-(2-(trifluoromethyl)phenyl)-1,2-dihydroquinoline-6-carboxamide | 417 (M + H) |

TABLE 23

| Example No. | Structural Formula | Compound Name | MS |
|---|---|---|---|
| 226 | | 1-ethyl-N-methyl-2-oxo-4-(propan-2-yl)-N-(4-(trifluoromethyl)phenyl)-1,2-dihydroquinoline-6-carboxamide | 417 (M + H) |
| 227 | | N-(3,4-difluorophenyl)-1-ethyl-N-methyl-2-oxo-4-(propan-2-yl)-1,2-dihydroquinoline-6-carboxamide | 385 (M + H) |
| 228 | | 1-ethyl-N-(4-fluoro-3-(trifluoromethyl)phenyl)-N-methyl-2-oxo-4-(propan-2-yl)-1,2-dihydroquinoline-6-carboxamide | 435 (M + H) |
| 229 | | 1-ethyl-N-methyl-2-oxo-N-(3-oxo-2,3-dihydro-1H-isoindol-5-yl)-4-(propan-2-yl)-1,2-dihydroquinoline-6-carboxamide | 404 (M + H) |

TABLE 23-continued

| Example No. | Structural Formula | Compound Name | MS |
|---|---|---|---|
| 230 | | 1-ethyl-4-(4-hydroxypiperidin-1-yl)-N-methyl-2-oxo-N-(3-(trifluoromethyl)phenyl)-1,2-dihydroquinoline-6-carboxamide | 474 (M + H) |
| 231 | | 1-ethyl-N-methyl-N-(2-methyl-3-oxo-2,3-dihydro-1H-isoindol-5-yl)-2-oxo-4-(propan-2-yl)-1,2-dihydroquinoline-6-carboxamide | 418 (M + H) |
| 232 | | 1-ethyl-4-(3-hydroxyazetidin-1-yl)-N-methyl-2-oxo-N-(3-(trifluoromethyl)phenyl)-1,2-dihydroquinoline-6-carboxamide | 446 (M + H) |
| 233 | | 1-ethyl-4-(4-(2-hydroxyethyl)piperidin-1-yl)-N-methyl-2-oxo-N-(3-(trifluoromethyl)phenyl)-1,2-dihydroquinoline-6-carboxamide | 502 (M + H) |
| 234 | | 4-(dimethylamino)-1-ethyl-N-methyl-2-oxo-N-(3-(trifluoromethyl)phenyl)-1,2-dihydroquinoline-6-carboxamide | 418 (M + H) |

TABLE 24

| Example No. | Structural Formula | Compound Name | MS |
|---|---|---|---|
| 235 | | N,1-dimethyl-N-(4-methylphenyl)-4-(1-methylpiperidin-4-yl)-2-oxo-1,2-dihydroquinoline-6-carboxamide | 404 (M + H) |
| 236 | | 1-ethyl-4-methyl-6-(2-oxo-5-phenyl-2,3-dihydro-1H-imidazol-1-yl)quinolin-2(1H)-one | 346 (M + H) |
| 237 | | 1-ethyl-6-(2-oxo-5-phenyl-2,3-dihydro-1H-imidazol-1-yl)-4-(piperidin-1-yl)quinolin-2(1H)-one | 415 (M + H) |
| 238 | | 1-ethyl-4-methyl-6-(3-methyl-2-oxo-5-phenyl-2,3-dihydro-1H-imidazol-1-yl)quinolin-2(1H)-one | 360 (M + H) |
| 239 | | 6-(3-benzyl-2-oxo-5-phenyl-2,3-dihydro-1H-imidazol-1-yl)-1-ethyl-4-methylquinolin-2(1H)-one | 436 (M + H) |

TABLE 24-continued

| Example No. | Structural Formula | Compound Name | MS |
|---|---|---|---|
| 240 | | 1-ethyl-6-(3-methyl-2-oxo-5-phenyl-2,3-dihydro-1H-imidazol-1-yl)-4-(piperidin-1-yl)quinolin-2(1H)-one | 429 (M + H) |
| 241 | | 6-(3-benzyl-2-oxo-5-phenyl-2,3-dihydro-1H-imidazol-1-yl)-1-ethyl-4-(piperidin-1-yl)quinolin-2(1H)-one | 505 (M + H) |
| 242 | | 1-ethyl-4-(1-methylpiperidin-4-yl)-6-(2-oxo-5-phenylimidazolidin-1-yl)quinolin-2(1H)-one | 431 (M + H) |

TABLE 25

| Example No. | Structural Formula | Compound Name | MS |
|---|---|---|---|
| 243 | | 1-ethyl-4-(1-methyl-1,2,3,6-tetrahydropyridin-4-yl)-6-(2-oxo-5-phenyl-2,3-dihydro-1H-imidazol-1-yl)quinolin-2(1H)-one | 427 (M + H) |

TABLE 25-continued

| Example No. | Structural Formula | Compound Name | MS |
|---|---|---|---|
| 244 | | 1-ethyl-4-(1-methylpiperidin-4-yl)-6-(2-oxo-5-phenyl-2,3-dihydro-1H-imidazol-1-yl)quinolin-2(1H)-one | 429 (M + H) |

Example 245

Example 246

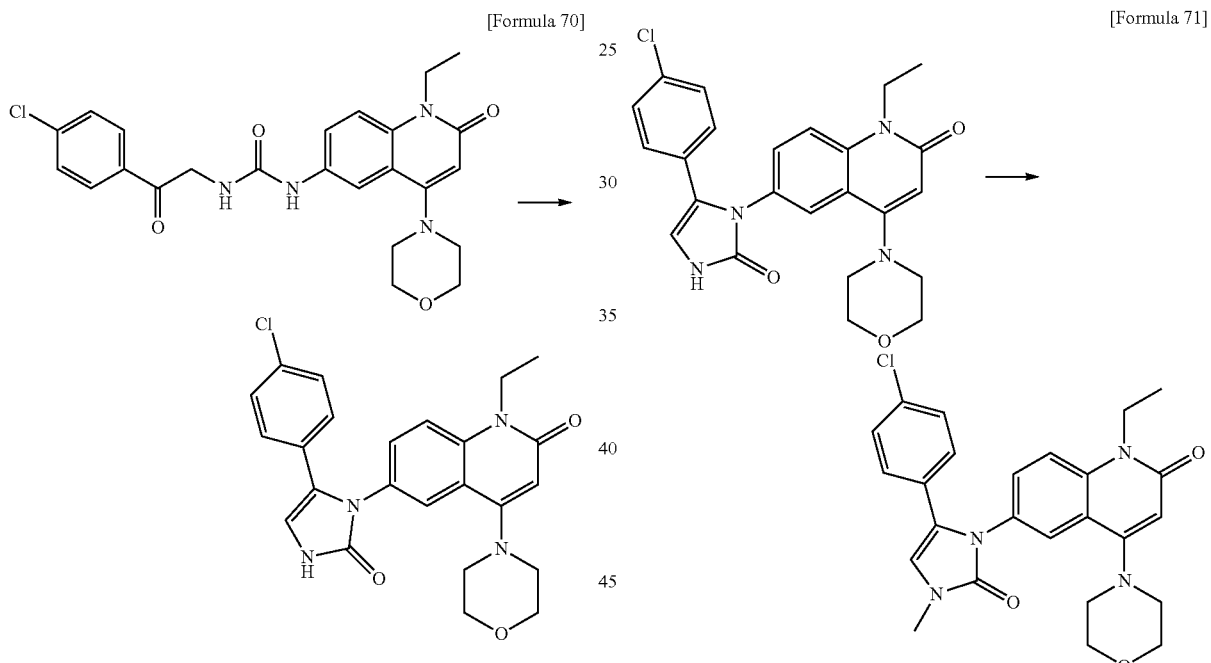

[Formula 70]

[Formula 71]

4.0 mL of Concentrated hydrochloric acid was added to a suspension of 0.70 g of 1-(2-(4-chlorophenyl)-2-oxoethyl)-3-(1-ethyl-4-(morpholin-4-yl)-2-oxo-1,2-dihydroquinolin-6-yl)urea in 4.0 mL of dioxane at room temperature, and the obtained mixture was then stirred for 2 hours. Thereafter, water was added to the reaction mixture, and a solid was collected by filtration, and was then washed with water and diisopropyl ether. The obtained solid was purified by silica gel column chromatography [gradient elution of chloroform:methanol=100:0-90:10]. To the obtained residue, diisopropyl ether was added, and a solid was then collected by filtration, so as to obtain 0.59 g of 6-(5-(4-chlorophenyl)-2-oxo-2,3-dihydro-1H-imidazol-1-yl)-1-ethyl-4-(morpholin-4-yl)quinolin-2(1H)-one in the form of a white solid.

$^1$H-NMR (DMSO-D$_6$) δ:1.19 (3H, t, J=6.8 Hz), 2.64-2.73 (4H, m), 3.50-3.57 (4H, m), 4.23 (2H, q, J=6.8 Hz), 6.00 (1H, s), 6.95 (1H, s), 7.07-7.13 (2H, m), 7.24 (1H, d, J=2.4 Hz), 7.32-7.38 (2H, m), 7.57 (1H, dd, J=9.1, 2.3 Hz), 7.65 (1H, d, J=9.0 Hz), 10.67 (1H, s).

MS (ESI, m/z): 451 (M+H), 449 (M−H)

30 mg of 60% Sodium hydride was added to a solution of 300 mg of 6-(5-(4-chlorophenyl)-2-oxo-2,3-dihydro-1H-imidazol-1-yl)-1-ethyl-4-(morpholin-4-yl)quinolin-2(1H)-one in 3 mL of N,N-dimethylformamide under cooling on ice, and the obtained mixture was then stirred for 5 minutes. Thereafter, 50 μL of methyl iodide was added to the reaction mixture under cooling on ice, and the obtained mixture was then stirred at room temperature for 2 hours. Thereafter, ethyl acetate and water were added to the reaction mixture under cooling on ice, and the obtained mixture was then adjusted to pH 2.0 with 1 mol/L hydrochloric acid. A solid was collected by filtration, and was then washed with water and diisopropyl ether, so as to obtain 203 mg of 6-(5-(4-chlorophenyl)-3-methyl-2-oxo-2,3-dihydro-1H-imidazol-1-yl)-1-ethyl-4-(morpholin-4-yl)quinolin-2(1H)-one in the form of a white solid.

$^1$H-NMR (DMSO-D$_6$): 1.19 (3H, t, J=7.0 Hz), 2.64-2.72 (4H, m), 3.28 (3H, s), 3.50-3.57 (4H, m), 4.23 (2H, q, J=6.8

Hz), 6.01 (1H, s), 7.05-7.12 (2H, m), 7.07 (1H, s), 7.26 (1H, d, J=2.4 Hz), 7.34-7.39 (2H, m), 7.57 (1H, dd, J=9.0, 2.4 Hz), 7.66 (1H, d, J=9.0 Hz).

MS (ESI, m/z): 465 (M+H)

Example 247

[Formula 72]

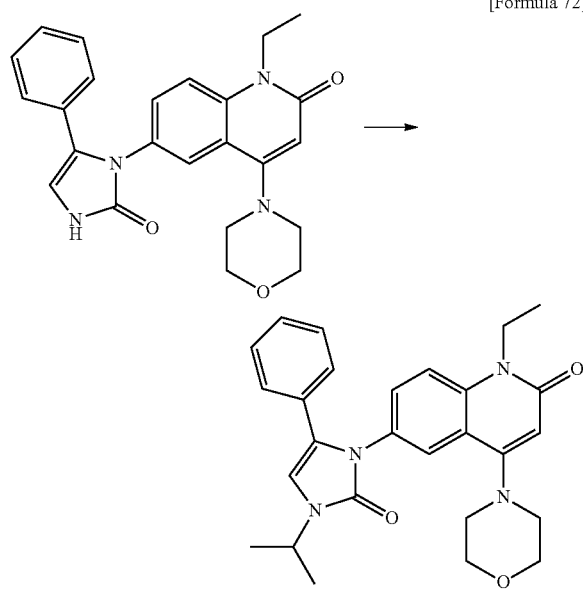

35 mg of 60% Sodium hydride was added to a suspension of 330 mg of 1-ethyl-4-(morpholin-4-yl)-6-(2-oxo-5-phenyl-2,3-dihydro-1H-imidazol-1-yl)quinolin-2(1H)-one in 2 mL of N,N-dimethylacetamide under cooling on ice, and the obtained mixture was then stirred for 5 minutes. Thereafter, 119 μL of 2-iodopropane was added to the reaction mixture under cooling on ice, and the obtained mixture was then stirred at room temperature for 1 hour. Thereafter, 60 μL of 2-iodopropane was added to the reaction mixture, and the obtained mixture was then stirred at room temperature for 1 hour. After that, to the reaction mixture, ethyl acetate and water were added under cooling on ice, and the obtained mixture was then adjusted to pH 2.0 with 1 mol/L hydrochloric acid. An organic layer was separated, was then washed with water and a saturated sodium chloride aqueous solution, and was then dried over anhydrous magnesium sulfate. The solvent was distilled away under reduced pressure. The obtained residue was purified by silica gel column chromatography [ethyl acetate→gradient elution of chloroform:methanol=95:5-90:10]. Diisopropyl ether and ethyl acetate were added to the obtained residue, and a solid was then collected by filtration. The obtained solid was purified by silica gel column chromatography [ethyl acetate]. Diisopropyl ether and ethyl acetate were added to the obtained residue, and a solid was then collected by filtration, so as to obtain 68 mg of 1-ethyl-4-(morpholin-4-yl)-6-(2-oxo-5-phenyl-3-(propan-2-yl)-2,3-dihydro-1H-imidazol-1-yl)quinolin-2(1H)-one in the form of a light brown solid.

$^1$H-NMR (CDCl$_3$) δ: 1.36 (3H, t, J=7.1 Hz), 1.43 (6H, d, J=6.8 Hz), 2.63-2.70 (4H, m), 3.55-3.62 (4H, m), 4.32 (2H, q, J=7.2 Hz), 4.55 (1H, quint, J=6.8 Hz), 6.09 (1H, s), 6.51 (1H, s), 7.07-7.12 (2H, m), 7.15-7.28 (3H, m), 7.33 (1H, d, J=2.4 Hz), 7.43 (1H, d, J=9.0 Hz), 7.72 (1H, dd, J=9.0, 2.4 Hz).

Example 248

[Formula 73]

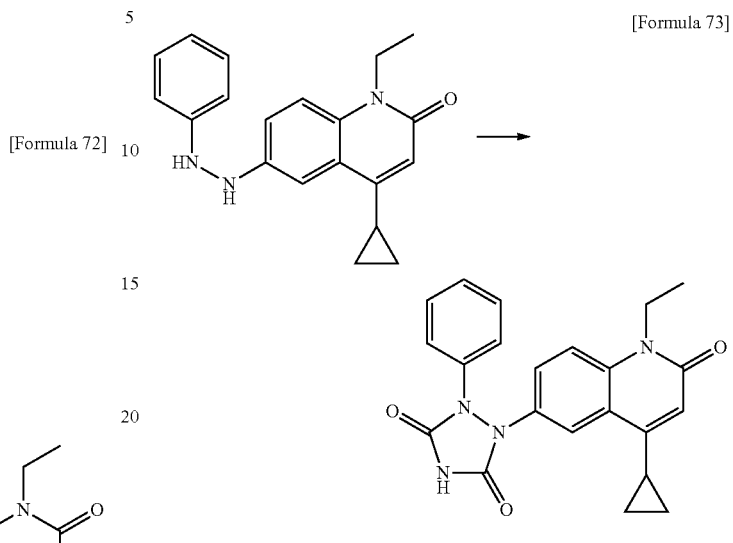

A mixture of 100 mg of 4-cyclopropyl-1-ethyl-6-(2-phenylhydrazinyl)quinolin-2(1H)-one, 46 mg of ethyl carbamoylcarbamate and 3 mL of toluene was stirred using a microwave apparatus at 140° C. for 1 hour 30 minutes. Thereafter, the reaction mixture was cooled to room temperature, and ethyl acetate and water were then added thereto. An organic layer was separated, was then successively washed with water and a saturated sodium chloride aqueous solution and was then dried over anhydrous magnesium sulfate. The solvent was distilled away under reduced pressure. The obtained residue was purified by silica gel column chromatography [gradient elution of hexane:ethyl acetate=50:50-0:100]. To the obtained residue, chloroform was added, and a solid was then collected by filtration, so as to obtain 15 mg of 1-(4-cyclopropyl-1-ethyl-2-oxo-1,2-dihydroquinolin-6-yl)-2-phenyl-1,2,4-triazolidine-3,5-dione in the form of a light brown solid.

$^1$H-NMR (DMS O-D$_6$) δ:0.57-0.65 (2H, m), 0.92-1.01 (2H, m), 1.14 (3H, t, J=7.0 Hz), 2.03-2.14 (1H, m), 4.20 (2H, q, J=7.1 Hz), 6.29 (1H, s), 7.20-7.27 (1H, m), 7.34-7.47 (4H, m), 7.60 (1H, d, J=9.3 Hz), 7.70 (1H, dd, J=9.1, 2.6 Hz), 8.03 (1H, d, J=2.4 Hz), 12.09 (1H, s).

Example 249

[Formula 74]

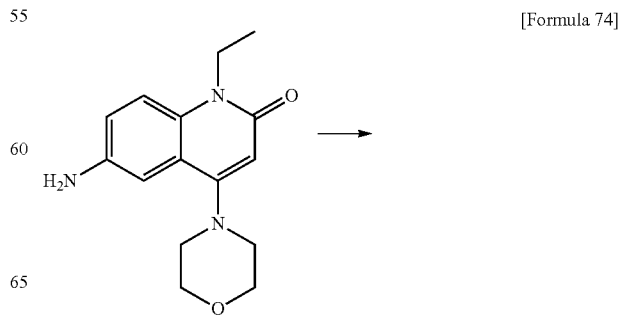

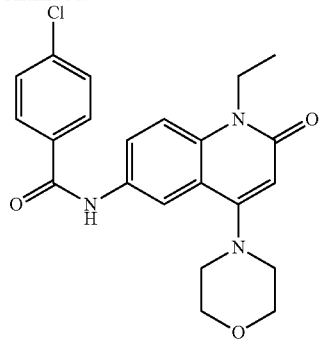

1.12 mL of 4-Chlorobenzoyl chloride was added to a suspension of 2.0 g of 6-amino-1-ethyl-4-(morpholin-4-yl)quinolin-2(1H)-one in 10 mL of pyridine under cooling on ice, and the obtained mixture was then stirred at room temperature for 1 hour. Thereafter, under cooling on ice, ethyl acetate and water were added to the reaction mixture, and the obtained mixture was then adjusted to pH 2.0 with 2 mol/L hydrochloric acid. A solid was collected by filtration, and was then washed with water and diisopropyl ether, so as to obtain 3.01 g of 4-chloro-N-(1-ethyl-4-(morpholin-4-yl)-2-oxo-1,2-dihydroquinolin-6-yl)benzamide in the form of a white solid.

$^1$H-NMR (DMSO-D$_6$): 1.19 (3H, t, J=7.0 Hz), 3.03-3.13 (4H, m), 3.81-3.90 (4H, m), 4.24 (2H, q, J=7.1 Hz), 6.04 (1H, s), 7.59 (1H, d, J=9.3 Hz), 7.64 (2H, d, J=8.5 Hz), 7.98 (1H, dd, J=9.3, 2.4 Hz), 8.01 (2H, d, J=8.5 Hz), 8.35 (1H, d, J=2.2 Hz), 10.48 (1H, s).

Example 250

[Formula 75]

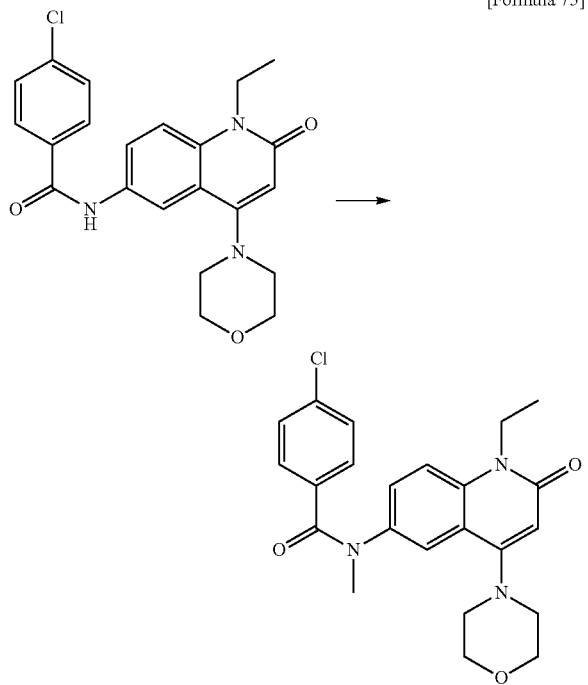

0.35 g of 60% sodium hydride was added to a suspension of 3.0 g of 4-chloro-N-(1-ethyl-4-(morpholin-4-yl)-2-oxo-1,2-dihydroquinolin-6-yl)benzamide in 24 mL of N,N-dimethylacetamide under cooling on ice, and the obtained mixture was then stirred for 10 minutes. Thereafter, under cooling on ice, 0.68 mL of methyl iodide was added to the reaction mixture, and the obtained mixture was then stirred at room temperature for 1 hour. Thereafter, ethyl acetate and ice water were added to the reaction mixture, and the obtained mixture was then adjusted to pH 2.0 with 2 mol/L hydrochloric acid. An organic layer was separated, was then washed with water and a saturated sodium chloride aqueous solution and was then dried over anhydrous magnesium sulfate. The solvent was distilled away under reduced pressure. To the obtained residue, diisopropyl ether and ethyl acetate were added, and a solid was collected by filtration and was then washed with diisopropyl ether, so as to obtain 2.55 g of 4-chloro-N-(1-ethyl-4-(morpholin-4-yl)-2-oxo-1,2-dihydroquinolin-6-yl)-N-methylbenzamide in the form of a white solid.

$^1$H-NMR (DMSO-D$_6$): 1.16 (3H, t, J=7.1 Hz), 2.45-2.60 (4H, m), 3.42 (3H, s), 3.60-3.71 (4H, m), 4.19 (2H, q, J=6.9 Hz), 5.96 (1H, s), 7.21 (1H, s), 7.28 (2H, d, J=8.3 Hz), 7.33 (2H, d, J=8.3 Hz), 7.60 (1H, d, J=9.0 Hz), 7.68 (1H, dd, J=9.0, 2.2 Hz).

Example 251

[Formula 76]

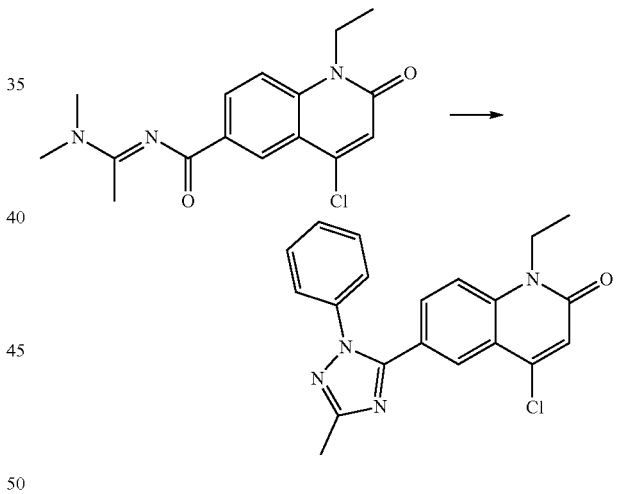

A mixture of 1.5 g of 4-chloro-N-((1E)-1-(dimethylamino)ethylidene)-1-ethyl-2-oxo-1,2-dihydroquinoline-6-carboxamide, 0.51 ml of phenyl hydrazine and 12 mL of acetic acid was stirred at an external temperature of 120° C. for 2 hours. Thereafter, the reaction mixture was cooled to room temperature, and the solvent was then distilled away under reduced pressure. To the obtained residue, diisopropyl ether and ethyl acetate were added, and a solid was collected by filtration and was then washed with diisopropyl ether, so as to obtain 1.37 g of 4-chloro-1-ethyl-6-(3-methyl-1-phenyl-1H-1,2,4-triazol-5-yl)quinolin-2(1H)-on e in the form of a light brown solid.

$^1$H-NMR (DMSO-D$_6$) δ:1.18 (3H, t, J=7.1 Hz), 2.41 (3H, s), 4.25 (2H, q, J=6.9 Hz), 6.97 (1H, s), 7.44-7.58 (5H, m), 7.72 (1H, d, J=9.0 Hz), 7.77 (1H, dd, J=9.0, 2.0 Hz), 7.99 (1H, d, J=2.0 Hz).

Example 252

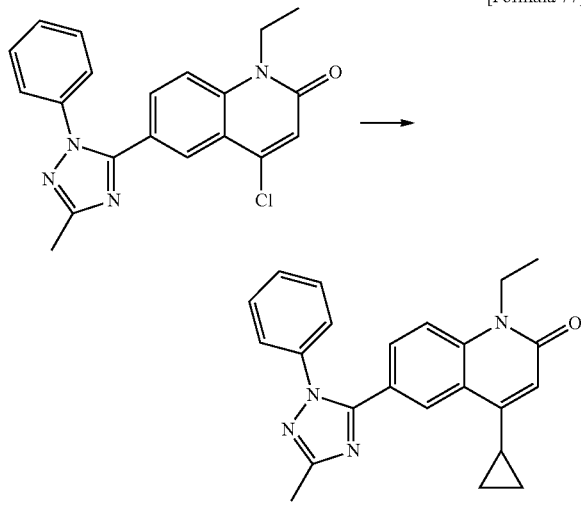

[Formula 77]

A mixture of 1.37 g of 4-chloro-1-ethyl-6-(3-methyl-1-phenyl-1H-1,2,4-triazol-5-yl)quinolin-2(1H)-on e, 0.48 g of cyclopropylboric acid, 1.6 g of tripotassium phosphate, 0.26 g of bis(di-tert-butyl(4-dimethylaminophenyl)phosphine)dichloropalladium(II), 15 mL of dioxane and 3.0 mL of water was stirred under a nitrogen atmosphere, at an external temperature of 100° C. to 110° C. for 3 hours. Thereafter, the reaction mixture was cooled to room temperature, and ethyl acetate and water were then added thereto. An organic layer was separated, was then successively washed with water and a saturated sodium chloride aqueous solution and was then dried over anhydrous magnesium sulfate. The solvent was distilled away under reduced pressure. The obtained residue was purified by silica gel column chromatography [gradient elution of hexane:ethyl acetate=50:50-0:100]. To the obtained residue, diisopropyl ether and cyclohexane were added, and a solid was then collected by filtration, so as to obtain 1.10 g of 4-cyclopropyl-1-ethyl-6-(3-methyl-1-phenyl-1H-1,2,4-triazol-5-yl)quinolin-2(1H)-one in the form of a slightly brown solid.

$^1$H-NMR (DMS O-D$_6$) δ:0.54-0.61 (2H, m), 0.70-0.79 (2H, m), 1.17 (3H, t, J=7.1 Hz), 1.70-1.79 (1H, m), 2.40 (3H, s), 4.23 (2H, q, J=7.1 Hz), 6.31 (1H, s), 7.42-7.57 (5H, m), 7.64 (1H, d, J=9.0 Hz), 7.81 (1H, dd, J=8.9, 2.1 Hz), 8.03 (1H, d, J=2.0 Hz).

Example 253

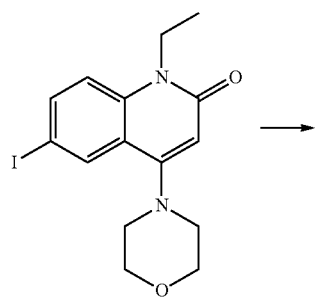

[Formula 78]

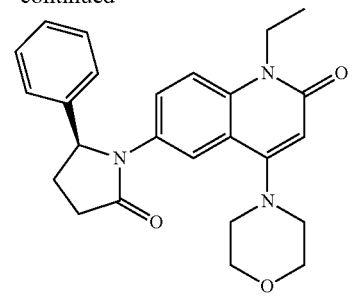

A mixture of 41 mg of 1-ethyl-6-iodo-4-(morpholin-4-yl)quinolin-2(1H)-one, 17 mg of (5S)-5-phenylpyrrolidin-2-one, 1 mg of copper(I) iodide, 4 mg of 4,7-dimethoxy-1,10-phenanthroline, 48 mg of cesium carbonate and 0.5 mL of N-methyl-2-pyrrolidone was stirred at an external temperature of 130° C. to 135° C. for 30 minutes. Thereafter, the reaction mixture was cooled to room temperature, ethyl acetate was then added to the reaction mixture, and insoluble matters were then removed by filtration. Water and a saturated sodium chloride aqueous solution were added to the filtrate. An organic layer was separated, was then washed with a saturated sodium chloride aqueous solution and was then dried over anhydrous sodium sulfate. The solvent was distilled away under reduced pressure. The obtained residue was purified by basic silica gel chromatography [gradient elution of hexane:ethyl acetate=70:30-40:60]. To the obtained residue, diisopropyl ether was added, and a solid was then collected by filtration, so as to obtain 23 mg of 1-ethyl-4-(morpholin-4-yl)-6-((5S)-2-oxo-5-phenylpyrrolidin-1-yl)quinolin-2(1H)-one in the form of a light yellow solid.

$^1$H-NMR (CDCl$_3$) δ: 1.29 (3H, t, J=7.2 Hz), 2.02-2.08 (1H, m), 2.60-2.97 (7H, m), 3.73-3.80 (4H, m), 4.20-4.33 (2H, m), 5.29-5.32 (1H, m), 6.11 (1H, s), 7.23-7.35 (6H, m), 7.75 (1H, d, J=2.4 Hz), 7.81 (1H, dd, J=8.8, 2.4 Hz).

Example 254

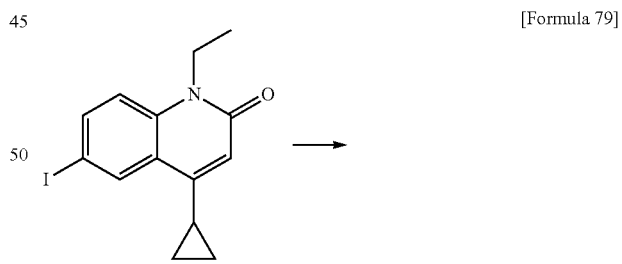

[Formula 79]

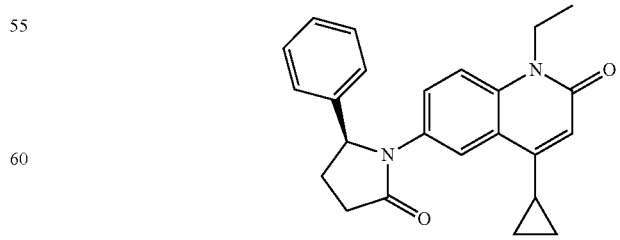

A mixture of 38 mg of 4-cyclopropyl-1-ethyl-6-iodoquinolin-2(1H)-one, 18 mg of (5S)-5-phenylpyrrolidin-2-one, 1 mg of copper(I) iodide, 4 mg of 4,7-dimethoxy-1,10- phenanthroline, 51 mg of cesium carbonate and 0.5 mL of N-methyl-2-pyrrolidone was stirred at an external temperature of 130° C. to 135° C. for 1 hour 15 minutes. Thereafter, the reaction mixture was cooled to room temperature, ethyl acetate was then added to the reaction mixture, and insoluble matters were then removed by filtration. Water and a saturated sodium chloride aqueous solution were added to the filtrate. An organic layer was separated, was then washed with a saturated sodium chloride aqueous solution and was then dried over anhydrous sodium sulfate. The solvent was distilled away under reduced pressure. The obtained residue was purified by basic silica gel chromatography [gradient elution of hexane:ethyl acetate=80: 20-60:40], to obtain 22 mg of 4-cyclopropyl-1-ethyl-6-((5S)-2-oxo-5-phenylpyrrolidin-1-yl)quinolin-2(1H)-one in the form of a light yellow solid.

¹H-NMR (CDCl₃) δ:0.50-0.57 (1H, m), 0.6-00.71 (1H, m), 0.82-0.99 (2H, m), 1.28 (3H, t, J=7.2 Hz), 1.79-1.86 (1H, m), 2.05-2.12 (1H, m), 2.63-2.85 (3H, m), 4.26 (2H, q, J=7.5 Hz), 5.27-5.30 (1H, m), 6.39 (1H, d, J=1.2 Hz), 7.25-7.40 (6H, m), 7.79 (1H, dd, J=9.2, 2.4 Hz), 7.99 (1H, d, J=2.4 Hz).

Example 255

[Formula 80]

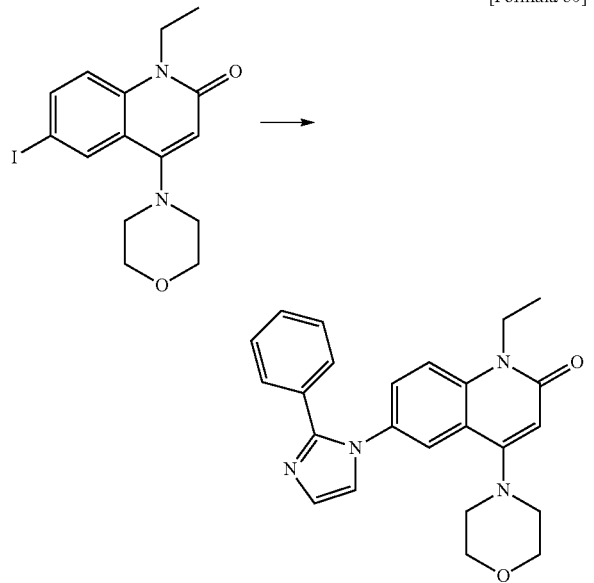

A mixture of 60 mg of 1-ethyl-6-iodo-4-(morpholin-4-yl)quinolin-2(1H)-one, 25 mg of 2-phenyl-1H-imidazole, 1.1 mg of copper(I) oxide, 5.6 mg of 4,7-dimethoxy-1,10-phenanthroline, 29 mg of polyethylene glycol, 71 mg of cesium carbonate and 4 mL of butyronitrile was stirred under a nitrogen atmosphere, using a microwave apparatus, at 170° C. for 40 minutes. Thereafter, the reaction mixture was cooled to room temperature, and ethyl acetate and water were then added thereto. An organic layer was separated, was then washed with a saturated sodium chloride aqueous solution and was then dried over anhydrous sodium sulfate. The solvent was distilled away under reduced pressure. The obtained residue was purified by preparative thin layer chromatography. To the obtained residue, hexane was added, and a solid was then collected by filtration, so as to obtain 10 mg of 1-ethyl-4-(morpholin-4-yl)-6-(2-phenyl-1H-imidazol-1-yl)quinolin-2(1H)-one in the form of a white solid.

¹H-NMR (DMS O-D₆) δ: 1.20 (3H, t, J=7.3 Hz), 2.57-2.66 (4H, m), 3.42-3.52 (4H, m), 4.26 (2H, q, J=6.8 Hz), 6.03 (1H, s), 7.22 (1H, d, J=1.3 Hz), 7.28-7.38 (6H, m), 7.59 (1H, s), 7.71-7.77 (2H, m).

MS (ESI, m/z): 401 (M+H)

Example 256

[Formula 81]

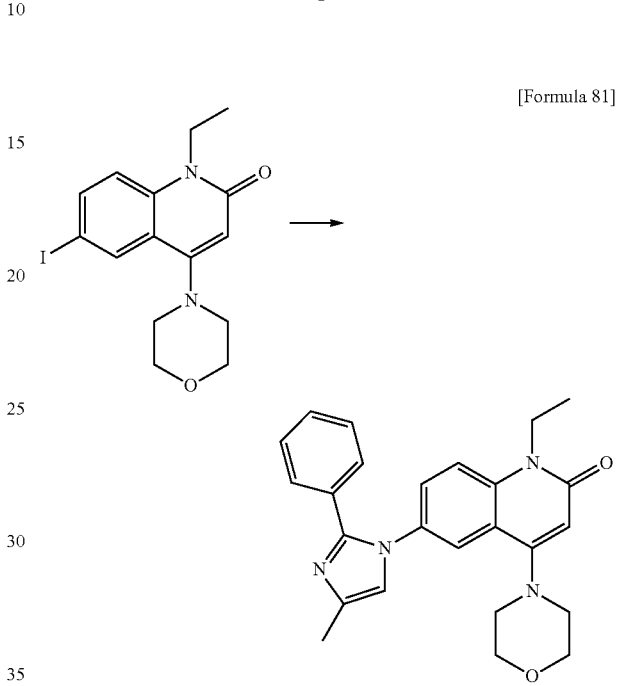

A mixture of 50 mg of 1-ethyl-6-iodo-4-(morpholin-4-yl)quinolin-2(1H)-one, 23 mg of 4-methyl-2-phenyl-1H-imidazole, 1.9 mg of copper(I) oxide, 6.2 mg of 4,7-dimethoxy-1,10-phenanthroline, 25 mg of polyethylene glycol, 64 mg of cesium carbonate and 1.5 mL of butyronitrile was stirred under a nitrogen atmosphere, using a microwave apparatus, at 210° C. for 45 minutes. Thereafter, 1.9 mg of copper(I) oxide was added to the reaction mixture, and the obtained mixture was then stirred using a microwave apparatus at 225° C. for 45 minutes. Thereafter, 6.0 mg of copper(I) oxide and 6.2 mg of 4,7-dimethoxy-1,10-phenanthroline were added to the reaction mixture, and the obtained mixture was then stirred using a microwave apparatus at 230° C. for 1 hour 30 minutes. Thereafter, the reaction mixture was cooled to room temperature, insoluble matters were then removed by filtration, and ethyl acetate and water were then added to the residue. An organic layer was separated, was then washed with a saturated sodium chloride aqueous solution, and was then dried over anhydrous sodium sulfate. The solvent was distilled away under reduced pressure. The obtained residue was purified by preparative thin layer chromatography. To the obtained residue, diisopropyl ether was added, and a solid was then collected by filtration, so as to obtain 5 mg of 1-ethyl-6-(4-methyl-2-phenyl-1H-imidazol-1-yl)-4-(morpholin-4-yl)quinolin-2(1H)-one in the form of a white solid.

¹H-NMR (DMSO-D₆) δ:1.20 (3H, t, J=6.9 Hz), 2.23 (3H, s), 2.56-2.66 (4H, m), 3.41-3.51 (4H, m), 4.20-4.30 (2H, m), 6.02 (1H, s), 7.22-7.36 (7H, m), 7.67-7.76 (2H, m).

MS (ESI, m/z): 415 (M+H)

Example 257

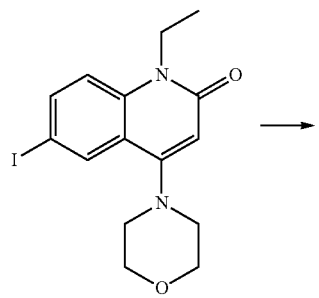

→

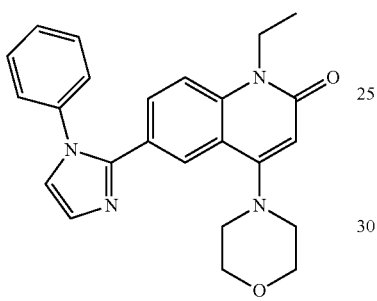

A mixture of 50 mg of 1-ethyl-6-iodo-4-(morpholin-4-yl) quinolin-2(1H)-one, 28 mg of 1-phenyl-1H-imidazole, 50 mg of copper(I) iodide, 1.5 mg of palladium acetate and 2 mL of N,N-dimethylacetamide was stirred under a nitrogen atmosphere, using a microwave apparatus, at 185° C. for 30 minutes. The reaction mixture was further stirred at 205° C. for 20 minutes. Thereafter, the reaction mixture was cooled to room temperature, and N,N-dimethylacetamide was then distilled away under reduced pressure. To the obtained residue, methanol was added, and a solid was then collected by filtration. To the obtained solid, chloroform was added, and the obtained mixture was then heated to reflux for 10 minutes. Thereafter, the reaction mixture was cooled to room temperature, insoluble matters were then removed by filtration, and the filtrate was then purified by silica gel column chromatography [chloroform:methanol]. To the obtained residue, hexane and ethyl acetate were added, and a solid was then collected by filtration, so as to obtain 10 mg of 1-ethyl-4-(morpholin-4-yl)-6-(1-phenyl-1H-imidazol-2-yl)quinolin-2(1H)-one in the form of a light brown solid.

$^1$H-NMR (DMSO-D$_6$) δ:1.16 (3H, t, J=6.9 Hz), 2.64-2.73 (4H, m), 3.47-3.57 (4H, m), 4.19 (2H, q, J=7.0 Hz), 5.97 (1H, s), 7.23-7.38 (3H, m), 7.39-7.63 (6H, m), 7.74-7.85 (1H, m).

MS (ESI, m/z): 401 (M+H)

[Formula 82]

Example 258

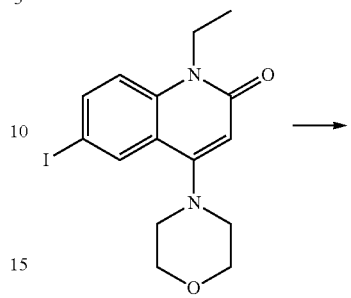

→

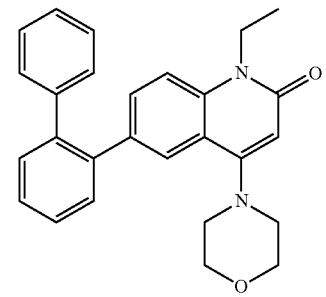

[Formula 83]

A mixture of 50 mg of 1-ethyl-6-iodo-4-(morpholin-4-yl) quinolin-2(1H)-one, 28 mg of biphenyl-2-ylboronic acid, 6 mg of tris(dibenzylideneacetone)dipalladium(0), 85 mg of cesium carbonate and 2 mL of dioxane was stirred under a nitrogen atmosphere, using a microwave apparatus, at 150° C. for 30 minutes. Then, the reaction mixture was further stirred at 160° C. for 30 minutes. Thereafter, the reaction mixture was cooled to room temperature, insoluble matters were then removed by filtration, and the solvent was then distilled away under reduced pressure. The obtained residue was purified by silica gel column chromatography [hexane:ethyl acetate]. To the obtained residue, hexane and ethyl acetate were added, and a solid was then collected by filtration, so as to obtain 6 mg of 6-(biphenyl-2-yl)-1-ethyl-4-(morpholin-4-yl)quinolin-2(1H)-one in the form of a white solid.

$^1$H-NMR (DMSO-D$_6$) δ:1.19 (3H, t, J=6.9 Hz), 2.46-2.55 (4H, m), 3.50-3.58 (4H, m), 4.23 (2H, q, J=7.0 Hz), 5.93 (1H, s), 7.13-7.22 (3H, m), 7.23-7.31 (3H, m), 7.42-7.53 (4H, m), 7.59-7.70 (2H, m).

MS (ESI, m/z): 411 (M+H)

Example 259 to 276

In accordance with the procedures described in the present description, the obtained compounds were subjected to a known reaction such as condensation, addition, oxidation, reduction, transposition, substitution, halogenation, dehydration or hydrolysis, or by combining these reactions with one another, as appropriate, so as to produce the compounds shown in Tables 26 to 28.

TABLE 26

| Example No. | Structural Formula | Compound Name | MS |
|---|---|---|---|
| 259 | | 1-ethyl-4-(morpholin-4-yl)-6-(2-oxo-5-phenyl-3-(2-(piperidin-1-yl)ethyl)-2,3-dihydro-1H-imidazol-1-yl)quinolin-2(1H)-one | 528 (M + H) |
| 260 | | 1-ethyl-4-(morpholin-4-yl)-6-(3-(2-morpholin-4-yl)ethyl)-2-oxo-5-phenyl-2,3-dihydro-1H-imidazol-1-yl)quinolin-2(1H)-one | 530 (M + H) |
| 261 | | 6-(3-(2-(dimethylamino)ethyl)-2-oxo-5-phenyl-2,3-dihydro-1H-imidazol-1-yl)-1-ethyl-4-(morpholin-4-yl)quinolin-2(1H)-one | 488 (M + H) |
| 262 | | 1-ethyl-6-(3-(2-hydroxyethyl)-2-oxo-5-phenyl-2,3-dihydro-1H-imidazol-1-yl)-4-(morpholin-4-yl)quinolin-2(1H)-one | 461 (M + H) |

TABLE 26-continued

| Example No. | Structural Formula | Compound Name | MS |
|---|---|---|---|
| 263 | | 1-ethyl-6-(3-(2-methoxyethyl)-2-oxo-5-phenyl-2,3-dihydro-1H-imidazol-1-yl)-4-(morpholin-4-yl)quinolin-2(1H)-one | 475 (M + H) |
| 264 | | 6-(3-butyl-2-oxo-5-phenyl-2,3-dihydro-1H-imidazol-1-yl)-1-ethyl-4-(morpholin-4-yl)quinolin-2(1H)-one | 473 (M + H) |
| 265 | | 1-ethyl-4-(morpholin-4-yl)-6-(2-oxo-5-phenyl-3-propyl-2,3-dihydro-1H-imidazol-1-yl)quinolin-2(1H)-one | 459 (M + H) |
| 266 | | 1-ethyl-6-(3-ethyl-2-oxo-5-phenyl-2,3-dihydro-1H-imidazol-1-yl)-4-(morpholin-4-yl)quinolin-2(1H)-one | 445 (M + H) |

TABLE 27

| Example No. | Structural Formula | Compound Name | MS |
|---|---|---|---|
| 267 | | 4-cyclopropyl-1-ethyl-6-(3-methyl-2-oxo-5-(4-(trifluoromethyl)phenyl)-2,3-dihydro-1H-imidazol-1-yl)quinolin-2(1H)-one | 454 (M + H) |
| 268 | | 4-cyclopropyl-1-ethyl-6-(2-oxo-5-(4-(trifluoromethyl)phenyl)-2,3-dihydro-1H-imidazol-1-yl)quinolin-2(1H)-one | 440 (M + H) |
| 269 | | 6-(5-(4-chlorophenyl)-3-methyl-2-oxo-2,3-dihydro-1H-imidazol-1-yl)-4-cyclopropyl-1-ethylquinolin-2(1H)-one | 420 (M + H) |
| 270 | | 1-ethyl-6-(3-methyl-2-oxo-5-(4-(trifluoromethyl)phenyl)-2,3-dihydro-1H-imidazol-1-yl)-4-(morpholin-4-yl)quinolin-2(1H)-one | 499 (M + H) |

TABLE 27-continued

| Example No. | Structural Formula | Compound Name | MS |
|---|---|---|---|
| 271 | | 6-(5-(4-chlorophenyl)-2-oxo-2,3-dihydro-1H-imidazol-1-yl)-4-cyclopropyl-1-ethylquinolin-2(1H)-one | 406 (M + H) |
| 272 | | 1-ethyl-6-(2-oxo-5-(4-(trifluoromethyl)phenyl)-2,3-dihydro-1H-imidazol-1-yl)-4-(morpholin-4-yl)quinolin-2(1H)-one | 485 (M + H) |
| 273 | | 1-ethyl-6-(3-methyl-5-(4-methylphenyl)-2-oxo-2,3-dihydro-1H-imidazol-1-yl)-4-(morpholin-4-yl)quinolin-2(1H)-one | 445 (M + H) |

TABLE 28

| Example No. | Structural Formula | Compound Name | MS |
|---|---|---|---|
| 274 | | 1-ethyl-6-(5-(4-methylphenyl)-2-oxo-2,3-dihydro-1H-imidazol-1-yl)-4-(morpholin-4-yl)quinolin-2(1H)-one | 431 (M + H) |

TABLE 28-continued

| Example No. | Structural Formula | Compound Name | MS |
|---|---|---|---|
| 275 | | 4-cyclopropyl-1-ethyl-6-(3-methyl-(5-(4-methylphenyl)-2-oxo-2,3-dihydro-1H-imidazol-1-yl)quinolin-2(1H)-one | 400 (M + H) |
| 276 | | 4-cyclopropyl-1-ethyl-6-(5-(4-methylphenyl)-2-oxo-2,3-dihydro-1H-imidazol-1-yl)quinolin-2(1H)-one | 386 (M + H) |

Example 277

[Formula 84]

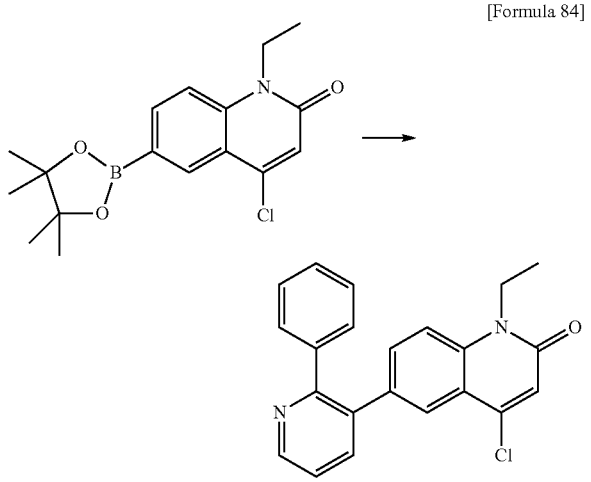

A mixture of 0.17 g of 4-chloro-1-ethyl-6-(4,4,5,5-tetramethyl-1,3,2-dioxaborolan-2-yl)quinolin-2(1H)-one, 0.11 g of 3-bromo-2-phenylpyridine, 0.20 g of tripotassium phosphate, 33 mg of bis(di-tert-butyl(4-dimethylaminophenyl)phosphine)dichloropalladium(II), 6 mL of dioxane and 2 mL of water was stirred under a nitrogen atmosphere at an external temperature of 100° C. to 110° C. for 1 hour. Thereafter, the reaction mixture was cooled to room temperature, and ethyl acetate and water were then added thereto. An organic layer was separated, and a water layer was then extracted with ethyl acetate. The organic layer was gathered with the extract, and the obtained mixture was then washed with a saturated sodium chloride aqueous solution and was then dried over anhydrous sodium sulfate. The solvent was distilled away under reduced pressure. The obtained residue was purified by silica gel chromatography [gradient elution of hexane:ethyl acetate=100:0-60:40], to obtain 134 mg of 4-chloro-1-ethyl-6-(2-phenylpyridin-3-yl)quinolin-2(1H)-one in the form of a white foam.

$^1$H-NMR (CDCl$_3$) δ:1.33 (3H, t, J=7.1 Hz), 4.31 (2H, q, J=7.1 Hz), 6.89 (1H, s), 7.24-7.29 (3H, m), 7.32-7.42 (5H, m), 7.81 (1H, dd, J=7.6, 1.7 Hz), 7.94 (1H, d, J=2.2 Hz), 8.74 (1H, dd, J=4.8, 1.7 Hz).

Example 278

[Formula 85]

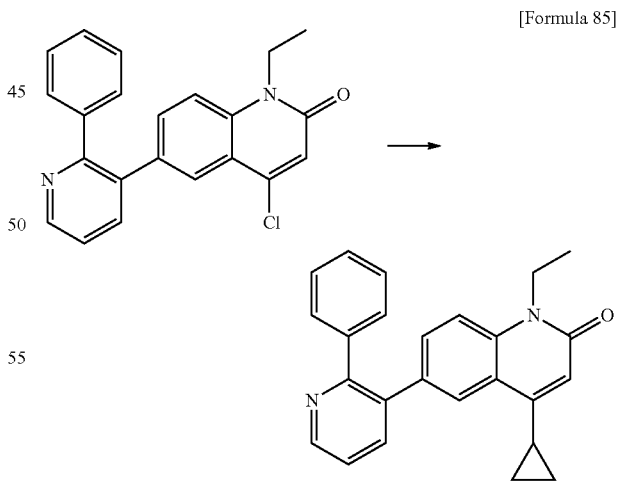

A mixture of 36 mg of 4-chloro-1-ethyl-6-(2-phenylpyridin-3-yl)quinolin-2(1H)-one, 17 mg of cyclopropylboric acid, 43 mg of tripotassium phosphate, 8 mg of bis(di-tert-butyl(4-dimethylaminophenyl)phosphine)dichloropalladium(II), 0.6 mL of dioxane and 0.2 mL of water was stirred using a microwave apparatus at 120° C. for 15 minutes.

Thereafter, the reaction mixture was cooled to room temperature, and ethyl acetate and water were then added thereto. An organic layer was separated, and a water layer was then extracted with ethyl acetate. The organic layer was gathered with the extract, and the solvent was then distilled away under reduced pressure. The obtained residue was purified by silica gel chromatography [gradient elution of hexane:ethyl acetate=100:0-50:50]. To the obtained residue, hexane was added, and a solid was then collected by filtration, so as to obtain 3 mg of 4-cyclopropyl-1-ethyl-6-(2-phenylpyridin-3-yl)quinolin-2(1H)-one in the form of a white solid.

$^1$H-NMR (CDCl$_3$) δ: 0.53-0.59 (2H, m), 0.81-0.92 (2H, m), 1.34 (3H, t, J=7.1 Hz), 1.71-1.80 (1H, m), 4.33 (2H, q, J=7.3 Hz), 6.39-6.44 (1H, m), 7.20-7.49 (8H, m), 7.82 (1H, dd, J=7.6, 1.5 Hz), 7.87 (1H, d, J=2.2 Hz), 8.73 (1H, dd, J=4.6, 1.5 Hz).

Example 279

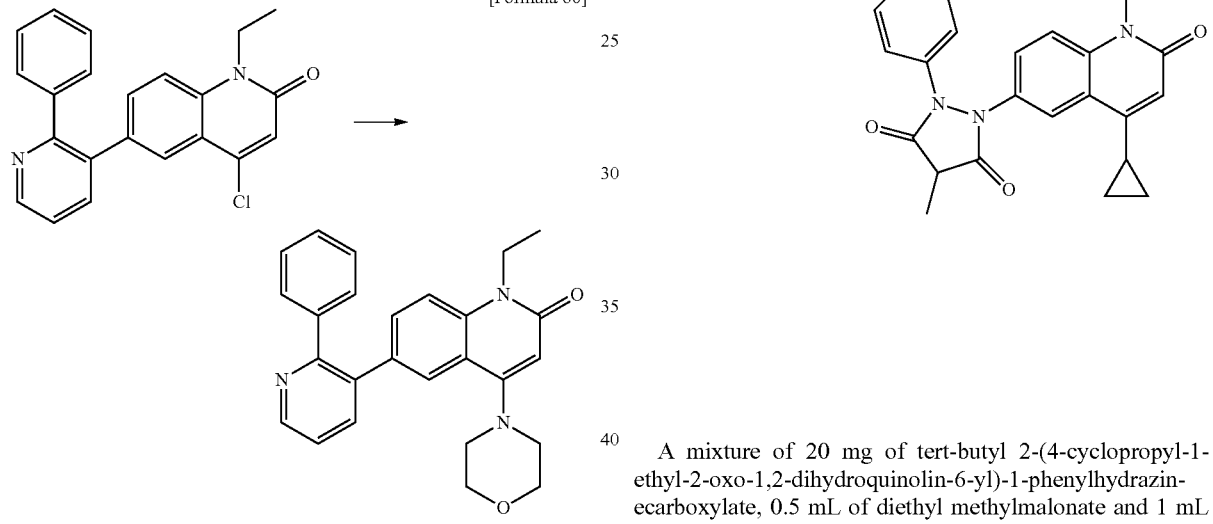

[Formula 86]

A mixture of 30 mg of 4-chloro-1-ethyl-6-(2-phenylpyridin-3-yl)quinolin-2(1H)-one, 0.7 mL of N,N-dimethylformamide, 35 mg of potassium carbonate and 21.5 μL of morpholine was stirred using a microwave apparatus at 150° C. for 5 minutes. Then, the reaction mixture was further stirred at 200° C. for 40 minutes. Thereafter, the reaction mixture was cooled to room temperature, and ethyl acetate and water were then added thereto. An organic layer was separated, and a water layer was then extracted with ethyl acetate. The organic layer was gathered with the extract, and the solvent was then distilled away under reduced pressure. The obtained residue was purified by silica gel chromatography [gradient elution of hexane:ethyl acetate=100:0-0:100-chloroform:methanol=95:5]. To the obtained residue, hexane and ethyl acetate were added, and a solid was then collected by filtration, so as to obtain 8 mg of 1-ethyl-4-(morpholin-4-yl)-6-(2-phenylpyridin-3-yl)quinolin-2(1H)-one in the form of a brown solid.

$^1$H-NMR (CDCl$_3$) δ: 1.38 (3H, t, J=7.1 Hz), 2.57-2.65 (4H, m), 3.57-3.66 (4H, m), 4.34 (2H, q, J=7.2 Hz), 6.09 (1H, s), 7.20-7.29 (2H, m), 7.35-7.49 (6H, m), 7.61 (1H, dd, J=8.7, 2.1 Hz), 7.74 (1H, dd, J=7.6, 1.7 Hz), 8.73 (1H, dd, J=4.9, 1.7 Hz).

Example 280

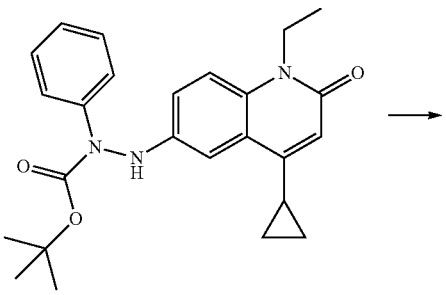

[Formula 87]

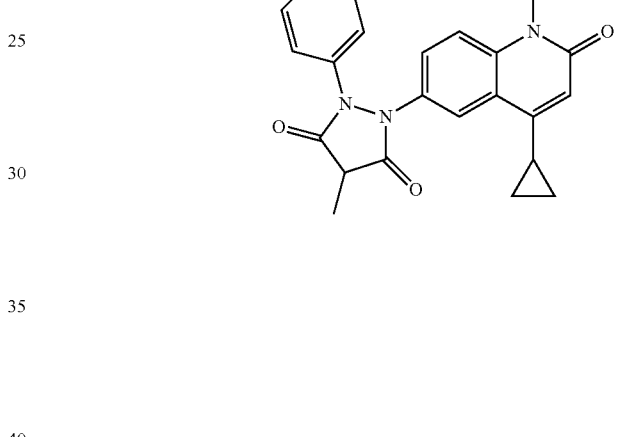

A mixture of 20 mg of tert-butyl 2-(4-cyclopropyl-1-ethyl-2-oxo-1,2-dihydroquinolin-6-yl)-1-phenylhydrazinecarboxylate, 0.5 mL of diethyl methylmalonate and 1 mL of a 20% sodium ethoxide-ethanol solution was stirred using a microwave apparatus at 180° C. for 3 minutes. Thereafter, the reaction mixture was cooled to room temperature, ethyl acetate and water were then added thereto, and the obtained mixture was then adjusted to pH 1.0 with 2 mol/L hydrochloric acid. An organic layer was separated, and a water layer was then extracted with ethyl acetate. The organic layer was gathered with the extract, and the obtained mixture was washed with a saturated sodium chloride aqueous solution and was then dried over anhydrous magnesium sulfate. The solvent was distilled away under reduced pressure. The obtained residue was purified by silica gel column chromatography [gradient elution of chloroform:methanol=100:0-95:5]. To the obtained residue, ethyl acetate was added, and a solid was then collected by filtration, so as to obtain 6 mg of 1-(4-cyclopropyl-1-ethyl-2-oxo-1,2-dihydroquinolin-6-yl)-4-methyl-2-phenylpyrazolidine-3,5-dione in the form of a white solid.

$^1$H-NMR (CDCl$_3$) δ: 0.58-0.65 (2H, m), 0.95-1.03 (2H, m), 1.30 (3H, t, J=7.1 Hz), 1.64 (3H, d, J=7.8 Hz), 1.84-1.94 (1H, m), 3.47 (1H, q, J=7.7 Hz), 4.27 (2H, q, J=7.2 Hz), 6.44 (1H, d, J=1.2 Hz), 7.18-7.24 (1H, m), 7.31-7.39 (5H, m), 7.61 (1H, dd, J=9.1 Hz, 2.6 Hz), 7.94 (1H, d, J=2.4 Hz).

Example 281

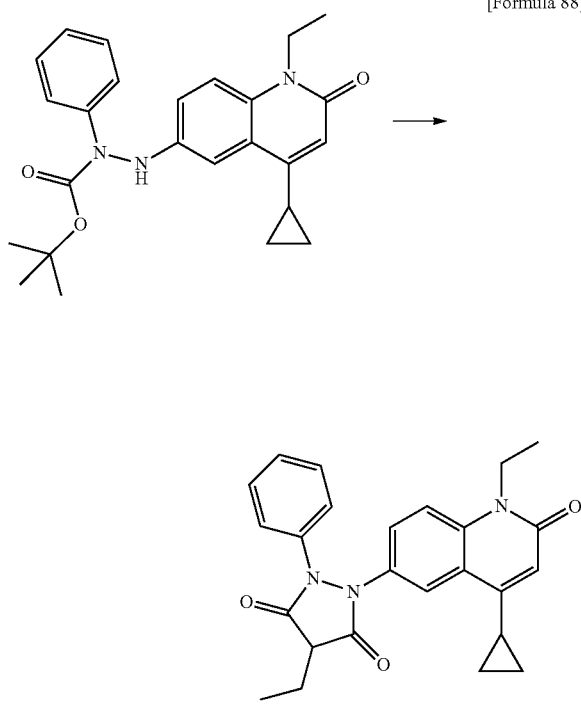

[Formula 88]

A mixture of 20 mg of tert-butyl 2-(4-cyclopropyl-1-ethyl-2-oxo-1,2-dihydroquinolin-6-yl)-1-phenylhydrazinecarboxylate, 0.5 mL of diethyl diethylmalonate and 1 mL of a 20% sodium ethoxide-ethanol solution was stirred using a microwave apparatus at 150° C. for 3 minutes. Thereafter, the reaction mixture was cooled to room temperature, ethyl acetate and water were then added thereto, and the obtained mixture was then adjusted to pH 1.0 with 2 mol/L hydrochloric acid. An organic layer was separated, and a water layer was then extracted with ethyl acetate. The organic layer was gathered with the extract, and the obtained mixture was washed with a saturated sodium chloride aqueous solution, and was then dried over anhydrous magnesium sulfate. The solvent was distilled away under reduced pressure. The obtained residue was purified by silica gel column chromatography [gradient elution of chloroform:methanol=100:0-95:5]. To the obtained residue, diisopropyl ether was added, and a solid was then collected by filtration, so as to obtain 8 mg of 1-(4-cyclopropyl-1-ethyl-2-oxo-1,2-dihydroquinolin-6-yl)-4-ethyl-2-phenylpyrazolidine-3,5-dione in the form of a light yellow solid.

$^1$H-NMR (CDCl$_3$) δ:0.58-0.65 (2H, m), 0.95-1.02 (2H, m), 1.10-1.18 (3H, m), 1.30 (3H, t, J=7.2 Hz), 1.85-1.94 (1H, m), 2.15-2.24 (2H, m), 3.42 (1H, t, J=5.5 Hz), 4.27 (2H, q, J=7.2 Hz), 6.42-6.45 (1H, m), 7.18-7.24 (1H, m), 7.31-7.40 (5H, m), 7.61 (1H, dd, J=9.1 Hz, 2.6 Hz), 7.95 (1H, d, J=2.4 Hz).

Example 282a, 282b

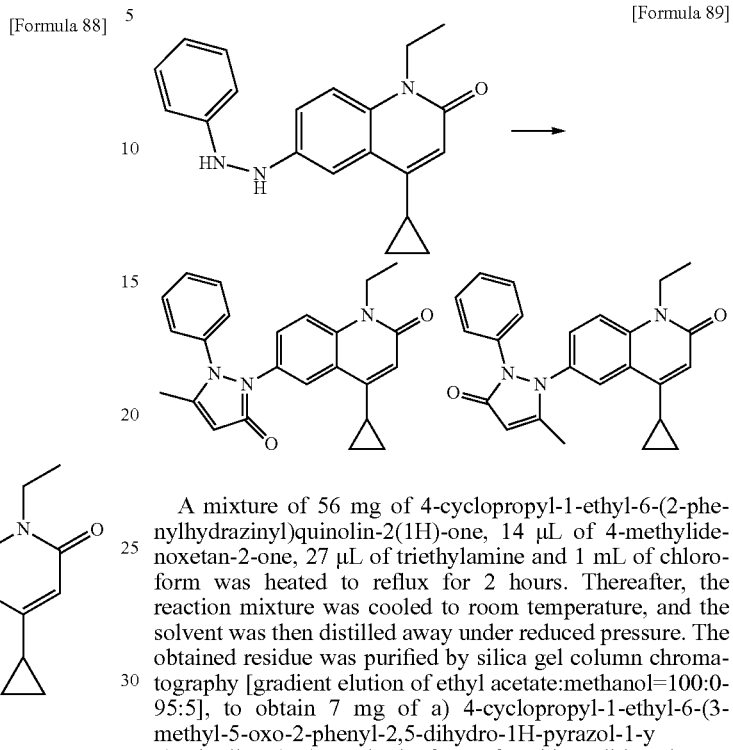

[Formula 89]

A mixture of 56 mg of 4-cyclopropyl-1-ethyl-6-(2-phenylhydrazinyl)quinolin-2(1H)-one, 14 μL of 4-methylidenoxetan-2-one, 27 μL of triethylamine and 1 mL of chloroform was heated to reflux for 2 hours. Thereafter, the reaction mixture was cooled to room temperature, and the solvent was then distilled away under reduced pressure. The obtained residue was purified by silica gel column chromatography [gradient elution of ethyl acetate:methanol=100:0-95:5], to obtain 7 mg of a) 4-cyclopropyl-1-ethyl-6-(3-methyl-5-oxo-2-phenyl-2,5-dihydro-1H-pyrazol-1-y 1)quinolin-2(1H)-one in the form of a white solid, and 4 mg of b) 4-cyclopropyl-1-ethyl-6-(5-methyl-3-oxo-2-phenyl-2,3-dihydro-1H-pyrazol-1-y 1)quinolin-2(1H)-one in the form of a white solid.

a)
4-Cyclopropyl-1-ethyl-6-(3-methyl-5-oxo-2-phenyl-2,5-dihydro-1H-pyrazol-1-y 1)quinolin-2(1H)-one $^1$H-NMR (CDCl$_3$) δ:0.63-0.69 (2H, m), 0.99-1.05 (2H, m), 1.28 (3H, t, J=7.2 Hz), 1.91-2.00 (1H, m), 2.12 (3H, d, J=1.0 Hz), 4.26 (2H, q, J=7.0 Hz), 5.61 (1H, d, J=0.7 Hz), 6.40 (1H, d, J=1.0 Hz), 7.21-7.39 (6H, m), 7.71 (1H, dd, J=9.3 Hz, 2.4 Hz), 7.95 (1H, d, J=2.4 Hz).

b)
4-Cyclopropyl-1-ethyl-6-(5-methyl-3-oxo-2-phenyl-2,3-dihydro-1H-pyrazol-1-yl)quinolin-2(1H)-one $^1$H-NMR (CDCl$_3$) δ: 0.64-0.70 (2H, m), 1.02-1.09 (2H, m), 1.30 (3H, t, J=7.1 Hz), 1.90-1.99 (1H, m), 2.14 (3H, s), 4.27 (2H, q, J=7.0 Hz), 5.61-5.65 (1H, m), 6.44-6.48 (1H, m), 7.13 (1H, t, J=7.3 Hz), 7.22-7.42 (6H, m), 7.87 (1H, d, J=2.2 Hz).

Example 283

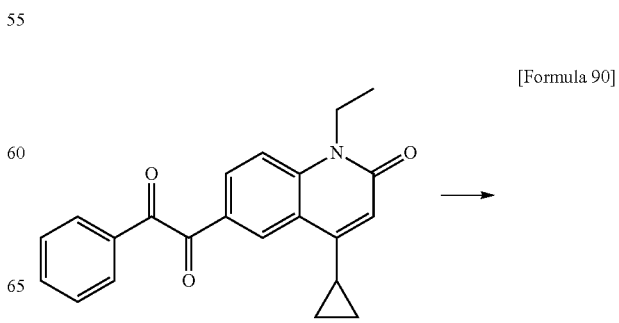

[Formula 90]

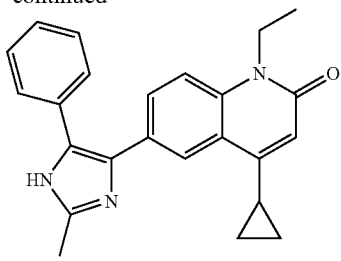

A mixture of 40 mg of 1-(4-cyclopropyl-1-ethyl-2-oxo-1,2-dihydroquinolin-6-yl)-2-phenylethane-1,2-dione, 1 mL of acetic acid, 89 mg of ammonium acetate and 32 μL of acetaldehyde was stirred using a microwave apparatus at 120° C. for 5 minutes. Then, the reaction mixture was further stirred at 140° C. for 5 minutes. Thereafter, the reaction mixture was cooled to room temperature, and ethyl acetate and a saturated sodium hydrogen carbonate aqueous solution were added thereto. An organic layer was separated, and a water layer was then extracted with ethyl acetate. The organic layer was gathered with the extract, and the obtained mixture was washed with a saturated sodium chloride aqueous solution and was then dried over anhydrous magnesium sulfate. The solvent was distilled away under reduced pressure. The obtained residue was purified by silica gel chromatography [gradient elution of ethyl acetate:methanol=100:0-90:10]. To the obtained residue, diisopropyl ether was added, and a solid was then collected by filtration, so as to obtain 4.7 mg of 4-cyclopropyl-1-ethyl-6-(2-methyl-5-phenyl-1H-imidazol-4-yl)quinolin-2(1H)-one in the form of a white solid.

$^1$H-NMR (CDCl$_3$) δ:0.59-0.67 (2H, m), 0.75-0.85 (2H, m), 1.34 (3H, t, J=7.2 Hz), 1.79-1.90 (1H, m), 2.55 (3H, s), 4.33 (2H, q, J=7.2 Hz), 6.36-6.42 (1H, m), 6.72 (1H, s), 7.20-7.41 (4H, m), 7.42-7.55 (1H, m), 7.75-7.79 (1H, m), 8.19-8.26 (1H, m).

Example 284

[Formula 91]

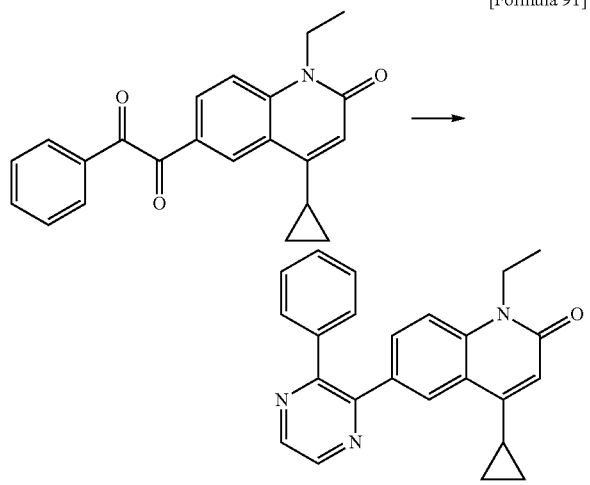

A mixture of 27 mg of 1-(4-cyclopropyl-1-ethyl-2-oxo-1,2-dihydroquinolin-6-yl)-2-phenylethane-1,2-dione and 1 mL of polyethylene glycol 400 was stirred using a microwave apparatus at 100° C. for 5 minutes. To the reaction mixture, 5.2 μL of ethane-1,2-diamine was added, and the obtained mixture was then stirred using a microwave apparatus at 150° C. for 7 minutes. Then, the reaction mixture was further stirred at 160° C. for 10 minutes. Thereafter, the reaction mixture was cooled to room temperature, and ethyl acetate and water were then added thereto. An organic layer was separated, was then washed with water and a saturated sodium chloride aqueous solution and was then dried over anhydrous magnesium sulfate. The solvent was distilled away under reduced pressure. The obtained residue was purified by silica gel chromatography [gradient elution of hexane:ethyl acetate=50:50-0:100]. To the obtained residue, diisopropyl ether was added, and a solid was then collected by filtration, so as to obtain 2 mg of 4-cyclopropyl-1-ethyl-6-(3-phenylpyrazin-2-yl)quinolin-2(1H)-one in the form of a white solid.

$^1$H-NMR (CDCl$_3$) δ:0.52-0.58 (2H, m), 0.77-0.85 (2H, m), 1.34 (3H, t, J=7.2 Hz), 1.65-1.75 (1H, m), 4.33 (2H, q, J=7.2 Hz), 6.37-6.41 (1H, m), 7.31-7.41 (4H, m), 7.47-7.54 (2H, m), 7.86 (1H, dd, J=8.9 Hz, 2.1 Hz), 8.13 (1H, d, J=2.2 Hz), 8.63 (2H, dd, J=6.8 Hz, 2.4 Hz)

Example 285

[Formula 92]

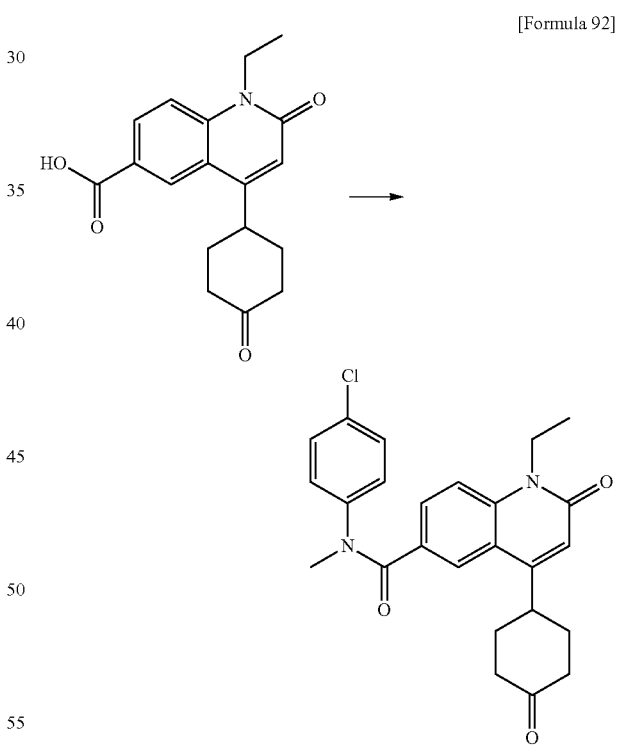

A mixture of 72 mg of 4-chloro-N-methylaniline, 0.27 mL of triethylamine and 216 mg of bis(2-oxo-3-oxazolidinyl)phosphinic chloride was added to a suspension of 134 mg of 1-ethyl-2-oxo-4-(4-oxocyclohexyl)-1,2-dihydroquinoline-6-carboxylic acid in 5 mL of dichloromethane, and the obtained mixture was then stirred at room temperature for 9 hours. Thereafter, to the reaction mixture, 72 mg of N-methyl-4-chloroaniline, 0.27 mL of triethylamine and 216 mg of bis(2-oxo-3-oxazolidinyl)phosphinic chloride were added, and the obtained mixture was then stirred at room temperature for 15 hours. Thereafter, the solvent was distilled away from the obtained reaction mixture under reduced pressure. The obtained residue was purified by silica gel column chromatography [ethyl acetate]. Diisopropyl ether and ethyl acetate were added to the obtained residue, and a solid was then collected by filtration, so as to obtain 73 mg of N-(4-chlorophenyl)-1-ethyl-N-methyl-2-oxo-4-(4-oxocyclohexyl)-1,2-dihydroquinoline-6-carboxamide in the form of a white solid.

$^1$H-NMR (CDCl$_3$) δ: 1.32 (3H, t, J=7.2 Hz), 1.74-1.88 (2H, m), 1.95-2.04 (2H, m), 2.42-2.61 (4H, m), 3.07-3.17 (1H, m), 3.55 (3H, s), 4.30 (2H, q, J=7.1 Hz), 6.55-6.58 (1H, m), 7.03 (2H, d, J=8.8 Hz), 7.22-7.33 (3H, m), 7.66 (1H, dd, J=8.9 Hz, 2.1 Hz), 7.71 (1H, d, J=1.7 Hz).

Example 286 under reduced pressure. The obtained residue was purified by silica gel column chromatography [gradient elution of ethyl acetate:methanol=100:0-90:10]. To the obtained residue, diisopropyl ether was added, and a solid was then collected by filtration, so as to obtain 41 mg of N-(4-chlorophenyl)-1-ethyl-4-(4-hydroxycyclohexyl)-N-methyl-2-oxo-1,2-dihydroquinoline-6-carboxamide in the form of a white solid.

$^1$H-NMR (CDCl$_3$) δ: 1.32 (3H, t, J=7.2 Hz), 1.36-1.70 (6H, m), 2.09-2.20 (2H, m), 2.50-2.61 (1H, m), 3.54 (3H, s), 3.60-3.75 (1H, m), 4.29 (2H, q, J=7.0 Hz), 6.51-6.55 (1H, m), 7.02 (2H, d, J=8.8 Hz), 7.20-7.35 (3H, m), 7.55 (1H, d, J=2.0 Hz), 7.72 (1H, dd, J=8.8 Hz, 2.0 Hz).

Example 287

[Formula 93]

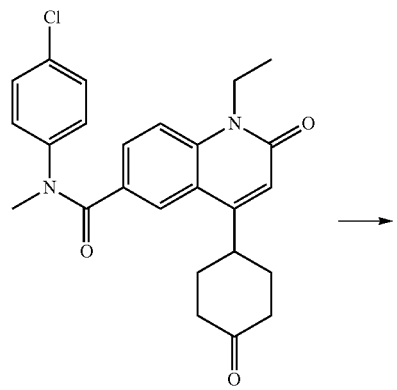

[Formula 94]

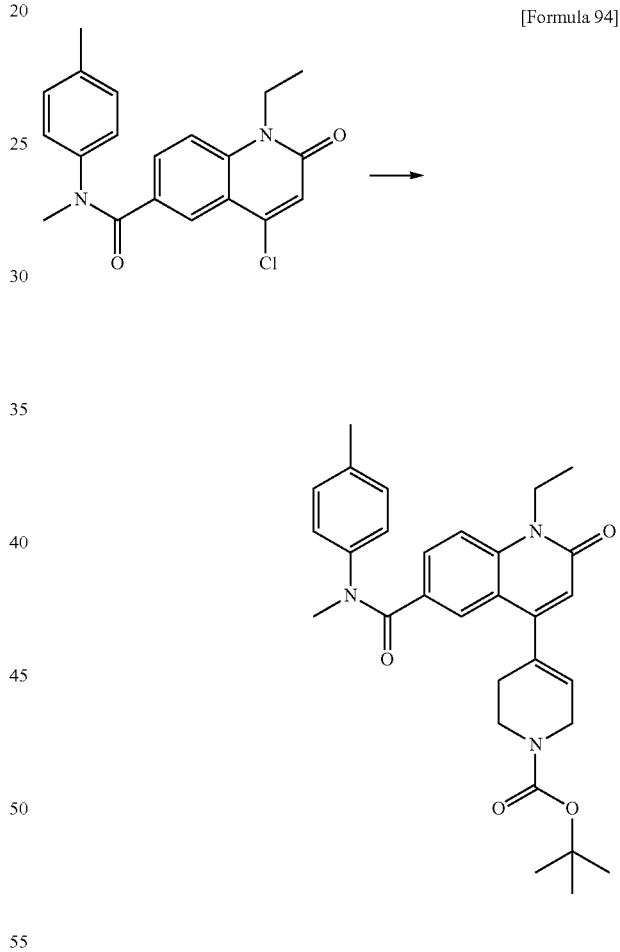

A mixture of 51 mg of N-(4-chlorophenyl)-1-ethyl-N-methyl-2-oxo-4-(4-oxocyclohexyl)-1,2-dihydroquinoline-6-carboxamide, 8.8 mg of sodium borohydride and 1.0 mL of methanol was stirred at room temperature for 1 hour. Thereafter, to the reaction mixture, ethyl acetate and 1 mol/L hydrochloric acid were added. An organic layer was separated, and a water layer was then extracted with ethyl acetate. The organic layer was gathered with the extract, and the obtained mixture was washed with a saturated sodium chloride aqueous solution and was then dried over anhydrous magnesium sulfate. The solvent was distilled away tert-Butyl 4-(1-ethyl-6-(methyl(4-methylphenyl)carbamoyl)-2-oxo-1,2-dihydroquinolin-4-yl)-3,6-dihydropyridine-1(2H)-carboxylate was obtained from 4-chloro-1-ethyl-N-methyl-N-(4-methylphenyl)-2-oxo-1,2-dihydroquinoline-6-carboxamide by the same method as that of Example 5.

MS (ESI, m/z): 502 (M+H)

Example 288

[Formula 95]

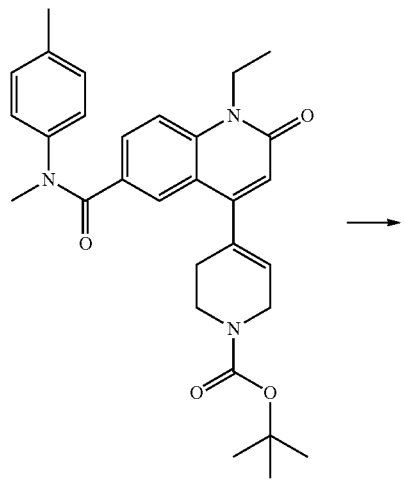

→

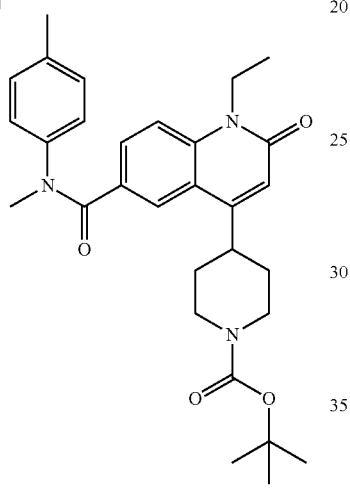

tert-Butyl 4-(1-ethyl-6-(methyl(4-methylphenyl)carbamoyl)-2-oxo-1,2-dihydroquinolin-4-yl)piperidine-1-carboxylate was obtained from tert-butyl 4-(1-ethyl-6-(methyl(4-methylphenyl)carbamoyl)-2-oxo-1,2-dihydroquinolin-4-yl)-3,6-dihydropyridine-1(2H)-carboxylate by the same method as that of Example 6.

MS (ESI, m/z): 504 (M+H)

Example 289

[Formula 96]

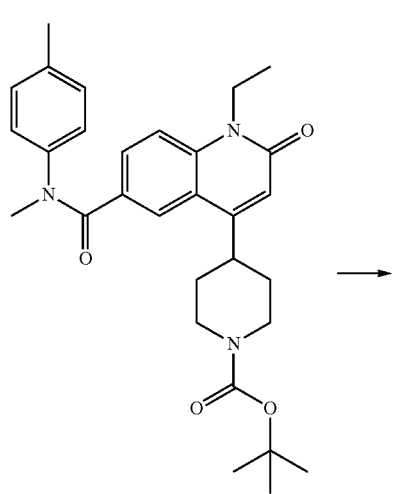

→

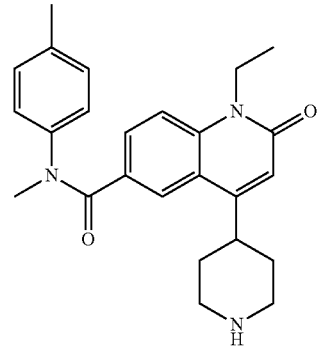

1-Ethyl-N-methyl-N-(4-methylphenyl)-2-oxo-4-(piperidin-4-yl)-1,2-dihydroquinoline-6-carboxamide was obtained from tert-butyl 4-(1-ethyl-6-(methyl(4-methylphenyl)carbamoyl)-2-oxo-1,2-dihydroquinolin-4-yl)piperidine-1-carboxylate by the same method as that of Example 7.

MS (ESI, m/z): 404 (M+H)

Example 290

[Formula 97]

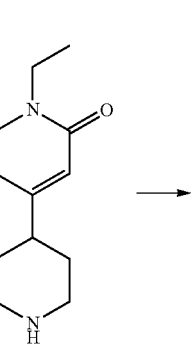

→

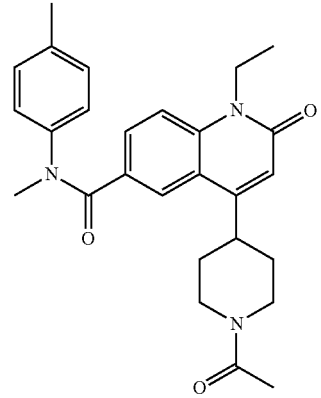

A mixture of 50 mg of 1-ethyl-N-methyl-N-(4-methylphenyl)-2-oxo-4-(piperidin-4-yl)-1,2-dihydroquinoline-6-carboxamide, 20 μL of acetyl chloride, 0.1 mL of triethylamine and 1 mL of dichloromethane was stirred at room temperature for 20 minutes. Thereafter, the reaction mixture was purified by silica gel column chromatography [gradient elution of chloroform:methanol=100:0-80:20]. To the obtained residue, hexane and ethyl acetate were added, and a solid was then collected by filtration, so as to obtain 13 mg of 4-(1-acetylpiperidin-4-yl)-1-ethyl-N-methyl-N-(4-methylphenyl)-2-oxo-1,2-dihydroquinoline-6-carboxamide in the form of a yellow solid.

$^1$H-NMR (DMSO-D$_6$) δ: 1.12-1.55 (7H, m), 2.05 (3H, s), 2.20 (3H, s), 2.57-2.69 (1H, m), 2.86-2.99 (1H, m), 3.10-3.23 (1H, m), 3.40 (3H, s), 3.87 (1H, d, J=13.9 Hz), 4.20 (2H, q, J=6.9 Hz), 4.49 (1H, d, J=12.9 Hz), 6.37 (1H, s), 7.06-7.13 (4H, m), 7.52-7.62 (2H, m), 7.74 (1H, d, J=8.8 Hz).

Example 291

[Formula 98]

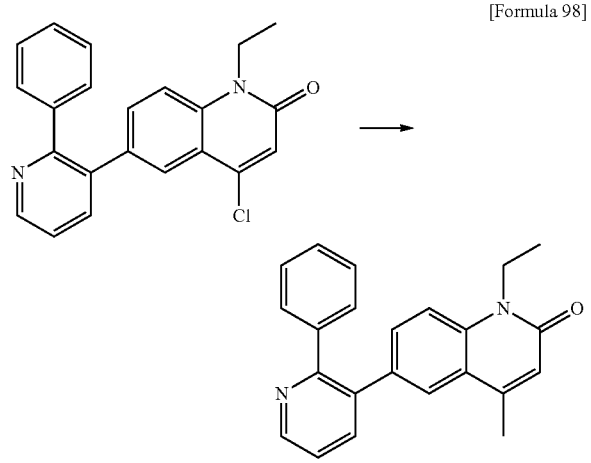

A mixture of 30 mg of 4-chloro-1-ethyl-6-(2-phenylpyridin-3-yl)quinolin-2(1H)-one, 10 mg of methylboric acid, 35 mg of tripotassium phosphate, 6 mg of bis(di-tert-butyl(4-dimethylaminophenyl)phosphine)dichloropalladium(II), 0.5 mL of dioxane and 0.2 mL of water was stirred using a microwave apparatus at 120° C. for 10 minutes. Thereafter, the reaction mixture was cooled to room temperature. The reaction mixture was purified by silica gel chromatography [gradient elution of hexane:ethyl acetate=100:0-30:70]. To the obtained residue, hexane was added, and a solid was then collected by filtration, so as to obtain 5 mg of 1-ethyl-4-methyl-6-(2-phenylpyridin-3-yl)quinolin-2(1H)-one in the form of a white solid.

$^1$H-NMR (CDCl$_3$) δ: 1.34 (3H, t, J=7.3 Hz), 2.21 (3H, d, J=1.0 Hz), 4.33 (2H, q, J=7.3 Hz), 6.55 (1H, d, J=0.96 Hz), 7.23-7.32 (4H, m), 7.34-7.42 (4H, m), 7.48 (1H, d, J=1.9 Hz), 7.81 (1H, dd, J=7.8, 1.7 Hz), 8.73 (1H, dd, J=4.9, 1.7 Hz).

MS (ESI, m/z): 341 (M+H)

Example 292 to 294

In accordance with the procedures described in the present description, the obtained compounds were subjected to a known reaction such as condensation, addition, oxidation, reduction, transposition, substitution, halogenation, dehydration or hydrolysis, or by combining these reactions with one another, as appropriate, so as to produce the compounds shown in Table 29.

TABLE 29

| Example No. | Structural Formula | Compound Name | MS |
|---|---|---|---|
| 292 | | 1-ethyl-N-(3-fluoro-4-methylphenyl)-N-methyl-4-(1-methylpiperidin-4-yl)-2-oxo-1,2-dihydroquinoline-6-carboxamide | 436 (M + H) |
| 293 | | N-(3-chloro-4-methylphenyl)-1-ethyl-N-methyl-4-(1-methylpiperidin-4-yl)-2-oxo-1,2-dihydroquinoline-6-carboxamide | 452 (M + H) |

TABLE 29-continued

| Example No. | Structural Formula | Compound Name | MS |
|---|---|---|---|
| 294 | | N-(3,4-dimethylphenyl)-1-ethyl-N-methyl-4-(1-methylpiperidin-4-yl)-2-oxo-1,2-dihydroquinoline-6-carboxamide | 432 (M + H) |

Test Example 1

(Binding Assay)

BRD2 BD1, BRD3 BD1 and BRD4 BD1 (Cisbio), [Lys(Ac)5/8/12/16]-Histone H4(1-25)-GSGSK (Biotin) (hereinafter referred to as "Peptide-Biotin," AnaSpec), and EPIgeneous (registered trademark) Binding Domain Kit A (Cisbio) were used to carry out an assay. That is to say, per well, 4 μL of BRD2 BD1, BRD3 BD1 or BRD4 BD1, which was adjusted to 20 nmol/L with Diluent buffer; 4 μL of 25 nmol/L Peptide-Biotin; 2 μL of Dilution buffer (Cisbio) containing dimethyl sulfoxide (DMSO) or a test compound that was serially diluted with DMSO; 5 μL of 2.5 nmol/L Streptavidin-d2; and 5 μL of Anti-Gst-Eu+$^{3+}$ Cryptate Conjugate 50-fold diluted with Detection Buffer were added to a 384-well plate (Corning).

Moreover, BRD2 BD2, BRD3 BD2 and BRD4 BD2 (Cisbio), Peptide-Biotin (AnaSpec), and EPIgeneous (registered trademark) Binding Domain Kit B (Cisbio) were used to carry out an assay. That is, per well, 4 μL of BRD2 BD2, BRD3 BD2 or BRD4 BD2, which was adjusted to 20 nmol/L with Diluent buffer; 4 μL of 250 nmol/L Peptide-Biotin; 2 μL of Dilution buffer (Cisbio) containing DMSO or a test compound that was serially diluted with DMSO; 5 μL of 25 nmol/L Streptavidin-XL665; 5 μL of Anti-Gst-Eu+$^{3+}$ Cryptate Conjugate 50-fold diluted with Detection Buffer were added to a 384-well plate (Corning).

The obtained mixture was left at rest at room temperature for 20 hours, and thereafter, the fluoresence intensity at 665 nm and 620 nm was measured using Envision plate reader (Perkin Elmer), so that the inhibition percentage (%) of the test compound against the binding of a bromodomain in a bromodomain-containing protein to Peptide-Biotin was calculated.

Binding inhibition percentage (%)=[1−{(fluorescence intensity at 665 nm of test compound–added well)/(fluorescence intensity at 620 nm of test compound–added well)}/{(fluorescence intensity at 665 nm of DMSO–added well)/(fluorescence intensity at 665 nm of DMSO–added well)}]×100

Moreover, using Graphpad prism 5 (GraphPad software), 50% inhibitory concentration [IC50 (nmol/L)] was calculated according to a non-linear regression analysis (log (inhibitor) vs. response—Variable slope (four parameters)). The results are shown in Table 30.

TABLE 30

| | IC50 (nmol/L) | | | | | |
|---|---|---|---|---|---|---|
| Example | BRD2 | | BRD3 | | BRD4 | |
| No. | BD1 | BD2 | BD1 | BD2 | BD1 | BD2 |
| 14 | 9 | 94 | 4 | 70 | 5 | 27 |
| 17 | 5 | 33 | 3 | 14 | 3 | 10 |
| 245 | 61 | 7 | 37 | 4 | 20 | 3 |
| 246 | 144 | 18 | 91 | 12 | 40 | 7 |
| 290 | 45 | 86 | 15 | 59 | 6 | 22 |

Regarding other test compounds, each compound was diluted with DMSO to a final concentration of 300 nmol/L by the same method as that described above, and the binding inhibition percentage (%) of each test compound at 300 nmol/L against the binding of bromodomain in a bromodomain-containing protein to acetylated histone was calculated. The results are shown in Table 31.

TABLE 31

| | Binding inhibition percentage (%) | | | | | |
|---|---|---|---|---|---|---|
| Example | BRD2 | | BRD3 | | BRD4 | |
| No. | BD1 | BD2 | BD1 | BD2 | BD1 | BD2 |
| 2 | 52 | 89 | 85 | 91 | 85 | 86 |
| 3 | 91 | 89 | 94 | 91 | 94 | 89 |
| 8 | 93 | 79 | 94 | 67 | 94 | 74 |
| 11 | 94 | 79 | 94 | 83 | 94 | 83 |
| 14 | 93 | 74 | 94 | 83 | 93 | 82 |
| 16 | 44 | 87 | 79 | 92 | 70 | 88 |
| 17 | 93 | 85 | 94 | 91 | 94 | 88 |
| 18 | 89 | 86 | 93 | 88 | 94 | 85 |
| 179 | 93 | 88 | 94 | 92 | 95 | 88 |
| 183 | 81 | 71 | 92 | 80 | 94 | 83 |
| 191 | 94 | 87 | 95 | 92 | 94 | 88 |
| 235 | 94 | 82 | 94 | 89 | 95 | 87 |
| 245 | 79 | 89 | 90 | 92 | 91 | 88 |
| 246 | 34 | 82 | 55 | 90 | 67 | 84 |
| 247 | 83 | 90 | 93 | 91 | 94 | 89 |
| 248 | 93 | 90 | 95 | 91 | 95 | 90 |
| 250 | 74 | 88 | 91 | 92 | 91 | 88 |
| 252 | 82 | 86 | 92 | 90 | 94 | 88 |
| 253 | 70 | 87 | 90 | 89 | 92 | 85 |
| 255 | 79 | 89 | 92 | 90 | 94 | 87 |
| 256 | 84 | 86 | 93 | 92 | 94 | 88 |
| 257 | 84 | 85 | 92 | 91 | 95 | 88 |
| 258 | 26 | 81 | 67 | 83 | 64 | 72 |
| 260 | 88 | 87 | 93 | 91 | 94 | 88 |
| 262 | 87 | 89 | 94 | 92 | 94 | 88 |

TABLE 31-continued

| | Binding inhibition percentage (%) | | | | | |
|---|---|---|---|---|---|---|
| Example | BRD2 | | BRD3 | | BRD4 | |
| No. | BD1 | BD2 | BD1 | BD2 | BD1 | BD2 |
| 264 | 92 | 88 | 94 | 91 | 95 | 88 |
| 265 | 91 | 89 | 95 | 92 | 94 | 87 |
| 266 | 91 | 90 | 94 | 91 | 93 | 88 |
| 267 | 32 | 87 | 53 | 90 | 68 | 87 |
| 268 | 48 | 86 | 62 | 92 | 73 | 87 |
| 269 | 36 | 85 | 58 | 92 | 71 | 87 |
| 270 | 87 | 89 | 94 | 91 | 94 | 89 |
| 271 | 60 | 88 | 72 | 92 | 77 | 88 |
| 272 | 87 | 89 | 93 | 91 | 93 | 90 |
| 273 | 93 | 90 | 94 | 93 | 94 | 89 |
| 278 | 83 | 89 | 94 | 91 | 93 | 89 |
| 279 | 91 | 88 | 93 | 91 | 93 | 89 |
| 280 | 83 | 88 | 90 | 92 | 93 | 90 |
| 281 | 87 | 89 | 92 | 91 | 94 | 88 |
| 282a | 94 | 90 | 94 | 91 | 95 | 89 |
| 282b | 71 | 88 | 89 | 92 | 91 | 87 |
| 283 | 68 | 86 | 87 | 92 | 90 | 87 |
| 284 | 83 | 88 | 93 | 92 | 93 | 89 |
| 286 | 91 | 89 | 94 | 93 | 95 | 89 |
| 291 | 64 | 83 | 88 | 91 | 85 | 84 |
| 292 | 93 | 81 | 94 | 87 | 95 | 85 |
| 293 | 94 | 88 | 93 | 90 | 94 | 87 |
| 294 | 94 | 84 | 95 | 90 | 94 | 85 |

From the aforementioned results, it was demonstrated that the compound of the example of the present invention has an ability to inhibit the binding of bromodomain in a bromodomain-containing protein to acetylated histone.

Test Example 2

(Cell Growth Test Performed on Cancer Cells)

The human undifferentiated thymoma cell line Ty-82 (JCRB), the human acute myeloid leukemia cell lines MV4-11 (ATCC), MOLM-13 (ATCC) and RS4-11 (ATCC), the human lymphoma cell line Raji (JCRB), the human cervical epidermoid carcinoma cell line Hela (JCRB), the human lung adenocarcinoma cell line A549 (ATCC), the human colon cancer cell lines DLD1 (DS Pharma) and HCT116 (DS Pharma), and the human pancreatic cancer cell line MIAPACA-2 (ATCC) were used to carry out a cell growth test.

Ty-82, MV4-11, MOLM-13, RS4-11, Raji and DLD1 were each seeded in a well plate, in which Roswell Park Memorial Institute (RPMI)-1640 medium supplemented with penicillin/streptomycin and fetal bovine serum (FBS) with a final concentration of 10% was placed. Hela was seeded in Dulbecco's Modified Eagle's medium (DMEM) supplemented with penicillin/streptomycin and FBS with a final concentration of 10%. A549 and MIAPACA-2 were each seeded in a well plate, in which Minimum Essential Medium (MEM) supplemented with penicillin/streptomycin and FBS with a final concentration of 10% was placed. HCT116 was seeded in a well plate, in which McCoy's 5A medium supplemented with penicillin/streptomycin and FBS with a final concentration of 10% was placed.

Thereafter, a medium containing a test compound serially diluted with DMSO, or DMSO, was added to each well of the plate, in which the cells had been seeded, and the obtained mixture was then cultured under conditions of 37° C. and 5% $CO_2$ for 3 to 5 days. Cell Titer Glo reaction solution (Promega) was added to the culture, and the amount of luminescence was then measured using Envision plate reader (PerkinElmer). Since the amount of luminescence is in proportion to the concentration of adenosine triphosphate (ATP) in cells, the amount of luminescence was used as an indicator of the number of living cells. The growth inhibition percentage of the test compound in each concentration was calculated according to the following equation.

Growth inhibition percentage (%)=(amount of luminescence in test compound–added well)/(amount of luminescence in DMSO–added well)×100

The growth inhibition percentage of the test compound in each concentration was plotted by performing a non-linear regression analysis [(log (inhibitor) vs. response—Variable slope (four parameters)], using Graphpad prism 5, and a 50% growth inhibitory concentration [GI50 (nmol/L)] was then calculated.

The GI50 (nmol/L) values regarding Ty-82, MV4-11 and MOLM-13 are shown in Table 32.

TABLE 32

| | GI50 (nmol/L) | | | | | |
|---|---|---|---|---|---|---|
| Cell line name | Ex. 11 | Ex. 14 | Ex. 17 | Ex. 245 | Ex. 246 | Ex. 247 |
| Ty-82 | 23 | 12 | 6 | 10 | 17 | 11 |
| MV4-11 | 22 | 16 | 8 | 15 | 16 | 16 |
| MOLM-13 | 44 | 32 | 16 | 37 | 43 | 43 |

The GI50 (nmol/L) values regarding other cell lines are shown in Table 33.

TABLE 33

| | Cell line- | GI50 (nmol/L) | | |
|---|---|---|---|---|
| Cell line name | derived cancer species | Ex. 14 | Ex. 17 | Ex. 245 |
| RS4-11 | Acute myeloid leukemia | 66 | 30 | 85 |
| Raji | Lymphoma | 60 | 23 | 97 |
| Hela | Cervical epidermoid carcinoma | 570 | 314 | 1860 |
| A549 | Lung adenocarcinoma | 665 | 292 | 1735 |
| DLD1 | Colon cancer | 361 | 165 | 1336 |
| HCT116 | Colon cancer | 241 | 116 | 628 |
| MIAPACA-2 | Pancreatic cancer | 1416 | 307 | 760 |

Moreover, the compound of Example 14 was subjected to a cell growth test using various types of cell lines.

All cell lines other than the below-noticed cells were each seeded in a well plate, in which an RPMI-1640 medium supplemented with penicillin/streptomycin and FBS with a final concentration of 10% was placed. The human prostate cancer cell line VCaP (ATCC) was seeded in a well plate, in which DMEM medium supplemented with penicillin/streptomycin and FBS with a final concentration of 10% was placed. The human lymphoma cell line OCI-Ly7 (DSMZ) was seeded in a well plate, in which Iscove's Modified Dulbecco's Medium (IMDM) supplemented with gentamicin with a final concentration of 0.05 mg/mL and FBS with a final concentration of 20% was placed. Thereafter, a medium containing a test compound serially diluted with DMSO, or DMSO, was added to each well of the plate, in which the cells had been seeded, and the obtained mixture was then cultured under conditions of 37° C. and 5% $CO_2$ for 3 days. Cell Titer Blue reaction solution (Promega) was added to the culture, and the obtained mixture was then cultured for 4 hours. Thereafter, using Enspire Multimode Plate Reader (PerkinElmer), the amount of fluorescence at an excitation wavelength of 531 nm and a fluorescence wavelength of 615 nm was measured. Since the amount of fluorescence is in proportion to the concentration of a florescent product resorufin that is converted from resazurin as a redox dye by living cells, the amount of fluorescence was used as an indicator of the number of living cells. The growth inhibition percentage of the test compound in each concentration was calculated according to the following equation.

Growth inhibition percentage (%)=(amount of fluorescence in test compound−added well)/(amount of fluorescence in DMSO−added well)×100

The growth inhibition percentage of the test compound in each concentration was plotted by performing a 4-parameter non-linear regression analysis using Oncotest Data Warehouse Software, and a GI50 (nmol/L) value was then calculated. The results are shown in Table 34.

TABLE 34

| Cell line name | Cell line-derived cancer species | Supply source | GI50 (nmol/L) Ex. 14 |
|---|---|---|---|
| T-24 | Bladder cancer | ATCC | 3035 |
| HT-29 | Colon cancer | NCI | 120 |
| HCT-15 | Colon cancer | NCI | 505 |
| KM12 | Colon cancer | NCI | 1494 |
| SW-620 | Colon cancer | NCI | 273 |
| MKN45 | Stomach cancer | JCRB | 2184 |
| KG-1 | Acute myeloid leukemia | DSMZ | 57 |
| NOMO-1 | Acute myeloid leukemia | DSMZ | 62 |
| HL-60 | Acute myeloid leukemia | DSMZ | 27 |
| KG-1A | Acute myeloid leukemia | DSMZ | 119 |
| Jurkat | Acute lymphoblastic leukemia | DSMZ | 129 |
| CCRF-CEM | Acute lymphoblastic leukemia | DSMZ | 65 |
| MOLT-3 | Acute lymphoblastic leukemia | ATCC, DSMZ | 317 |
| MOLT-4 | Acute lymphoblastic leukemia | NCI, DSMZ | 57 |
| K-562 | Chronic myeloid leukemia | NCI, DSMZ | 17 |
| SK-HEP-1 | Liver cancer | DSMZ | 2495 |
| HOP-62 | Lung cancer | NCI | 143 |
| NCI-H69 | Lung cancer | NCI | 975 |
| NCI-H522 | Lung cancer | NCI | 155 |
| NCI-H1299 | Lung cancer | NCI | 422 |
| NCI-H460 | Lung cancer | NCI | 2031 |
| Raji | Lymphoma | DSMZ | 203 |
| U-937 | Lymphoma | DSMZ | 286 |
| WSU-DLCL2 | Lymphoma | DSMZ | 91 |
| SU-DHL-4 | Lymphoma | DSMZ | 49 |
| Daudi | Lymphoma | DSMZ | 165 |
| OCI-LY7 | Lymphoma | DSMZ | 274 |
| SU-DHL-1 | Lymphoma | DSMZ | 1255 |
| MDA-MB-231 | Breast cancer | ATCC | 85 |
| MDA-MB-453 | Breast cancer | ATCC | 115 |
| MDA-MB-468 | Breast cancer | ATCC | 1195 |
| MCF-7 | Breast cancer | DSMZ | 689 |
| T47D | Breast cancer | ECACC | 286 |
| MDA-MB-435 | Melanoma | NCI | 2782 |
| MM.1S | Myeloma | Oncotest | 84 |
| A2780 | Ovarian cancer | NCI | 582 |
| BxPC-3 | Pancreatic cancer | ATCC | 2550 |
| PANC-1 | Pancreatic cancer | CLS | 2985 |
| VCaP | Prostate cancer | ATCC | 361 |
| LNCaP | Prostate cancer | DSMZ | 64 |
| PC-3 | Prostate cancer | DSMZ | 175 |
| DU-145 | Prostate cancer | NCI | 1431 |
| Saos-2 | Sarcoma | DSMZ | 2622 |

From the aforementioned results, it was found that the compound of the example of the present invention exhibited cell growth inhibitory activity on various types of cancer cells.

Test Example 3

(Medicinal Effect Test Using MV4-11-Subcutaneously-Transplanted Cancer-Bearing Mouse Models)

The human acute myeloid leukemia cell line MV4-11 (ATCC) was suspended in a mixture of RPMI-1640 medium and Matrigel (Corning), and the obtained mixture was then subcutaneously transplanted into 6-week-old female BALB/c nu/nu mice (CLEA Japan, Inc.). After confirming that the average tumor volume exceeded 200 mm$^3$, a test compound was dissolved in a solvent (a 0.5% methyl cellulose aqueous solution or water containing 1 equivalent of hydrochloric acid), and the obtained solution was then orally administered to the mice at a daily dose of 10 to 30 mg/kg, once per day, for 14 days. As a negative control, a solvent administration group involving administration of a 0.5% methyl cellulose aqueous solution was established. The tumor diameter was measured on a daily basis, and the tumor volume was calculated. The tumor volume was calculated by measuring the major axis and minor axis of the tumor and then applying the following equation.

Tumor volume (mm$^3$)=[major axis (mm)×minor axis (mm)×minor axis (mm)]/2

T/C (%) was calculated from the average tumor volume of each group according to the following equation, and medicinal effects were then evaluated.

T/C(%)=[1−(average tumor volume of drug administration group)/(average tumor volume of solvent administration group)]×100%

The results are shown in Table 35.

TABLE 35

|  | Ex. 14 | | Ex. 17 | | Ex. 246 | | Ex. 245 | Ex. 247 |
|---|---|---|---|---|---|---|---|---|
| Dose (mg/kg) | 10 | 30 | 10 | 30 | 10 | 30 | 30 | 30 |
| T/C (%) | 34 | 45 | 21 | 49 | 13 | 33 | 42 | 33 |

Moreover, using the above-described mouse models, medicinal effects obtained upon intravenous administration were evaluated.

The human acute myeloid leukemia cell line MV4-11 (ATCC) was suspended in a mixture of RPMI-1640 radium and Matrigel (Corning), and the obtained mixture was then subcutaneously transplanted into 6-week-old female BALB/c nu/nu mice (CLEA Japan, Inc.). After confirming that the average tumor volume exceeded 200 mm$^3$, a test compound was dissolved in a solvent (a normal saline containing 1 equivalent of hydrochloric acid), and the obtained solution was then intravenously administered to the mice at a daily dose of 10 to 30 mg/kg, once per day, for 25 days. As a negative control, a solvent administration group involving administration of a normal saline was established. The tumor diameter was measured on a daily basis, and the tumor volume was calculated. In the same manner as described above, the tumor volume and T/C (%) were calculated, and medicinal effects were then evaluated.

The results are shown in Table 36.

TABLE 36

|  | Ex. 14 Dose (mg/kg) | |
|---|---|---|
|  | 10 | 30 |
| T/C (%) | 66 | 78 |

From the aforementioned results, it was demonstrated that the compounds of the Examples of the present invention have tumor growth inhibitory effects on the above-described models, and it became clear that the compounds of the present invention can be used as antitumor agents.

Test Example 4

(Pharmacological Action Confirmation Test on Cancer Cells)

It has been known that the antitumor action of a bromodomain inhibitor is associated with a c-Myc protein. Please refer to, for example, Non-Patent Document 3: Delmore J E et al., Cell, Vol. 146, pp. 904 to 917, 2011. With reference to the method described in Non-Patent Document 3, the ability of the compound of the present example to inhibit the expression of a c-Myc protein in cancer cells was evaluated according to Western blotting.

The human undifferentiated thymoma cell line Ty-82 (JCRB) used in the evaluation was seeded in a 6-well plate, in which an RPMI-1640 medium supplemented with penicillin/streptomycin and FBS with a final concentration of 10% was placed. A medium containing a test compound serially diluted with dimethyl sulfoxide (DMSO), or DMSO, was added to each well of the 6-well plate in which the cells had been seeded, and the obtained mixture was then cultured under conditions of 37° C. and 5% $CO_2$ for 24 hours. Thereafter, the cells were recovered, and were then washed with PBS. After that, Lysis Buffer (10-fold diluted Cell Lysis Buffer (10×) (CST Japan), to which Halt Protease and Phosphatase Inhibitor Cocktail (Thermofisher Scientific) were added) was added to the resulting cells. The above-described cell suspension was subjected to an ultrasonic treatment to disintegrate the cells, and was then centrifuged to recover a supernatant. Sample buffer was added thereto, and the obtained mixture was then heated at 95° C. for 5 minutes.

A sample prepared from the above-described supernatant was loaded at a protein mass of 10 μg/lane on XV PANTERA GEL 7.5%-15% (D.R.C), and was then subjected to electrophoresis. The electrophoresed protein was transcribed on a transcription membrane, and was then inoculated with Anti-Myc antibody (CST, Catalog No. 9402) and then with IRDye® 680LT Donkey anti-Rabbit IgG (H+L) (LI-COR). Using Odessey (LI-COR), the fluorescence intensity at an excitation wavelength of 700 nm was measured, and the expression level of the c-Myc protein was then quantified.

When the compounds of Example 14, Example 17, and Example 245 were used at a concentration of 100 nmol/L, the expression level of c-Myc was significantly reduced.

Test Example 5

(Analysis of Fluctuation in Expression of c-Myc, IL-7R and HEXIM1 Genes in MV4-11 Cells)

It has been known that the gene expression of c-Myc and Interleukin-7 receptor subunit alpha (IL-7R) is decreased by a treatment with a bromodomain inhibitor whereas the gene expression of Hexamethylene bisacetamide inducible 1 (HEXIM1) is increased. Please refer to, for example, Non-Patent Document 4: Dyana T. Saenz et al., Leukemia, Vol. 31, pp. 678 to 687, 2017.

A fluctuation in the expression of c-Myc, IL-7R and HEXIM1 genes in MV4-11 (ATCC) cells treated with the test compound was analyzed according to a reverse transcription polymerase chain reaction (RT-PCR) method.

MV4-11 cells were cultured for 6 hours in an RPMI-1640 medium supplemented with penicillin/streptomycin and FBS with a final concentration of 10%, to which the compound of Example 14 was added to a concentration of 10 nmol/L, 30 nmol/L or 100 nmol/L. On the other hand, a non-treatment group (Non-treatment) was established by culturing MV4-11 cells for 6 hours in the above-described medium, to which the compound of Example 14 was not added. Using Rneasy (registered trademark) (Qiagen), RNA was extracted from the above-described MV4-11 cells in accordance with the instruction manual included with the aforementioned device. Buffer RLT was added to the cells, and the cells were then disintegrated. After that, the lysate was directly added to QIAshredder Spin Column, using a pipette, and was then centrifuged at 20,000 g for 2 minutes. The resultant was added to gDNA Eliminator Spin Column, and was then centrifuged at 8,000 g for 1 minute, and thereafter, ethanol was added to the resultant. Thereafter, the obtained mixture was added to RNeasy Spin Column, and was then washed with Buffer RW1 and Buffer RPE. Thereafter, RNase-Free Water was added to the resultant for recovery. Thereafter, using PrimeScript RT reagent Kit (Takara), a reverse transcription reaction was carried out at 42° C. for 30 minutes, and the enzyme was then inactivated at 95° C. for 5 minutes, so as to prepare cDNA. The prepared cDNA was used as template DNA, and initial denaturation was carried out at 95° C. for 30 seconds and the primers described below were used. Thereafter, a PCR reaction was carried out for 40 cycles (a cycle consisting of 95° C.-5 seconds and 60° C.-30 seconds.) Subsequently, the obtained reaction product was measured.

GAPDH primer: PrimePCR SYBR (registered trademark) Green Assay: GAPDH, Human (BioRad)

c-Myc primer: PrimePCR SYBR (registered trademark) Green Assay: MYC, Human (BioRad)

IL-7R primer: PrimePCR SYBR (registered trademark) Green Assay: IL7R, Human (BioRad)

HEXIM1 primer: PrimePCR SYBR (registered trademark) Green Assay: HEXIM1, Human (BioRad)

As a housekeeping gene, the expression level of GAPDH (Glyceraldehyde 3-phosphate dehydrogenase) was also evaluated. The ratio of the expression level of the mRNA of each of c-Myc, IL-7R and HEXIM1 to the expression level of GAPDH was calculated, and the expression level of each gene (relative expression level) was then quantified. In this RT-PCR, SYBR (registered trademark) Premix Ex Taq II (Takara) was used.

As a result, as shown in FIG. 1 to FIG. 3, it could be confirmed that when the MV4-11 cells were treated with the compound of Example 14, the expression of c-Myc and IL-7R was decreased in a compound concentration-dependent manner, whereas the expression of HEXIM1 was increased.

Test Example 6

(Analysis of Fluctuation in Intratumoral Expression of c-Myc Gene in MV4-11-Subcutaneously-Transplanted Cancer-Bearing Mouse Models)

According to an RT-PCR method, a fluctuation in the intratumoral expression of a c-Myc gene in MV4-11-subcutaneously-transplanted cancer-bearing mouse models, to which a test compound had been administered, was analyzed.

The compound of Example 14 was dissolved in a solvent (a 0.5% methyl cellulose aqueous solution or water containing 1 equivalent of hydrochloric acid), and the obtained solution was then orally administered to the mice at a dose of 30 mg/kg. As a negative control, a solvent administration group (vehicle) involving administration of a 0.5% methyl cellulose aqueous solution was established. Moreover, the test compound was dissolved in a solvent (a normal saline containing 1 equivalent of hydrochloric acid), and the obtained solution was then intravenously administered to the mice at a dose of 30 mg/kg. As a negative control, a solvent administration group (vehicle) involving administration of a normal saline was established. From MV4-11-subcutaneously-transplanted cancer-bearing mice involving oral or intravenous administration of the test compound, tumor was excised 1, 3, 6 and 24 hours (hr) after the administration. The excised tumor was disintegrated in a frozen state, using Multi-beads Shocker (Yasui Kikai Corporation). Using RNeasy(Qiagen), RNA was extracted from the disintegrated tumor sample in accordance with the instruction manual, and cDNA was then prepared using PrimeScript RT reagent Kit (Takara). A PCR reaction was carried out by the same method as that of Test Example 5, and a fluctuation in the gene expression of GAPDH and c-Myc in the tumor was then evaluated.

As a result, as shown in FIG. 4 and FIG. 5, it could be confirmed that the intratumoral expression of the c-Myc gene was decreased by administration of the compound of Example 14.

Test Example 7

(Intravenous Administration Toxicity Test on Rats)

It has been reported that oral administration of a bromodomain inhibitor causes weight reduction. In addition, it has also been reported that the activity and area under the blood concentration-time curve (AUC) of a bromodomain inhibitor are correlated with a weight reduction percentage. Moreover, it has further been reported that BRD4 inhibition induces disorders to gastrointestinal epithelial stem cells. Please refer to, for example, Non-Patent 5: P. Newham et al., "In vivo and in vitro models of bromodomain and extraterminal domain inhibitor-induced intestinal stem cell loss and villous atrophy reveal differential human vs pre-clinal species sensitivity," Basel Life Sciences Week 2015, Reference Document for Poster Session, Sep. 21, 2015).

With reference to the above-described findings, the compound of the present example was administered to rats via repeated intravenous administration, and the influence of the compound on the body weight and the digestive tract was then evaluated.

The compound of Example 14 was dissolved in a solvent (a normal saline containing 1 equivalent of hydrochloric acid), and the obtained solution was then intravenously administered to 6-week-old male SD rats (Charles River Laboratories Japan) at a dose of 30 to 60 mg/kg, once a day, for 7 days. As a negative control, a solvent administration group involving administration of a normal saline was established. At the time of the final administration, the plasma concentration of the compound of Example 14 was measured. As a result, it was confirmed that the plasma concentration was increased in proportion to the applied dose. Moreover, a weight reduction was not observed during the administration period. Furthermore, on the day following the final administration, pathological evaluation was carried out. As a result, no disorders were found in gastrointestinal epithelial cells including gastrointestinal epithelial stem cells.

In the case of using the compound of Example 14, a weight reduction was not observed in AUC that was 3.8 times higher than the AUC upon intravenous administration in Test Example 3. In Non-Patent Document 4, it has been reported that BRD4 inhibition induces disorders to gastrointestinal epithelial stem cells. However, it became clear that such gastrointestinal epithelial disorders are not caused by intravenous administration of the compound of Example 14.

INDUSTRIAL APPLICABILITY

The antitumor agent and the bromodomain inhibitor, which are represented by the formula [1], have an excellent bromodomain inhibitory activity and are useful as treatment agents in the prevention and/or therapy of tumor associated with a bromodomain, and the like.

The invention claimed is:
1. A method for treating tumor, comprising administering a therapeutically effective amount of a compound represented by the following formula [1] or a salt thereof, wherein the tumor is blood cancer, thymoma, myeloma, liver cancer, pancreatic cancer, ovarian cancer, prostate cancer, lung cancer, osteosarcoma, colon cancer, breast cancer, skin cancer, epithelial cell cancer, bladder cancer, lymphoma or stomach cancer:

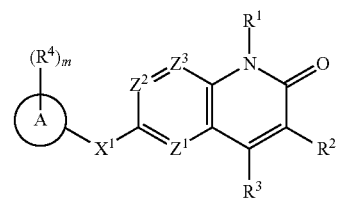

[1]

wherein $R^1$ represents an optionally substituted $C_{1-6}$ alkyl group;
$R^2$ represents a hydrogen atom;
$R^3$ represents an optionally substituted $C_{1-6}$ alkyl group, an optionally substituted $C_{3-8}$ cycloalkyl group, or an optionally substituted heterocyclic group;
$Z^1$, $Z^2$ and $Z^3$ each represents CH;
$X^1$ represents
(1) a group represented by the formula $C(=O)N(R^6)$ (wherein the carbon atom binds to Ring A, and $R^6$ represents a hydrogen atom, an amino-protecting group, or an optionally substituted $C_{1-6}$ alkyl group),
(2) a group represented by the formula $N(R^7)C(=O)$ (wherein the nitrogen atom binds to Ring A, and $R^7$ represents a hydrogen atom, an amino-protecting group, or an optionally substituted $C_{1-6}$ alkyl group; or $R^7$ represents, together with one substituent $R^4$ of Ring A, an optionally substituted $C_{2-4}$ alkylene group,
(3) an optionally substituted divalent cyclic hydrocarbon group that is formed by removing each one hydrogen atom on the two adjacent atoms, or
(4) an optionally substituted divalent heterocyclic group that is formed by removing each one hydrogen atom on the two adjacent atoms;
Ring A represents an aryl group;
an m number of $R^4$, which are the same or different, each represents a halogen atom, an optionally substituted $C_{1-6}$ alkyl group,
an optionally substituted $C_{2-5}$ alkylene group formed together by the two adjacent $R^4$, an optionally substituted C$_{2-4}$ alkylene group formed by one R$^4$ together with R$^7$, and m represents an integer from 0 to 2.

2. The method according to claim 1, wherein
R$^3$ represents an optionally substituted C$_{3-8}$ cycloalkyl group or an optionally substituted heterocyclic group.

3. The method according to claim 1, wherein
R$^3$ represents any one of the following heterocyclic groups:

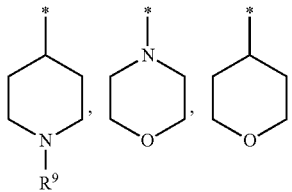

wherein R$^9$ represents a hydrogen atom, an amino-protecting group, or an optionally substituted C$_{1-6}$ alkyl group, and * represents a binding site.

4. The method according to claim 1, wherein
X$^1$ represents
(2) a group represented by the formula N(R$^7$)C(=O) (wherein the nitrogen atom binds to Ring A, and R$^7$ represents a hydrogen atom, an amino-protecting group, or an optionally substituted C$_{1-6}$ alkyl group; or R$^7$ represents, together with one substituent R$^4$ of Ring A, an optionally substituted C$_{2-4}$ alkylene group, or
(4) an optionally substituted divalent heterocyclic group that is formed by removing each one hydrogen atom on the two adjacent atoms.

5. The method according to claim 1, wherein
the compound is represented by the following formula [1-1]:

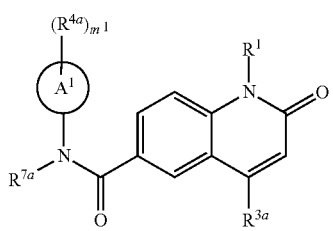

wherein R$^1$ represents a hydrogen atom;

R$^{3a}$ represents an optionally substituted C$_{1-6}$ alkyl group, an optionally substituted C$_{3-8}$ cycloalkyl group, or an optionally substituted heterocyclic group;

Ring A$^1$ represents an aryl group;

R$^{7a}$ represents an amino-protecting group or an optionally substituted C$_{1-6}$ alkyl group; or R$^{7a}$ represents, together with one substituent R$^{4a}$ of Ring A$^1$, an optionally substituted C$_{2-3}$ alkylene group, an m$^1$ number of R$^{4a}$, which are the same or different, each represents a halogen atom, an optionally substituted C$_{1-3}$ alkyl group, an optionally substituted C$_{2-5}$ alkylene group formed together by the two adjacent R$^{4a}$, an optionally substituted C$_{2-3}$ alkylene group formed by one R$^{4a}$ together with R$^{7a}$, and m$^1$ represents an integer from 0 to 2.

6. The method according to claim 1, wherein
X$^1$ represents an optionally substituted dihydrooxoimidazole-1,5-diyl group, an optionally substituted imidazole-1,2-diyl group, an optionally substituted imidazole-4,5-diyl group, an optionally substituted 1,2,4-triazole-1,5-diyl group, an optionally substituted 1H-pyrazole-4,5-dihyl group, an optionally substituted oxopyrrolidine-1,2-diyl group, an optionally substituted dioxotriazolidine-1,2-diyl group, an optionally substituted dioxopyrazolidine-1,2-diyl group, an optionally substituted oxopyrazoline-1,2-diyl group, an optionally substituted pyridine-2,3-diyl group, or an optionally substituted pyrazine-2,3-diyl group.

7. The method according to claim 1, wherein
the compound is at least one selected from the group consisting of:

N-(4-cyclopropyl-1-ethyl-2-oxo-1,2-dihydroquinolin-6-yl)-N-methylbenzamide,1-ethyl-4-(1-ethylpiperidin-4-yl)-N-methyl-2-oxo-N-phenyl-1,2-dihydroquinoline-6-carboxamide, 6-(3,4-dihydroquinolin-1(2H)-ylcarbonyl)-1-ethyl-4-(1-methylpiperidin-4-yl)quinolin-2(1H)-one, 1-ethyl-N-methyl-N-(4-methylphenyl)-4-(1-methylpiperidin-4-yl)-2-oxo-1,2-dihydroquinoline-6-carboxamide, N-(2,3-dihydro-1H-inden-5-yl)-1-ethyl-N-methyl-4-(1-methylpiperidin-4-yl)-2-oxo-1,2-dihydroquinoline-6-carboxamide, 6-(5-(4-chlorophenyl)-2-oxo-2,3-dihydro-1H-imidazol-1-yl)-1-ethyl-4-(morpholin-4-yl)quinolin-2(1H)-one, 6-(5-(4-chlorophenyl)-3-methyl-2-oxo-2,3-dihydro-1H-imidazol-1-yl)-1-ethyl-4-(morpholin-4-yl)quinolin-2(1H)-one, 1-ethyl-4-(morpholin-4-yl)-6-(2-oxo-5-phenyl-3-(propan-2-yl)-2,3-dihydro-1H-imidazol-1-yl)quinolin-2(1H)-one, 1-(4-cyclopropyl-1-ethyl-2-oxo-1,2-dihydroquinolin-6-yl)-2-phenyl-1,2,4-triazolidine-3,5-dione, 4-chloro-N-(1-ethyl-4-(morpholin-4-yl)-2-oxo-1,2-dihydroquinolin-6-yl)-N-methylbenzamide, 4-(1-acetylpiperidin-4-yl)-1-ethyl-N-methyl-N-(4-methylphenyl)-2-oxo-1,2-dihydroquinoline-6-carboxamide, 1-ethyl-N-(3-fluoro-4-methylphenyl)-N-methyl-4-(1-methylpiperidin-4-yl)-2-oxo-1,2-dihydroquinoline-6-carboxamide, N-(3-chloro-4-methylphenyl)-1-ethyl-N-methyl-4-(1-methylpiperidin-4-yl)-2-oxo-1,2-dihydroquinoline-6-carboxamide, and N-(3,4-dimethylphenyl)-1-ethyl-N-methyl-4-(1-methylpiperidin-4-yl)-2-oxo-1,2-dihydroquinoline-6-carboxamide.

8. The method according to claim 1, wherein
the tumor is blood cancer, thymoma, myeloma, liver cancer, pancreatic cancer, ovarian cancer, prostate cancer, lung cancer, osteosarcoma, colon cancer, breast cancer, skin cancer, or epithelial cell cancer.

9. A method of inhibiting bromodomains wherein diseases treatable by such inhibition include diseases selected from the group consisting of blood cancer, thymoma, myeloma, liver cancer, pancreatic cancer, ovarian cancer, prostate cancer, lung cancer, osteosarcoma, colon cancer, breast cancer, skin cancer, epithelial cell cancer, bladder cancer, lymphoma or stomach cancer, said method comprising administering a therapeutically effective amount of a compound represented by the formula [1] or a salt thereof:

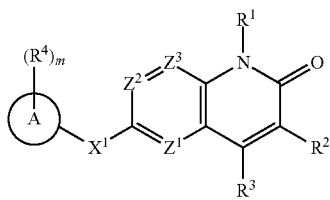

wherein $R^1$ represents an optionally substituted $C_{1-6}$ alkyl group;
$R^2$ represents a hydrogen atom;
$R^3$ represents an optionally substituted $C_{1-6}$ alkyl group, an optionally substituted $C_{3-8}$ cycloalkyl group or an optionally substituted heterocyclic group;
$Z^1$, $Z^2$ and $Z^3$ each represents CH;
$X^1$ represents
(1) a group represented by the formula $C(=O)N(R^6)$ (wherein the carbon atom binds to Ring A, and $R^6$ represents a hydrogen atom, an amino-protecting group, or an optionally substituted $C_{1-6}$ alkyl group,
(2) a group represented by the formula $N(R^7)C(=O)$ (wherein the nitrogen atom binds to Ring A, and $R^7$ represents a hydrogen atom, an amino-protecting group, or an optionally substituted $C_{1-6}$ alkyl group; or $R^7$ represents, together with one substituent $R^4$ of Ring A, an optionally substituted $C_{2-4}$ alkylene group,
(3) an optionally substituted divalent cyclic hydrocarbon group that is formed by removing each one hydrogen atom on the two adjacent atoms, or
(4) an optionally substituted divalent heterocyclic group that is formed by removing each one hydrogen atom on the two adjacent atoms;
Ring A represents an aryl group;
an m number of $R^4$, which are the same or different, each represents a halogen atom, an optionally substituted $C_{1-6}$ alkyl group,
an optionally substituted $C_{2-5}$ alkylene group formed together by the two adjacent $R^4$,
an optionally substituted $C_{2-4}$ alkylene group formed by one $R^4$ together with $R^7$, and
m represents an integer from 0 to 2.

10. The method according to claim 9, which inhibits the binding of bromodomain to acetylated histone.

11. The method according to claim 9, wherein the bromodomain is a protein domain comprised in a BET family protein.

* * * * *